US007189889B2

(12) United States Patent
Tarczynski et al.

(10) Patent No.: US 7,189,889 B2
(45) Date of Patent: Mar. 13, 2007

(54) METHODS FOR IMPROVING SEED CHARACTERISTICS

(75) Inventors: Mitchell C. Tarczynski, West Des Moines, IA (US); Odd-Arne Olsen, Johnston, IA (US); Bo Shen, Johnston, IA (US); Stein E. Lid, As (NO); Changjiang Li, Urbandale, IA (US); Rudolf Jung, Des Moines, IA (US); Darren B. Gruis, Des Moines, IA (US); Jennifer A. Lorentzen, West Des Moines, IA (US); Evgueni Ananiev, Johnston, IA (US); Scott E. Nichols, Westchester, PA (US); Cunxi Wang, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 185 days.

(21) Appl. No.: 10/208,948

(22) Filed: Jul. 30, 2002

(65) Prior Publication Data
US 2003/0074689 A1 Apr. 17, 2003

Related U.S. Application Data

(60) Provisional application No. 60/337,444, filed on Oct. 25, 2001, provisional application No. 60/309,719, filed on Aug. 2, 2001.

(51) Int. Cl.
C12N 15/29 (2006.01)
C12N 15/82 (2006.01)
C12N 15/87 (2006.01)
C12N 5/04 (2006.01)
A01H 5/00 (2006.01)
A01H 5/10 (2006.01)

(52) U.S. Cl. ............ 800/278; 800/298; 800/287; 800/290; 435/320.1; 435/410; 435/419; 435/252.3; 536/23.1; 536/23.6

(58) Field of Classification Search ............... 800/290, 800/278, 298, 320, 312, 287, 281; 536/23.1, 536/23.6; 435/252.3, 468, 419
See application file for complete search history.

(56) References Cited
FOREIGN PATENT DOCUMENTS
EP 1 033 405 A2 6/2000

OTHER PUBLICATIONS

Bowie et al, Science 247:1306-1310, 1990.*
McConnell et al, Nature 411 (6838):709-713, 2001.*
Fourgoux-Nicol et al (1999, Plant Molecular Biology 40 :857-872).*
Larkin et al (1994, The Plant Cell 6:1065-1076).*
Whetten et al (1999, NCBI Accession No. AW043258).*
Lid et al (2002, PNAS 99(8):5460-5465).*

Clonetech Laboratories, Inc. (1997, Protocol # PT3003-5, Version #PR7Y564, www.genomex.com/vector_maps/PT3003-5_map.pdf).*
Becraft et al., CRINKLY4: A TNFR-Like Receptor Kinase Involved in Maize Epidermal Differentiation, Science (1996) 273:1406-1409.
Becraft et al., Positional cues specify and maintain aleurone cell fate in maize endosperm development, Development (2000) 127:4039-4048.
Bonnard et al., Nucleotide sequence, evolutionary origin and biological role of a rearranged cytokinin gene isolated from a wide hose range biotype III *Agrobacterium* strain, Mol Gen. Genet. (1989) 216:428-438.
Hargin et al., Triglyceride Deposits in the Starchy Endosperm of Wheat, Cereal Chem. (1980) 57(5):320-325.
Hargin et al., The Distribution of Acyl Lipids in the Germ, Aleurone, Starch and Non-starch Endosperm of Four Wheat Varieties, J. Sci. Food Agric. (1980) 31:877-888.
Kalla et al., The promoter of the barley aleurone-specific gene encoding a putative 7 kDa lipid transfer protein confers aleurone cell-specific expression in transgenic rice, Plant Journal (1994) 6(6):849-860.
Shen et al., Sa/1 determines the number of aleurone cell layers in maize endosperm and encodes a class E vacuolar sorting protein, Proc. Natl. Acad. Sci. USA (2003) 100(11):6552-6557.
Thompson, R.D., Turning fields into grains, Nature (2000) 408:39-41.
Wang et al., The Calpain Domain of the Maize DEK1 Protein Contains the Conserved Catalytic Triad and Functions as a Cysteine Proteinase, J. Biol. Chem. (2003) 278(36):34467-34474.
Welch et al., Improving the mineral reserves and protein quality of maize (*Zea mays* L.) kernels using unique genes, Plant and Soil (1993) 155(156):215-218.
Wolf et al., Maize with Multilayer Aleurone of High Protein Content, Crop Science (1972) 12:440-442.
Yang et al., Molecular Characterization of *NbCHMP1* Encoding of Homolog of Human *CHMP1* in *Nicotiana benthamiana*, Mol. Cells (2004) 17(2):255-261.
Olsen et al., In search of gene hierarchies regulating endosperm development: an effort involving forward and reverse genetics, functional genomics and proteomics, Plant Biology (2001) pp. 64-65 and Joint Annual Meetings of the American Society of Plant Biologists and the Canadian Society of Plant (Jul. 2001) Abstract #220.
Kessler et al., Characterization of xcl (extra cell layers), a mutation affecting planes of cell division during maize development, Plant Biology (2000) pp. 48 and Annual Meeting of the American Society of Plant Physiologists (Jul. 2000) Abstract #131.
Gavazzi et al., Dap (Defective aleurone pigmentation) mutations affect maize aleurone development, Mol. Gen. Genet. (1997) 256:223-230.
DATABASE EMBL, *Zea mays* PCO082662 mRNA sequence (2002) Accession No. AY104483.

* cited by examiner

*Primary Examiner*—Stuart F. Baum
(74) *Attorney, Agent, or Firm*—Pioneer Hi-Bred International, Inc.; Kathryn K. Lappegard

(57) ABSTRACT

Methods are provided for altering grain characteristics by introducing into plants, isolated nucleic acid molecules that can be used to produce transgenic plants characterized by altered number, type, or configuration of aleurone cells within the seed. Also provided are isolated nucleic acids that encode maize dek1 proteins, vectors capable of expressing such nucleic acid molecules, host cells containing such vectors, and polypeptides encoded by such nucleic acids.

20 Claims, No Drawings

METHODS FOR IMPROVING SEED CHARACTERISTICS

CROSS-REFERENCE TO RELATED APPLICATIONS

This application claims priority to U.S. Provisional Application Ser. No. 60/309,719 filed Aug. 2, 2001 and U.S. Provisional Application Ser. No. 60/337,444 filed Oct. 25, 2001, the contents of which are incorporated herein by reference.

TECHNICAL FIELD

The present invention relates to the field of crop improvement. Specifically, the present invention relates to the identification and use of genes encoding molecules involved in altering the number and characteristics of aleurone cells in plant seeds and the use of these genes and mutants thereof to improve nutritional, industrial, and agricultural traits in seed and grain.

BACKGROUND OF THE INVENTION

Most common cereal grains contain cells called aleurone cells that occur as the most external layer of the endosperm. Aleurone cells are generally oil and protein-rich and secrete enzymes allowing the mobilization of endosperm reserves during seed germination. Barley, oats, and some varieties of rice have been reported to have 2 to 4 layers of aleurone cells (Sawicki et al., 1952, and Hoshikawa et al, 1967). Maize commonly has only a single layer making up only 2% or less of the weight of the kernel (Hinton et al, 1953). A South American race of maize, Coroico, has been found to contain from 2 to 6 layers of aleurone cells (Wolf et al, 1972). This characteristic has been referred to as the Mal (multiple aleurone) phenotype by Welch et al, 1993.

When compared to grains having only a single layer of aleurone cells, varieties having multiple aleurone cell layers contain increased amounts of minerals (Welch et al., 1993) and protein (Wolf, ibid). However, the Mal phenotype is inherited as a partially dominant trait and is highly variable in the Coroico line. To date, a reliable, multiple aleurone trait has not been available in maize or other cereal crops that could be used in a breeding program to take advantage of the unique characteristics of aleurone cells.

Thus, a transgenic or breeding approach that alters the number of aleurone cells in a grain crop as well as the characteristics of the aleurone cells would be highly desirable.

SUMMARY OF THE INVENTION

Several genes have been isolated that are known to affect the differentiation of the aleurone layer in crop seeds. This invention foresees using these nucleic acids, or polypeptides, or variants thereof, to improve seed and grain quality by altering the number, type, and/or characteristics of aleurone cells.

DETAILED DESCRIPTION OF THE INVENTION

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By "seed" or "kernel" is intended to include the grain or ripened ovule of a plant, or more broadly, a propagative plant structure. The terms "seed" and "kernel" are used interchangeably herein.

The term "grain" as used herein means the mature seed produced by commercial growers for purposes other than growing or reproducing the species.

As used herein the term "recombinant" means having parts combined in a configuration not found in nature.

The term "coding sequence" or "coding region" refers to a nucleotide sequence that codes for a specific amino acid sequence.

The term "expression" as used herein, refers to the transcription and accumulation of sense (mRNA) or antisense RNA derived from a nucleic acid fragment of the invention. Expression may also refer to translation of mRNA into a polypeptide.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, the term "nucleic acid" means a polynucleotide and includes single or multi-stranded polymers of deoxyribonucleotide or ribonucleotide bases. Nucleic acids may also include fragments and modified nucleotides. Therefore, as used herein, the terms "nucleic acid" and "polynucleotide" are used interchangably.

As used herein, "polypeptide" means proteins, protein fragments, modified proteins (e.g., glycosylated, phosphorylated, or other modifications), amino acid sequences and synthetic amino acid sequences. The polypeptide can be modified or not. Therefore, as used herein, "polypeptide" and "protein" are used interchangably.

As used herein, "plant" includes plants and plant parts including but not limited to plant cells and plant tissues such as leaves, stems, roots, flowers, pollen, and seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Fragments of a nucleotide sequence may encode protein fragments that retain the biological activity of the native nucleic acid ie: "functional fragments". Alternatively, fragments of a nucleotide sequence that can be useful as hybridization probes may not encode fragment proteins retaining biological activity. Thus, fragments of a nucleotide sequence are generally greater than 25, 50, 100, 150, 200, 250, 300, 350, 400, 450, 500, 600, or 700 nucleotides and up to and including the entire nucleotide sequence encoding the proteins of the invention. Generally the probes are less than 1000 nucleotides and often less than 500 nucleotides. Fragments of the invention include antisense sequences used to decrease expression of the inventive polynucleotides. Such antisense fragments may vary in length ranging from greater than 25, 50, 100, 200, 300, 400, 500, 600, or 700 nucleotides and up to and including the entire coding sequence.

By "functional equivalent" as applied to a polynucleotide or a protein is intended a polynucleotide or a protein of sufficient length to modulate the level of protein activity in a plant cell. A polynucleotide functional equivalent can be in sense or antisense orientation.

By "variants" is intended substantially similar sequences. Generally, nucleic acid sequence variants of the invention will have at least 60%, 65%, 70%, 75%, 80%, 85%, 86%, 87%, 88%, 89%, 90%, 91%, 92%, 93%, 94%, 95%, 96%, 97%, 98% or 99% sequence identity to the native nucleotide sequence, wherein the % sequence identity is based on the entire sequence and is determined by GAP 10 analysis using default parameters. Generally, polypeptide sequence variants of the invention will have at least about 60%, 65%, 70%, 75%, 80%, 85%, 90%, 95% or 98% sequence identity to the native protein, wherein the % sequence identity is based on the entire sequence and is determined by GAP 10 analysis using default parameters. GAP uses the algorithm of Needleman and Wunsch (*J. Mol. Biol.* 48:443–453, 1970) to find the alignment of two complete sequences that maximizes the number of matches and minimizes the number of gaps.

As used herein "transformation" includes stable transformation and transient transformation.

As used herein "stable transformation" refers to the transfer of a nucleic acid fragment into a genome of a host organism (this includes both nuclear and organelle genomes) resulting in genetically stable inheritance. In addition to traditional methods, stable transformation includes the alteration of gene expression by any means including chimeraplasty or transposon insertion.

"Non-ruminant animal" means an animal with a simple stomach divided into the esophageal, cardia, fundus and pylorus regions. A non-ruminant animal additionally implies a species of animal without a functional rumen. A rumen is a section of the digestive system where feedstuff/food is soaked and subjected to digestion by microorganisms before passing on through the digestive tract. This phenomenon does not occur in a non-ruminant animal. The term non-ruminant animal includes, but is not limited to: humans, swine, poultry, cats and dogs.

The term "aleurone cell" as used herein refers to an epidermis-like cell layer in the seeds of many crop species. This aleurone layer functions as "an important source of hydrolytic enzymes required for remobilization of stored starch and protein during germination" (Becraft et al., *Science*, 1996 273:1406–1409.)

Wild-type aleurone cells contain oil bodies, phytic acid inclusions and protein carbohydrate bodies. Storage proteins are in the form of globulins. Wild-type aleurone cells contain very little or no starch granules. As a seed matures, aleurone cells go through a maturation and desiccation program. After seed desiccation, mature aleurone cells respond to GA stimulation by initiation of transcription of genes encoding amylases, proteases and glucanases upon inhibition. A marker of aleurone cells is that they can activate transcription from the barley Ltp2 promoter (Kalla, R. et al., 1994). Sudan red can be used to visualize the high concentration of oil bodies in the aleurone layer, as well as the low amount of oil bodies in nearby starchy endosperm cells. Aleurone cells may also be transgenically manipulated to alter expression in—including but not limited to—type or amount of: oil bodies and their contents, storage proteins, protein-carbohydrate bodies, phytate deposition, and responsiveness to GA in the form of transcriptional activation of one or more of the genes activated in germinating seeds.

It is expected that modulating the expression of the nucleic acids of the present invention will modulate signaling in the aleurone cell developmental pathway providing methods to alter the number and characteristics of the aleurone cells.

Increasing the aleurone cell number is a mechanism for increasing the concentration of plant sterols (phytosterols) and their derivatives. Phytosterols have been shown to have important applications to human health by, for example, decreasing serum cholesterol concentrations. Sitostanol, a sterol derivative that is particularly effective in reducing cholesterol, is found at unusually high concentrations in maize aleurone cells.

As used herein, "Dek1" is a polynucleotide of the present invention that encodes a polypeptide which is a protein involved in aleurone cell differentiation, and refers to one or more amino acid sequences, in modified or unmodified form, that is necessary and sufficient for aleurone cell fate determination in a transformed plant. The term is also inclusive of fragments, variants, homologs, alleles or precursors (e.g., preproproteins or proproteins) that, when introduced into a plant or plant germ line by way of—but not limited to—transformation or breeding, result in changes in the aleurone cells.

The Dek1 gene has been identified as a calpain based on the presence of the cystein proteinase domain shared by all members of the calpain super gene family. The sequence of the single copy gene ZmDek1-calpain spans about 24 000 bp (SEQ ID NO: 25). A transcriptional start-site is predicted at bp1440 and the coding sequence is between bp 2682–23732, containing 31 exons. Arabidopsis thaliana also has a single copy Del1-calpain orthologue (SEQ ID NO: 28) that shares a remarkable conservation with the maize gene, including an identical exon structure.

The maize Dek1 coding region is 7110 bp, compared with 6453 bp for Arabidopsis. Based on MPSS transcript profiling technology (Lynx Therapeutics, Inc. 25861 Industrial Blvd. Hayward, Calif. 94545). Maize Dek1 is expressed at a low level in many tissues of the maize plant, including kernel, roots, tassel, stem sheaths, leaf, seedlings and roots. Using RT-PCR, the transcript is detected in unfertilized ovules and in developing grains up to 15 DAP, but very little at 22 DAP.

The isolated maize dek1 promoter region is characterized by a putative TATA box at positions 2283–2287 of SEQ ID NO:25 and a putative CAAT box at positions 2333–2337 of SEQ ID NO:25.

Kernels of the dek1 corn mutant lack aleurone cells and the endosperm of such mutants consists of starchy endosperm cells in the periphery normally occupied by aleurone cells. Positional cues specify and maintain aleurone cell fate in maize endosperm development. A reversion of a dek1 mutant allele to wild-type restores aleurone cell identity to peripheral starchy endosperm cells in which this event occurs (Becraft et al., *Development*, 127(18):4039–48, 2000).

The maize DEK1 protein is 2159 amino acid residues (239.0 kDa) and 2151 amino acids for Arabidopis: the two protein sharing 70% overall identity. The DEK1 proteins are identified as members of the calpain superfamily by their conserved cystein proteinase domain II (from aa position 1708–2013 of SEQ ID NO:24) shared by all members of this superfamily, plus similarity in domain III (from aa position 2014–2163) present in many calpains. The identity between maize and Arabidopsis in these two domains is 88 and 83%, respectively.

DEK1 proteins from maize and Arabidopsis differ from conventional calpains by their N-terminal extensions of 1435 amino acids. This part of the protein contains five distinguishable domains, including a predicted plasma membrane targeting signal in the N-terminus (positions 1–30 of SEQ ID NO:24). This region is followed by a predicted membrane spanning peptide sequence (positions 31–335 of SEQ ID NO:24). A similar domain, containing 15 predicted membrane-spanning peptide sequences, is found further downstream (positions 620–1108 of SEQ ID NO:24). The identity between maize and Arabidopsis in these two regions is 72% and 64%, respectively. The two membrane spanning domains are separated by a loop region (positions 336–628 of SEQ ID NO:24). This region is the least conserved part of the maize and Arabidopis DEK1 proteins, with 57% identity.

Over-expression or modification of this protein can increase the number of aleurone layer cells, or the production of aleurone cells in parts of the seed that do not normally possess these cells. Further, creation of a dominant version of the dek1 protein would render the signal transduction pathway responsible for aleurone cell fate specification constitutively active in the cells expressing the gene— inducing formation of aleurone layers independent of the positional cues proposed to be involved in aleurone cell formation.

The crinkly 4 (cr4)(Becraft, P. W., *Science*, 1996, 273: 1406–1409) gene encodes a putative receptor kinase that is involved in the signaling pathway controlling aleurone layer differentiation. Over-expression or modification of this protein can increase the number of aleurone layer cells.

A dominant version of cr4 can be obtained by functional screening mutated cr4 gene. The cr4 kinase domain as described in Becraft can be fused to the extracellular domain of the clv1 (Clark S. E., et al. *Cell.* 1997 May 16;89(4): 575–85) or bri1 (Wang Z. Y., et al, *Nature.* 2001 Mar 15;410(6826):380-3) gene to form a chimeric receptor that can be activated by CLV3 (Trotochaud A. E., et al, *Science* Jul. 28, 2000 289(5479):613–7) or brassinosteroid.

As used herein "Superal" is a polynucleotide of the present invention that encodes a polypeptide involved in or interacts with the signal transduction pathway that determines aleurone cell fate. The kernels of superal mutants are characterized by as many as eight layers of aleurone cells. Down regulation of this protein can increase the number of aleurone cells in the seed.

Nucleic Acids

The isolated nucleic acids of the present invention can be made using standard recombinant methods, synthetic techniques, or combinations thereof known in the art. In some embodiments, the polynucleotides of the present invention can be cloned, amplified, or otherwise constructed from monocots or dicots. Typical plants include maize, barley, wheat, rice, rye, oats, millet, soybeans, arabidopsis, tobacco, canola, sunflower, or sorghum.

Functional fragments included in the invention can be obtained using primers which selectively hybridize under stringent conditions. Primers are generally at least 12 bases in length and can be as high as 200 bases, but will generally be from 15 to 75, or more likely from 15 to 50 bases. Functional fragments can be identified using a variety of techniques such as restriction analysis, Southern analysis, primer extension analysis, and DNA sequence analysis.

The present invention includes a plurality of polynucleotides that encode for the DEK1 amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, pages 8.0.3–8.5.9 *Current Protocols in Molecular Biology,* Ausubel et al., Eds., Greene Publishing and Wiley-Interscience, New York (1995). Also, see generally, McPherson (ed.), *DIRECTED MUTAGENESIS: A Practical Approach,* (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences which alter, add or delete a single amino acid or a small percentage of amino acids in the encoded sequence. A "conservatively modified variant" is an alteration which results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J. H., et al., *Proc. Natl. Acad. Sci. USA* 94:4504–4509 (1997).

The present invention also includes a promoter region natively associated with the maize dek1 coding region. By "natively associated" is meant a promoter region as it exists prior to its isolation from its associated in vivo coding region.

The present invention also includes the use of 5' and/or 3' UTR regions for modulation of translation of heterologous coding sequences. Positive sequence motifs include translational initiation consensus sequences (Kozak, *Nucleic Acids Res.*15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides of the present invention can be modified to alter codon usage. Altered codon usage can be employed to alter translational efficiency. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387–395 (1984)) or MacVector 4.1 (Eastman Kodak Co., New Haven, Conn.).

For example, the inventive nucleic acids can be optimized for enhanced expression in plants of interest. See, for example, EPA0359472; WO91/16432; Perlak et al. (1991) *Proc. Natl. Acad. Sci. USA* 88:3324–3328; and Murray et al. (1989) *Nucleic Acids Res.* 17:477–498. In this manner, the polynucleotides can be synthesized utilizing plant-preferred codons. See, for example, Murray et al. (1989) *Nucleic Acids Res.* 17:477–498, the disclosure of which is incorporated herein by reference.

The present invention provides subsequences comprising isolated nucleic acids containing at least 20 contiguous bases of the inventive sequences. For example the isolated nucleic acid includes those comprising at least 20, 30, 40, 50, 60, 70, 80, 90, 100, 200, 300, 400, 500, 600, 700 or 800 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics* 37:327–336 (1996). Other methods for producing full-length libraries are known in the art. See, e.g., Edery et al., *Mol. Cell Biol.* 15(6):3363–3371 (1995); and PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18(19):5705–5711 (1990); Patanjali et al., *Proc. Natl. Acad. U.S.A.* 88:1943–1947 (1991); U.S. Pat. Nos. 5,482,685 and 5,637,685; and Soares et al., *Proc. Natl. Acad. Sci. USA* 91:9228–9232 (1994).

Subtracted cDNA libraries are another means to increase the proportion of less abundant cDNA species. See, Foote et al., in *Plant Molecular Biology: A Laboratory Manual*, Clark, Ed., Springer-Verlag, Berlin (1997); Kho and Zarbl, *Technique* 3(2):58–63 (1991); Sive and St. John, *Nucl. Acids Res.* 16(22):10937 (1988); *Current Protocols in Molecular Biology*, Ausubel et al., Eds., Greene Publishing and Wiley-Interscience, New York (1995); and, Swaroop et al., *Nucl. Acids Res.* 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook et al., *Molecular Cloning: A Laboratory Manual*, 2nd Ed., Cold Spring Harbor Laboratory, Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous polynucleotides in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5× to 1×SSC at 55° C. Exemplary high stringency conditions include hybridization in 50% formamide, 1 M NaCl, 1% SDS at 37° C., and a wash in 0.1×SSC at 60° C. Typically the time of hybridization is from 4 to 16 hours.

An extensive guide to the hybridization of nucleic acids is found in Tijssen, *Laboratory Techniques in Biochemistry and Molecular Biology—Hybridization with Nucleic Acid Probes,* Part I, Chapter 2 *"Overview of principles of hybridization and the strategy of nucleic acid probe assays",* Elsevier, New York (1993); and *Current Protocols in Molecular Biology,* Chapter 2, Ausubel et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related polynucleotides directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications,* Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products. PCR-based screening methods have also been described. Wilfinger et al. describe a PCR-based method in which the longest cDNA is identified in the first step so that incomplete clones can be eliminated from study. *BioTechniques,* 22(3): 481–486 (1997).

In one aspect of the invention, nucleic acids can be amplified from a plant nucleic acid library. The nucleic acid library may be a cDNA library, a genomic library, or a library generally constructed from nuclear transcripts at any stage of intron processing. Libraries can be made from a variety of plant tissues such as ears, seedlings, leaves, stalks, roots, pollen, or seeds. Good results have been obtained using tissues such as corn nucellus 5 days after silking, corn embryos 20 days after pollination, and dissected embryo sacs at 4, 5, and 6, days after pollination.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al., (1989) *Molecular Cloning: A Laboratory Manual* (2d ed., Cold Spring Harbor Laboratory Press, Plainview, N.Y.). and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.* 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Regulatory Sequences

Transformation of organisms with exogenous DNA sequences can provide commercially desirable strains. In the case of plants, transformation can lead to new varieties having heritable traits of insect resistance, herbicide resistance, and other agronomically important nutritional or morphological properties.

Diverse regulatory sequences are needed as undesirable biochemical interactions result from using the same regulatory sequence to control more than one gene. For example, transformation with multiple copies of a regulatory element may cause homologous recombination between two or more expression systems, formation of hairpin loops caused from two copies of the same promoter or enhancer in opposite orientation in close proximity, competition between identical expression systems for binding to common promoter-specific regulatory factors, and inappropriate expression levels of an exogenous gene due to trans effects of a second promoter or enhancer.

The limited number of known regulatory sequences does not cover the desired range of conditions for transgenic expression. Accordingly, any new sequence having a regulatory role in promoting, enhancing or otherwise regulating gene expression could be used in new combinations with known regulatory sequences and would be a valuable contribution to the art.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus the promoter regions disclosed herein are generally further defined by comprising upstream regulatory elements such as those responsible for tissue and temporal expression of the coding sequence, enhancers and the like. In the same manner, the promoter elements which enable expression in the desired tissue such as the seed can be identified, isolated, and used with other core promoters to confirm seed-preferred expression.

It is recognized that the promoters may be used with their native coding sequences to increase or decrease expression resulting in a change in phenotype in the transformed plant.

A regulatory sequence "variant" is a modified form of a regulatory sequence wherein one or more bases have been modified, removed or added. For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to remove progressively nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions. After digestion, mung bean nuclease removes single stranded DNA overhangs and the blunt ends are ligated with T4 DNA ligase.

One example of a regulatory sequence variant is a promoter formed by one or more deletions from a larger promoter. The 5' portion of a promoter up to the TATA box near the transcription start site can be deleted without abolishing promoter activity, as described by Zhu et al., *The Plant Cell* 7:1681–89 (1995).

Those fragments of promoter nucleotide sequences disclosed herein that operate to promote the seed-preferred expression of an operably linked heterologous nucleotide sequence, are referred to as "functional fragments". These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York). Again, variants of these promoter fragments, such as those resulting from site-directed mutagenesis, are encompassed by the compositions of the present invention.

An artisan can modify the regulatory sequences as summarized above and expect to obtain a functional product. Others have made these kinds of simple modifications resulting in functional fragments. For example, Rieping and Schoffl reported that "[c]omplete reconstruction of a native (heat shock) promoter region increased" transgenic expression "only very little, but deletion of CCAAT box sequences reduced CAT expression five-fold." *Mol. Gen. Genet.* 231:226–32 (1992). The same authors also reported using a "series of deletion mutants of a soybean heat shock (hs) promoter" and that heat inducible "activities were detected except in plants containing a transcriptional fusion devoid of all but 18 nucleotides at the 5' terminus of the hs gene transcript." *Mol. Gen. Genet.* 217:246–53 (1989).

The coding sequence expressed by the promoters of the invention may be used for varying the phenotype of the seeds. Various changes in phenotype are of interest including modifying the fatty acid composition in seeds, altering the starch or carbohydrate profile, altering the amino acid content of the seed, and the like. These results can be achieved by providing expression of heterologous or increased expression of endogenous products in seeds. Alternatively, the results can be achieved by providing for a reduction of expression of one or more endogenous products, particularly enzymes or cofactors in the seed. These changes result in a change in phenotype of the transformed seed.

A wide variety of polypeptides or RNA, such as an antisense sequence, can be expressed transgenically under the control of an inventive regulatory sequence. In practice, DNA that codes for a desired polypeptide or RNA is fused to a promoter to achieve a high level of expression. In many cases, the controlled polypeptide or RNA may not be native to the organism in which it is expressed. DNA coding for the polypeptide may be modified to reflect preferred codon usage in the particular species that is the transformation target.

In cases where the controlled gene is to be expressed in a plant seed or tissue, especially desired are regulatory elements of a "seed tissue-preferred" or "seed tissue-specific" promoter, that is, a promoter that drives high expression of the heterologous DNA segment in seed tissue where control of genes involved in seed metabolism is desired, and little or no expression in other parts of the plant. Manufacture of the protein encoded by the heterologous DNA segment in other parts of the plant needlessly expends the plant's energy.

A regulatory sequence of the invention is advantageously combined with a selectable marker gene, in physical proximity to the introduced DNA segment. The marker gene allows recovery of transformed cells by positive genetic selection or screening. The selectable marker gene also provides continuing selection pressure on a transgenic plant population, to ensure that the introduced DNA segment is retained by the transgenic organism.

Many commonly used positive selectable marker genes for transformation have been isolated from bacteria and code for enzymes that metabolically detoxify a selective chemical agent which may be an antibiotic or a herbicide. Other positive selection marker genes encode an altered target which is insensitive to the inhibitor.

In order to create an expression vector containing the gene and a regulatory sequence to control the gene, an expression cassette first is made by inserting a cloned gene, or a DNA segment comprising the desired regulatory sequences fused to a DNA sequence encoding a desired high-value protein as described above, into a plasmid.

One or more copies of the expression cassette containing the introduced DNA is transferred to an expression vector. In a preferred embodiment, the vector also contains a gene encoding a selection marker which functionally is linked to a promoter regulatory sequence that controls transcription initiation.

Transformation protocols as well as protocols for introducing nucleotide sequences into plants may vary depending on the type of plant or plant cell, i.e., monocot or dicot, targeted for transformation as described further herein.

Expression Cassettes

Expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook et al.; *Molecular Cloning: A*

*Laboratory Manual;* Cold Spring Harbor, N.Y.; (1989); Gelvin et al.; *Plant Molecular Biology Manual* (1990); *Plant Biotechnology: Commercial Prospects and Problems,* eds. Prakash et al.; Oxford & IBH Publishing Co.; New Delhi, India; (1993); and Heslot et al.; *Molecular Biology and Genetic Engineering of Yeasts;* CRC Press, Inc., USA; (1992); each incorporated herein in its entirety by reference.

For example, plant expression vectors may include one or more cloned plant genes under the transcriptional control of 5' and 3' regulatory sequences and a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'- promoter derived from T-DNA of *Agrobacterium tumefaciens,* the actin promoter, the ubiquitin promoter, the histone H2B promoter (Nakayama et al., 1992, *FEBS Lett* 30:167–170), the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known in the art.

Examples of inducible promoters are the Adh1 promoter which is inducible by hypoxia or cold stress, the Hsp70 promoter which is inducible by heat stress, the PPDK promoter which is inducible by light, the In2 promoter which is safener induced, the ERE promoter which is estrogen induced and the Pepcarboxylase promoter which is light induced.

Examples of promoters under developmental control include promoters that initiate transcription preferentially in certain tissues, such as leaves, roots, fruit, pollen, seeds, or flowers. An exemplary promoter is the anther specific promoter 5126 (U.S. Pat. Nos. 5,689,049 and 5,689,051). Examples of seed-preferred promoters include, but are not limited to, 22 kDa zein promoter, 27 kD gamma zein promoter and waxy promoter, (Boronat, A., et al., *Plant Sci.* 47:95–102 (1986); Reina, M., et al., *Nucleic Acids Res.* 18(21):6426 (1990); Kloesgen, R. B., et al., *Mol. Gen. Genet.* 203:237–244 (1986)), as well as the globulin 1, oleosin and the phaseolin promoters. A typical aleurone-preferred promoter is the Ltp2 promoter (Kalla, R., et al., *Plant Journal,* 4:849–860, 1994; see also SEQ ID NO:18). The barley nuc1 promoter (see SEQ ID NO:17), and cim1 promoter (U.S. Pat. No. 6,225,529 issued May 1, 2001) are examples of nucellus tissue preferred promoters. Developing endosperm promoters that may be used are the end1 and end2 promoters (see SEQ ID NOS:19 and 20). The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395–4405 (1988); Callis et al., *Genes Dev.* 1:1183–1200 (1987). Use of maize introns Adh1-S intron 1, 2, and 6, the Bronze-1 intron are known in the art. See generally, *The Maize Handbook,* Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene encodes antibiotic or herbicide resistance. Suitable genes include those coding for resistance to the antibiotics spectinomycin and streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., *Meth. In Enzymol.* 153:253–277 (1987). Exemplary *A. tumefaciens* vectors useful herein are plasmids pKYLX6 and pKYLX7 of Schardl et al., *Gene* 61:1–11 (1987) and Berger et al., *Proc. Natl. Acad. Sci. USA* 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Natl. Acad. Sci. USA* 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990) and U.S. Pat. No. 5,034,323.

Recent work has shown suppression with the use of double stranded RNA. Such work is described in Tabara et al., *Science* 282:5388:430–431 (1998), WO 99/53050 and WO 98/53083.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J. Am. Chem. Soc.* (1987) 109:1241–1243). Meyer, R. B., et al., *J. Am. Chem. Soc.* (1989) 111:8517–8519, effect covalent crosslinking to a target nucleotide using an alkylating agent complementary to the single-stranded target nucleotide sequence. A photo-activated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home et al., *J. Am. Chem. Soc.* (1990) 112:2435–2437. Use of N4, N4-ethanocytosine as an alkylating agent to crosslink to single-stranded oligonucleotides has also been described by Webb and Matteucci, *J. Am. Chem. Soc.* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

Proteins of the present invention include proteins having the disclosed sequences as well proteins coded by the disclosed polynucleotides. In addition, proteins of the present invention include proteins derived from the native protein by deletion, addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants can generally be made such that variants continue to possess the desired activity.

The isolated proteins of the present invention include a polypeptide comprising at least 25 contiguous amino acids encoded by any one of the nucleic acids of the present invention, or polypeptides that are conservatively modified variants thereof. The proteins of the present invention or variants thereof can comprise any number of contiguous amino acid residues from a polypeptide of the present invention, wherein that number is selected from the group of integers consisting of from 25 to the number of residues in a full-length polypeptide of the present invention. Optionally, this subsequence of contiguous amino acids is at least 25, 30, 40, 50, 60, 70, 80, 90, 100, 150, 200, 250, 300, 350, 400, 450, or 500 amino acids in length.

The present invention includes catalytically active polypeptides (i.e., enzymes). Catalytically active polypeptides will generally have a specific activity of at least about 20%, 30%, 40%, 50%, 60%, 70%, 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least about 30%, 40%, 50%, 60%, 70%, 80%, 90%, or 95% that of the native (non-synthetic), endogenous polypeptide. Methods of assaying and quantifying measures of enzymatic activity and substrate specificity ($k_{cat}/K_m$), are well known to those of skill in the art. See, e.g., Segel, *Biochemical Calculations*, $2^{nd}$ ed., John Wiley and Sons, New York (1976).

The present invention includes modifications that can be made to an inventive protein. In particular, it may be desirable to diminish the activity of the gene. Other modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Using the nucleic acids of the present invention, one may express a protein of the present invention in recombinantly engineered cells such as bacteria, yeast, insect, mammalian, or plant cells. The cells produce the protein in a non-natural condition (e.g., in quantity, composition, location, and/or time), because they have been genetically altered through human intervention to do so.

Typically, an intermediate host cell may be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes and eukaryotes. Prokaryotes include bacterial hosts such as *Eschericia coli*, *Salmonella typhimurium*, and *Serratia marcescens*. Eukaryotic hosts such as yeast, insect cells or filamentous fungi may also be used in this invention.

Commonly used prokaryotic control sequences include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using Bacillus sp. and Salmonella (Palva et al., *Gene* 22:229–235 (1983); Mosbach et al., *Nature* 302:543–545 (1983)).

Synthesis of heterologous proteins in yeast is well known. See Sherman, F., et al., *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The baculovirus expression system (BES) is a eukaryotic, helper-independent expression system which has been used to express hundreds of foreign genes (Luckow, V., Ch. 4 "Cloning and Expression of Heterologous Genes in Insect Cells with Baculovirus Vectors" in *Recombinant DNA Technology and Applications*, A. Prokop et al., Eds. McGraw-Hill, Inc. (1991); Luckow, V., Ch. 10 "Insect Expression Technology" in *Principles & Practice of Protein Engineering*, J. L. Cleland and C. S. Craig, Eds. John Wiley & Sons, (1994)).

Recombinant baculoviruses are generated by inserting the particular gene- or genes-of-interest into the baculovirus genome using established protocols with vectors and reagents from commercial suppliers (e.g., Invitrogen, Life Technologies Incorporated). Commercial vectors are readily available with various promoters, such as polyhedrin and p10, optional signal sequences for protein secretion, or affinity tags, such as 6×histidine. These recombinant viruses are grown, maintained and propagated in commercially available cell lines derived from several insect species including *Spodoptera frugiperda* and *Trichoplusia ni*. The insect cells can be cultured using well-established protocols in a variety of different media, for example, with and without bovine serum supplementation. The cultured cells are infected with the recombinant viruses and the gene-of-interest polypeptide is expressed. Proteins expressed with the baculovirus system have been extensively characterized and, in many cases, their post-translational modifications such as phosphorylation, acylation, etc., are identical to the natively expressed protein.

A protein of the present invention, once expressed, can be isolated from cells by lysing the cells and applying standard protein isolation techniques to the lysates. The monitoring of the purification process can be accomplished by using Western blot techniques or radioimmunoassay or other standard immunoassay techniques. Expression cassettes are also available which direct the expressed protein to be secreted from the cell into the media. In these cases, the expressed protein can be purified from the cell growth media using standard protein purification techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology*. Vol. 2 *Special Methods in Peptide Synthesis*, Part A.; Merrifield et al., *J. Am. Chem. Soc.* 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide)) are known to those of skill.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant.

The method comprises transforming a plant cell with an expression cassette comprising a polynucleotide of the present invention to obtain a transformed plant cell, growing the transformed plant cell under conditions allowing expression of the polynucleotide in the plant cell in an amount sufficient to modulate concentration and/or composition in the plant cell.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. One method of down-regulation of the protein involves using PEST sequences that provide a target for degradation of the protein.

In some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant growing conditions for a time sufficient to: alter the aleurone cells in the seeds of the plant, to increase the level of oil in the seeds of the plant, or to otherwise improve the grain characteristics of the seed of the plant. Plant growing conditions are well known in the art.

In general, content of the polypeptide is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucteotide of the present invention can also be controlled by exogenous administration of an effective amount of inducing compound. Inducible promoters and inducing compounds which activate expression from these promoters are well known in the art. In certain embodiments, the polypeptides of the present invention are modulated in monocots or dicots, for example: maize, wheat, rice, barley, soybean, arabidopsis, oats, sorghum, millet, rye, sunflower, safflower, alfalfa, canola, or cotton.

Means of detecting the proteins of the present invention are not critical aspects of the present invention. The proteins can be detected and/or quantified using any of a number of well-recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B. V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and Non-isotopic *Immunoassays*, Ngo, Ed., Plenum Press, NY (1988).

Typical methods include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of catalytically active polypeptides of the present invention. The method comprises contacting a polypeptide of the present invention with a compound whose ability to bind to or modulate enzyme activity is to be determined. The polypeptide employed will have at least 20%, 30%, 40%, 50%, 60%, 70%, 80%, 90% or 95% of the specific activity of the native, full-length polypeptide of the present invention (e.g., enzyme). Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256:495–497 (1975).

Other suitable techniques involve selection of libraries of recombinant antibodies in phage or similar vectors (see, e.g., Huse et al., *Science* 246:1275–1281 (1989); and Ward et al., *Nature* 341:544–546 (1989); and Vaughan et al., *Nature Biotechnology* 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.* 14:845–851

(1996). Also, recombinant immunoglobulins may be produced. See, Cabilly, U.S. Pat. No. 4,816,567; and Queen et al., *Proc. Natl. Acad. Sci. U.S.A.* 86:10029–10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention may be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transformation of Cells

The method of transformation is not critical to the present invention; various methods of transformation are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A DNA sequence coding for the desired polynucleotide of the present invention, for example a cDNA or a genomic sequence encoding a full length protein or functional portion thereof, can be used to construct an expression cassette which can be introduced into the desired plant. Isolated nucleic acid acids of the present invention can be introduced into plants according to techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet* 22:421–477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197–213 in *Plant Cell, Tissue and Organ Culture, Fundamental Methods*, Eds. O. L. Gamborg and G. C. Phillips, Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3:2717–2722 (1984). Electroporation techniques are described in Fromm et al., *Proc. Natl. Acad. Sci. U.S.A.* 82:5824 (1985). Ballistic transformation techniques are described in Klein et al., *Nature* 327:70–73 (1987).

*Agrobacterium tumefaciens*-meditated transformation techniques are well described in the scientific literature. See, for example Horsch et al., *Science* 233:496–498 (1984), and Fraley et al., *Proc. Natl. Acad. Sci.* 80:4803 (1983). For instance, *Agrobacterium* transformation of maize is described in U.S. Pat. No. 5,981,840; 5,591,616 and 5,731,179 herein incorporated in their entirety by reference. *Agrobacterium* transformation of soybean is described in U.S. Pat. No. 5,563,055.

Other methods of transformation include (1) *Agrobacterium rhizogenes*-mediated transformation (see, e.g., Lichtenstein and Fuller In: *Genetic Engineering*, Vol. 6, P. W. J. Rigby, Ed., London, Academic Press, 1987; and Lichtenstein, C. P. and Draper, J. In: *DNA Cloning*, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16, (2) liposome-mediated DNA uptake (see, e.g., Freeman et al., *Plant Cell Physiol.* 25:1353 (1984)), and (3) the vortexing method (see, e.g., Kindle, *Proc. Natl. Acad. Sci. USA* 87:1228 (1990)).

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding polynucleotides can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.* 75:30 (1987); and Benbrook et al., in *Proceedings Bio Expo 1986*, Butterworth, Stoneham, Mass., pp. 27–54 (1986).

Animal and lower eukaryotic (e.g., yeast) host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, Gordon-Kamm et al., *The Plant Cell* 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell*

*Culture,* Macmillan Publishing Company, New York, pp.124–176 (1983); and Binding, *Regeneration of Plants, Plant Protoplasts,* CRC Press, Boca Raton, pp. 21–73 (1985).

The regeneration of plants containing the foreign gene introduced by *Agrobacterium* can be achieved as described by Horsch et al., *Science* 227:1229–1231 (1985) and Fraley et al., *Proc. Natl. Acad. Sci. U.S.A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, *Methods for Plant Molecular Biology,* A. Weissbach and H. Weissbach, eds., Academic Press, Inc., San Diego, Calif. (1988). For maize cell culture and regeneration see generally, *The Maize Handbook,* Freeling and Walbot, Eds., Springer, N.Y. (1994); *Corn and Corn Improvement,* $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings, via production of apomictic seed, or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Transgenic plants of the present invention can be homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant (such as Coroico) are also contemplated. Alternatively, propagation of heterozygous transgenic plants could be accomplished through apomixis.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual,* Chapter 7, Clark, Ed., Springer-Verlag, Berlin (1997). For molecular marker methods, see generally, The DNA Revolution by Andrew H. Paterson 1996 (Chapter 2) in: *Genome Mapping in Plants* (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants which can be used in the method of the invention include monocotyledonous and dicotyledonous plants. Typical plants include: maize, wheat, rice, barley, soybean, arabidopsis, oats, sorghum, millet, rye, sunflower, safflower, alfalfa, canola, or cotton.

Seeds derived from plants regenerated from transformed plant cells, plant parts or plant tissues, or progeny derived from the regenerated transformed plants, may be used directly as feed or food, or further processing may occur. Plants grown from these seeds can be effectively used in breeding programs to further incorporate and select for desirable traits.

All publications cited in this application are herein incorporated by reference to the same extent as if each individual publication or patent application was specifically and individually indicated to be incorporated by reference.

The present invention will be further described by reference to the following detailed examples. It is understood, however, that there are many extensions, variations, and modifications on the basic theme of the present invention beyond that shown in the examples and description, which are within the spirit and scope of the present invention.

Other objects, features, advantages and aspects of the present invention will become apparent to those of skill from the following description. It should be understood, however, that the following description and the specific examples, while indicating certain embodiments of the invention, are given by way of illustration only. Various changes and modifications within the spirit and scope of the disclosed invention will become readily apparent to those skilled in the art from reading the following description and from reading the other parts of the present disclosure.

EXAMPLES

Example 1 cDNA Library Construction

A. Total RNA Isolation

Total RNA was isolated from maize tissues with TRIzol Reagent (Life Technology Inc. Gaithersburg, Md.) using a modification of the guanidine isothiocyanate/acid-phenol procedure described by Chomczynski and Sacchi (*Anal. Biochem.* 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

B. Poly(A)+RNA Isolation

The selection of poly(A)+RNA from total RNA was performed using PolyATract system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

C. cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between Not I and Sal I sites.

D. dek1 Isolation and Sequencing dek1 maize cDNA fragments were used as probes to screen a maize Mo17 genomic bacterial artificial chromosome (BAC) library. The HindIII and EcoRI subfragments homologous to calcium-requiring cysteine proteinases (calpain) cDNA were identified in selected BAC clones by gel blot hybridization, cloned into a plasmid vector pBK-SKS (Stratagene), and sequenced with the help of the ES::TN transposon insertion system (Epicentre Technologies, Madison, Wis.).

Example 2

Sequencing and cDNA Subtraction Procedures Used for Maize EST's

A. Sequencing Template Preparation

Individual colonies were picked and DNA was prepared either by PCR with M13 forward primers and M13 reverse primers, or by plasmid isolation. All the cDNA clones were sequenced using M13 reverse primers.

B. Q-bot Subtraction Procedure cDNA libraries subjected to the subtraction procedure were plated out on 22×22 cm$^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto individual agar plates with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in *Molecular Cloning: A Laboratory Manual*, 2$^{nd}$ Edition). The following probes were used in colony hybridization:

1. First strand cDNA from the same tissue from which the library was made to remove the most redundant clones.
2. 48–192 most redundant cDNA clones from the same library based on previous sequencing data.
3. 192 most redundant cDNA clones in the entire corn sequence database.
4. A Sal-A20 oligonucleotide removes clones containing a poly A tail but no cDNA. See SEQ ID NO:22.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

Example 3

Co-segregation Analysis of Superal Mutation

The maize superal mutation is characterized by multiple aleurone layers. Unlike wild-type maize, superal maize can have up to 8 layers of aleurone. It was isolated from the Pioneer TUSC population by phenotypic analysis; aleurone layers showed a red color when stained with the oil-specific stain red-fat7B. In the TUSC collection, a separate mutant with multiple aleurone layers was isolated by a microscopy screen, which when crossed to superal, demonstrated that this represents a second and independent allele.

The superal mutation is recessive and showed a simple 3:1 segregation in selfed ears.

Southern blots of the backcross population showed that a 1.6 kb BgIII fragment of mu1 (Del Giudice,L., et al, *Mol. Gen. Genet.* 222 (1), 71–76 (1990)) was co-segregated with the superal phenotype. When the band was cloned, the sequences flanking the mu1 insertion showed identity to SEQ ID NO:5. SEQ ID NO:5 showed complete co-segregation with the superal phenotype, consistent with this gene as the causal agent for the superal phenotype.

Mu1 was inserted in the 5'-UTR of the superal gene. A second independent allele with a mu8 (Fleenor, D., et al, *Nucleic Acids Res.* 18 (22), 6725 (1990)) insertion at 3'-UTR of superal gene showed the similar multiple aleurone layers, demonstrating that mutations resulting in down-regulation of SUPERAL was responsible for the multi-aleurone layer phenotype.

Example 4

Co-segregation Analysis of dek1 Mutation

The maize Dek1 mutation is characterized by a lack of aleurone layers.

Southern blots of a segregating population showed that plants with the Dek1 mutant phenotype did not contain a 3.0 kb Kpnl fragment representing the wild-type band. The plants were probed with the sequence flanking the co-segregating Mu1 insertion, indicating that maize Dek1 is responsible for the dek1 phenotype.

A second dek1 allele is being characterized.

Example 5

To Assay Gene Functionality

Dek1

Grain of the genotype dek1/dek1 (lacking aleurone cells) from Dek1/dek1 plants cultured in vitro had pericarp removed and were bombarded with constructs comprising maize Dek1 behind the beps promoter (Thorbjornsen, T. et al., 1996, *Biochem J.*, 313:149–154, pp 152) driving gene transcription in peripheral starchy endosperm cells, and were co-bombarded with constructs comprising anthocyanin activators c1 (Paz-Ares et al., *Embo J.* 6(12):3553–8, 1987) and Ic (Ludwig, S. R. et al., *Natl Acad Sci US* 86(18): 7092–6, 1989) behind the 35S promoter. Control constructs comprised only the activators with the 35S promoter.

Positive results were represented by kernels with red anthocyanine spots due to the presence of aleurone cells. Controls give no red spots due to lack of aleurone cells, as red anthocyanin coloration is expressed in aleurone cells but not starchy endosperm cells.

Alternatively, cyncytial stage dek1/dek1 endosperm of in vitro nucellus slab culture is micro injected with Dek1. Sectors of endosperm with aleurone cells, stemming from single nuclei or groups of nuclei in which Dek1 was incorporated, proves the function of Dek1 in aleurone cell signaling. The presence of aleurone cells was facilitated by using dek1/Dek1 plants that contained Ltp2::Gus gene constructs. In this genetic background, aleurone cells were detectable by the presence of the blue Gus stain. In these endosperms, the dek1/dek1 genotype of the endosperm was shown by the dek1/dek1 phenotype of the embryo, which lacks axis polarity. In these nucellus slab cultures, the embryos were never or extremely rarely transformed by injected DNA.

Superal

The function of the Superal gene as a negative regulator of aleurone cell fate in endosperm cells other than the peripheral layer of the endosperm was shown in co-bombardment experiments of in vitro cultivated colorless wild type grains with an Ltp2::superal cDNA construct and constructs comprising anthocyanin activators c1 (Paz-Ares, et al., *Embo J.* 6(12):3553–8, 1987) and Ic (Ludwig, S. R. et al., *Natl Acad Sci US* 86(18):7092–6, 1989) behind the 35S promoter. Control constructs comprised only the activators with the 35S promoter. Positive results were represented by kernels in which red anthocyanine spots did not appear or disappeared shortly after bombardment due to the de-differentiation of aleurone cells to starchy endosperm cells caused by ectopic expression of Superal in aleurone cells.

Alternatively, bombardment of in vitro cultivated grains with a genotype that gives red aleurone cells with the beps promoter::superal cDNA, demonstrate the wild-type function of SUPERAL as a suppressor of aleurone cell fate by the presence of white spots due to the de-differentiation of aleurone cells to starchy endosperm cells. Control bombardment with other genes under the control of the 35S promoter had no effect on aleurone cell coloration.

Alternatively, the function of Superal was demonstrated by the injection of Superal in homozygous superal syncytial endosperm of nucellus slab cultures. Endosperm with normal aleurone layers or sectors with normal aleurone layers demonstrated the wild-type function of Superal as a negative regulator of aleurone cell fate in deeper layers of the endosperm. Identification of the injected seeds as homozygous superal seeds was done by the embryo phenotype: homozygous superal embryos being arrested at an early developmental stage. The embryo was never or very rarely transformed by the injected DNA in nucellus slab cultures.

Alternatively, the function of SUPERAL is demonstrated by co-suppressing superal expression in transgenic seed. The superal gene introduced into plants under a seed specific promoter to silence endogenous superal gene expression, results in multi-aleurone layers.

Example 6

Vector Construction

All vectors are constructed using standard molecular biology techniques used by those of skill in the art (Sambrook et al., supra). Vectors are constructed for plant transformation using both particle bombardment and *Agrobacterium* transformation protocols. Plasmids are constructed by inserting the gene of interest into an expression cassette. For example, the Dek1 coding region, including the 5' UTR and 3' UTR is isolated from a full length EST clone. The fragment is ligated into an expression cassette comprising the beps promoter and nos terminator. Orientation is confirmed using a restriction enzyme digest. The expression cassette is linked to the selectable marker between the right and left borders of the T-DNA borders of an appropriate vector for *Agrobacterium* transformation. This vector is used for insert preparation for particle gun transformation as well as for generating *Agrobacterium* transformation vectors as described below. In this case, insert DNA for particle gun transformation is generated by isolating the insert from the vector.

The plasmid pSB11 is obtained from Japan Tobacco Inc. (Tokyo, Japan). The construction of pSB11 from pSB21 and the construction of pSB21 from starting vectors is described by Komari et al., 1996, *Plant J.* 10:165–174. The T-DNA of the plasmid is integrated in to the superbinary plasmid pSB1 (Saito et al., EP 672 752 A1) by homologous recombination between the two plasmids. The plasmid pSB1 is also obtained from Japan Tobacco Inc. These plasmids are either used for particle bombardment transformation, or for *Agrobacterium*-mediated transformation, after making a cointegrate in an appropriate *Agrobacterium* strain.

Competent cells of the *Agrobacterium* strain LBA4404 harboring pSB1 are created using the protocol as described by Lin (1995) in *Methods in Molecular Biology*, ed. Nickoloff, J. A. (Humana Press, Totowa, N.J.). The plasmid containing the expression cassettes is electroporated into competent cells of the *Agrobacterium* strain LBA4404 harboring pSB1 to create the cointegrate plasmid in *Agrobacterium*. Cells and DNA are prepared for electroporation by mixing 1 ul of plasmid DNA (~100 ng) with 20 ul of competent *Agrobacterium* cells in a 0.2 cm electrode gap cuvette (Bio-Rad Cat# 165-2086, Hercules, Calif.). Electroporation is performed in a Bio-Rad Micropulser (Cat# 165-2100, Hercules, Calif.) using the EC2 setting, which delivers 2.5 kV to the cells. Successful recombination is verified by restriction analysis of the plasmid after transformation of the cointegrate plasmid back into *E. coil* DH5α cells.

Example 7

Plant Transformation

A. Particle Bombardment Transformation and Regeneration of Maize Callus

Immature maize embryos from greenhouse or field grown High type II donor plants are bombarded with a plasmid containing a calpain polynucleotide of the invention operably linked to an appropriate promoter. If the polynucleotide does not include a selectable marker, another plasmid containing a selectable marker gene can be co-precipitated on the particles used for bombardment. For example, a plasmid containing the PAT gene (Wohlleben et al., 1988, *Gene* 70:25–37) which confers resistance to the herbicide Bialaphos can be used. Transformation is performed as follows.

The ears are surface sterilized in 50% Chlorox bleach plus 0.5% Micro detergent for 20 minutes, and rinsed two times with sterile water. The immature embryos are excised and placed embryo axis side down (scutellum side up), 25 embryos per plate. These are cultured on 560L agar medium 4 days prior to bombardment in the dark. Medium 560L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560L with high sucrose concentration).

A plasmid vector comprising a polynucleotide of the invention operably linked to the selected promoter is constructed. This plasmid DNA, plus plasmid DNA containing a PAT selectable marker if needed, is precipitated onto 1.1 μm (average diameter) tungsten pellets using a $CaCl_2$ precipitation procedure as follows: 100 μl prepared tungsten particles (0.6 mg) in water, 20 μl (2 μg) DNA in TrisEDTA buffer (1 μg total), 100 μl 2.5 M $CaCl_2$, 40 μl 0.1 M spermidine.

Each reagent is added sequentially to the tungsten particle suspension. The final mixture is sonicated briefly. After the precipitation period, the tubes are centrifuged briefly, liquid removed, washed with 500 ml 100% ethanol, and centrifuged again for 30 seconds. Again the liquid is removed, and 60 μl 100% ethanol is added to the final tungsten particle pellet. For particle gun bombardment, the tungsten/DNA particles are briefly sonicated and 5 μl spotted onto the center of each macrocarrier and allowed to dry about 2 minutes before bombardment.

The sample plates are bombarded at a distance of 8 cm from the stopping screen to the tissue, using a DuPont biolistics helium particle gun. All samples receive a single shot at 650 PSI, with a total of ten aliquots taken from each tube of prepared particles/DNA.

Four to 12 hours post bombardment, the embryos are moved to 560P (a low osmoticum callus initiation medium similar to 560L but with lower silver nitrate), for 3–7 days, then transferred to 560R selection medium, an N6 based medium similar to 560P containing 3 mg/liter Bialaphos, and subcultured every 2 weeks. After approximately 10 weeks of selection, callus clones are sampled for PCR and activity of the polynucleotide of interest. Positive lines are transferred to 288J medium, an MS-based medium with lower sucrose and hormone levels, to initiate plant regeneration. Following somatic embryo maturation (2–4 weeks), well-developed somatic embryos are transferred to medium for germination and transferred to the lighted culture room. Approximately 7–10 days later, developing plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to Classic™ 600 pots (1.6 gallon) and grown to maturity. Plants are monitored for expression of the polynucleotide of interest.

B. Agrobacterium-mediated Transformation and Regeneration of Maize Callus

For *Agrobacterum*-mediated transformation of maize of a nucleotide sequence encoding a protein of the present invention, the method of Zhao was employed (U.S. Pat. No. 5,981,840, and PCT patent publication WO98/32326; the contents of which are hereby incorporated by reference).

Briefly, immature embryos were isolated from maize and the embryos contacted with a suspension of *Agrobacterium* containing a polynucleotide of the present invention, where the bacteria are capable of transferring the nucleotide sequence of interest to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step is contemplated. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step), and calli grown on selective medium were cultured on solid medium to regenerate the plants.

C. DNA Isolation from Callus and Leaf Tissues

In order to screen putative transformation events for the presence of the transgene, genomic DNA is extracted from calluses or leaves using a modification of the CTAB (cetyl-triethylammonium bromide, Sigma H5882) method described by Stacey and Isaac (1994). Approximately 100–200 mg of frozen tissues is ground into powder in liquid nitrogen and homogenised in 1 ml of CTAB extraction buffer (2% CTAB, 0.02 M EDTA, 0.1 M Tris-Cl pH 8, 1.4 M NaCl, 25 mM DTT) for 30 min at 65° C. Homogenised samples are allowed to cool at room temperature for 15 min before a single protein extraction with approximately 1 ml 24:1 v/v chloroform:octanol is done. Samples are centrifuged for 7 min at 13,000 rpm and the upper layer of supernatant collected using wide-mouthed pipette tips. DNA is precipitated from the supernatant by incubation in 95% ethanol on ice for 1 h. DNA threads are spooled onto a glass hook, washed in 75% ethanol containing 0.2 M sodium acetate for 10 min, air-dried for 5 min and resuspended in TE buffer. Five μl RNAse A is added to the samples and incubated at 37° C. for 1 h.

For quantification of genomic DNA, gel electrophoresis is performed using a 0.8% agarose gel in 1×TBE buffer. One microliter of the samples are fractionated alongside 200, 400, 600 and 800 ng μl$^{-1}$ λ uncut DNA markers.

Example 8

Overexpression of CR4 in Transgenic Corn

The maize cr4 gene (SEQ ID NO:15) was overexpressed in endosperm under the control of the Itp2 promoter (Kalla, R., et al., 1994) (Itp2::cr4::pinII) and 22 kDa zein promoter (Boronat, A., et al.,1986) (22 kDa zein::cr4::22 kDa zein) constructed as generally described in Example 6. A single vector containing both constructs was introduced into maize by agrobacterial transformation (see Example 7B). Transgenic plants showed an extra layer of aleurone cells in the endosperm. This additional layer of cells stained red by red fat-7B, indicating oil accumulation in the extra aleurone cells.

Example 9

Expression of Functional Domains in Bacteria and Plants

Functional domains that were used in bacterial and plant expression constructs were as follows:
External loop region: positions 1063–1938 of SEQ ID NO: 23 corresponding to positions 337–628 of SEQ ID NO: 24
Cytoplasmic domain: positions 3679–6531 of SEQ ID NO: 23 corresponding to positions 1209–2159 of SEQ ID NO:24
calpain proteinase Domain II: positions 5164–6069 of SEQ ID NO:23 corresponding to positions 1704–2005 of SEQ ID NO:24
calpain proteinase Domain III: positions 6082–6531 of SEQ ID NO:23 corresponding to positions 2010–2159 of SEQ ID NO:24

A. Bacterial expression

Calpain proteinase Domains II+III, and the external loop region were cloned into the pGEX-4T-3 vector (Amersham Biosciences) for expression in *E. coli*. After induction with IPTG, the bacterial lysates were analyzed for the presence of expressed protein. Proteins are expressed as fusion proteins with the 26 kDa glutathione S-transferase. Both constucts were shown to have GST activity.

Sequence analysis has indicated that dek1 has domain features similar to calpain. Domain II & III of calpain are highly conserved in dek1. In addition, it is reported that domain II of m-calpain has cysteine protease activity. Therefore, bacteria-expressed domain II+III of dek1 was used to determine if dek1 has calpain activity.

The so called caseinolytic assay was used for this determination. In this assay, degradation of casein was evaluated by electrophoresis on SDS-PAGE with gel staining. With partially purified Domain II+III, casein was clearly shown to be degraded. Caseinolytic activity of partially purified Domain II+III was higher than that of domain II of human m-calpain as reported.

B. Plant Expression

The external loop region, cytoplasmic domain, calpain proteinase domain II, and calpain proteinase domain III are each operably linked to the Itp2 and/or 22 kDa zein promoter to express altered aleurone phenotypes in plants.

Over-expression of the external loop region is expected to phenocopy the dek1 mutation, ie: lack of aleurone cells.

Expression of the cytoplasmic domain, domain II, and domain III are expected to increase the number of aleurone layers.

Sequence Listing Table

| SEQ ID NO. | Description | Nucleotide (NT) or Amino Acid (AA) |
| --- | --- | --- |
| 1 | maize dek1 cDNA incomplete sequence | NT |
| 2 | maize dek1 incomplete sequence | AA |
| 3 | Arabidopsis calpain cDNA | NT |
| 4 | Arabidopsis calpain | AA |
| 5 | maize superal cDNA | NT |
| 6 | maize SUPERAL | AA |
| 7 | Arabidopsis superal cDNA homolog 1 | NT |
| 8 | Arabidopsis SUPERAL homolog 1 | AA |
| 9 | Arabidopsis superal cDNA homolog 2 | NT |
| 10 | Arabidopsis SUPERAL homolog 2 | AA |
| 11 | Rice superal homolog | NT |
| 12 | Wheat superal homolog | NT |
| 13 | Soybean superal homolog | NT |
| 14 | Barley superal homolog | NT |
| 15 | maize crinkly4 (cr4) cDNA | NT |
| 16 | maize CRINKLY 4 | AA |
| 17 | barley nuc1 promoter | NT |
| 18 | barley Ltp2 promoter | NT |
| 19 | maize end1 promoter | NT |
| 20 | maize end2 promoter | NT |
| 21 | barley beps promoter | NT |
| 22 | Sal A20 primer | NT |
| 23 | maize dek1 cDNA from B73 | NT |
| 24 | maize DEK1 from B73 | AA |
| 25 | maize Mo17 dek1 (genomic) | NT |
| 26 | Arabidopsis dek1 cDNA | NT |
| 27 | Arabidopsis DEK1 | AA |
| 28 | Arabidopsis dek1 (genomic) | NT |

What is claimed is:

1. A method for altering maize seed characteristics, the method comprising:
   a. introducing into a maize plant cell a recombinant expression cassette comprising a polynucleotide that encodes the polypeptide of SEQ ID NO:24 or functional fragment thereof, wherein a plant transformed with the functional fragment has an altered number or configuration of aleurone cells in the maize seed, wherein the polynucleotide is operably linked to a promoter capable of expressing the polynucleotide in the seed;
   b. culturing the plant cell under plant forming conditions to produce a plant; and,
   c. expressing the polynucleotide for a time sufficient to alter the number or configuration of aleurone cells in the seeds of the maize plant.

2. The method of claim 1 wherein the promoter is selected from the group consisting of nuc1, Ltp2, end1, end2, cim1, beps, 22 kDa zein, and 27 kDa zein promoters.

3. The method of claim 1 wherein the polynucleotide is SEQ ID NO: 23.

4. A transgenic plant produced by the method of claim 1.

5. A transgenic seed produced by the transgenic plant of claim 4, wherein the seed comprises the recombinant expression cassette.

6. A method for increasing oil content of maize seeds, the method comprising:
   a. introducing into a maize plant cell a recombinant expression cassette comprising a polynucleotide that encodes the polypeptide of SEQ ID NO:24 or functional fragment thereof, wherein a plant transformed with the functional fragment has an altered number or configuration of aleurone cells in the maize seed, wherein the polynucleotide is operably linked to a promoter capable of expressing the polynucleotide in the seed;
   b. culturing the plant cell under plant forming conditions to produce a plant; and,
   c. expressing the polynucleotide for a time sufficient to increase the level of oil in the seeds of the maize plant.

7. The method of claim 6 wherein the promoter is selected from the group consisting of: nuc1, Ltp2, end1, end2, cim1, beps, 22 kDa zein, and 27 kDa zein.

8. The method of claim 6 wherein the polynucleotide is SEQ ID NO: 23.

9. A transgenic plant produced by the method of claim 6.

10. A transgenic seed of the transgenic plant of claim 9, wherein the seed comprises the recombinant expression cassette.

11. An isolated nucleic acid comprising a polynucleotide encoding the DEK1 polypeptide of SEQ ID NO: 24, wherein the polynucleotide is capable of altering the number, or configuration of aleurone cells within seed.

12. An expression cassette comprising the nucleic acid of claim 11 operably linked to a promoter.

13. A non-human host cell stably transformed with the expression cassette of claim 12.

14. The host cell of claim 13 that is a plant cell.

15. The host cell of claim 13 that is a bacterial cell.

16. A plant stably transformed with the expression cassette of claim 12.

17. An isolated nucleic acid comprising a functional fragment of SEQ ID NO:24 encoding at least one of: a cystein proteinase domain II, or a calpain proteinase domain III, wherein a maize plant transformed with the functional fragment has an altered number or configuration of aleurone cells in seeds of the maize plant.

18. A transgenic maize seed comprising the expression cassette of the method of claim 1 upon whose expression, the number, or configuration of aleurone cells within seed is altered.

19. The method of claim 1 wherein the promoter is a seed-preferred promoter.

20. The method of claim 1 wherein the polynucleotide is overexpressed.

* * * * *

SEQUENCE LISTING

<160> NUMBER OF SEQ ID NOS: 28

<210> SEQ ID NO 1
<211> LENGTH: 4857
<212> TYPE: DNA
<213> ORGANISM: Zea mays
<220> FEATURE:
<221> NAME/KEY: CDS
<222> LOCATION: (1)...(4857)
<223> OTHER INFORMATION: maize dek1

<400> SEQUENCE: 1

```
ctc tca ttt gct gtt ccc ata tgg ata cgc aat ggt tac agt ttc tgg      48
Leu Ser Phe Ala Val Pro Ile Trp Ile Arg Asn Gly Tyr Ser Phe Trp
 1               5                  10                  15 att cct gga agg gag ttt gca aat cgt gaa aat gtt agt caa gct cca      96
Ile Pro Gly Arg Glu Phe Ala Asn Arg Glu Asn Val Ser Gln Ala Pro
             20                  25                  30 gga gag aaa gag cgg gct ctc ttt gtt atc acc att gct gtt ttc act     144
Gly Glu Lys Glu Arg Ala Leu Phe Val Ile Thr Ile Ala Val Phe Thr
         35                  40                  45 gca tca att att ggc ctt ggt gca ata gtg tca gca aag cct tta gac     192
Ala Ser Ile Ile Gly Leu Gly Ala Ile Val Ser Ala Lys Pro Leu Asp
     50                  55                  60 gct cta ggc tat aaa gga tgg gat gct gat aag aac agc tcc tat tct     240
Ala Leu Gly Tyr Lys Gly Trp Asp Ala Asp Lys Asn Ser Ser Tyr Ser
 65                  70                  75                  80 ccc tat gca aca tca atg tat ctt gga tgg gca ttg tct tca aca att     288
Pro Tyr Ala Thr Ser Met Tyr Leu Gly Trp Ala Leu Ser Ser Thr Ile
                 85                  90                  95 gct gtg att acc aca ggg ttg ata cct att gtt gct tgg ttt gca aca     336
Ala Val Ile Thr Thr Gly Leu Ile Pro Ile Val Ala Trp Phe Ala Thr
            100                 105                 110 tac cgg ttt tca cct tca tca gct ata tgt gtt ggc ctc ttt gca act     384
Tyr Arg Phe Ser Pro Ser Ser Ala Ile Cys Val Gly Leu Phe Ala Thr
        115                 120                 125 gtt ctt gtg tct ttt tgc ggt gca tcc tac tgg gga gtg gta aat tca     432
Val Leu Val Ser Phe Cys Gly Ala Ser Tyr Trp Gly Val Val Asn Ser
    130                 135                 140 cga gag gat ggt gtt cct cta aag gct gat ttc ctt gca gca tta ctt     480
Arg Glu Asp Gly Val Pro Leu Lys Ala Asp Phe Leu Ala Ala Leu Leu
145                 150                 155                 160 ccc ttg ctt tgc att cca gca ttt ttc tca ctg ttc act ggg ctt tac     528
Pro Leu Leu Cys Ile Pro Ala Phe Phe Ser Leu Phe Thr Gly Leu Tyr
                165                 170                 175 aaa tgg aag gat gat gat tgg aag att tct cgt ggt gtt tac ctt ttt     576
Lys Trp Lys Asp Asp Asp Trp Lys Ile Ser Arg Gly Val Tyr Leu Phe
            180                 185                 190 gtt ggc atg gga atg ttg ctg ttg ttt ggt gca gtt gca gct gtt att     624
Val Gly Met Gly Met Leu Leu Leu Phe Gly Ala Val Ala Ala Val Ile
        195                 200                 205 gtc aca atc agg ccc tgg act gtt gga gtt gct tgc ctc gta gcc att     672
Val Thr Ile Arg Pro Trp Thr Val Gly Val Ala Cys Leu Val Ala Ile
    210                 215                 220 ctg ttc ctt gta ttt gtt att ggg gtc atc cac tac tgg aca tct aac     720
Leu Phe Leu Val Phe Val Ile Gly Val Ile His Tyr Trp Thr Ser Asn
225                 230                 235                 240 aac ttc tat cta acg agg act cag atg ttg ctt gtt tgt tcc att gct     768
Asn Phe Tyr Leu Thr Arg Thr Gln Met Leu Leu Val Cys Ser Ile Ala
                245                 250                 255
```

-continued

| | |
|---|---|
| ttt ctc tta gcc ttg gct gcc ttc ctg atg ggt tta ttt cac gga aag<br>Phe Leu Leu Ala Leu Ala Ala Phe Leu Met Gly Leu Phe His Gly Lys<br>260                        265                      270 | 816 |
| cct ttt gtt gga gca tct ata ggt tat ttc tca ttt ata ttt ctt ctc<br>Pro Phe Val Gly Ala Ser Ile Gly Tyr Phe Ser Phe Ile Phe Leu Leu<br>        275                      280                      285 | 864 |
| act gga agg gct ttg act gtc ctt cta tca ccg cca atc gta gtg tat<br>Thr Gly Arg Ala Leu Thr Val Leu Leu Ser Pro Pro Ile Val Val Tyr<br>290                        295                      300 | 912 |
| tcg cca aga gta ttg cct gta tac gtt tat gat gct cat gca gac tct<br>Ser Pro Arg Val Leu Pro Val Tyr Val Tyr Asp Ala His Ala Asp Ser<br>305                      310                      315                  320 | 960 |
| gct aaa aat gtt agc tat gcc ttt ctt att ctg tat ggg att gca tta<br>Ala Lys Asn Val Ser Tyr Ala Phe Leu Ile Leu Tyr Gly Ile Ala Leu<br>        325                      330                      335 | 1008 |
| gca act gaa gtt tgg ggt gtt att gct agt cta ata atg aat cca cca<br>Ala Thr Glu Val Trp Gly Val Ile Ala Ser Leu Ile Met Asn Pro Pro<br>340                        345                      350 | 1056 |
| ttt gtt ggg gct ggc gtt tct gct act act ctt gta att gct ttc agt<br>Phe Val Gly Ala Gly Val Ser Ala Thr Thr Leu Val Ile Ala Phe Ser<br>        355                      360                      365 | 1104 |
| ttt gct gtt tct cga cca tgc ctg act ctt aag atg atg gag gat gca<br>Phe Ala Val Ser Arg Pro Cys Leu Thr Leu Lys Met Met Glu Asp Ala<br>370                        375                      380 | 1152 |
| gtt cat ttt ctc agc aag gat aca gtt gtg caa gcg atg tca cgg tct<br>Val His Phe Leu Ser Lys Asp Thr Val Val Gln Ala Met Ser Arg Ser<br>385                      390                      395                  400 | 1200 |
| gct aat aaa act aga aat gct ata tct ggg act tac tca gca cct cag<br>Ala Asn Lys Thr Arg Asn Ala Ile Ser Gly Thr Tyr Ser Ala Pro Gln<br>        405                      410                      415 | 1248 |
| agg tcc gca agt tct gct gct ctt ttg gtt gga gat cct gct ctt aca<br>Arg Ser Ala Ser Ser Ala Ala Leu Leu Val Gly Asp Pro Ala Leu Thr<br>420                        425                      430 | 1296 |
| ttg gac agg gct ggg aac ttt gtg ctt cct agg gct gat gtt atg aaa<br>Leu Asp Arg Ala Gly Asn Phe Val Leu Pro Arg Ala Asp Val Met Lys<br>        435                      440                      445 | 1344 |
| ctg aga gat cgt ttg aga aat gaa gaa att gct gca gga tct ttc tta<br>Leu Arg Asp Arg Leu Arg Asn Glu Glu Ile Ala Ala Gly Ser Phe Leu<br>450                        455                      460 | 1392 |
| tgt gga gta aaa gat tgt tta cta att tgc ccc cag tcc ctg tca aac<br>Cys Gly Val Lys Asp Cys Leu Leu Ile Cys Pro Gln Ser Leu Ser Asn<br>465                      470                      475                  480 | 1440 |
| ata gat tat cgg agg aat atg tgt gcc cat gca cgt att ttg gct ttg<br>Ile Asp Tyr Arg Arg Asn Met Cys Ala His Ala Arg Ile Leu Ala Leu<br>        485                      490                      495 | 1488 |
| gaa gaa gca att gat aca gaa tgg gtg tat atg tgg gac aaa ttt ggt<br>Glu Glu Ala Ile Asp Thr Glu Trp Val Tyr Met Trp Asp Lys Phe Gly<br>500                        505                      510 | 1536 |
| ggt tat tta ctt ctg ttg ctt gga ttg act gcc aaa gct gaa caa ata<br>Gly Tyr Leu Leu Leu Leu Leu Gly Leu Thr Ala Lys Ala Glu Gln Ile<br>        515                      520                      525 | 1584 |
| cag gat gaa gtt cgt cta aga ctc ttt ttg gat agc ata ggc ctt tcc<br>Gln Asp Glu Val Arg Leu Arg Leu Phe Leu Asp Ser Ile Gly Leu Ser<br>530                        535                      540 | 1632 |
| gat ttg agt gcc aaa gaa att aag aaa tgg atg cct gaa gat cgg agg<br>Asp Leu Ser Ala Lys Glu Ile Lys Lys Trp Met Pro Glu Asp Arg Arg<br>545                      550                      555                  560 | 1680 |
| caa ttt gag ctt att caa gaa agc tac ata agg gaa aaa gaa atg gaa<br>Gln Phe Glu Leu Ile Gln Glu Ser Tyr Ile Arg Glu Lys Glu Met Glu | 1728 |

```
                              -continued 565                 570                 575
gag gag gct ttg atg caa aga cga gag gaa gaa ggg aag gga aga gaa    1776
Glu Glu Ala Leu Met Gln Arg Arg Glu Glu Glu Gly Lys Gly Arg Glu
            580                 585                 590 agg agg agg gca ttg cta gag aga gag gag cga aaa tgg aag gag ctc    1824
Arg Arg Arg Ala Leu Leu Glu Arg Glu Glu Arg Lys Trp Lys Glu Leu
        595                 600                 605 gaa ata tca ttg ctt tct tcc att cca aat act gga agc agg gat gct    1872
Glu Ile Ser Leu Leu Ser Ser Ile Pro Asn Thr Gly Ser Arg Asp Ala
    610                 615                 620 gca gct atg gca gca gct gtc aga gct gtt gga ggt gat tct gcc ctg    1920
Ala Ala Met Ala Ala Ala Val Arg Ala Val Gly Gly Asp Ser Ala Leu
625                 630                 635                 640 gaa gat tct ttt gca aga gat agg gtc tct tca ata gcc aat cac ata    1968
Glu Asp Ser Phe Ala Arg Asp Arg Val Ser Ser Ile Ala Asn His Ile
                645                 650                 655 cga aag gca caa ttg gct cgg cga gca gaa cag act ggt att cca ggc    2016
Arg Lys Ala Gln Leu Ala Arg Arg Ala Glu Gln Thr Gly Ile Pro Gly
            660                 665                 670 act ata tgc ata ctc gat gat gaa cca agg agt act ggg cgt cat tgt    2064
Thr Ile Cys Ile Leu Asp Asp Glu Pro Arg Ser Thr Gly Arg His Cys
        675                 680                 685 gga gag ctt gac ttg tgc ctc tgt caa agt caa aag gtt act ttg tct    2112
Gly Glu Leu Asp Leu Cys Leu Cys Gln Ser Gln Lys Val Thr Leu Ser
    690                 695                 700 att gct gtc atg gtt cag cct gta tct ggc cca gtg tgt ctt ttt gga    2160
Ile Ala Val Met Val Gln Pro Val Ser Gly Pro Val Cys Leu Phe Gly
705                 710                 715                 720 agt gaa ttc caa aag gtt tgt tgg gaa atc tta gtg gca gga tca gaa    2208
Ser Glu Phe Gln Lys Val Cys Trp Glu Ile Leu Val Ala Gly Ser Glu
                725                 730                 735 cag ggt atg gaa gct gga caa gtt ggt ctt cga tta gta act aag ggt    2256
Gln Gly Met Glu Ala Gly Gln Val Gly Leu Arg Leu Val Thr Lys Gly
            740                 745                 750 gaa agg atg act act gtt gct aaa gag tgg aat att ggt gcg tct agt    2304
Glu Arg Met Thr Thr Val Ala Lys Glu Trp Asn Ile Gly Ala Ser Ser
        755                 760                 765 att gca gat ggc agg tgg cat ctt gtc act gta act tta gat gcc gac    2352
Ile Ala Asp Gly Arg Trp His Leu Val Thr Val Thr Leu Asp Ala Asp
    770                 775                 780 cta ggt gaa gca act tct ttc att gat gga gtt tat gat gga tat cag    2400
Leu Gly Glu Ala Thr Ser Phe Ile Asp Gly Val Tyr Asp Gly Tyr Gln
785                 790                 795                 800 aat ggg ttg ccg ttg cca aca gat aac ggt att tgg gaa cct gga act    2448
Asn Gly Leu Pro Leu Pro Thr Asp Asn Gly Ile Trp Glu Pro Gly Thr
                805                 810                 815 gat att tgg gtt ggt gct agg cca ccc atg gac tta gat gcc ttt ggt    2496
Asp Ile Trp Val Gly Ala Arg Pro Pro Met Asp Leu Asp Ala Phe Gly
            820                 825                 830 agg tca gat agc gaa ggt tct gac tca aag atg cag atc atg gat gct    2544
Arg Ser Asp Ser Glu Gly Ser Asp Ser Lys Met Gln Ile Met Asp Ala
        835                 840                 845 ttt cta tgg gga aga tgt ctc agt gaa gat gag gtt act gtt tta cat    2592
Phe Leu Trp Gly Arg Cys Leu Ser Glu Asp Glu Val Thr Val Leu His
    850                 855                 860 act gcc atg tct cct gct gag tat gga ttt ttt gac ctt gca ccc ggc    2640
Thr Ala Met Ser Pro Ala Glu Tyr Gly Phe Phe Asp Leu Ala Pro Gly
865                 870                 875                 880 gat gct tgg cat gga agt tat tct gca agg gtg gat gac tgg gaa agc    2688
```

```
Asp Ala Trp His Gly Ser Tyr Ser Ala Arg Val Asp Asp Trp Glu Ser
            885                 890                 895 gaa gag gct tat gag ctt tat gat caa ggg gat gtc gaa tgg gat gga    2736
Glu Glu Ala Tyr Glu Leu Tyr Asp Gln Gly Asp Val Glu Trp Asp Gly
        900                 905                 910 cag tac tca agt ggt agg aaa cgt ccg gta cat gat gct gta gct att    2784
Gln Tyr Ser Ser Gly Arg Lys Arg Pro Val His Asp Ala Val Ala Ile
            915                 920                 925 gac ctt gac tcc ttt gct agg aga cca aga aaa cca agg ttt gag aca    2832
Asp Leu Asp Ser Phe Ala Arg Arg Pro Arg Lys Pro Arg Phe Glu Thr
        930                 935                 940 cgt gat gaa gtc aac cag cgt atg ctt tct gtt gaa agg gct gtc agg    2880
Arg Asp Glu Val Asn Gln Arg Met Leu Ser Val Glu Arg Ala Val Arg
945                 950                 955                 960 gat gct ctt atc gcg aaa gga gag aga aac ttc act gat caa gag ttc    2928
Asp Ala Leu Ile Ala Lys Gly Glu Arg Asn Phe Thr Asp Gln Glu Phe
                965                 970                 975 cct cca gag gat cgt tct tta ttt gta gat ccg atg aat cca cct ctg    2976
Pro Pro Glu Asp Arg Ser Leu Phe Val Asp Pro Met Asn Pro Pro Leu
            980                 985                 990 aaa ctg cag gtt gtt tct gag tgg atg agg cct tct gac ata gca aag    3024
Lys Leu Gln Val Val Ser Glu Trp Met Arg Pro Ser Asp Ile Ala Lys
        995                 1000                1005 gat ata tct atc agt tgt cag cct tgc ttg ttt tcg ggt tct gtg aat    3072
Asp Ile Ser Ile Ser Cys Gln Pro Cys Leu Phe Ser Gly Ser Val Asn
    1010                1015                1020 tcc tca gat gtg tgt cag ggt cgg ttg gga gac tgt tgg ttc cta agt    3120
Ser Ser Asp Val Cys Gln Gly Arg Leu Gly Asp Cys Trp Phe Leu Ser
1025                1030                1035                1040 gca gtc gca gtt tta act gag atg tct cgg ata tca gaa gtt ata atc    3168
Ala Val Ala Val Leu Thr Glu Met Ser Arg Ile Ser Glu Val Ile Ile
                1045                1050                1055 act ccc gag tac aat gat gaa ggg att tat aca gtc aga ttc tgt att    3216
Thr Pro Glu Tyr Asn Asp Glu Gly Ile Tyr Thr Val Arg Phe Cys Ile
            1060                1065                1070 cag ggt gag tgg gtg gcc gtg gtt gtt gat gat tgg att cct tgc gag    3264
Gln Gly Glu Trp Val Ala Val Val Val Asp Asp Trp Ile Pro Cys Glu
        1075                1080                1085 tct ccg ggg aaa cca gca ttt gct act agt aga aag caa aac gag ctt    3312
Ser Pro Gly Lys Pro Ala Phe Ala Thr Ser Arg Lys Gln Asn Glu Leu
    1090                1095                1100 tgg gta tcc att ctt gag aag gct tat gca aaa ctt cat ggc tct tat    3360
Trp Val Ser Ile Leu Glu Lys Ala Tyr Ala Lys Leu His Gly Ser Tyr
1105                1110                1115                1120 gag gca ttg gaa ggt ggg ctt gtt caa gat gct cta gtc gat ctc aca    3408
Glu Ala Leu Glu Gly Gly Leu Val Gln Asp Ala Leu Val Asp Leu Thr
                1125                1130                1135 gga gga gct ggt gaa gag att gat atg cga agt cct caa gcc caa ctt    3456
Gly Gly Ala Gly Glu Glu Ile Asp Met Arg Ser Pro Gln Ala Gln Leu
            1140                1145                1150 gat ctt gct agt gga aga ttg tgg tcg cag ttg ttg cat ttc aaa caa    3504
Asp Leu Ala Ser Gly Arg Leu Trp Ser Gln Leu Leu His Phe Lys Gln
        1155                1160                1165 gaa ggt ttt ctt ctt ggt gct gga agt cct tct gga tct gat gct cac    3552
Glu Gly Phe Leu Leu Gly Ala Gly Ser Pro Ser Gly Ser Asp Ala His
    1170                1175                1180 atc tca tca agt ggc att gtt cag gga cat gcg tac tca att ttg cag    3600
Ile Ser Ser Ser Gly Ile Val Gln Gly His Ala Tyr Ser Ile Leu Gln
1185                1190                1195                1200
```

|     |     |
| --- | --- |
| gta aga gaa gtt gat ggc cac aaa ctc atc caa atc aga aat cca tgg<br>Val Arg Glu Val Asp Gly His Lys Leu Ile Gln Ile Arg Asn Pro Trp<br>                   1205                        1210                    1215 | 3648 |
| gca aat gaa gtt gaa tgg aat gga cca tgg tca gac tcg tca cca gag<br>Ala Asn Glu Val Glu Trp Asn Gly Pro Trp Ser Asp Ser Ser Pro Glu<br>                   1220                        1225                    1230 | 3696 |
| tgg acg gaa cgg atg aag cat aag ctc atg cat gtt cca cag tcg aag<br>Trp Thr Glu Arg Met Lys His Lys Leu Met His Val Pro Gln Ser Lys<br>                   1235                        1240                    1245 | 3744 |
| aat ggg gta ttc tgg atg tct tgg caa gat ttt cag att cac ttt cgg<br>Asn Gly Val Phe Trp Met Ser Trp Gln Asp Phe Gln Ile His Phe Arg<br>                   1250                        1255                    1260 | 3792 |
| tca ata tat gtt tgt cgt gtt tat cca cct gag atg cgt tac tct gtc<br>Ser Ile Tyr Val Cys Arg Val Tyr Pro Pro Glu Met Arg Tyr Ser Val<br>1265                      1270                       1275                    1280 | 3840 |
| cat ggg caa tgg cgt ggc tac aat gca ggt ggt tgc caa gat tat gac<br>His Gly Gln Trp Arg Gly Tyr Asn Ala Gly Gly Cys Gln Asp Tyr Asp<br>                   1285                        1290                    1295 | 3888 |
| tcg tgg cac caa aat cca cag tat cga ctt aga gta aca gga cgt gat<br>Ser Trp His Gln Asn Pro Gln Tyr Arg Leu Arg Val Thr Gly Arg Asp<br>                   1300                        1305                    1310 | 3936 |
| gca cta tac cct gtt cac gtt ttt att acc ctt act cag ggt gtt ggt<br>Ala Leu Tyr Pro Val His Val Phe Ile Thr Leu Thr Gln Gly Val Gly<br>                   1315                        1320                    1325 | 3984 |
| ttc tct aga aag acg aat ggt ttt cgg aac tac caa tct agc cat gat<br>Phe Ser Arg Lys Thr Asn Gly Phe Arg Asn Tyr Gln Ser Ser His Asp<br>                   1330                        1335                    1340 | 4032 |
| tct tca atg ttt tac att gga atg agg ata ctc aag aca cag ggc tgc<br>Ser Ser Met Phe Tyr Ile Gly Met Arg Ile Leu Lys Thr Gln Gly Cys<br>1345                      1350                       1355                    1360 | 4080 |
| cgt gct gct tac aat atc tac atg cat gaa agc gct ggt gga aca gat<br>Arg Ala Ala Tyr Asn Ile Tyr Met His Glu Ser Ala Gly Gly Thr Asp<br>                   1365                        1370                    1375 | 4128 |
| tac gtt aac tcg agg gag ata tca tgc gaa ctg gtc ttg gat cct tat<br>Tyr Val Asn Ser Arg Glu Ile Ser Cys Glu Leu Val Leu Asp Pro Tyr<br>                   1380                        1385                    1390 | 4176 |
| ccc aaa ggg tac aca att gtg cca act acc atc cac cct ggg gag gaa<br>Pro Lys Gly Tyr Thr Ile Val Pro Thr Thr Ile His Pro Gly Glu Glu<br>                   1395                        1400                    1405 | 4224 |
| gca cct ttt gtt ttg tca gtt ttt tca aaa gca tca atc aga cta gag<br>Ala Pro Phe Val Leu Ser Val Phe Ser Lys Ala Ser Ile Arg Leu Glu<br>                   1410                        1415                    1420 | 4272 |
| gct gtt tag ttc aag att gag atc cca tgt gtt tga tgg tag ctg cgt<br>Ala Val * Phe Lys Ile Glu Ile Pro Cys Val * Trp * Leu Arg<br>1425                      1430                       1435 | 4320 |
| ctg ctg ggc acc cgt gca cgc agg atc cag ctg tgg gtt ctc ggg aac<br>Leu Leu Gly Thr Arg Ala Arg Arg Ile Gln Leu Trp Val Leu Gly Asn<br>                   1440                        1445                    1450 | 4368 |
| tag ata atg ggt ata gga att gcc tcc tgg aca act tca atc aat ctt<br>* Ile Met Gly Ile Gly Ile Ala Ser Trp Thr Thr Ser Ile Asn Leu<br>                   1455                        1460                    1465 | 4416 |
| gct gca tgc aag tac cta agt tcg gtt gct tgt tgc aga tct gac aaa<br>Ala Ala Cys Lys Tyr Leu Ser Ser Val Ala Cys Cys Arg Ser Asp Lys<br>                   1470                        1475                    1480 | 4464 |
| cgg caa tgc ttc ttg tgc tga agg gaa agg aga gaa ggc atg atc cat<br>Arg Gln Cys Phe Leu Cys * Arg Glu Arg Arg Glu Gly Met Ile His<br>1485                      1490                       1495 | 4512 |
| ggt tct ttg gta gct gcg caa agt gca ggg tga gag gct tgg ttc aat<br>Gly Ser Leu Val Ala Ala Gln Ser Ala Gly * Glu Ala Trp Phe Asn<br>1500                      1505                       1510 | 4560 |

-continued

```
gtt tgt aga tag ccg tgg taa ctg acc tgg tag ccc atc cta tgt ata    4608
Val Cys Arg *   Pro Trp *   Leu Thr Trp *   Pro Ile Leu Cys Ile
1515                1520                1525 ggt gtc ccg ttt acc ctg taa atg cta tag agt tag gtt agg tag cct    4656
Gly Val Pro Phe Thr Leu *   Met Leu *   Ser *   Val Arg *   Pro
        1530                1535 gtc gtt cct gtt aac gca tag ggc tct tat gca gct gtg aaa tgt ctt    4704
Val Val Pro Val Asn Ala *   Gly Ser Tyr Ala Ala Val Lys Cys Leu
1540                1545                1550 gtt ggc aag ctg cag ttt tgc tga ttt gag cgt gga gta gtc ggc cat    4752
Val Gly Lys Leu Gln Phe Cys *   Phe Glu Arg Gly Val Val Gly His
1555                1560                1565 agc tgt tcc cat tgg ttt gcc ctg tat gta atc gga atc tga tgt cat    4800
Ser Cys Ser His Trp Phe Ala Leu Tyr Val Ile Gly Ile *   Cys His
1570                1575                1580 tca atg aac cta ttt ttt ggg tgc cat gcg aag ctg tct aaa aaa aaa    4848
Ser Met Asn Leu Phe Phe Gly Cys His Ala Lys Leu Ser Lys Lys Lys
1585                1590                1595                1600 aaa aaa aaa                                                        4857
Lys Lys Lys
```

<210> SEQ ID NO 2
<211> LENGTH: 1603
<212> TYPE: PRT
<213> ORGANISM: Zea mays

<400> SEQUENCE: 2

```
Leu Ser Phe Ala Val Pro Ile Trp Ile Arg Asn Gly Tyr Ser Phe Trp
1               5                   10                  15

Ile Pro Gly Arg Glu Phe Ala Asn Arg Glu Asn Val Ser Gln Ala Pro
            20                  25                  30

Gly Glu Lys Glu Arg Ala Leu Phe Val Ile Thr Ile Ala Val Phe Thr
        35                  40                  45

Ala Ser Ile Ile Gly Leu Gly Ala Ile Val Ser Ala Lys Pro Leu Asp
    50                  55                  60

Ala Leu Gly Tyr Lys Gly Trp Asp Ala Asp Lys Asn Ser Ser Tyr Ser
65                  70                  75                  80

Pro Tyr Ala Thr Ser Met Tyr Leu Gly Trp Ala Leu Ser Ser Thr Ile
                85                  90                  95

Ala Val Ile Thr Thr Gly Leu Ile Pro Ile Val Ala Trp Phe Ala Thr
            100                 105                 110

Tyr Arg Phe Ser Pro Ser Ser Ala Ile Cys Val Gly Leu Phe Ala Thr
        115                 120                 125

Val Leu Val Ser Phe Cys Gly Ala Ser Tyr Trp Gly Val Val Asn Ser
    130                 135                 140

Arg Glu Asp Gly Val Pro Leu Lys Ala Asp Phe Leu Ala Leu Leu
145                 150                 155                 160

Pro Leu Leu Cys Ile Pro Ala Phe Phe Ser Leu Phe Thr Gly Leu Tyr
                165                 170                 175

Lys Trp Lys Asp Asp Trp Lys Ile Ser Arg Gly Val Tyr Leu Phe
            180                 185                 190

Val Gly Met Gly Met Leu Leu Phe Gly Ala Val Ala Val Ile
        195                 200                 205

Val Thr Ile Arg Pro Trp Thr Val Gly Val Ala Cys Leu Val Ala Ile
    210                 215                 220

Leu Phe Leu Val Phe Val Ile Gly Val Ile His Tyr Trp Thr Ser Asn
```

```
            225                 230                 235                 240

Asn Phe Tyr Leu Thr Arg Thr Gln Met Leu Leu Val Cys Ser Ile Ala
                245                 250                 255

Phe Leu Leu Ala Leu Ala Ala Phe Leu Met Gly Leu Phe His Gly Lys
                260                 265                 270

Pro Phe Val Gly Ala Ser Ile Gly Tyr Phe Ser Phe Ile Phe Leu Leu
                275                 280                 285

Thr Gly Arg Ala Leu Thr Val Leu Leu Ser Pro Pro Ile Val Val Tyr
                290                 295                 300

Ser Pro Arg Val Leu Pro Val Tyr Val Asp Ala His Ala Asp Ser
305                 310                 315                 320

Ala Lys Asn Val Ser Tyr Ala Phe Leu Ile Leu Tyr Gly Ile Ala Leu
                325                 330                 335

Ala Thr Glu Val Trp Gly Val Ile Ala Ser Leu Ile Met Asn Pro Pro
                340                 345                 350

Phe Val Gly Ala Gly Val Ser Ala Thr Thr Leu Val Ile Ala Phe Ser
                355                 360                 365

Phe Ala Val Ser Arg Pro Cys Leu Thr Leu Lys Met Met Glu Asp Ala
                370                 375                 380

Val His Phe Leu Ser Lys Asp Thr Val Gln Ala Met Ser Arg Ser
385                 390                 395                 400

Ala Asn Lys Thr Arg Asn Ala Ile Ser Gly Thr Tyr Ser Ala Pro Gln
                405                 410                 415

Arg Ser Ala Ser Ala Ala Leu Leu Val Gly Asp Pro Ala Leu Thr
                420                 425                 430

Leu Asp Arg Ala Gly Asn Phe Val Leu Pro Arg Ala Asp Val Met Lys
                435                 440                 445

Leu Arg Asp Arg Leu Arg Asn Glu Glu Ile Ala Ala Gly Ser Phe Leu
450                 455                 460

Cys Gly Val Lys Asp Cys Leu Leu Ile Cys Pro Gln Ser Leu Ser Asn
465                 470                 475                 480

Ile Asp Tyr Arg Arg Asn Met Cys Ala His Ala Arg Ile Leu Ala Leu
                485                 490                 495

Glu Glu Ala Ile Asp Thr Glu Trp Val Tyr Met Trp Asp Lys Phe Gly
                500                 505                 510

Gly Tyr Leu Leu Leu Leu Gly Leu Thr Ala Lys Ala Glu Gln Ile
                515                 520                 525

Gln Asp Glu Val Arg Leu Arg Leu Phe Leu Asp Ser Ile Gly Leu Ser
                530                 535                 540

Asp Leu Ser Ala Lys Glu Ile Lys Lys Trp Met Pro Glu Asp Arg Arg
545                 550                 555                 560

Gln Phe Glu Leu Ile Gln Glu Ser Tyr Ile Arg Glu Lys Glu Met Glu
                565                 570                 575

Glu Glu Ala Leu Met Gln Arg Glu Glu Gly Lys Gly Arg Glu
                580                 585                 590

Arg Arg Arg Ala Leu Leu Glu Arg Glu Arg Lys Trp Lys Glu Leu
                595                 600                 605

Glu Ile Ser Leu Leu Ser Ser Ile Pro Asn Thr Gly Ser Arg Asp Ala
                610                 615                 620

Ala Ala Met Ala Ala Ala Val Arg Ala Val Gly Gly Asp Ser Ala Leu
625                 630                 635                 640

Glu Asp Ser Phe Ala Arg Asp Arg Val Ser Ser Ile Ala Asn His Ile
                645                 650                 655
```

```
Arg Lys Ala Gln Leu Ala Arg Arg Ala Glu Gln Thr Gly Ile Pro Gly
            660                 665                 670
Thr Ile Cys Ile Leu Asp Asp Glu Pro Arg Ser Thr Gly Arg His Cys
        675                 680                 685
Gly Glu Leu Asp Leu Cys Leu Cys Gln Ser Gln Lys Val Thr Leu Ser
    690                 695                 700
Ile Ala Val Met Val Gln Pro Val Ser Pro Val Cys Leu Phe Gly
705                 710                 715                 720
Ser Glu Phe Gln Lys Val Cys Trp Glu Ile Leu Val Ala Gly Ser Glu
                725                 730                 735
Gln Gly Met Glu Ala Gly Gln Val Gly Leu Arg Leu Val Thr Lys Gly
            740                 745                 750
Glu Arg Met Thr Thr Val Ala Lys Glu Trp Asn Ile Gly Ala Ser Ser
        755                 760                 765
Ile Ala Asp Gly Arg Trp His Leu Val Thr Val Thr Leu Asp Ala Asp
    770                 775                 780
Leu Gly Glu Ala Thr Ser Phe Ile Asp Gly Val Tyr Asp Gly Tyr Gln
785                 790                 795                 800
Asn Gly Leu Pro Leu Pro Thr Asp Asn Gly Ile Trp Glu Pro Gly Thr
                805                 810                 815
Asp Ile Trp Val Gly Ala Arg Pro Pro Met Asp Leu Asp Ala Phe Gly
            820                 825                 830
Arg Ser Asp Ser Glu Gly Ser Asp Ser Lys Met Gln Ile Met Asp Ala
        835                 840                 845
Phe Leu Trp Gly Arg Cys Leu Ser Glu Asp Glu Val Thr Val Leu His
    850                 855                 860
Thr Ala Met Ser Pro Ala Glu Tyr Gly Phe Phe Asp Leu Ala Pro Gly
865                 870                 875                 880
Asp Ala Trp His Gly Ser Tyr Ser Ala Arg Val Asp Asp Trp Glu Ser
                885                 890                 895
Glu Glu Ala Tyr Glu Leu Tyr Asp Gln Gly Asp Val Glu Trp Asp Gly
            900                 905                 910
Gln Tyr Ser Ser Gly Arg Lys Arg Pro Val His Asp Ala Val Ala Ile
        915                 920                 925
Asp Leu Asp Ser Phe Ala Arg Arg Pro Arg Lys Pro Arg Phe Glu Thr
    930                 935                 940
Arg Asp Glu Val Asn Gln Arg Met Leu Ser Val Glu Arg Ala Val Arg
945                 950                 955                 960
Asp Ala Leu Ile Ala Lys Gly Glu Arg Asn Phe Thr Asp Gln Glu Phe
                965                 970                 975
Pro Pro Glu Asp Arg Ser Leu Phe Val Asp Pro Met Asn Pro Pro Leu
            980                 985                 990
Lys Leu Gln Val Val Ser Glu Trp Met Arg Pro Ser Asp Ile Ala Lys
        995                 1000                1005
Asp Ile Ser Ile Ser Cys Gln Pro Cys Leu Phe Ser Gly Ser Val Asn
    1010                1015                1020
Ser Ser Asp Val Cys Gln Gly Arg Leu Gly Asp Cys Trp Phe Leu Ser
1025                1030                1035                1040
Ala Val Ala Val Leu Thr Glu Met Ser Arg Ile Ser Glu Val Ile Ile
                1045                1050                1055
Thr Pro Glu Tyr Asn Asp Glu Gly Ile Tyr Thr Val Arg Phe Cys Ile
            1060                1065                1070
```

-continued

```
Gln Gly Glu Trp Val Ala Val Val Asp Asp Trp Ile Pro Cys Glu
        1075                1080                1085
Ser Pro Gly Lys Pro Ala Phe Ala Thr Ser Arg Lys Gln Asn Glu Leu
    1090                1095                1100
Trp Val Ser Ile Leu Glu Lys Ala Tyr Ala Lys Leu His Gly Ser Tyr
1105                1110                1115                1120
Glu Ala Leu Glu Gly Gly Leu Val Gln Asp Ala Leu Val Asp Leu Thr
                1125                1130                1135
Gly Gly Ala Gly Glu Glu Ile Asp Met Arg Ser Pro Gln Ala Gln Leu
        1140                1145                1150
Asp Leu Ala Ser Gly Arg Leu Trp Ser Gln Leu Leu His Phe Lys Gln
        1155                1160                1165
Glu Gly Phe Leu Leu Gly Ala Gly Ser Pro Ser Gly Ser Asp Ala His
        1170                1175                1180
Ile Ser Ser Ser Gly Ile Val Gln Gly His Ala Tyr Ser Ile Leu Gln
1185                1190                1195                1200
Val Arg Glu Val Asp Gly His Lys Leu Ile Gln Ile Arg Asn Pro Trp
                1205                1210                1215
Ala Asn Glu Val Glu Trp Asn Gly Pro Trp Ser Asp Ser Ser Pro Glu
        1220                1225                1230
Trp Thr Glu Arg Met Lys His Lys Leu Met His Val Pro Gln Ser Lys
        1235                1240                1245
Asn Gly Val Phe Trp Met Ser Trp Gln Asp Phe Gln Ile His Phe Arg
        1250                1255                1260
Ser Ile Tyr Val Cys Arg Val Tyr Pro Pro Glu Met Arg Tyr Ser Val
1265                1270                1275                1280
His Gly Gln Trp Arg Gly Tyr Asn Ala Gly Gly Cys Gln Asp Tyr Asp
                1285                1290                1295
Ser Trp His Gln Asn Pro Gln Tyr Arg Leu Arg Val Thr Gly Arg Asp
        1300                1305                1310
Ala Leu Tyr Pro Val His Val Phe Ile Thr Leu Thr Gln Gly Val Gly
        1315                1320                1325
Phe Ser Arg Lys Thr Asn Gly Phe Arg Asn Tyr Gln Ser Ser His Asp
        1330                1335                1340
Ser Ser Met Phe Tyr Ile Gly Met Arg Ile Leu Lys Thr Gln Gly Cys
1345                1350                1355                1360
Arg Ala Ala Tyr Asn Ile Tyr Met His Glu Ser Ala Gly Gly Thr Asp
                1365                1370                1375
Tyr Val Asn Ser Arg Glu Ile Ser Cys Glu Leu Val Leu Asp Pro Tyr
        1380                1385                1390
Pro Lys Gly Tyr Thr Ile Val Pro Thr Thr Ile His Pro Gly Glu Glu
        1395                1400                1405
Ala Pro Phe Val Leu Ser Val Phe Ser Lys Ala Ser Ile Arg Leu Glu
        1410                1415                1420
Ala Val Phe Lys Ile Glu Ile Pro Cys Val Trp Leu Arg Leu Leu Gly
1425                1430                1435                1440
Thr Arg Ala Arg Arg Ile Gln Leu Trp Val Leu Gly Asn Ile Met Gly
                1445                1450                1455
Ile Gly Ile Ala Ser Trp Thr Thr Ser Ile Asn Leu Ala Ala Cys Lys
        1460                1465                1470
Tyr Leu Ser Ser Val Ala Cys Cys Arg Ser Asp Lys Arg Gln Cys Phe
        1475                1480                1485
Leu Cys Arg Glu Arg Arg Glu Gly Met Ile His Gly Ser Leu Val Ala
```

```
                        1490                1495                1500
Ala Gln Ser Ala Gly Glu Ala Trp Phe Asn Val Cys Arg Pro Trp Leu
1505                1510                1515                1520

Thr Trp Pro Ile Leu Cys Ile Gly Val Pro Phe Thr Leu Met Leu Ser
                1525                1530                1535

Val Arg Pro Val Val Pro Val Asn Ala Gly Ser Tyr Ala Ala Val Lys
                1540                1545                1550

Cys Leu Val Gly Lys Leu Gln Phe Cys Phe Glu Arg Gly Val Val Gly
                1555                1560                1565

His Ser Cys Ser His Trp Phe Ala Leu Tyr Val Ile Gly Ile Cys His
                1570                1575                1580

Ser Met Asn Leu Phe Phe Gly Cys His Ala Lys Leu Ser Lys Lys Lys
1585                1590                1595                1600

Lys Lys Lys

<210> SEQ ID NO 3
<211> LENGTH: 6467
<212> TYPE: DNA
<213> ORGANISM: Arabidopsis
<220> FEATURE:
<221> NAME/KEY: CDS
<222> LOCATION: (120)...(6465)
<223> OTHER INFORMATION: Arabidopsis calpain

<400> SEQUENCE: 3
cttggttggt tttaagctgc ggatttgatg atttgtgcgc aagcttgggg tttcagcttt      60
tttttgtgat ggaattttga tttccgagtt gcatggtgtt gtaggtggga gaagaagcc      119 atg gaa ggg gat gag cga gga gtc tta ctt gct tgt gta att tcg ggt      167
Met Glu Gly Asp Glu Arg Gly Val Leu Leu Ala Cys Val Ile Ser Gly
1               5                   10                  15 acc ctt ttc acg gtt ttc ggt tcg ggt tcg ttt tgg ata ctt tgg gct      215
Thr Leu Phe Thr Val Phe Gly Ser Gly Ser Phe Trp Ile Leu Trp Ala
                20                  25                  30 gtt aat tgg cgg cca tgg cgt ctc tac agt tgg atc ttt gct aga aaa      263
Val Asn Trp Arg Pro Trp Arg Leu Tyr Ser Trp Ile Phe Ala Arg Lys
            35                  40                  45 tgg cca aaa gta ttg caa ggt cct cag ctt gat ata cta tgt ggt gtt      311
Trp Pro Lys Val Leu Gln Gly Pro Gln Leu Asp Ile Leu Cys Gly Val
        50                  55                  60 cta tct ctt ttt gct tgg att gtg gta gta tcc cct att gca atc ttg      359
Leu Ser Leu Phe Ala Trp Ile Val Val Val Ser Pro Ile Ala Ile Leu
65                  70                  75                  80 ata gga tgg ggt tct tgg ctg att gtg ata ttg gat cga cat atc att      407
Ile Gly Trp Gly Ser Trp Leu Ile Val Ile Leu Asp Arg His Ile Ile
                85                  90                  95 ggg ctg gcg ata ata atg gct gga aca gcc ctt tta ctg gca ttc tac      455
Gly Leu Ala Ile Ile Met Ala Gly Thr Ala Leu Leu Leu Ala Phe Tyr
            100                 105                 110 tca atc atg ctt tgg tgg agg acc cag tgg caa agc tca aga gct gtc      503
Ser Ile Met Leu Trp Trp Arg Thr Gln Trp Gln Ser Ser Arg Ala Val
        115                 120                 125 gct tta ctt ctc ctt ctt ggt gtt gcc tta cta tgt gcg tat gaa ctc      551
Ala Leu Leu Leu Leu Leu Gly Val Ala Leu Leu Cys Ala Tyr Glu Leu
130                 135                 140 tgt gct gtc tat gtt acg gct ggt gcg cat gca tct cag caa tat tct      599
Cys Ala Val Tyr Val Thr Ala Gly Ala His Ala Ser Gln Gln Tyr Ser
145                 150                 155                 160 cct tct ggt ttc ttt ttc ggt gta tca gca atc gcg ttg gca att aac      647
```

| | | |
|---|---|---|
| Pro Ser Gly Phe Phe Phe Gly Val Ser Ala Ile Ala Leu Ala Ile Asn<br>                   165                      170                  175 | | |
| atg cta ttt atc tgc cgc atg gtc ttt aat gga aat ggt tta gat gtg<br>Met Leu Phe Ile Cys Arg Met Val Phe Asn Gly Asn Gly Leu Asp Val<br>             180                  185                 190 | 695 |
| gac gaa tat gta agg agg gca tat aaa ttt gct tat tca gat tgt ata<br>Asp Glu Tyr Val Arg Arg Ala Tyr Lys Phe Ala Tyr Ser Asp Cys Ile<br>        195                     200                 205 | 743 |
| gaa gtg ggt cct gtg gct tgt ttg cct gaa cct cct gat cct aat gaa<br>Glu Val Gly Pro Val Ala Cys Leu Pro Glu Pro Pro Asp Pro Asn Glu<br>210                     215                     220 | 791 |
| tta tat ccc cgg caa acc agc agg gct tca cat ctt ggc ctt ctg tac<br>Leu Tyr Pro Arg Gln Thr Ser Arg Ala Ser His Leu Gly Leu Leu Tyr<br>225                         230                    235                  240 | 839 |
| ctg ggc tca ctc gta gtt ctc ctt gcc tac tca gtc cta tat ggt ctc<br>Leu Gly Ser Leu Val Val Leu Leu Ala Tyr Ser Val Leu Tyr Gly Leu<br>                   245                     250                 255 | 887 |
| aca gct agg gaa tca cgt tgg ctt gga gga atc aca tca gct gca gtt<br>Thr Ala Arg Glu Ser Arg Trp Leu Gly Gly Ile Thr Ser Ala Ala Val<br>             260                  265                 270 | 935 |
| att gtt ctt gac tgg aat att ggg gca tgc ttg tat ggg ttt aag ctt<br>Ile Val Leu Asp Trp Asn Ile Gly Ala Cys Leu Tyr Gly Phe Lys Leu<br>        275                     280                 285 | 983 |
| ctt cag aat cgt gtt ctg gca ctt ttt gtt gct ggc ata tcc cgt ctt<br>Leu Gln Asn Arg Val Leu Ala Leu Phe Val Ala Gly Ile Ser Arg Leu<br>290                     295                    300 | 1031 |
| ttc cta ata tgt ttt ggc ata cac tac tgg tac cta ggg cat tgt att<br>Phe Leu Ile Cys Phe Gly Ile His Tyr Trp Tyr Leu Gly His Cys Ile<br>305                     310                    315                 320 | 1079 |
| agt tac att ttc gta gca tca gtt cta tca ggt gct gct gtt tct cgg<br>Ser Tyr Ile Phe Val Ala Ser Val Leu Ser Gly Ala Ala Val Ser Arg<br>                   325                     330                 335 | 1127 |
| cat cta tct ata aca gac cca tca gct gca aga aga gat gcc tta cag<br>His Leu Ser Ile Thr Asp Pro Ser Ala Ala Arg Arg Asp Ala Leu Gln<br>             340                  345                 350 | 1175 |
| agc aca gtg atc cgc ttg aga gaa ggt ttt cgg aga aaa gag cag aat<br>Ser Thr Val Ile Arg Leu Arg Glu Gly Phe Arg Arg Lys Glu Gln Asn<br>        355                     360                 365 | 1223 |
| agt tct tca agt tct tca gat ggt tgt ggc tca agt ata aaa aga agt<br>Ser Ser Ser Ser Ser Ser Asp Gly Cys Gly Ser Ser Ile Lys Arg Ser<br>370                     375                    380 | 1271 |
| agt agt atc gat gct ggc cat act ggt tgt act aat gaa gca aat cgt<br>Ser Ser Ile Asp Ala Gly His Thr Gly Cys Thr Asn Glu Ala Asn Arg<br>385                     390                    395                 400 | 1319 |
| acg gca gaa tct tgc acg gct gac aat cta act cga aca ggc agc tct<br>Thr Ala Glu Ser Cys Thr Ala Asp Asn Leu Thr Arg Thr Gly Ser Ser<br>                   405                     410                 415 | 1367 |
| cag gag gga atc aat agc gac aaa agc gaa gaa agt gga aga cca agc<br>Gln Glu Gly Ile Asn Ser Asp Lys Ser Glu Glu Ser Gly Arg Pro Ser<br>             420                  425                 430 | 1415 |
| tta ggt tta cgt agt agt tca tgt cgt tct gtg gtc caa gag ccc gaa<br>Leu Gly Leu Arg Ser Ser Ser Cys Arg Ser Val Val Gln Glu Pro Glu<br>        435                     440                 445 | 1463 |
| gca gga acg tct tat ttt atg gac aaa gtt tct gat caa aat aac act<br>Ala Gly Thr Ser Tyr Phe Met Asp Lys Val Ser Asp Gln Asn Asn Thr<br>450                     455                    460 | 1511 |
| ctt gtt gtt tgt tcg agc agt ggt cta gat agc caa ggt tac gag tct<br>Leu Val Val Cys Ser Ser Ser Gly Leu Asp Ser Gln Gly Tyr Glu Ser<br>465                     470                    475                 480 | 1559 |

-continued

| | |
|---|---|
| agc aca tcg aat tct gca aac cag cag ctt ttg gat atg aat ttg gct<br>Ser Thr Ser Asn Ser Ala Asn Gln Gln Leu Leu Asp Met Asn Leu Ala<br>                485                        490                  495 | 1607 |
| ctt gct ttc cag gac cag tta aac aat cct agg ata gcc tcg ata ctt<br>Leu Ala Phe Gln Asp Gln Leu Asn Asn Pro Arg Ile Ala Ser Ile Leu<br>        500                        505                        510 | 1655 |
| aag aag aaa gca aaa gaa ggt gat ctt gaa ctg act aat ttg ctg caa<br>Lys Lys Lys Ala Lys Glu Gly Asp Leu Glu Leu Thr Asn Leu Leu Gln<br>                515                        520                  525 | 1703 |
| gac aag ggg ttg gac cct aac ttt gct gta atg ttg aag gaa aaa aac<br>Asp Lys Gly Leu Asp Pro Asn Phe Ala Val Met Leu Lys Glu Lys Asn<br>530                        535                        540 | 1751 |
| ttg gat cct act ata ttg gca cta ctt cag agg agt agt ttg gat gca<br>Leu Asp Pro Thr Ile Leu Ala Leu Leu Gln Arg Ser Ser Leu Asp Ala<br>545                        550                        555                  560 | 1799 |
| gat aga gat cac cgc gac aat act gat att aca atc att gac tca aac<br>Asp Arg Asp His Arg Asp Asn Thr Asp Ile Thr Ile Ile Asp Ser Asn<br>                        565                        570                  575 | 1847 |
| agt gtt gac aat act ttg cca aat cag att tct tta tcc gaa gaa ttg<br>Ser Val Asp Asn Thr Leu Pro Asn Gln Ile Ser Leu Ser Glu Glu Leu<br>        580                        585                        590 | 1895 |
| aga ctc cgt gga cta gag aag tgg ctt aag ttg tct aga ctt ctt ctg<br>Arg Leu Arg Gly Leu Glu Lys Trp Leu Lys Leu Ser Arg Leu Leu Leu<br>                595                        600                  605 | 1943 |
| cac cat gta gcg ggg aca cca gag aga gca tgg ggc ctc ttt agt ctt<br>His His Val Ala Gly Thr Pro Glu Arg Ala Trp Gly Leu Phe Ser Leu<br>610                        615                        620 | 1991 |
| gtc ttt atc ctt gaa aca atc att gtg gcc att ttt cgc cca aag acc<br>Val Phe Ile Leu Glu Thr Ile Ile Val Ala Ile Phe Arg Pro Lys Thr<br>625                        630                        635                  640 | 2039 |
| atc acg att ata aat tct agt cat caa cag ttc gaa ttt ggt ttc tct<br>Ile Thr Ile Ile Asn Ser Ser His Gln Gln Phe Glu Phe Gly Phe Ser<br>                        645                        650                  655 | 2087 |
| gtg ctg cta ttg tca cct gtt gtc tgt tca ata atg gct ttt ctt cgg<br>Val Leu Leu Leu Ser Pro Val Val Cys Ser Ile Met Ala Phe Leu Arg<br>        660                        665                        670 | 2135 |
| tct ctt caa gtt gag gaa atg gcc ttg aca tca aaa tct cgc aag tat<br>Ser Leu Gln Val Glu Glu Met Ala Leu Thr Ser Lys Ser Arg Lys Tyr<br>                675                        680                  685 | 2183 |
| ggc ttt gtt gcc tgg ctt ctg agc aca tca gtt gga ttg tca ctc tcg<br>Gly Phe Val Ala Trp Leu Leu Ser Thr Ser Val Gly Leu Ser Leu Ser<br>690                        695                        700 | 2231 |
| ttc ttg agt aaa tcg tca gta ctt ctg gga ata tcc ttg act gtg ccc<br>Phe Leu Ser Lys Ser Ser Val Leu Leu Gly Ile Ser Leu Thr Val Pro<br>705                        710                        715                  720 | 2279 |
| ctc atg gca gca tgc ctg tct att gct gtt ccc ata tgg atg cat aat<br>Leu Met Ala Ala Cys Leu Ser Ile Ala Val Pro Ile Trp Met His Asn<br>                        725                        730                  735 | 2327 |
| ggg tac caa ttt tgg gtt cca cag tta tca tgt ggt gac cag gca aga<br>Gly Tyr Gln Phe Trp Val Pro Gln Leu Ser Cys Gly Asp Gln Ala Arg<br>        740                        745                        750 | 2375 |
| gat tta cga tct ccc agg ata aag ggg ttt att ctt tgg att tgt gtt<br>Asp Leu Arg Ser Pro Arg Ile Lys Gly Phe Ile Leu Trp Ile Cys Val<br>                755                        760                  765 | 2423 |
| gtg ttg ttt gcg ggt tct gta att tct ctt ggt gcg att ata tct gct<br>Val Leu Phe Ala Gly Ser Val Ile Ser Leu Gly Ala Ile Ile Ser Ala<br>770                        775                        780 | 2471 |
| aaa cct ttg gat gat tta aag tat aag ctg ttt agt gcc aga gaa aac<br>Lys Pro Leu Asp Asp Leu Lys Tyr Lys Leu Phe Ser Ala Arg Glu Asn<br>785                        790                        795                  800 | 2519 |

```
aac gtc acg tca cca tat aca tct tct gta tac ctt ggt tgg gca atg       2567
Asn Val Thr Ser Pro Tyr Thr Ser Ser Val Tyr Leu Gly Trp Ala Met
            805                 810                 815 tca tct gga att gct tta gta gtt acc gcc att cta cca ata gtt tca       2615
Ser Ser Gly Ile Ala Leu Val Val Thr Ala Ile Leu Pro Ile Val Ser
        820                 825                 830 tgg ttt gca act tat agg ttt tcc cac tct tct gct gtc tgt ctc atg       2663
Trp Phe Ala Thr Tyr Arg Phe Ser His Ser Ser Ala Val Cys Leu Met
835                 840                 845 ata ttc tca gtt gtt ctc gtg gca ttt tgt gga act tca tat ttg gaa       2711
Ile Phe Ser Val Val Leu Val Ala Phe Cys Gly Thr Ser Tyr Leu Glu
    850                 855                 860 gtt gta aaa tct aga gat gat cag ttg ccc aca aag ggt gat ttc ctt       2759
Val Val Lys Ser Arg Asp Asp Gln Leu Pro Thr Lys Gly Asp Phe Leu
865                 870                 875                 880 gcg gcc ttg ctt cca ctt gca tgc att ccg gcg ctg ctt tca cta tgc       2807
Ala Ala Leu Leu Pro Leu Ala Cys Ile Pro Ala Leu Leu Ser Leu Cys
                885                 890                 895 tgt ggg atg gtt aaa tgg aag gac gat tgt tgg ata ctc tct cga ggt       2855
Cys Gly Met Val Lys Trp Lys Asp Asp Cys Trp Ile Leu Ser Arg Gly
            900                 905                 910 gta tat gtt ttc ttt tca ata ggt ctt ctt ctt ttt ggt gcg ata           2903
Val Tyr Val Phe Phe Ser Ile Gly Leu Leu Leu Phe Gly Ala Ile
        915                 920                 925 gca gct gtc att gca gtc aaa cca tgg acg ata ggc gta tct ttt ctc       2951
Ala Ala Val Ile Ala Val Lys Pro Trp Thr Ile Gly Val Ser Phe Leu
930                 935                 940 tta gtt ctt ttc ctt atg gtg gta aca att ggt gta atc cat ctt tgg       2999
Leu Val Leu Phe Leu Met Val Val Thr Ile Gly Val Ile His Leu Trp
945                 950                 955                 960 gcg tca aac aat ttc tat tta acc agg aaa cag aca tcc ttt gtc tgc       3047
Ala Ser Asn Asn Phe Tyr Leu Thr Arg Lys Gln Thr Ser Phe Val Cys
                965                 970                 975 ttt ctt gct ctt ctt ttg ggt ttg gcc gca ttc ctt ctc gga tgg cat       3095
Phe Leu Ala Leu Leu Leu Gly Leu Ala Ala Phe Leu Leu Gly Trp His
            980                 985                 990 caa gat aaa gca ttt gct gga gca tct gtt ggt tac ttt aca ttc ctg       3143
Gln Asp Lys Ala Phe Ala Gly Ala Ser Val Gly Tyr Phe Thr Phe Leu
        995                 1000                1005 tct ctg ttg gct gga aga gca tta gct gtt ctt cta tcc cca cca att       3191
Ser Leu Leu Ala Gly Arg Ala Leu Ala Val Leu Leu Ser Pro Pro Ile
    1010                1015                1020 gta gta tat tct cca agg gtg cta cca gta tat gtc tac gat gct cat       3239
Val Val Tyr Ser Pro Arg Val Leu Pro Val Tyr Val Tyr Asp Ala His
1025                1030                1035                1040 gct gat tgc gga aag aat gtc agt gct gca ttt ctt gtc ctg tat gga       3287
Ala Asp Cys Gly Lys Asn Val Ser Ala Ala Phe Leu Val Leu Tyr Gly
                1045                1050                1055 att gct ttg gca aca gaa ggc tgg ggt gtt gtt gct agt ctg ata att       3335
Ile Ala Leu Ala Thr Glu Gly Trp Gly Val Val Ala Ser Leu Ile Ile
            1060                1065                1070 tat cct ccg ttt gcg ggt gct gct gta tca gct atc acc ctt gta gta       3383
Tyr Pro Pro Phe Ala Gly Ala Ala Val Ser Ala Ile Thr Leu Val Val
        1075                1080                1085 gcc ttt ggg ttt gct gtt tct cgc cca tgt ttg act ctt gag atg atg       3431
Ala Phe Gly Phe Ala Val Ser Arg Pro Cys Leu Thr Leu Glu Met Met
    1090                1095                1100 gag gtt gct gta cgc ttt ctt agc aag gat act ata gtg caa gct atc       3479
Glu Val Ala Val Arg Phe Leu Ser Lys Asp Thr Ile Val Gln Ala Ile
```

-continued

| | | | | |
|---|---|---|---|---|
| 1105 | 1110 | 1115 | 1120 | |
| tct cga tct gcc acg aaa aca aga aat gct cta tcc ggc acg tat tca<br>Ser Arg Ser Ala Thr Lys Thr Arg Asn Ala Leu Ser Gly Thr Tyr Ser<br>　　　　　　　　1125　　　　　　　　1130　　　　　　　　1135 | | | | 3527 |
| gct ccc caa agg tcc gcc agc tct gca gct ctt ctg gtt ggg gat ccc<br>Ala Pro Gln Arg Ser Ala Ser Ser Ala Ala Leu Leu Val Gly Asp Pro<br>　　　　　1140　　　　　　　　1145　　　　　　　　1150 | | | | 3575 |
| tct gca atg cgt gat aaa gca ggg aac ttt gtg ctt cct aga gat gat<br>Ser Ala Met Arg Asp Lys Ala Gly Asn Phe Val Leu Pro Arg Asp Asp<br>1155　　　　　　　　1160　　　　　　　　1165 | | | | 3623 |
| gtc atg aaa tta agg gat cgt ctc agg aac gaa gaa aga gtt gct gga<br>Val Met Lys Leu Arg Asp Arg Leu Arg Asn Glu Glu Arg Val Ala Gly<br>　　　　1170　　　　　　　　1175　　　　　　　　1180 | | | | 3671 |
| tca atc ttc tac aaa atg caa tgc agg aaa gga ttc cgt cat gaa cca<br>Ser Ile Phe Tyr Lys Met Gln Cys Arg Lys Gly Phe Arg His Glu Pro<br>1185　　　　　　　　1190　　　　　　　　1195　　　　　　　　1200 | | | | 3719 |
| cct aca aat gta gat tat aga aga gac atg tgt gcc cat gca aga gtt<br>Pro Thr Asn Val Asp Tyr Arg Arg Asp Met Cys Ala His Ala Arg Val<br>　　　　　　　　1205　　　　　　　　1210　　　　　　　　1215 | | | | 3767 |
| ttg gca ctg gaa gag gca att gat aca gaa tgg gtg tat atg tgg gac<br>Leu Ala Leu Glu Glu Ala Ile Asp Thr Glu Trp Val Tyr Met Trp Asp<br>　　　　1220　　　　　　　　1225　　　　　　　　1230 | | | | 3815 |
| aaa ttt ggt ggt tat tta cta cta ttg tta ggt ttg aca gct aag gcg<br>Lys Phe Gly Gly Tyr Leu Leu Leu Leu Gly Leu Thr Ala Lys Ala<br>　　　　　　　1235　　　　　　　　1240　　　　　　　　1245 | | | | 3863 |
| gag aga gtt cag gat gag gta cgg ttg cgg ctc ttc tta gat agc att<br>Glu Arg Val Gln Asp Glu Val Arg Leu Arg Leu Phe Leu Asp Ser Ile<br>　　　1250　　　　　　　　1255　　　　　　　　1260 | | | | 3911 |
| ggg ttc tcg gat tta agt gcc aga aaa atc agt aaa tgg aag cca gag<br>Gly Phe Ser Asp Leu Ser Ala Arg Lys Ile Ser Lys Trp Lys Pro Glu<br>1265　　　　　　　　1270　　　　　　　　1275　　　　　　　　1280 | | | | 3959 |
| gat aga aga caa ttc gaa att att caa gag agt tat ctg aga gag aaa<br>Asp Arg Arg Gln Phe Glu Ile Ile Gln Glu Ser Tyr Leu Arg Glu Lys<br>　　　　　　　　1285　　　　　　　　1290　　　　　　　　1295 | | | | 4007 |
| gag atg gaa gag gaa agc ctt atg cag aga cgt gaa gaa gaa ggg aga<br>Glu Met Glu Glu Glu Ser Leu Met Gln Arg Arg Glu Glu Glu Gly Arg<br>　　　　1300　　　　　　　　1305　　　　　　　　1310 | | | | 4055 |
| ggt aaa gaa aga agg aaa gct ctt ttg gag aag gaa gag cgc aaa tgg<br>Gly Lys Glu Arg Arg Lys Ala Leu Leu Glu Lys Glu Glu Arg Lys Trp<br>　　　　　　　1315　　　　　　　　1320　　　　　　　　1325 | | | | 4103 |
| aag gaa att gaa gcg tcc ctt att cca tct att cct aat gct ggt agc<br>Lys Glu Ile Glu Ala Ser Leu Ile Pro Ser Ile Pro Asn Ala Gly Ser<br>　　　1330　　　　　　　　1335　　　　　　　　1340 | | | | 4151 |
| agg gag gca gca gcc atg gca gct gca ata cgt gct gtt ggg ggt gat<br>Arg Glu Ala Ala Ala Met Ala Ala Ala Ile Arg Ala Val Gly Gly Asp<br>1345　　　　　　　　1350　　　　　　　　1355　　　　　　　　1360 | | | | 4199 |
| tct gtc ctt gag gat tcc ttc gca aga gag agg gtc tcg ggt att gca<br>Ser Val Leu Glu Asp Ser Phe Ala Arg Glu Arg Val Ser Gly Ile Ala<br>　　　　　　　　1365　　　　　　　　1370　　　　　　　　1375 | | | | 4247 |
| cgt agg ata cgc act gct caa cta gaa cga cgt gca caa cag act gga<br>Arg Arg Ile Arg Thr Ala Gln Leu Glu Arg Arg Ala Gln Gln Thr Gly<br>　　　　1380　　　　　　　　1385　　　　　　　　1390 | | | | 4295 |
| ata tct ggg gca gtt tgt gtt ctt gat gat gaa cca atg ata agt ggt<br>Ile Ser Gly Ala Val Cys Val Leu Asp Asp Glu Pro Met Ile Ser Gly<br>　　　　　　　1395　　　　　　　　1400　　　　　　　　1405 | | | | 4343 |
| aaa cat tgc ggc caa atg gac tca agt gtc tgt caa agt cag aag att<br>Lys His Cys Gly Gln Met Asp Ser Ser Val Cys Gln Ser Gln Lys Ile<br>　　　1410　　　　　　　　1415　　　　　　　　1420 | | | | 4391 |
| agc ttt tcc gtt aca gca atg atc caa tcc gat tct gga cct gta tgt | | | | 4439 |

```
                                                                             -continued Ser Phe Ser Val Thr Ala Met Ile Gln Ser Asp Ser Gly Pro Val Cys
1425                1430                1435                1440 ctt ttt ggc act gaa ttt caa aag aaa gta tgt tgg gag att ctg gtt    4487
Leu Phe Gly Thr Glu Phe Gln Lys Lys Val Cys Trp Glu Ile Leu Val
                1445                1450                1455 gct ggt tct gag caa gga att gag gct ggc caa gtt ggg ctt agg ttg    4535
Ala Gly Ser Glu Gln Gly Ile Glu Ala Gly Gln Val Gly Leu Arg Leu
            1460                1465                1470 ata aca aaa ggt gag agg cag aca acc gtt gct aga gag tgg tat att    4583
Ile Thr Lys Gly Glu Arg Gln Thr Thr Val Ala Arg Glu Trp Tyr Ile
        1475                1480                1485 ggt gca acc agc ata act gat gga agg tgg cat aca gtg aca atc aca    4631
Gly Ala Thr Ser Ile Thr Asp Gly Arg Trp His Thr Val Thr Ile Thr
    1490                1495                1500 att gat gct gat gcg ggg gaa gct act tgt tac ata gat ggt ggg ttt    4679
Ile Asp Ala Asp Ala Gly Glu Ala Thr Cys Tyr Ile Asp Gly Gly Phe
1505                1510                1515                1520 gat ggc tac cag aat ggg tta cct cta agt att ggc agt gcc att tgg    4727
Asp Gly Tyr Gln Asn Gly Leu Pro Leu Ser Ile Gly Ser Ala Ile Trp
                1525                1530                1535 gaa caa gga gct gaa gtt tgg ttg ggt gtt agg cca cct ata gat gtt    4775
Glu Gln Gly Ala Glu Val Trp Leu Gly Val Arg Pro Pro Ile Asp Val
            1540                1545                1550 gat gca ttc ggg aga tca gat agt gat ggc gtc gaa tca aag atg cat    4823
Asp Ala Phe Gly Arg Ser Asp Ser Asp Gly Val Glu Ser Lys Met His
        1555                1560                1565 att atg gat gtt ttc ctt tgg ggg aaa tgc tta agt gaa gaa gag gcc    4871
Ile Met Asp Val Phe Leu Trp Gly Lys Cys Leu Ser Glu Glu Glu Ala
    1570                1575                1580 gct tct ttg cat gca gcc att ggc atg gct gac tta gac atg att gat    4919
Ala Ser Leu His Ala Ala Ile Gly Met Ala Asp Leu Asp Met Ile Asp
1585                1590                1595                1600 ttg tct gat gac aat tgg caa tgg acg gat tca ccc ccc aga gtc gat    4967
Leu Ser Asp Asp Asn Trp Gln Trp Thr Asp Ser Pro Pro Arg Val Asp
                1605                1610                1615 ggt tgg gat agt gat cct gcc gat gtt gat ctc tat gat agg gat gac    5015
Gly Trp Asp Ser Asp Pro Ala Asp Val Asp Leu Tyr Asp Arg Asp Asp
            1620                1625                1630 gta gat tgg gat gga caa tat tcc agt ggg agg aaa aga aga tca ggt    5063
Val Asp Trp Asp Gly Gln Tyr Ser Ser Gly Arg Lys Arg Arg Ser Gly
        1635                1640                1645 cgg gat ttt gta atg agt gtc gat tcc ttt gcc agg aga cac agg aaa    5111
Arg Asp Phe Val Met Ser Val Asp Ser Phe Ala Arg Arg His Arg Lys
    1650                1655                1660 ccc agg atg gag aca caa gaa gat ata aat caa aga atg cgt tca gtt    5159
Pro Arg Met Glu Thr Gln Glu Asp Ile Asn Gln Arg Met Arg Ser Val
1665                1670                1675                1680 gag ttg gct gtc aaa gaa gct ctc tct gca cga ggt gat aag caa ttt    5207
Glu Leu Ala Val Lys Glu Ala Leu Ser Ala Arg Gly Asp Lys Gln Phe
                1685                1690                1695 act gac cag gaa ttt cct cca aat gat cgc tct tta ttt gtg gat aca    5255
Thr Asp Gln Glu Phe Pro Pro Asn Asp Arg Ser Leu Phe Val Asp Thr
            1700                1705                1710 caa aat ccc cca tca aaa ttg cag gtt gtt tct gaa tgg atg aga cct    5303
Gln Asn Pro Pro Ser Lys Leu Gln Val Val Ser Glu Trp Met Arg Pro
        1715                1720                1725 gac tcc att gtg aaa gaa aac ggt agt gat tcc cgt ccc tgc ctg ttc    5351
Asp Ser Ile Val Lys Glu Asn Gly Ser Asp Ser Arg Pro Cys Leu Phe
    1730                1735                1740
```

-continued

| | |
|---|---|
| tct ggg gat gca aat cct tca gat gtt tgc cag ggg cgt ttg ggg gat<br>Ser Gly Asp Ala Asn Pro Ser Asp Val Cys Gln Gly Arg Leu Gly Asp<br>1745     1750     1755     1760 | 5399 |
| tgt tgg ttc tta agc gcc gtt gca gtt ttg aca gag gtt tca cga ata<br>Cys Trp Phe Leu Ser Ala Val Ala Val Leu Thr Glu Val Ser Arg Ile<br>    1765     1770     1775 | 5447 |
| tct gaa gtg atc att act cct gaa tac aac gag gaa ggg atc tac act<br>Ser Glu Val Ile Ile Thr Pro Glu Tyr Asn Glu Glu Gly Ile Tyr Thr<br>1780     1785     1790 | 5495 |
| gtt cgt ttt tgt att cag ggt gag tgg gtt cct gtt gtt atc gat gac<br>Val Arg Phe Cys Ile Gln Gly Glu Trp Val Pro Val Val Ile Asp Asp<br>1795     1800     1805 | 5543 |
| tgg att cca tgt gaa tca cct ggt aaa cca gct ttt gct act agc aga<br>Trp Ile Pro Cys Glu Ser Pro Gly Lys Pro Ala Phe Ala Thr Ser Arg<br>1810     1815     1820 | 5591 |
| aag ctc aat gaa ctc tgg gtc tcc atg gtg gag aaa gca tat gcc aag<br>Lys Leu Asn Glu Leu Trp Val Ser Met Val Glu Lys Ala Tyr Ala Lys<br>1825     1830     1835     1840 | 5639 |
| ctc cat ggt tct tat gag gca ctg gag ggg gga ctg gtt cag gat gct<br>Leu His Gly Ser Tyr Glu Ala Leu Glu Gly Gly Leu Val Gln Asp Ala<br>    1845     1850     1855 | 5687 |
| ctt gtc gac cta act gga gga gct ggt gag gag att gac ttg cgg agt<br>Leu Val Asp Leu Thr Gly Gly Ala Gly Glu Glu Ile Asp Leu Arg Ser<br>1860     1865     1870 | 5735 |
| gct caa gca caa ata gat ctt gca agt ggc aga ttg tgg tct caa ttg<br>Ala Gln Ala Gln Ile Asp Leu Ala Ser Gly Arg Leu Trp Ser Gln Leu<br>1875     1880     1885 | 5783 |
| tta cgt ttt aaa caa gag ggg ttc tta ctt ggt gct gga agt cca tca<br>Leu Arg Phe Lys Gln Glu Gly Phe Leu Leu Gly Ala Gly Ser Pro Ser<br>1890     1895     1900 | 5831 |
| gga tct gat gtt cat gta tct tcc agt ggc att gtg caa ggg cat gct<br>Gly Ser Asp Val His Val Ser Ser Ser Gly Ile Val Gln Gly His Ala<br>1905     1910     1915     1920 | 5879 |
| tac tcc gtc tta cag gtg aga gag gtt gat ggg cac aga ctt gtt cag<br>Tyr Ser Val Leu Gln Val Arg Glu Val Asp Gly His Arg Leu Val Gln<br>    1925     1930     1935 | 5927 |
| att cga aat cca tgg gct aat gaa gtt gag tgg aat ggt ccc tgg tca<br>Ile Arg Asn Pro Trp Ala Asn Glu Val Glu Trp Asn Gly Pro Trp Ser<br>1940     1945     1950 | 5975 |
| gac tca tcc cca gag tgg act gat agg atg aag cac aag ctg aag cat<br>Asp Ser Ser Pro Glu Trp Thr Asp Arg Met Lys His Lys Leu Lys His<br>1955     1960     1965 | 6023 |
| gtt cca cag atg cgc tac tct gta aat ggc caa tgg cga ggt tat agt<br>Val Pro Gln Met Arg Tyr Ser Val Asn Gly Gln Trp Arg Gly Tyr Ser<br>1970     1975     1980 | 6071 |
| gcc ggt ggc tgc caa gat tat agc tca tgg cat caa aat cca caa ttc<br>Ala Gly Gly Cys Gln Asp Tyr Ser Ser Trp His Gln Asn Pro Gln Phe<br>1985     1990     1995     2000 | 6119 |
| agg ctg agg gca act ggt tct gat gca tct tta cca att cat ggc gta<br>Arg Leu Arg Ala Thr Gly Ser Asp Ala Ser Leu Pro Ile His Gly Val<br>    2005     2010     2015 | 6167 |
| ggt ttc tcg aga aca act cct gga ttt cgt aac tac caa tca agc cat<br>Gly Phe Ser Arg Thr Thr Pro Gly Phe Arg Asn Tyr Gln Ser Ser His<br>2020     2025     2030 | 6215 |
| gat tca cag ttg ttc tat atc gga ttg agg att ctt aaa act cgt gga<br>Asp Ser Gln Leu Phe Tyr Ile Gly Leu Arg Ile Leu Lys Thr Arg Gly<br>2035     2040     2045 | 6263 |
| cgt cgt gct gct tac aac ata ttt ctt cat gaa tct gtt ggt gga aca<br>Arg Arg Ala Ala Tyr Asn Ile Phe Leu His Glu Ser Val Gly Gly Thr<br>2050     2055     2060 | 6311 |

```
gac tat gtg aat tcc cgt gag att tca tgt gaa atg gtt ctt gac cct      6359
Asp Tyr Val Asn Ser Arg Glu Ile Ser Cys Glu Met Val Leu Asp Pro
2065                2070                2075                2080 gat cct aag ggt tat act att gtc cca acc acg ata cac cca ggg gaa      6407
Asp Pro Lys Gly Tyr Thr Ile Val Pro Thr Thr Ile His Pro Gly Glu
            2085                2090                2095 gaa gca cct ttt gtc ctt tca gtc ttc aca aaa gca tcc att gtt ctt      6455
Glu Ala Pro Phe Val Leu Ser Val Phe Thr Lys Ala Ser Ile Val Leu
        2100                2105                2110 gaa gct ttg tag                                                       6467
Glu Ala Leu
    2115

<210> SEQ ID NO 4
<211> LENGTH: 2115
<212> TYPE: PRT
<213> ORGANISM: arabidopsis

<400> SEQUENCE: 4

Met Glu Gly Asp Glu Arg Gly Val Leu Leu Ala Cys Val Ile Ser Gly
1               5                   10                  15

Thr Leu Phe Thr Val Phe Gly Ser Gly Ser Phe Trp Ile Leu Trp Ala
            20                  25                  30

Val Asn Trp Arg Pro Trp Arg Leu Tyr Ser Trp Ile Phe Ala Arg Lys
        35                  40                  45

Trp Pro Lys Val Leu Gln Gly Pro Gln Leu Asp Ile Leu Cys Gly Val
    50                  55                  60

Leu Ser Leu Phe Ala Trp Ile Val Val Ser Pro Ile Ala Ile Leu
65                  70                  75                  80

Ile Gly Trp Gly Ser Trp Leu Ile Val Ile Leu Asp Arg His Ile Ile
                85                  90                  95

Gly Leu Ala Ile Ile Met Ala Gly Thr Ala Leu Leu Ala Phe Tyr
            100                 105                 110

Ser Ile Met Leu Trp Trp Arg Thr Gln Trp Gln Ser Ser Arg Ala Val
        115                 120                 125

Ala Leu Leu Leu Leu Leu Gly Val Ala Leu Leu Cys Ala Tyr Glu Leu
    130                 135                 140

Cys Ala Val Tyr Val Thr Ala Gly Ala His Ala Ser Gln Gln Tyr Ser
145                 150                 155                 160

Pro Ser Gly Phe Phe Phe Gly Val Ser Ala Ile Ala Leu Ala Ile Asn
                165                 170                 175

Met Leu Phe Ile Cys Arg Met Val Phe Asn Gly Asn Gly Leu Asp Val
            180                 185                 190

Asp Glu Tyr Val Arg Arg Ala Tyr Lys Phe Ala Tyr Ser Asp Cys Ile
        195                 200                 205

Glu Val Gly Pro Val Ala Cys Leu Pro Glu Pro Pro Asp Pro Asn Glu
    210                 215                 220

Leu Tyr Pro Arg Gln Thr Ser Arg Ala Ser His Leu Gly Leu Leu Tyr
225                 230                 235                 240

Leu Gly Ser Leu Val Val Leu Ala Tyr Ser Val Leu Tyr Gly Leu
                245                 250                 255

Thr Ala Arg Glu Ser Arg Trp Leu Gly Gly Ile Thr Ser Ala Ala Val
            260                 265                 270

Ile Val Leu Asp Trp Asn Ile Gly Ala Cys Leu Tyr Gly Phe Lys Leu
        275                 280                 285
```

-continued

| | | | | | | | | | | | |
|---|---|---|---|---|---|---|---|---|---|---|---|
|Leu|Gln|Asn|Arg|Val|Leu|Ala|Leu|Phe|Val|Ala|Gly|Ile|Ser|Arg|Leu|
| |290| | | |295| | | |300| | | | | | |

Phe Leu Ile Cys Phe Gly Ile His Tyr Trp Tyr Leu Gly His Cys Ile
305                 310                 315                 320

Ser Tyr Ile Phe Val Ala Ser Val Leu Ser Gly Ala Ala Val Ser Arg
                325                 330                 335

His Leu Ser Ile Thr Asp Pro Ser Ala Ala Arg Arg Asp Ala Leu Gln
            340                 345                 350

Ser Thr Val Ile Arg Leu Arg Glu Gly Phe Arg Arg Lys Glu Gln Asn
        355                 360                 365

Ser Ser Ser Ser Ser Asp Gly Cys Gly Ser Ser Ile Lys Arg Ser
    370                 375                 380

Ser Ser Ile Asp Ala Gly His Thr Gly Cys Thr Asn Glu Ala Asn Arg
385                 390                 395                 400

Thr Ala Glu Ser Cys Thr Ala Asp Asn Leu Thr Arg Thr Gly Ser Ser
                405                 410                 415

Gln Glu Gly Ile Asn Ser Asp Lys Ser Glu Ser Gly Arg Pro Ser
            420                 425                 430

Leu Gly Leu Arg Ser Ser Cys Arg Ser Val Val Gln Glu Pro Glu
        435                 440                 445

Ala Gly Thr Ser Tyr Phe Met Asp Lys Val Ser Asp Gln Asn Asn Thr
    450                 455                 460

Leu Val Val Cys Ser Ser Ser Gly Leu Asp Ser Gln Gly Tyr Glu Ser
465                 470                 475                 480

Ser Thr Ser Asn Ser Ala Asn Gln Gln Leu Leu Asp Met Asn Leu Ala
                485                 490                 495

Leu Ala Phe Gln Asp Gln Leu Asn Asn Pro Arg Ile Ala Ser Ile Leu
            500                 505                 510

Lys Lys Lys Ala Lys Glu Gly Asp Leu Glu Leu Thr Asn Leu Leu Gln
        515                 520                 525

Asp Lys Gly Leu Asp Pro Asn Phe Ala Val Met Leu Lys Glu Lys Asn
    530                 535                 540

Leu Asp Pro Thr Ile Leu Ala Leu Leu Gln Arg Ser Ser Leu Asp Ala
545                 550                 555                 560

Asp Arg Asp His Arg Asp Asn Thr Asp Ile Thr Ile Asp Ser Asn
                565                 570                 575

Ser Val Asp Asn Thr Leu Pro Asn Gln Ile Ser Leu Ser Glu Glu Leu
            580                 585                 590

Arg Leu Arg Gly Leu Glu Lys Trp Leu Lys Leu Ser Arg Leu Leu Leu
        595                 600                 605

His His Val Ala Gly Thr Pro Glu Arg Ala Trp Gly Leu Phe Ser Leu
    610                 615                 620

Val Phe Ile Leu Glu Thr Ile Val Ala Ile Phe Arg Pro Lys Thr
625                 630                 635                 640

Ile Thr Ile Ile Asn Ser Ser His Gln Gln Phe Glu Phe Gly Phe Ser
                645                 650                 655

Val Leu Leu Leu Ser Pro Val Val Cys Ser Ile Met Ala Phe Leu Arg
            660                 665                 670

Ser Leu Gln Val Glu Glu Met Ala Leu Thr Ser Lys Ser Arg Lys Tyr
        675                 680                 685

Gly Phe Val Ala Trp Leu Leu Ser Thr Ser Val Gly Leu Ser Leu Ser
    690                 695                 700

Phe Leu Ser Lys Ser Ser Val Leu Leu Gly Ile Ser Leu Thr Val Pro

-continued

```
            705                 710                 715                 720
Leu Met Ala Ala Cys Leu Ser Ile Ala Val Pro Ile Trp Met His Asn
                725                 730                 735
Gly Tyr Gln Phe Trp Val Pro Gln Leu Ser Cys Gly Asp Gln Ala Arg
                740                 745                 750
Asp Leu Arg Ser Pro Arg Ile Lys Gly Phe Ile Leu Trp Ile Cys Val
                755                 760                 765
Val Leu Phe Ala Gly Ser Val Ile Ser Leu Gly Ala Ile Ile Ser Ala
                770                 775                 780
Lys Pro Leu Asp Asp Leu Lys Tyr Lys Leu Phe Ser Ala Arg Glu Asn
785                 790                 795                 800
Asn Val Thr Ser Pro Tyr Thr Ser Ser Val Tyr Leu Gly Trp Ala Met
                805                 810                 815
Ser Ser Gly Ile Ala Leu Val Val Thr Ala Ile Leu Pro Ile Val Ser
                820                 825                 830
Trp Phe Ala Thr Tyr Arg Phe Ser His Ser Ser Ala Val Cys Leu Met
                835                 840                 845
Ile Phe Ser Val Val Leu Val Ala Phe Cys Gly Thr Ser Tyr Leu Glu
                850                 855                 860
Val Val Lys Ser Arg Asp Asp Gln Leu Pro Thr Lys Gly Asp Phe Leu
865                 870                 875                 880
Ala Ala Leu Leu Pro Leu Ala Cys Ile Pro Ala Leu Leu Ser Leu Cys
                885                 890                 895
Cys Gly Met Val Lys Trp Lys Asp Asp Cys Trp Ile Leu Ser Arg Gly
                900                 905                 910
Val Tyr Val Phe Phe Ser Ile Gly Leu Leu Leu Phe Gly Ala Ile
                915                 920                 925
Ala Ala Val Ile Ala Val Lys Pro Trp Thr Ile Gly Val Ser Phe Leu
                930                 935                 940
Leu Val Leu Phe Leu Met Val Val Thr Ile Gly Val Ile His Leu Trp
945                 950                 955                 960
Ala Ser Asn Asn Phe Tyr Leu Thr Arg Lys Gln Thr Ser Phe Val Cys
                965                 970                 975
Phe Leu Ala Leu Leu Leu Gly Leu Ala Ala Phe Leu Leu Gly Trp His
                980                 985                 990
Gln Asp Lys Ala Phe Ala Gly Ala Ser Val Gly Tyr Phe Thr Phe Leu
                995                 1000                1005
Ser Leu Leu Ala Gly Arg Ala Leu Ala Val Leu Leu Ser Pro Pro Ile
                1010                1015                1020
Val Val Tyr Ser Pro Arg Val Leu Pro Val Tyr Val Tyr Asp Ala His
1025                1030                1035                1040
Ala Asp Cys Gly Lys Asn Val Ser Ala Phe Leu Val Leu Tyr Gly
                1045                1050                1055
Ile Ala Leu Ala Thr Glu Gly Trp Gly Val Val Ala Ser Leu Ile Ile
                1060                1065                1070
Tyr Pro Pro Phe Ala Gly Ala Ala Val Ser Ala Ile Thr Leu Val Val
                1075                1080                1085
Ala Phe Gly Phe Ala Val Ser Arg Pro Cys Leu Thr Leu Glu Met Met
                1090                1095                1100
Glu Val Ala Val Arg Phe Leu Ser Lys Asp Thr Ile Val Gln Ala Ile
1105                1110                1115                1120
Ser Arg Ser Ala Thr Lys Thr Arg Asn Ala Leu Ser Gly Thr Tyr Ser
                1125                1130                1135
```

-continued

```
Ala Pro Gln Arg Ser Ala Ser Ala Ala Leu Leu Val Gly Asp Pro
        1140                1145                1150

Ser Ala Met Arg Asp Lys Ala Gly Asn Phe Val Leu Pro Arg Asp Asp
        1155                1160                1165

Val Met Lys Leu Arg Asp Arg Leu Arg Asn Glu Glu Arg Val Ala Gly
        1170                1175                1180

Ser Ile Phe Tyr Lys Met Gln Cys Arg Lys Gly Phe Arg His Glu Pro
1185                1190                1195                1200

Pro Thr Asn Val Asp Tyr Arg Arg Asp Met Cys Ala His Ala Arg Val
        1205                1210                1215

Leu Ala Leu Glu Glu Ala Ile Asp Thr Glu Trp Val Tyr Met Trp Asp
        1220                1225                1230

Lys Phe Gly Gly Tyr Leu Leu Leu Leu Gly Leu Thr Ala Lys Ala
        1235                1240                1245

Glu Arg Val Gln Asp Glu Val Arg Leu Arg Leu Phe Leu Asp Ser Ile
        1250                1255                1260

Gly Phe Ser Asp Leu Ser Ala Arg Lys Ile Ser Lys Trp Lys Pro Glu
1265                1270                1275                1280

Asp Arg Arg Gln Phe Glu Ile Ile Gln Glu Ser Tyr Leu Arg Glu Lys
        1285                1290                1295

Glu Met Glu Glu Glu Ser Leu Met Gln Arg Arg Glu Glu Glu Gly Arg
        1300                1305                1310

Gly Lys Glu Arg Arg Lys Ala Leu Leu Glu Lys Glu Glu Arg Lys Trp
        1315                1320                1325

Lys Glu Ile Glu Ala Ser Leu Ile Pro Ser Ile Pro Asn Ala Gly Ser
        1330                1335                1340

Arg Glu Ala Ala Ala Met Ala Ala Ile Arg Ala Val Gly Gly Asp
1345                1350                1355                1360

Ser Val Leu Glu Asp Ser Phe Ala Arg Glu Arg Val Ser Gly Ile Ala
        1365                1370                1375

Arg Arg Ile Arg Thr Ala Gln Leu Glu Arg Arg Ala Gln Gln Thr Gly
        1380                1385                1390

Ile Ser Gly Ala Val Cys Val Leu Asp Asp Glu Pro Met Ile Ser Gly
        1395                1400                1405

Lys His Cys Gly Gln Met Asp Ser Ser Val Cys Gln Ser Gln Lys Ile
        1410                1415                1420

Ser Phe Ser Val Thr Ala Met Ile Gln Ser Asp Ser Gly Pro Val Cys
1425                1430                1435                1440

Leu Phe Gly Thr Glu Phe Gln Lys Lys Val Cys Trp Glu Ile Leu Val
        1445                1450                1455

Ala Gly Ser Glu Gln Gly Ile Glu Ala Gly Gln Val Gly Leu Arg Leu
        1460                1465                1470

Ile Thr Lys Gly Glu Arg Gln Thr Thr Val Ala Arg Glu Trp Tyr Ile
        1475                1480                1485

Gly Ala Thr Ser Ile Thr Asp Gly Arg Trp His Thr Val Thr Ile Thr
        1490                1495                1500

Ile Asp Ala Asp Ala Gly Glu Ala Thr Cys Tyr Ile Asp Gly Gly Phe
1505                1510                1515                1520

Asp Gly Tyr Gln Asn Gly Leu Pro Leu Ser Ile Gly Ser Ala Ile Trp
        1525                1530                1535

Glu Gln Gly Ala Glu Val Trp Leu Gly Val Arg Pro Pro Ile Asp Val
        1540                1545                1550
```

-continued

Asp Ala Phe Gly Arg Ser Asp Ser Asp Gly Val Glu Ser Lys Met His
            1555                1560                1565

Ile Met Asp Val Phe Leu Trp Gly Lys Cys Leu Ser Glu Glu Ala
        1570                1575                1580

Ala Ser Leu His Ala Ala Ile Gly Met Ala Asp Leu Asp Met Ile Asp
1585                1590                1595                1600

Leu Ser Asp Asp Asn Trp Gln Trp Thr Asp Ser Pro Pro Arg Val Asp
            1605                1610                1615

Gly Trp Asp Ser Asp Pro Ala Asp Val Asp Leu Tyr Asp Arg Asp Asp
            1620                1625                1630

Val Asp Trp Asp Gly Gln Tyr Ser Ser Gly Arg Lys Arg Arg Ser Gly
            1635                1640                1645

Arg Asp Phe Val Met Ser Val Asp Ser Phe Ala Arg Arg His Arg Lys
        1650                1655                1660

Pro Arg Met Glu Thr Gln Glu Asp Ile Asn Gln Arg Met Arg Ser Val
1665                1670                1675                1680

Glu Leu Ala Val Lys Glu Ala Leu Ser Ala Arg Gly Asp Lys Gln Phe
            1685                1690                1695

Thr Asp Gln Glu Phe Pro Pro Asn Asp Arg Ser Leu Phe Val Asp Thr
        1700                1705                1710

Gln Asn Pro Pro Ser Lys Leu Gln Val Val Ser Glu Trp Met Arg Pro
        1715                1720                1725

Asp Ser Ile Val Lys Glu Asn Gly Ser Asp Ser Arg Pro Cys Leu Phe
        1730                1735                1740

Ser Gly Asp Ala Asn Pro Ser Asp Val Cys Gln Gly Arg Leu Gly Asp
1745                1750                1755                1760

Cys Trp Phe Leu Ser Ala Val Ala Val Leu Thr Glu Val Ser Arg Ile
            1765                1770                1775

Ser Glu Val Ile Ile Thr Pro Glu Tyr Asn Glu Glu Gly Ile Tyr Thr
        1780                1785                1790

Val Arg Phe Cys Ile Gln Gly Glu Trp Val Pro Val Ile Asp Asp
        1795                1800                1805

Trp Ile Pro Cys Glu Ser Pro Gly Lys Pro Ala Phe Ala Thr Ser Arg
        1810                1815                1820

Lys Leu Asn Glu Leu Trp Val Ser Met Val Glu Lys Ala Tyr Ala Lys
1825                1830                1835                1840

Leu His Gly Ser Tyr Glu Ala Leu Glu Gly Gly Leu Val Gln Asp Ala
            1845                1850                1855

Leu Val Asp Leu Thr Gly Gly Ala Gly Glu Glu Ile Asp Leu Arg Ser
            1860                1865                1870

Ala Gln Ala Gln Ile Asp Leu Ala Ser Gly Arg Leu Trp Ser Gln Leu
            1875                1880                1885

Leu Arg Phe Lys Gln Glu Gly Phe Leu Leu Gly Ala Gly Ser Pro Ser
            1890                1895                1900

Gly Ser Asp Val His Val Ser Ser Gly Ile Val Gln Gly His Ala
1905                1910                1915                1920

Tyr Ser Val Leu Gln Val Arg Glu Val Asp Gly His Arg Leu Val Gln
                1925                1930                1935

Ile Arg Asn Pro Trp Ala Asn Glu Val Glu Trp Asn Gly Pro Trp Ser
            1940                1945                1950

Asp Ser Ser Pro Glu Trp Thr Asp Arg Met Lys His Lys Leu Lys His
            1955                1960                1965

Val Pro Gln Met Arg Tyr Ser Val Asn Gly Gln Trp Arg Gly Tyr Ser

|  |  |  |  |  |  |  |  |  |  |  |  |  | 1970 |  |  |  | 1975 |  |  |  | 1980 |  |  |  |
|---|---|---|---|---|---|---|---|---|---|---|---|---|---|---|---|---|---|---|---|---|---|---|---|---|

Ala Gly Gly Cys Gln Asp Tyr Ser Ser Trp His Gln Asn Pro Gln Phe
　　1985　　　　　　　　1990　　　　　　　　1995　　　　　　　　2000

Arg Leu Arg Ala Thr Gly Ser Asp Ala Ser Leu Pro Ile His Gly Val
　　　　　　　　2005　　　　　　　　2010　　　　　　　　2015

Gly Phe Ser Arg Thr Thr Pro Gly Phe Arg Asn Tyr Gln Ser Ser His
　　　　　　　　2020　　　　　　　　2025　　　　　　　　2030

Asp Ser Gln Leu Phe Tyr Ile Gly Leu Arg Ile Leu Lys Thr Arg Gly
　　　　　　2035　　　　　　　　2040　　　　　　　　2045

Arg Arg Ala Ala Tyr Asn Ile Phe Leu His Glu Ser Val Gly Gly Thr
　　2050　　　　　　　　2055　　　　　　　　2060

Asp Tyr Val Asn Ser Arg Glu Ile Ser Cys Glu Met Val Leu Asp Pro
2065　　　　　　　　2070　　　　　　　　2075　　　　　　　　2080

Asp Pro Lys Gly Tyr Thr Ile Val Pro Thr Thr Ile His Pro Gly Glu
　　　　　　　　2085　　　　　　　　2090　　　　　　　　2095

Glu Ala Pro Phe Val Leu Ser Val Phe Thr Lys Ala Ser Ile Val Leu
　　　　　　2100　　　　　　　　2105　　　　　　　　2110

Glu Ala Leu
　　　　2115

<210> SEQ ID NO 5
<211> LENGTH: 1007
<212> TYPE: DNA
<213> ORGANISM: zea mays
<220> FEATURE:
<221> NAME/KEY: CDS
<222> LOCATION: (150)...(762)
<223> OTHER INFORMATION: maize superal

<400> SEQUENCE: 5

| | |
|---|---|
| gtcgtcaaaa aatccccatt cgttcccctt ctcgcctcca cgagccttca caaattgccc | 60 |
| tctcagctct tctcctaatc tcactctagc cctagccaaa tcccagaccc atcccagccc | 120 |
| tagcgacacc aaccagctcg ccagcgacc atg ggg aac ccg gag aag ctg atg | 173 |
|                                                        Met Gly Asn Pro Glu Lys Leu Met<br>                                                       1               5 | |
| aat cag atc ttc gac ctc aag ttc acc tcc aag tcg ctg cag cgg cag<br>Asn Gln Ile Phe Asp Leu Lys Phe Thr Ser Lys Ser Leu Gln Arg Gln<br>    10                 15                 20 | 221 |
| gcg cgc aag tgc gag aag gag gag aag gag cag aag ctc aag gtc aag<br>Ala Arg Lys Cys Glu Lys Glu Glu Lys Glu Gln Lys Leu Lys Val Lys<br>25               30                 35                 40 | 269 |
| aag gcg atc gag aag ggc aac atg gac ggc gcc cgc atc tac gcc gag<br>Lys Ala Ile Glu Lys Gly Asn Met Asp Gly Ala Arg Ile Tyr Ala Glu<br>               45                 50                 55 | 317 |
| aac gcc atc cgc aag cgc acc gag cac atg aac tac ctc cgc ctc gcc<br>Asn Ala Ile Arg Lys Arg Thr Glu His Met Asn Tyr Leu Arg Leu Ala<br>               60                 65                 70 | 365 |
| tct cgc ctc gac gcc gtc gtg gcc cgc ctc gac acg cag gcc aag atg<br>Ser Arg Leu Asp Ala Val Val Ala Arg Leu Asp Thr Gln Ala Lys Met<br>    75                 80                 85 | 413 |
| cag gtc atc ggc aag tcc atg cag tcc atc gtc aag tcg ctc gac tcc<br>Gln Val Ile Gly Lys Ser Met Gln Ser Ile Val Lys Ser Leu Asp Ser<br>90               95                 100 | 461 |
| tcg ctc gcc acc ggg aac ctc cag aag atg tcc gag acc atg gac aat<br>Ser Leu Ala Thr Gly Asn Leu Gln Lys Met Ser Glu Thr Met Asp Asn<br>105               110               115               120 | 509 |
| ttc gag cgc cag ttc gtc aac atg gag gtc cag gcc gag ttc atg gag<br>Phe Glu Arg Gln Phe Val Asn Met Glu Val Gln Ala Glu Phe Met Glu | 557 |

|  |  |  |  |  |  |  |  |  |  |  |  |  |  |  |  |
|---|---|---|---|---|---|---|---|---|---|---|---|---|---|---|---|
|  |  |  |  | 125 |  |  |  | 130 |  |  |  | 135 |  |  |  |
| ggc | gcc | atg | gcc | ggc | tcc | acc | tcc | ctc | tcc | acg | ccg | gag | acc | gag | gtc | 605 |
| Gly | Ala | Met | Ala | Gly | Ser | Thr | Ser | Leu | Ser | Thr | Pro | Glu | Thr | Glu | Val |
|  |  |  | 140 |  |  |  | 145 |  |  |  | 150 |  |  |  |  |
| aac | agc | ctc | atg | cag | cag | gtc | gcg | gac | gac | tac | ggg | ctc | gag | gtc | tcc | 653 |
| Asn | Ser | Leu | Met | Gln | Gln | Val | Ala | Asp | Asp | Tyr | Gly | Leu | Glu | Val | Ser |
|  |  | 155 |  |  |  | 160 |  |  |  | 165 |  |  |  |  |  |
| gtc | ggt | ctg | ccg | cag | gca | gcc | gcc | cac | gcc | atc | cct | gcc | gcc | aag | gat | 701 |
| Val | Gly | Leu | Pro | Gln | Ala | Ala | Ala | His | Ala | Ile | Pro | Ala | Ala | Lys | Asp |
|  | 170 |  |  |  | 175 |  |  |  | 180 |  |  |  |  |  |  |
| aag | gag | aaa | gtc | gac | gag | gat | gac | ctt | tct | cgc | cgc | ctc | gcc | gag | ctt | 749 |
| Lys | Glu | Lys | Val | Asp | Glu | Asp | Asp | Leu | Ser | Arg | Arg | Leu | Ala | Glu | Leu |
| 185 |  |  |  | 190 |  |  |  | 195 |  |  |  | 200 |  |  |  |
| aag gcc cgc ggc t gagagggtgt tcaggcttt atcagatgcg attcaggctt | | | | | | | | | | | | | | | | 802 |
| Lys Ala Arg Gly | | | | | | | | | | | | | | | | |
| atgctgttga gccgcaatga cccattgtcc tgtggactgc tactcatgtt tggtagattc | | | | | | | | | | | | | | | | 862 |
| gtaaatacta ctgttatatg cttgaaggcg tgtgttggca ttgccatgtg gggtttgtgt | | | | | | | | | | | | | | | | 922 |
| gactcgatgg aaactttgct gtcttattgt actttaaaat ccaataattt cgcgcgattgc | | | | | | | | | | | | | | | | 982 |
| ggacaaaaaa aaaacaaaa aaaaa | | | | | | | | | | | | | | | | 1007 |

<210> SEQ ID NO 6
<211> LENGTH: 204
<212> TYPE: PRT
<213> ORGANISM: zea mays

<400> SEQUENCE: 6

Met Gly Asn Pro Glu Lys Leu Met Asn Gln Ile Phe Asp Leu Lys Phe
1               5                   10                  15

Thr Ser Lys Ser Leu Gln Arg Gln Ala Arg Lys Cys Glu Lys Glu Glu
            20                  25                  30

Lys Glu Gln Lys Leu Lys Val Lys Lys Ala Ile Glu Lys Gly Asn Met
        35                  40                  45

Asp Gly Ala Arg Ile Tyr Ala Glu Asn Ala Ile Arg Lys Arg Thr Glu
    50                  55                  60

His Met Asn Tyr Leu Arg Leu Ala Ser Arg Leu Asp Ala Val Val Ala
65                  70                  75                  80

Arg Leu Asp Thr Gln Ala Lys Met Gln Val Ile Gly Lys Ser Met Gln
                85                  90                  95

Ser Ile Val Lys Ser Leu Asp Ser Ser Leu Ala Thr Gly Asn Leu Gln
            100                 105                 110

Lys Met Ser Glu Thr Met Asp Asn Phe Glu Arg Gln Phe Val Asn Met
        115                 120                 125

Glu Val Gln Ala Glu Phe Met Glu Gly Ala Met Ala Gly Ser Thr Ser
    130                 135                 140

Leu Ser Thr Pro Glu Thr Glu Val Asn Ser Leu Met Gln Gln Val Ala
145                 150                 155                 160

Asp Asp Tyr Gly Leu Glu Val Ser Val Gly Leu Pro Gln Ala Ala Ala
                165                 170                 175

His Ala Ile Pro Ala Ala Lys Asp Glu Lys Val Asp Glu Asp Asp
            180                 185                 190

Leu Ser Arg Arg Leu Ala Glu Leu Lys Ala Arg Gly
        195                 200

<210> SEQ ID NO 7
<211> LENGTH: 612
<212> TYPE: DNA

<213> ORGANISM: arabidopsis
<220> FEATURE:
<221> NAME/KEY: CDS
<222> LOCATION: (1)...(612)
<223> OTHER INFORMATION: arabidopsis superal homolog 1

<400> SEQUENCE: 7

```
atg ggt aac aca gat aag ctg atg aat cag ata ttc gat ttg aaa ttt      48
Met Gly Asn Thr Asp Lys Leu Met Asn Gln Ile Phe Asp Leu Lys Phe
 1               5                  10                  15 acg tca aag tct ctg caa agg caa tca agg aag tgt gag aag gaa gag      96
Thr Ser Lys Ser Leu Gln Arg Gln Ser Arg Lys Cys Glu Lys Glu Glu
            20                  25                  30 aaa gca gag aaa ttg aag gtg aag aag gct atc gag aag ggt aat atg     144
Lys Ala Glu Lys Leu Lys Val Lys Lys Ala Ile Glu Lys Gly Asn Met
        35                  40                  45 gat ggt gct cgg atc tac gct gag aac gcc att cgt aag cgt agc gag     192
Asp Gly Ala Arg Ile Tyr Ala Glu Asn Ala Ile Arg Lys Arg Ser Glu
    50                  55                  60 cag atg aac tat ctc cgt ctc gct tct cgc ctt gac gct gtt gtt gct     240
Gln Met Asn Tyr Leu Arg Leu Ala Ser Arg Leu Asp Ala Val Val Ala
65                  70                  75                  80 cgt ctt gat act cag gct aag atg acc acc atc acc aaa tcc atg acc     288
Arg Leu Asp Thr Gln Ala Lys Met Thr Thr Ile Thr Lys Ser Met Thr
                85                  90                  95 aat atc gtc aaa tcc ctt gag tct tct ctt gcc aca ggg aat cta cag     336
Asn Ile Val Lys Ser Leu Glu Ser Ser Leu Ala Thr Gly Asn Leu Gln
            100                 105                 110 aag atg tca gag aca atg gat tca ttc gag aag cag ttt gtg aac atg     384
Lys Met Ser Glu Thr Met Asp Ser Phe Glu Lys Gln Phe Val Asn Met
        115                 120                 125 gag gtc caa gct gag ttc atg gag aat gct atg gct ggt tca act tca     432
Glu Val Gln Ala Glu Phe Met Glu Asn Ala Met Ala Gly Ser Thr Ser
    130                 135                 140 ttg tcc act cca gaa ggc gaa gtc aac agc ctt atg cag cag gtg gca     480
Leu Ser Thr Pro Glu Gly Glu Val Asn Ser Leu Met Gln Gln Val Ala
145                 150                 155                 160 gat gac tat ggt ttg gaa gtc tct gtg ggg ctt cct cag cct gct ggt     528
Asp Asp Tyr Gly Leu Glu Val Ser Val Gly Leu Pro Gln Pro Ala Gly
                165                 170                 175 cat gcc att cct act aag act gag gag aaa gtc gat gag gat gat ttg     576
His Ala Ile Pro Thr Lys Thr Glu Glu Lys Val Asp Glu Asp Asp Leu
            180                 185                 190 tcg agg agg ctt gcg gag ctt aaa gcc aga gga taa                     612
Ser Arg Arg Leu Ala Glu Leu Lys Ala Arg Gly *
        195                 200
```

<210> SEQ ID NO 8
<211> LENGTH: 203
<212> TYPE: PRT
<213> ORGANISM: arabidopsis

<400> SEQUENCE: 8

```
Met Gly Asn Thr Asp Lys Leu Met Asn Gln Ile Phe Asp Leu Lys Phe
 1               5                  10                  15

Thr Ser Lys Ser Leu Gln Arg Gln Ser Arg Lys Cys Glu Lys Glu Glu
            20                  25                  30

Lys Ala Glu Lys Leu Lys Val Lys Lys Ala Ile Glu Lys Gly Asn Met
        35                  40                  45

Asp Gly Ala Arg Ile Tyr Ala Glu Asn Ala Ile Arg Lys Arg Ser Glu
    50                  55                  60
```

```
Gln Met Asn Tyr Leu Arg Leu Ala Ser Arg Leu Asp Ala Val Val Ala
 65                  70                  75                  80

Arg Leu Asp Thr Gln Ala Lys Met Thr Thr Ile Thr Lys Ser Met Thr
                 85                  90                  95

Asn Ile Val Lys Ser Leu Glu Ser Ser Leu Ala Thr Gly Asn Leu Gln
            100                 105                 110

Lys Met Ser Glu Thr Met Asp Ser Phe Glu Lys Gln Phe Val Asn Met
        115                 120                 125

Glu Val Gln Ala Glu Phe Met Glu Asn Ala Met Ala Gly Ser Thr Ser
    130                 135                 140

Leu Ser Thr Pro Glu Gly Val Asn Ser Leu Met Gln Gln Val Ala
145                 150                 155                 160

Asp Asp Tyr Gly Leu Glu Val Ser Val Gly Leu Pro Gln Pro Ala Gly
                165                 170                 175

His Ala Ile Pro Thr Lys Thr Glu Glu Lys Val Asp Glu Asp Asp Leu
            180                 185                 190

Ser Arg Arg Leu Ala Glu Leu Lys Ala Arg Gly
        195                 200
```

<210> SEQ ID NO 9
<211> LENGTH: 669
<212> TYPE: DNA
<213> ORGANISM: arabidopsis
<220> FEATURE:
<221> NAME/KEY: CDS
<222> LOCATION: (1)...(669)
<223> OTHER INFORMATION: arabidopsis superal homolog 2

<400> SEQUENCE: 9

```
atg ggt aat aca gat aag ctg atg aac cag atc ttt gaa ttg aaa ttt    48
Met Gly Asn Thr Asp Lys Leu Met Asn Gln Ile Phe Glu Leu Lys Phe
  1               5                  10                  15 acg tca aag tct ctg cag agg caa gct agg aag tgc gaa aaa gag gag    96
Thr Ser Lys Ser Leu Gln Arg Gln Ala Arg Lys Cys Glu Lys Glu Glu
             20                  25                  30 aga tcg gag aag ctc aag gta aag aaa gcc att gag aaa ggt aac atg   144
Arg Ser Glu Lys Leu Lys Val Lys Lys Ala Ile Glu Lys Gly Asn Met
         35                  40                  45 gat ggt gct cgg atc tat gcc gag aac gcc att cgc aaa cgc agc gag   192
Asp Gly Ala Arg Ile Tyr Ala Glu Asn Ala Ile Arg Lys Arg Ser Glu
     50                  55                  60 cag atg aac tac ctt cgt ctc tct tct cga ttg gac gct gtt gtt gct   240
Gln Met Asn Tyr Leu Arg Leu Ser Ser Arg Leu Asp Ala Val Val Ala
 65                  70                  75                  80 cga ctc gat acc cag gct aag atg gct acc atc acc aaa tcg atg acc   288
Arg Leu Asp Thr Gln Ala Lys Met Ala Thr Ile Thr Lys Ser Met Thr
                 85                  90                  95 aac att gtc aaa tcc ctc gaa tcg tct ctt acc act ggc aac tta cag   336
Asn Ile Val Lys Ser Leu Glu Ser Ser Leu Thr Thr Gly Asn Leu Gln
            100                 105                 110 aag atg tct gag acg atg gat tcg ttt gag aaa cag ttt gtg aac atg   384
Lys Met Ser Glu Thr Met Asp Ser Phe Glu Lys Gln Phe Val Asn Met
        115                 120                 125 gaa gtc caa gct gag ttc atg gat aat gca atg gct ggc tct act tca   432
Glu Val Gln Ala Glu Phe Met Asp Asn Ala Met Ala Gly Ser Thr Ser
    130                 135                 140 ttg tcg act cca gaa gga gaa gtc aac agc ttg atg cag caa gta gca   480
Leu Ser Thr Pro Glu Gly Glu Val Asn Ser Leu Met Gln Gln Val Ala
145                 150                 155                 160
```

```
gat gat tac ggt ctt gaa gtt tct gtt gga cta cct cag cct gct ggt     528
Asp Asp Tyr Gly Leu Glu Val Ser Val Gly Leu Pro Gln Pro Ala Gly
            165                 170                 175 cat gcc att cct acc aag act gaa gag aaa gtt gag gag gat gat tta     576
His Ala Ile Pro Thr Lys Thr Glu Glu Lys Val Glu Glu Asp Asp Leu
        180                 185                 190 acc agg aga ctt gcc gag ctt aaa gcc aga gat gtg tct ctg gta gta     624
Thr Arg Arg Leu Ala Glu Leu Lys Ala Arg Asp Val Ser Leu Val Val
            195                 200                 205 gtt cca cca aat ttt cca ggt cca gaa agg aat aca ctg gag taa         669
Val Pro Pro Asn Phe Pro Gly Pro Glu Arg Asn Thr Leu Glu *
        210                 215                 220

<210> SEQ ID NO 10
<211> LENGTH: 222
<212> TYPE: PRT
<213> ORGANISM: arabidopsis

<400> SEQUENCE: 10

Met Gly Asn Thr Asp Lys Leu Met Asn Gln Ile Phe Glu Leu Lys Phe
 1               5                  10                  15

Thr Ser Lys Ser Leu Gln Arg Gln Ala Arg Lys Cys Glu Lys Glu
            20                  25                  30

Arg Ser Glu Lys Leu Lys Val Lys Lys Ala Ile Glu Lys Gly Asn Met
        35                  40                  45

Asp Gly Ala Arg Ile Tyr Ala Glu Asn Ala Ile Arg Lys Arg Ser Glu
    50                  55                  60

Gln Met Asn Tyr Leu Arg Leu Ser Ser Arg Leu Asp Ala Val Val Ala
65                  70                  75                  80

Arg Leu Asp Thr Gln Ala Lys Met Ala Thr Ile Thr Lys Ser Met Thr
                85                  90                  95

Asn Ile Val Lys Ser Leu Glu Ser Ser Leu Thr Thr Gly Asn Leu Gln
            100                 105                 110

Lys Met Ser Glu Thr Met Asp Ser Phe Glu Lys Gln Phe Val Asn Met
        115                 120                 125

Glu Val Gln Ala Glu Phe Met Asp Asn Ala Met Ala Gly Ser Thr Ser
    130                 135                 140

Leu Ser Thr Pro Glu Gly Glu Val Asn Ser Leu Met Gln Gln Val Ala
145                 150                 155                 160

Asp Asp Tyr Gly Leu Glu Val Ser Val Gly Leu Pro Gln Pro Ala Gly
                165                 170                 175

His Ala Ile Pro Thr Lys Thr Glu Glu Lys Val Glu Glu Asp Asp Leu
            180                 185                 190

Thr Arg Arg Leu Ala Glu Leu Lys Ala Arg Asp Val Ser Leu Val Val
        195                 200                 205

Val Pro Pro Asn Phe Pro Gly Pro Glu Arg Asn Thr Leu Glu
    210                 215                 220

<210> SEQ ID NO 11
<211> LENGTH: 607
<212> TYPE: DNA
<213> ORGANISM: Oryza sativa
<220> FEATURE:
<221> NAME/KEY: allele
<222> LOCATION: (1)...(607)
<223> OTHER INFORMATION: Rice superal homolog
<220> FEATURE:
<221> NAME/KEY: misc_feature
<222> LOCATION: (1)...(607)
```

<223> OTHER INFORMATION: n = A,T,C or G

<400> SEQUENCE: 11

```
tgaattcggc acgaggcnna atcccccaat ccgatctgcc tttcctcttc ctcctcgtca    60
aaccctagcc aaatccacga tcggggctag ctcgtcggcg gcggcgatgg ggaacccgga   120
gaagctgatg acccagatct tcgacctcaa gttcacctcc aagtcgctgc agcggcaggc   180
gcgcaagtgc gagaaggagg agaaggagca gaagctcaag gtgaagaagg cgatcgagaa   240
ggggaacatg gacggcgcgc ggatctacgc cgagaacgcc atccgcaagc gcaccgagca   300
catgaactac ctccgcctcg cctcccgcct cgacgccgtc gtcgcgcgcc tcgacaccca   360
ggcgaagatg caggtcatcg gcaagtccat ggccaacatc gtcaagtcgc tcgactccgc   420
gctcgccacg gggaacctgc agaagatgtc cgagaccatg acaacttcg agcgccagtt    480
cgtcaacatg gaggtccagg ccgagttcat ggagggcgcc atggccggct ccacctcgct   540
ctccacgccc gagaccgnnn tcaacagcct catgcagcaa gtcgccgacg actacggcct   600
tgaggtc                                                             607
```

<210> SEQ ID NO 12
<211> LENGTH: 529
<212> TYPE: DNA
<213> ORGANISM: Triticum aestivum
<220> FEATURE:
<221> NAME/KEY: allele
<222> LOCATION: (1)...(529)
<223> OTHER INFORMATION: Wheat superal homolog

<400> SEQUENCE: 12

```
gcacgaggcc caatcccga tctcccgacc ccgaccccg acgaaaccct agccagcaaa      60
ccgcggcggc ggcggcaatg ggcaacccgg agaagctgat ggcgcagatc ttcgacctca   120
agttcacgtc caagtcgctg cagcggcagg cgcgcaagtg cgagaaggag gagaaggagc   180
agaagctcaa ggtgaagaag gccatcgaga agggcaacgt cgacggcgcg cggatctacg   240
ccgagaacgc catccgcaag cgcaccgagc acatgaacta cctccgcctc gcctcccgcc   300
tcgacgccgt cgtcgcgcgc tcgacacgc aggccaagat gcaggccatc ggcaagtcca   360
tgggcagcat cgtcaagtcg cttgactcct ccctcgccac gggcaacctc cagaagatgt   420
ccgagaccat ggacagcttc gagcgccagt tcgtcaacat ggaggtccag gccgagttca   480
tggagggcgc catggccggc tccacctccc tctccacgcc cgagaccga              529
```

<210> SEQ ID NO 13
<211> LENGTH: 469
<212> TYPE: DNA
<213> ORGANISM: Glycine max
<220> FEATURE:
<221> NAME/KEY: allele
<222> LOCATION: (1)...(469)
<223> OTHER INFORMATION: Soybean superal homolog

<400> SEQUENCE: 13

```
ggaacacgga gaagctgatg aaccagatca tggaattgaa gttcacgtcg aaatcgctgc    60
agcggcaatc gcgtaagtgc gagaaggagg agaaatcgga gaagctgaag gtgaagaagg   120
cgatcgagaa aggcaacatg gacggagcgc ggatctacgc ggagaacgcg atccgtaagc   180
gcacggagca gatgaactac ctccggcttg cctcgcgcct ggacgccgtc gtggcccgcc   240
tcgacacgca ggcgaagatg acgacgatca gcaagtcgat gggcaacatc gtcaaatcgc   300
tggagtcgtc gctggccacg gggaacctcc agaagatgtc ggagaccatg gactcgttcg   360
```

```
agaagcagtt cgtgaacatg gaggtccagg ccgagttcat ggagagcgcc atggcgggat      420
ccacctccct ctccactccc gaaggagagg tcaacagcct catgcagca                  469

<210> SEQ ID NO 14
<211> LENGTH: 484
<212> TYPE: DNA
<213> ORGANISM: Hordeum vulgare
<220> FEATURE:
<221> NAME/KEY: allele
<222> LOCATION: (1)...(484)
<223> OTHER INFORMATION: Barley superal homolog

<400> SEQUENCE: 14
gcacgagggt cgccctccct ccctaaaaa atccccaatc ctcctctcgc cccctcccc        60 aatcccgacc cccgacgaaa ccctagctaa caaccggcgg cggcggcgat gggcaacccg      120
gagaagctga tggcgcagat cttcgacctc aagttcacct ccaagtcgct gcagcggcag      180
gcgcgcaagt gcgagaagga ggagaaggac cagaagctca aggtcaagaa ggccatcgag      240
aagggcaacg tcgacggcgc gcggatctac gccgagaacg ccatccgcaa gcgcaccgag      300
cacatgaact acctccgcct cgcctcccgc ctcgacgccg tcgtctcccg cctcgacacg      360
caggccaaga tgcaggccat cggaaagtcc atgggcaaca tcgtcaagtc gctcgactcc      420
tccctcgcca ccggcaacct ccagaagatg tccgagacca tggacaactt cgagcgccag      480
ttcg                                                                   484

<210> SEQ ID NO 15
<211> LENGTH: 3346
<212> TYPE: DNA
<213> ORGANISM: Zea mays
<220> FEATURE:
<221> NAME/KEY: CDS
<222> LOCATION: (157)...(2862)
<223> OTHER INFORMATION: maize cr4

<400> SEQUENCE: 15
caggggcctg gtgaaatgct gcgcagcgag ggtgactgac tggccactcc gcccgccgac      60
ccccgtttcg tgcttactgg catgctcgca gcataaagga atcttctcgg aattagcccc      120
ccttcctgtg gtcgtgacgg ccccaagttt caagac atg gac cat gtg ccg gct       174
                                          Met Asp His Val Pro Ala
                                           1               5 cta gtt ctt gcc ggg tgc tgc ttc ctg gcc ctg ctg cct ggc tgg gcc        222
Leu Val Leu Ala Gly Cys Cys Phe Leu Ala Leu Leu Pro Gly Trp Ala
                 10                  15                  20 tgt ggc ctt ggc tcc atg tcg tcc att gcg gtg tcc tat ggg gag gat        270
Cys Gly Leu Gly Ser Met Ser Ser Ile Ala Val Ser Tyr Gly Glu Asp
         25                  30                  35 ggt ccg gtg ttc tgt ggc ctc aac tcc gac ggc tcc cac ctc gtc gcc        318
Gly Pro Val Phe Cys Gly Leu Asn Ser Asp Gly Ser His Leu Val Ala
     40                  45                  50 tgc ttc ggt gct gat gca tct gtc ctg tac ggc gca cca ccc aac atc        366
Cys Phe Gly Ala Asp Ala Ser Val Leu Tyr Gly Ala Pro Pro Asn Ile
 55                  60                  65                  70 cct ttc ctt ggc ctc acg gca ggg gat ggg ttc gtg tgt ggc ctc ctg        414
Pro Phe Leu Gly Leu Thr Ala Gly Asp Gly Phe Val Cys Gly Leu Leu
                 75                  80                  85 ctc gac acc agg cag cca tac tgc tgg ggt agc aac tcc tat gtc aag        462
Leu Asp Thr Arg Gln Pro Tyr Cys Trp Gly Ser Asn Ser Tyr Val Lys
         90                  95                 100
```

```
                                                    -continued agc ggg gtg cca cag ccg atg gtt gag ggc gca agg tac tct gag ctc      510
Ser Gly Val Pro Gln Pro Met Val Glu Gly Ala Arg Tyr Ser Glu Leu
            105                 110                 115 agt gcg ggg gac aac cac ctc tgc gca ctg aga gct gct caa gat ggg      558
Ser Ala Gly Asp Asn His Leu Cys Ala Leu Arg Ala Ala Gln Asp Gly
        120                 125                 130 ggt cgt ggt tcc agt gct gct aca tcg ctg att gac tgc tgg gga tac      606
Gly Arg Gly Ser Ser Ala Ala Thr Ser Leu Ile Asp Cys Trp Gly Tyr
135                 140                 145                 150 aat atg acc gcc aca cat gct gtt gat gaa gcc gtg tcg act gtt tca      654
Asn Met Thr Ala Thr His Ala Val Asp Glu Ala Val Ser Thr Val Ser
                155                 160                 165 gct ggt tcg gtg ttc aat tgt ggc ttg ttt gct cgg aac agg acg gtg      702
Ala Gly Ser Val Phe Asn Cys Gly Leu Phe Ala Arg Asn Arg Thr Val
            170                 175                 180 ttc tgc tgg ggc gac gag acg gtg agt ggt gtc gtt ggg ctg gca ccg      750
Phe Cys Trp Gly Asp Glu Thr Val Ser Gly Val Val Gly Leu Ala Pro
        185                 190                 195 agg gat ctg cac ttt cag tct ata ggc gcg ggc ggt tac cat gtc tgt      798
Arg Asp Leu His Phe Gln Ser Ile Gly Ala Gly Gly Tyr His Val Cys
200                 205                 210 ggg gtg ttg gag aat gca cag gtg ttc tgc tgg ggc agg agc ttg gag      846
Gly Val Leu Glu Asn Ala Gln Val Phe Cys Trp Gly Arg Ser Leu Glu
215                 220                 225                 230 atg cag cag gtg gtg cca tcc agt gct atc ggt gat ggt gat gtg aac      894
Met Gln Gln Val Val Pro Ser Ser Ala Ile Gly Asp Gly Asp Val Asn
                235                 240                 245 ata gtg ccg atg gat gca atg agc act gtg gtt ggc ggg cgg ttc cat      942
Ile Val Pro Met Asp Ala Met Ser Thr Val Val Gly Gly Arg Phe His
            250                 255                 260 gct tgt ggc atc agg agc ctt gac cac caa gtg gct tgc tgg ggc ttc      990
Ala Cys Gly Ile Arg Ser Leu Asp His Gln Val Ala Cys Trp Gly Phe
        265                 270                 275 act ctt cat aac agt aca tcg cca cca aaa ggg ctg aag atg tat gct     1038
Thr Leu His Asn Ser Thr Ser Pro Pro Lys Gly Leu Lys Met Tyr Ala
    280                 285                 290 ctt gtg gct ggg gat tac ttc act tgt gga gtg cct gct gag act tcg     1086
Leu Val Ala Gly Asp Tyr Phe Thr Cys Gly Val Pro Ala Glu Thr Ser
295                 300                 305                 310 ctg atg ccg agg tgc tgg ggc aac agt ggg cca ttg gca tta ccc atg     1134
Leu Met Pro Arg Cys Trp Gly Asn Ser Gly Pro Leu Ala Leu Pro Met
                315                 320                 325 gcc gta cct cct ggg att tgt gta cct act gca tgc agc cat ggg tac     1182
Ala Val Pro Pro Gly Ile Cys Val Pro Thr Ala Cys Ser His Gly Tyr
            330                 335                 340 tat gaa tat gtg aac cat ggt gaa gtt ggc agc atc aag gtg tgt aag     1230
Tyr Glu Tyr Val Asn His Gly Glu Val Gly Ser Ile Lys Val Cys Lys
        345                 350                 355 cct gca aac tct aga ctc tgc ttg ccc tgt agt aca ggt tgc ccg gaa     1278
Pro Ala Asn Ser Arg Leu Cys Leu Pro Cys Ser Thr Gly Cys Pro Glu
    360                 365                 370 ggc ttg tat gag tca tct cct tgc aat gca aca gct gac cgt gtt tgc     1326
Gly Leu Tyr Glu Ser Ser Pro Cys Asn Ala Thr Ala Asp Arg Val Cys
375                 380                 385                 390 cag ttt gat tgc ttg aag tgt gtc aca gat gag tgc ctg tca ttc tgc     1374
Gln Phe Asp Cys Leu Lys Cys Val Thr Asp Glu Cys Leu Ser Phe Cys
                395                 400                 405 tta tca cag aag cgg acc aag agc cgc aag ttg atg gct ttt cag atg     1422
Leu Ser Gln Lys Arg Thr Lys Ser Arg Lys Leu Met Ala Phe Gln Met
            410                 415                 420
```

-continued

| | |
|---|---|
| cgc atc ttt gtt gca gag att gtc ttt gct gtc gtc ttg gta ctc agc<br>Arg Ile Phe Val Ala Glu Ile Val Phe Ala Val Val Leu Val Leu Ser<br>425                            430                         435 | 1470 |
| gtg tca gta acc act tgc ctg tat gtc cgg cac aag ctt cga cat tgc<br>Val Ser Val Thr Thr Cys Leu Tyr Val Arg His Lys Leu Arg His Cys<br>440                            445                         450 | 1518 |
| caa tgc tca aat aga gag ctg aga ctg gct aag agc aca gca tac tct<br>Gln Cys Ser Asn Arg Glu Leu Arg Leu Ala Lys Ser Thr Ala Tyr Ser<br>455                            460                         465                        470 | 1566 |
| ttc cgg aag gat aac atg aag atc cag cct gat atg gag gac ttg aag<br>Phe Arg Lys Asp Asn Met Lys Ile Gln Pro Asp Met Glu Asp Leu Lys<br>475                            480                         485 | 1614 |
| atc agg aga gct cag gaa ttc tcc tat gaa gag tta gag caa gca acc<br>Ile Arg Arg Ala Gln Glu Phe Ser Tyr Glu Glu Leu Glu Gln Ala Thr<br>490                            495                         500 | 1662 |
| ggt ggc ttc tca gag gat tca caa gtc ggc aaa ggc agc ttc tca tgt<br>Gly Gly Phe Ser Glu Asp Ser Gln Val Gly Lys Gly Ser Phe Ser Cys<br>505                            510                         515 | 1710 |
| gta ttc aag ggc ata ctg aga gat ggg aca gtg gtt gct gtg aag cgt<br>Val Phe Lys Gly Ile Leu Arg Asp Gly Thr Val Val Ala Val Lys Arg<br>520                            525                         530 | 1758 |
| gca ata aaa gca tca gat gtg aag aag agc tca aag gag ttt cac aac<br>Ala Ile Lys Ala Ser Asp Val Lys Lys Ser Ser Lys Glu Phe His Asn<br>535                            540                         545                        550 | 1806 |
| gaa ctt gac ctc cta tcc agg ctc aac cat gca cat ttg ctg aat ttg<br>Glu Leu Asp Leu Leu Ser Arg Leu Asn His Ala His Leu Leu Asn Leu<br>555                            560                         565 | 1854 |
| ctt ggt tac tgc gag gat ggc agt gag agg ctc ttg gtt tat gag ttc<br>Leu Gly Tyr Cys Glu Asp Gly Ser Glu Arg Leu Leu Val Tyr Glu Phe<br>570                            575                         580 | 1902 |
| atg gct cat gga tcc ctg tac cag cat ctg cat ggc aag gat cca aac<br>Met Ala His Gly Ser Leu Tyr Gln His Leu His Gly Lys Asp Pro Asn<br>585                            590                         595 | 1950 |
| ttg aaa aag cga cta aac tgg gca agg cgg gtc acc att gct gta cag<br>Leu Lys Lys Arg Leu Asn Trp Ala Arg Arg Val Thr Ile Ala Val Gln<br>600                            605                         610 | 1998 |
| gct gct agg gga att gag tac ttg cat ggc tat gct tgc cct cct gta<br>Ala Ala Arg Gly Ile Glu Tyr Leu His Gly Tyr Ala Cys Pro Pro Val<br>615                            620                         625                        630 | 2046 |
| att cac cgg gac atc aag tcg tca aac ata ttg att gat gag gat cac<br>Ile His Arg Asp Ile Lys Ser Ser Asn Ile Leu Ile Asp Glu Asp His<br>635                            640                         645 | 2094 |
| aat gcc cgt gtt gct gac ttt ggt ctg tct ata ttg ggt cct gca gat<br>Asn Ala Arg Val Ala Asp Phe Gly Leu Ser Ile Leu Gly Pro Ala Asp<br>650                            655                         660 | 2142 |
| agc ggt acc cca ctg tct gag ctg cca gca ggg act ctt ggc tac ctt<br>Ser Gly Thr Pro Leu Ser Glu Leu Pro Ala Gly Thr Leu Gly Tyr Leu<br>665                            670                         675 | 2190 |
| gac cct gag tac tac cgt ctc cac tac ttg act aca aaa tct gat gtc<br>Asp Pro Glu Tyr Tyr Arg Leu His Tyr Leu Thr Thr Lys Ser Asp Val<br>680                            685                         690 | 2238 |
| tac agc ttc ggg gtt gtt ctc ctg gag ata cta agt ggc agg aaa gcg<br>Tyr Ser Phe Gly Val Val Leu Leu Glu Ile Leu Ser Gly Arg Lys Ala<br>695                            700                         705                        710 | 2286 |
| atc gac atg cag ttc gag gag ggg aac att gtt gaa tgg gca gta cct<br>Ile Asp Met Gln Phe Glu Glu Gly Asn Ile Val Glu Trp Ala Val Pro<br>715                            720                         725 | 2334 |
| ctg atc aaa gca ggg gac att ttt gcc atc ctt gat cca gtc tta tct<br>Leu Ile Lys Ala Gly Asp Ile Phe Ala Ile Leu Asp Pro Val Leu Ser | 2382 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 730 |     |     |     |     | 735 |     |     |     |     | 740 |     |      |
| cct | ccc | tca | gac | ctt | gag | gcc | ctc | aag | aag | att | gct | tct | gtg | gca | tgt | 2430 |
| Pro | Pro | Ser | Asp | Leu | Glu | Ala | Leu | Lys | Lys | Ile | Ala | Ser | Val | Ala | Cys |      |
|     |     | 745 |     |     |     |     | 750 |     |     |     |     | 755 |     |     |     |      |
| aag | tgt | gtc | aga | atg | cga | ggt | aaa | gat | cgg | cct | tcc | atg | gat | aag | gtg | 2478 |
| Lys | Cys | Val | Arg | Met | Arg | Gly | Lys | Asp | Arg | Pro | Ser | Met | Asp | Lys | Val |      |
|     | 760 |     |     |     |     | 765 |     |     |     |     | 770 |     |     |     |     |      |
| acg | aca | gct | cta | gag | cac | gcc | ctt | gca | ctg | ctg | atg | ggc | agc | ccc | tgc | 2526 |
| Thr | Thr | Ala | Leu | Glu | His | Ala | Leu | Ala | Leu | Leu | Met | Gly | Ser | Pro | Cys |      |
| 775 |     |     |     |     | 780 |     |     |     |     | 785 |     |     |     |     | 790 |      |
| atc | gag | cag | ccc | att | cta | ccg | acc | gag | gtt | gtt | ctt | gga | agc | agc | cgc | 2574 |
| Ile | Glu | Gln | Pro | Ile | Leu | Pro | Thr | Glu | Val | Val | Leu | Gly | Ser | Ser | Arg |      |
|     |     |     |     | 795 |     |     |     |     | 800 |     |     |     |     | 805 |     |      |
| atg | cac | aag | gtg | tca | cag | atg | tcc | tct | aac | cac | tcc | tgc | tca | gag | aac | 2622 |
| Met | His | Lys | Val | Ser | Gln | Met | Ser | Ser | Asn | His | Ser | Cys | Ser | Glu | Asn |      |
|     |     |     | 810 |     |     |     |     | 815 |     |     |     |     | 820 |     |     |      |
| gag | ctt | gct | gac | ggg | gag | gac | cag | ggg | atc | ggg | tac | agg | gca | cct | tcc | 2670 |
| Glu | Leu | Ala | Asp | Gly | Glu | Asp | Gln | Gly | Ile | Gly | Tyr | Arg | Ala | Pro | Ser |      |
|     |     | 825 |     |     |     |     | 830 |     |     |     |     | 835 |     |     |     |      |
| tgg | ata | act | ttt | cct | agc | gtg | acc | tca | tca | cag | agg | agg | aaa | tca | tct | 2718 |
| Trp | Ile | Thr | Phe | Pro | Ser | Val | Thr | Ser | Ser | Gln | Arg | Arg | Lys | Ser | Ser |      |
|     | 840 |     |     |     |     | 845 |     |     |     |     | 850 |     |     |     |     |      |
| gca | tcc | gaa | gct | gac | atc | gtt | ggt | cga | agg | gcc | aca | gac | ggc | agg | aac | 2766 |
| Ala | Ser | Glu | Ala | Asp | Ile | Val | Gly | Arg | Arg | Ala | Thr | Asp | Gly | Arg | Asn |      |
| 855 |     |     |     |     | 860 |     |     |     |     | 865 |     |     |     |     | 870 |      |
| gtc | ggg | agc | agc | ata | ggt | gac | gga | ctg | cgg | tca | ctg | gag | gaa | gaa | atc | 2814 |
| Val | Gly | Ser | Ser | Ile | Gly | Asp | Gly | Leu | Arg | Ser | Leu | Glu | Glu | Glu | Ile |      |
|     |     |     |     | 875 |     |     |     |     | 880 |     |     |     |     | 885 |     |      |
| gct | cca | gct | tca | cca | caa | gag | aac | ctg | tac | ttg | cag | cac | aac | ttc | tga | 2862 |
| Ala | Pro | Ala | Ser | Pro | Gln | Glu | Asn | Leu | Tyr | Leu | Gln | His | Asn | Phe | *   |      |
|     |     |     | 890 |     |     |     |     | 895 |     |     |     |     | 900 |     |     |      |

| | |
|---|---|
| agaaattcag gagatgcagg aacctgagca gcgactttct gccattgttg agcagtattt | 2922 |
| taagttcggc cttcatgcc ctgttgaagt gttcatacgt tctatataat agcagcctaa | 2982 |
| aaacagggag ctaattagta ctggaagaat tcttttagc gtccagaagc attcatctgt | 3042 |
| agattcgtat ggtccctttt attttcctgg tacaatttat cttctggtgg ctgcagttga | 3102 |
| tggattatcg tgtatcctta gcttgcaaaa ctgggtagtt tccttaatcc ttcagatcat | 3162 |
| ctctctggct cccgatgctg tttctgcatc ctaaatggca gtagctttgg gaaccaactg | 3222 |
| catgtctggg tcgggtcacc atgttcagca ttctttcgct tgtatccttg tggaaggttt | 3282 |
| cttcagttgc ttgatttgtg attcgcagca acaggctgtc tgcccaaaaa aaaaaaaaaa | 3342 |
| aaaa | 3346 |

<210> SEQ ID NO 16
<211> LENGTH: 901
<212> TYPE: PRT
<213> ORGANISM: Zea mays

<400> SEQUENCE: 16

Met Asp His Val Pro Ala Leu Val Leu Ala Gly Cys Cys Phe Leu Ala
1               5                   10                  15

Leu Leu Pro Gly Trp Ala Cys Gly Leu Gly Ser Met Ser Ser Ile Ala
            20                  25                  30

Val Ser Tyr Gly Glu Asp Gly Pro Val Phe Cys Gly Leu Asn Ser Asp
        35                  40                  45

Gly Ser His Leu Val Ala Cys Phe Gly Ala Asp Ala Ser Val Leu Tyr
    50                  55                  60

```
Gly Ala Pro Pro Asn Ile Pro Phe Leu Gly Leu Thr Ala Gly Asp Gly
 65                  70                  75                  80

Phe Val Cys Gly Leu Leu Asp Thr Arg Gln Pro Tyr Cys Trp Gly
                 85                  90                  95

Ser Asn Ser Tyr Val Lys Ser Gly Val Pro Gln Pro Met Val Glu Gly
                100                 105                 110

Ala Arg Tyr Ser Glu Leu Ser Ala Gly Asp Asn His Leu Cys Ala Leu
            115                 120                 125

Arg Ala Ala Gln Asp Gly Gly Arg Gly Ser Ser Ala Ala Thr Ser Leu
        130                 135                 140

Ile Asp Cys Trp Gly Tyr Asn Met Thr Ala Thr His Ala Val Asp Glu
145                 150                 155                 160

Ala Val Ser Thr Val Ser Ala Gly Ser Val Phe Asn Cys Gly Leu Phe
                165                 170                 175

Ala Arg Asn Arg Thr Val Phe Cys Trp Gly Asp Glu Thr Val Ser Gly
            180                 185                 190

Val Val Gly Leu Ala Pro Arg Asp Leu His Phe Gln Ser Ile Gly Ala
        195                 200                 205

Gly Gly Tyr His Val Cys Gly Val Leu Glu Asn Ala Gln Val Phe Cys
    210                 215                 220

Trp Gly Arg Ser Leu Glu Met Gln Gln Val Val Pro Ser Ser Ala Ile
225                 230                 235                 240

Gly Asp Gly Asp Val Asn Ile Val Pro Met Asp Ala Met Ser Thr Val
                245                 250                 255

Val Gly Gly Arg Phe His Ala Cys Gly Ile Arg Ser Leu Asp His Gln
            260                 265                 270

Val Ala Cys Trp Gly Phe Thr Leu His Asn Ser Thr Ser Pro Pro Lys
        275                 280                 285

Gly Leu Lys Met Tyr Ala Leu Val Ala Gly Asp Tyr Phe Thr Cys Gly
    290                 295                 300

Val Pro Ala Glu Thr Ser Leu Met Pro Arg Cys Trp Gly Asn Ser Gly
305                 310                 315                 320

Pro Leu Ala Leu Pro Met Ala Val Pro Pro Gly Ile Cys Val Pro Thr
                325                 330                 335

Ala Cys Ser His Gly Tyr Tyr Glu Tyr Val Asn His Gly Glu Val Gly
            340                 345                 350

Ser Ile Lys Val Cys Lys Pro Ala Asn Ser Arg Leu Cys Leu Pro Cys
        355                 360                 365

Ser Thr Gly Cys Pro Glu Gly Leu Tyr Glu Ser Ser Pro Cys Asn Ala
370                 375                 380

Thr Ala Asp Arg Val Cys Gln Phe Asp Cys Leu Lys Cys Val Thr Asp
385                 390                 395                 400

Glu Cys Leu Ser Phe Cys Leu Ser Gln Lys Arg Thr Lys Ser Arg Lys
                405                 410                 415

Leu Met Ala Phe Gln Met Arg Ile Phe Val Ala Glu Ile Val Phe Ala
            420                 425                 430

Val Val Leu Val Leu Ser Val Ser Val Thr Thr Cys Leu Tyr Val Arg
        435                 440                 445

His Lys Leu Arg His Cys Gln Cys Ser Asn Arg Glu Leu Arg Leu Ala
    450                 455                 460

Lys Ser Thr Ala Tyr Ser Phe Arg Lys Asp Asn Met Lys Ile Gln Pro
465                 470                 475                 480
```

```
Asp Met Glu Asp Leu Lys Ile Arg Arg Ala Gln Phe Ser Tyr Glu
            485                 490                 495

Glu Leu Glu Gln Ala Thr Gly Gly Phe Ser Glu Asp Ser Gln Val Gly
                500                 505                 510

Lys Gly Ser Phe Ser Cys Val Phe Lys Gly Ile Leu Arg Asp Gly Thr
                515                 520                 525

Val Val Ala Val Lys Arg Ala Ile Lys Ala Ser Asp Val Lys Lys Ser
        530                 535                 540

Ser Lys Glu Phe His Asn Glu Leu Asp Leu Leu Ser Arg Leu Asn His
545                 550                 555                 560

Ala His Leu Leu Asn Leu Leu Gly Tyr Cys Glu Asp Gly Ser Glu Arg
                    565                 570                 575

Leu Leu Val Tyr Glu Phe Met Ala His Gly Ser Leu Tyr Gln His Leu
                580                 585                 590

His Gly Lys Asp Pro Asn Leu Lys Lys Arg Leu Asn Trp Ala Arg Arg
                595                 600                 605

Val Thr Ile Ala Val Gln Ala Ala Arg Gly Ile Glu Tyr Leu His Gly
                610                 615                 620

Tyr Ala Cys Pro Pro Val Ile His Arg Asp Ile Lys Ser Ser Asn Ile
625                 630                 635                 640

Leu Ile Asp Glu Asp His Asn Ala Arg Val Ala Asp Phe Gly Leu Ser
                    645                 650                 655

Ile Leu Gly Pro Ala Asp Ser Gly Thr Pro Leu Ser Glu Leu Pro Ala
                660                 665                 670

Gly Thr Leu Gly Tyr Leu Asp Pro Glu Tyr Tyr Arg Leu His Tyr Leu
                675                 680                 685

Thr Thr Lys Ser Asp Val Tyr Ser Phe Gly Val Val Leu Leu Glu Ile
                690                 695                 700

Leu Ser Gly Arg Lys Ala Ile Asp Met Gln Phe Glu Glu Gly Asn Ile
705                 710                 715                 720

Val Glu Trp Ala Val Pro Leu Ile Lys Ala Gly Asp Ile Phe Ala Ile
                    725                 730                 735

Leu Asp Pro Val Leu Ser Pro Pro Ser Asp Leu Glu Ala Leu Lys Lys
                740                 745                 750

Ile Ala Ser Val Ala Cys Lys Cys Val Arg Met Arg Gly Lys Asp Arg
                755                 760                 765

Pro Ser Met Asp Lys Val Thr Thr Ala Leu Glu His Ala Leu Ala Leu
770                 775                 780

Leu Met Gly Ser Pro Cys Ile Glu Gln Pro Ile Leu Pro Thr Glu Val
785                 790                 795                 800

Val Leu Gly Ser Ser Arg Met His Lys Val Ser Gln Met Ser Ser Asn
                    805                 810                 815

His Ser Cys Ser Glu Asn Glu Leu Ala Asp Gly Glu Asp Gln Gly Ile
                    820                 825                 830

Gly Tyr Arg Ala Pro Ser Trp Ile Thr Phe Pro Ser Val Thr Ser Ser
                835                 840                 845

Gln Arg Arg Lys Ser Ser Ala Ser Glu Ala Asp Ile Val Gly Arg Arg
        850                 855                 860

Ala Thr Asp Gly Arg Asn Val Gly Ser Ser Ile Gly Asp Gly Leu Arg
865                 870                 875                 880

Ser Leu Glu Glu Glu Ile Ala Pro Ala Ser Pro Gln Glu Asn Leu Tyr
                    885                 890                 895

Leu Gln His Asn Phe
```

<210> SEQ ID NO 17
<211> LENGTH: 1091
<212> TYPE: DNA
<213> ORGANISM: Hordeum vulgare
<220> FEATURE:
<221> NAME/KEY: promoter
<222> LOCATION: (1)...(1091)
<223> OTHER INFORMATION: nuc1 promoter

<400> SEQUENCE: 17

```
aagctttacg tttgagacgt atcatgtcgc cgaggcgag gggacgcgag gggtacgcga       60
gaatttcctc cgtttgctag cagttgcaga tctatgcaat gattccgtgt gaagatggga      120
tgacggtaga tcctaagcgt gcgcatggag tacgcgttct ggaacaccta tgccggttgg     180
tactatcacc ttgatatgtg ggcagatgct gattagatgg tgctcattag tcatggcaca     240
tctttatact taggtgtagt gatttcgttt gccttgacga tgactttaga ttgatcgttg     300
tattcatttt gtgaggctgt gatgaataac taataaagat gactacatgc attattttga     360
tgcaaaggcc gggagcaatc tttcctttaa aaaaaaact tcacatcaag acacttaaaa     420
tggcaacctg tcccttacta ctgctaaaca gcaagtgggt gagcatcttt atgcagtaat     480
ttgcacgggt acgccatccc atataaacag cactgtatga agctgcatt cagttttctt      540
tctacatcag cacaggcagc ttcataaggt cttgtctggg cagaagaaag acgagtatcc     600
ggatattttt tgtggtctct gatttatctc cctacgtgca acagtacagt taaacgaagg     660
tgattaaact tacagtaagt cagtaacttg aactggtacc tcatcgcata aactgccact     720
gcattcagtt ttctttctat atcaacacag gcagctccat aactcataac caaccttaac    780
atccaaggtt attttcaggt gcaccagggc tagtgatagt acataaagtc tactttttgtt   840
cagaaaatga ataataccat ggcaaacttg gctacaggac acccaacatg acattttggg    900
ccatttaact tgctgcgaaa tactgaaata ctttactcgg ctgcattaca attatcaagg    960
tcaatgtcaa tattgccctc ggaactctaa tcctactgct atacaagtgc ccacactcag   1020
actttctgac gaagaacaga gccgccactc accacagcaa tcctcttccc ttcgccagca  1080
cgagcaagga g                                                        1091
```

<210> SEQ ID NO 18
<211> LENGTH: 869
<212> TYPE: DNA
<213> ORGANISM: Hordeum vulgare
<220> FEATURE:
<221> NAME/KEY: promoter
<222> LOCATION: (1)...(869)
<223> OTHER INFORMATION: Ltp2 promoter
<220> FEATURE:
<221> NAME/KEY: TATA_signal
<222> LOCATION: (761)...(765)

<400> SEQUENCE: 18

```
gatctcgatg tgtagtctac gagaagggtt aaccgtctct tcgtgagaat aaccgtggcc      60
taaaataag ccgatgagga taaataaaat gtggtggtac agtacttcaa gaggtttact      120
catcaagagg atgcttttcc gatgagctct agtagtacat cggacctcac atacctccat    180
tgtggtgaaa tattttgtgc tcatttagtg atgggtaaat tttgtttatg tcactctagg    240
ttttgacatt tcagttttgc cactcttagg ttttgacaaa taatttccat tccgcggcaa    300
aagcaaaaca attttatttt acttttacca ctcttagctt tcacaatgta tcacaaatgc    360
```

```
cactctagaa attctgttta tgccacagaa tgtgaaaaaa aacactcact tatttgaagc      420
caaggtgttc atggcatgga aatgtgacat aaagtaacgt tcgtgtataa gaaaaaattg      480
tactcctcgt aacaagagac ggaaacatca tgagacaatc gcgtttggaa ggctttgcat      540
cacctttgga tgatgcgcat gaatggagtc gtctgcttgc tagccttcgc ctaccgccca      600
ctgagtccgg gcggcaacta ccatcggcga acgacccagc tgacctctac cgaccggact      660
tgaatgcgct accttcgtca gcgacgatgg ccgcgtacgc tggcgacgtg ccccgcatg       720 catggcggca catggcgagc tcagaccgtg cgtggctggc tacaaatacg taccccgtga      780
gtgccctagc tagaaactta cacctgcaac tgcgagagcg agcgtgtgag tgtagccgag      840
tagatcaccg tacgacgacg acgagggggc                                      869

<210> SEQ ID NO 19
<211> LENGTH: 713
<212> TYPE: DNA
<213> ORGANISM: Zea mays
<220> FEATURE:
<221> NAME/KEY: promoter
<222> LOCATION: (1)...(713)
<223> OTHER INFORMATION: end1

<400> SEQUENCE: 19
ggctggtaaa aaccattatt aactttaaca tcgaatcaaa actgacaaat tttatacttt       60
cacagagcag cagaaattta tacaatatga ttgaatacaa gatgtaggac ccgatggaga      120 gaatttttttt gtctcctata tgcttgaata cccaacataa tatcttcgca gcatactatc     180
tatctaatag aaaaattata atatagttaa atacttaagt agtatctagt ggatagaatt      240
caatatctca tacatgcatg aggagtaata tctactagac atgcaacata tttttatcta     300
tctaatagaa tatatataat aaagttaaat attatatgca tcacctacta tatataatttt    360 gatatctttt agatgtataa gggactaaga ataaatctc tagcacacat gcaatgcatt      420
atctatctaa atatattata taatagttaa atattaatta tacgtagtct aaacctacat      480
ataagcctac ccatccccac ttagagatct cagtgtcaca catagaccat acatctcact      540
tcgccaagaa aatttcgtca acagttgaag ttatacccat ggcaaaacta ctcttgggtt     600
tgctccttgc ccttgctatt ctagggacaa catcggctgc tggttgtgta caagaagggc     660
gaattctgca gatatccatc acactggcgg ccgctcgagc atgcatctag agg            713

<210> SEQ ID NO 20
<211> LENGTH: 924
<212> TYPE: DNA
<213> ORGANISM: Zea mays
<220> FEATURE:
<221> NAME/KEY: promoter
<222> LOCATION: (1)...(924)
<223> OTHER INFORMATION: end2

<400> SEQUENCE: 20
agtttttggc agaaaaaatg atcaatgttt cacaaaccaa atatttttat aacttttgat       60
gaaagaagat caccacggtc atatctaggg gtggtaacaa attgcgatct aaatgtttct     120
tcataaaaaa taaggcttct taataaattt tagttcaaaa taaatacgaa taaagtctga     180
ttctaatctg attcgatcct taaatttat aatgcaaaat ttagagctca ttaccacctc      240
tagtcatatg tctagtctga ggtatatcca aaaagccctt tctctaaatt ccacacccaa     300
ctcagatgtt tgcaaataaa tactccgact ccaaaatgta ggtgaagtgc aactttctcc     360
attttatatc aacatttgtt attttttgtt taacatttca cactcaaaac taattaataa     420
```

```
aatacgtggt tgttgaacgt gcgcacatgt ctcccttaca ttatgttttt ttatttatgt      480
attattgttg ttttcctccg aacaacttgt caacatatca tcattggtct ttaatattta      540
tgaatatgga agcctagtta tttacacttg gctacacact agttgtagtt ttgccacttg      600
tctaacatgc aactctagta gttttgccac ttgcctggca cgcgactcta gtattgacac      660
ttgtatagca ataatgcca atacgacacc tggccttaca tgaaacatta tttttgacac       720
ttgtatacca tgcaacatta ccattgacat ttgtccatac acattatatc aaatatattg      780
agcgcatgtc acaaactcga tacaaagctg atgaccctc cctcaccaca tctataaaaa       840
cccgagcgct actgtaaatc actcacaaca caacacatat cttttagtaa cctttcaata      900
ggcgtccccc aagaactagt aaac                                             924

<210> SEQ ID NO 21
<211> LENGTH: 2140
<212> TYPE: DNA
<213> ORGANISM: Hordeum vugare
<220> FEATURE:
<221> NAME/KEY: promoter
<222> LOCATION: (1)...(2140)
<223> OTHER INFORMATION: beps promoter

<400> SEQUENCE: 21
gagctcgact ccggcgacga tgcggcaacg gtgactgcaa caactgaccg gcggggggtgc     60 ggaaatccta gggggttcca ttcccagggc taatgcggcg aaggggaa cctactggcg       120 gcgcaagaag cttgcgcttc tggccatggc ggaacgcgac agcgacgatg ctacgctacg     180
acgagcggat cgagcacgcg ggagagggca agagggtcta ctctgctcac ctaggttgca    240
ccgaaggcga gaacgaggcg cgcaggaaga agatgcttgg agcggcctgc tgcagtgaag    300
cttccgcgcc ggtgatgcga cgacggggcc gacgccatgg aggggctcg acctctccta     360 gcgcgggaac gggacaagga caatgccagc ttcctcgcgg gcgctcagac gccgcggaga    420
ggctgctgac gatgaaggag aaggcggaga cgacgaggat gatcccctgc tctcgctctg    480
aacctgacga tctctctctg aacttaccgg ggtaggagaa tgatggagtg gagaagaggg    540
atggcggcgg cgataggagg ggcgcggaac cctaggattg gcagggctat ataggcgcga    600
cgggagatgg acctcgacgt ccgtgagggc acggtggca cctcctctca cacgcgtgtct    660 cactctgacg gaaaagggag aaggagatgg cgacagtgcc gttagggggg agcttgggcc    720
acgcaggagg gtgatgggcc aggagagccc atctggcctt ctctctctct cactctcaaa    780
caagttctaa ttaaaatcaa acagaattga attaaaagcc aggggctagg gaaaggagtt    840
aaaaaaatcg ggcatctaaa atgttccccc atttacaaaa ataggcgtgg cattttagag    900
taaagaaaaa taaattggtt tatttgaaat tggctctgtt ttaaaataaa aacaaaggga    960
aaataaaacc cagaagagag tgttgccacc cgcaaatatt aaaaggattt tcaagagaag   1020
atgaacattt ttaatgggcc aaaacaaaaa ctttaaaaca accacaataa attgaaaaga   1080
gagggaaggg ttttatggtc atggtgcaac aagggttttg aagtggctct tgttgcaccc   1140
acactcatca cacaatcaac acaaagccac actcacaagg cactccactt tcaatcacca   1200 aagtgcaac acaaacaaca agacaagaca aaggatgatg ccatgcatga tgtctaatgc    1260
acatggatga agacacaatg atgggctcac accacgtata ataccatatc aaggttgaca   1320
tgcaaggaaa gattacaagg aggggaagaa atagcatagg ggctgtcaca aactattagt   1380
cctggagata atgtatgctg tcatgaatca tcaaaacttt caaggagca catgtgctttt   1440
```

-continued

| | |
|---|---|
| cacatgtagc ctccatcatc gagggaggcc atggatcact agacaatcat aacttaggag | 1500 |
| acaccaaaat agtgccttca atggtgagtc tcattcatac ggcttccaat gcgcatgcct | 1560 |
| tgtggaggga ggaattgtaa tgcatgtgaa tgaggttgtt gcgaggtgtg tgttttggaa | 1620 |
| gtaccttaag cacgtcggta gtcactaacg aaaagtagcc tttttgtttt ttgttgtggg | 1680 |
| tcagctggat ccttcgagag ttgtaagatt ctatgcagca tggcatcttt gtcactttct | 1740 |
| tccataaaag ttgtacacca ttcttgggca tgttctggaa ataagagagc catgtatgat | 1800 |
| ttttgtatgg ctaaactcga tgccaataaa gcgaagagca tatctagaac acaattttt | 1860 |
| tccagttcaa ctaatttcgt cgcacaaaac tatccatata tgttttttgt gtgtgaataa | 1920 |
| acttgttgcc aataaagcga agagcatatg tagtacgcca aaaactttac agcttgtcac | 1980 |
| atgcgaacta atttcgtcgc acatggatat tcatgtgctc ttttttgtac gtgcatatac | 2040 |
| ttccttcgcc tataaataaa agaagagttt cctatgact tcaaaagtga actcacacat | 2100 |
| cactcaatat ctatatcctt ccattttata tccctcggtg | 2140 |

<210> SEQ ID NO 22
<211> LENGTH: 36
<212> TYPE: DNA
<213> ORGANISM: Artificial Sequence
<220> FEATURE:
<223> OTHER INFORMATION: Sal A20 primer

<400> SEQUENCE: 22

| | |
|---|---|
| tcgacccacg cgtccgaaaa aaaaaaaaaa aaaaaa | 36 |

<210> SEQ ID NO 23
<211> LENGTH: 7110
<212> TYPE: DNA
<213> ORGANISM: zea mays
<220> FEATURE:
<221> NAME/KEY: CDS
<222> LOCATION: (55)...(6532)
<223> OTHER INFORMATION: dek1/calpain cDNA from B73

<400> SEQUENCE: 23

| | |
|---|---|
| cttgcaggct atccatgatt tttgcctaca aaggtgatt gaaaaggggg gagg atg<br>                                                                                                                             Met<br>                                                                                                                              1 | 57 |
| gaa ggg gag gga cac cac gga gtt gtt ttg gca tgc agc atc tgt ggg<br>Glu Gly Glu Gly His His Gly Val Val Leu Ala Cys Ser Ile Cys Gly<br>        5                   10                   15 | 105 |
| ttc ctc ttc gct gtc ctt agc cct ttc agc ttt tgg gtt tta tgg gct<br>Phe Leu Phe Ala Val Leu Ser Pro Phe Ser Phe Trp Val Leu Trp Ala<br>      20                 25                 30 | 153 |
| gtg aat tgg agg cca tgg agg tta tac agt tgg ata tat gca agg aaa<br>Val Asn Trp Arg Pro Trp Arg Leu Tyr Ser Trp Ile Tyr Ala Arg Lys<br>35                   40                 45 | 201 |
| tgg cca aca tat gtt caa gga cct caa ttg agc aca ctt tgc agc ctt<br>Trp Pro Thr Tyr Val Gln Gly Pro Gln Leu Ser Thr Leu Cys Ser Leu<br> 50                55                60                65 | 249 |
| ttg act ctt tgt gca tgg ctt gtt gtc att tcc cct ata gca gtt ctg<br>Leu Thr Leu Cys Ala Trp Leu Val Val Ile Ser Pro Ile Ala Val Leu<br>          70                   75                   80 | 297 |
| ctc gtg tgg gga agc gtc ctt att gct ctt atg gaa agg aat ata att<br>Leu Val Trp Gly Ser Val Leu Ile Ala Leu Met Glu Arg Asn Ile Ile<br>                 85                   90                   95 | 345 |
| ggt tta gct gtt ata atg gcg ggt gtt gct ttg ctc ctg tca ttc tac<br>Gly Leu Ala Val Ile Met Ala Gly Val Ala Leu Leu Leu Ser Phe Tyr<br>                100                  105                110 | 393 |

-continued

| | | |
|---|---|---|
| tct ata atg ctc tgg tgg aga aca caa tgg caa agc tca aag gct gtt<br>Ser Ile Met Leu Trp Trp Arg Thr Gln Trp Gln Ser Ser Lys Ala Val<br>115                    120                         125 | 441 |
| gct tac ctt ctc ctc ctg gca gta tgc ctg cta tgt gcc tac gat ttt<br>Ala Tyr Leu Leu Leu Leu Ala Val Cys Leu Leu Cys Ala Tyr Asp Phe<br>130                    135                    140                    145 | 489 |
| tgt gct att tat gtg aca gct ggt gct agt gct tcc gag ctt aat tct<br>Cys Ala Ile Tyr Val Thr Ala Gly Ala Ser Ala Ser Glu Leu Asn Ser<br>                    150                    155                    160 | 537 |
| cca tca ggg ttc ttc ttc ggg gtg tct gta ata tca ttg gcc atc aat<br>Pro Ser Gly Phe Phe Phe Gly Val Ser Val Ile Ser Leu Ala Ile Asn<br>          165                    170                    175 | 585 |
| atg ctt ttt ata tgt aaa ata ctg ttt aat gta agt gga ttt gat gtt<br>Met Leu Phe Ile Cys Lys Ile Leu Phe Asn Val Ser Gly Phe Asp Val<br>      180                    185                    190 | 633 |
| gat gaa tat gtg cgg agg tca tac aaa ttt gcc tat tct gac tgt gtt<br>Asp Glu Tyr Val Arg Arg Ser Tyr Lys Phe Ala Tyr Ser Asp Cys Val<br>195                    200                    205 | 681 |
| gaa gtg gct cct gtt tca tgc tct cct gag cca ccg gat cct agt gaa<br>Glu Val Ala Pro Val Ser Cys Ser Pro Glu Pro Pro Asp Pro Ser Glu<br>210                    215                    220                    225 | 729 |
| tta tac atg aca aaa tcc agc agg gtc aag cat tta ggg ctt ctg tac<br>Leu Tyr Met Thr Lys Ser Ser Arg Val Lys His Leu Gly Leu Leu Tyr<br>                    230                    235                    240 | 777 |
| att agc tct ctg ctt gtg ctt gtt ggt tat tcc atc ttg tac ggt ctt<br>Ile Ser Ser Leu Leu Val Leu Val Gly Tyr Ser Ile Leu Tyr Gly Leu<br>          245                    250                    255 | 825 |
| acg tca aaa gaa gct cgt tgg ttg ggt gct tta act tca gtt gca gtt<br>Thr Ser Lys Glu Ala Arg Trp Leu Gly Ala Leu Thr Ser Val Ala Val<br>      260                    265                    270 | 873 |
| gtt atc ctt gac tgg aat ctg ggc tta tgt tca ttt aga ttt gag ctt<br>Val Ile Leu Asp Trp Asn Leu Gly Leu Cys Ser Phe Arg Phe Glu Leu<br>275                    280                    285 | 921 |
| ctt aaa agt agg atg ata gtg tta ttt gtg gct gga aca tca agg gct<br>Leu Lys Ser Arg Met Ile Val Leu Phe Val Ala Gly Thr Ser Arg Ala<br>290                    295                    300                    305 | 969 |
| ttc ctt gta tcc ttt gga gtg cat tac tgg tac ctt ggc cat tgc atc<br>Phe Leu Val Ser Phe Gly Val His Tyr Trp Tyr Leu Gly His Cys Ile<br>                    310                    315                    320 | 1017 |
| agc tat gct ttt gta gca tct gtg ctt tta tct gct gct gtt tct tcc<br>Ser Tyr Ala Phe Val Ala Ser Val Leu Leu Ser Ala Ala Val Ser Ser<br>          325                    330                    335 | 1065 |
| tgg ctt tct att tca aac ccc tca gtt gca agg ata gac gct cta aga<br>Trp Leu Ser Ile Ser Asn Pro Ser Val Ala Arg Ile Asp Ala Leu Arg<br>      340                    345                    350 | 1113 |
| agt acg gta ata aag cta cga gag gga ttt cga aga aaa gga caa aat<br>Ser Thr Val Ile Lys Leu Arg Glu Gly Phe Arg Arg Lys Gly Gln Asn<br>355                    360                    365 | 1161 |
| agt tct tca aat tca tca gaa ggc tgt ggc tct agt gtg aag cgt agt<br>Ser Ser Ser Asn Ser Ser Glu Gly Cys Gly Ser Ser Val Lys Arg Ser<br>370                    375                    380                    385 | 1209 |
| agc ggt agt gtt gaa gct ggt caa aat ggt aat gca atg gat tct atg<br>Ser Gly Ser Val Glu Ala Gly Gln Asn Gly Asn Ala Met Asp Ser Met<br>                    390                    395                    400 | 1257 |
| tac aga agc aac tca caa agc gat ggt gtc aat tgg agc agt att cct<br>Tyr Arg Ser Asn Ser Gln Ser Asp Gly Val Asn Trp Ser Ser Ile Pro<br>          405                    410                    415 | 1305 |
| ttt gat cga tca aac agt tgt caa gaa ggc cgg agc tcc gac aag aac<br>Phe Asp Arg Ser Asn Ser Cys Gln Glu Gly Arg Ser Ser Asp Lys Asn | 1353 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 420 |     |     |     |     | 425 |     |     |     |     | 430 |     |     |     |      |
| ata | gat | agt | gca | cgt | gca | agc | tta | gct | cat | cgg | agt | aat | tca | tgc | tta | 1401 |
| Ile | Asp | Ser | Ala | Arg | Ala | Ser | Leu | Ala | His | Arg | Ser | Asn | Ser | Cys | Leu |      |
|     |     | 435 |     |     |     |     | 440 |     |     |     |     | 445 |     |     |     |      |
| tct | gcc | gtc | caa | gac | tct | gaa | acc | gct | gtt | gtt | tca | gta | gat | agg | cat | 1449 |
| Ser | Ala | Val | Gln | Asp | Ser | Glu | Thr | Ala | Val | Val | Ser | Val | Asp | Arg | His |      |
| 450 |     |     |     |     | 455 |     |     |     |     | 460 |     |     |     |     | 465 |      |
| gga | gat | ccc | att | act | tca | ctt | gtt | tgt | tct | agc | agt | ggt | ttg | gaa | agt | 1497 |
| Gly | Asp | Pro | Ile | Thr | Ser | Leu | Val | Cys | Ser | Ser | Ser | Gly | Leu | Glu | Ser |      |
|     |     |     |     | 470 |     |     |     |     | 475 |     |     |     |     | 480 |     |      |
| cat | ggc | tgt | gag | cct | agt | gga | tca | gcc | acc | acc | tca | ggt | aat | caa | cag | 1545 |
| His | Gly | Cys | Glu | Pro | Ser | Gly | Ser | Ala | Thr | Thr | Ser | Gly | Asn | Gln | Gln |      |
|     |     |     | 485 |     |     |     |     | 490 |     |     |     |     | 495 |     |     |      |
| cta | ttg | gat | ttg | aac | ctg | gca | gcg | ata | ttt | cag | gac | aga | tta | aat | gat | 1593 |
| Leu | Leu | Asp | Leu | Asn | Leu | Ala | Ala | Ile | Phe | Gln | Asp | Arg | Leu | Asn | Asp |      |
|     |     | 500 |     |     |     |     | 505 |     |     |     |     | 510 |     |     |     |      |
| cca | agg | att | tca | tct | atg | cta | aaa | aag | aat | ggt | gga | ctt | gga | gat | gta | 1641 |
| Pro | Arg | Ile | Ser | Ser | Met | Leu | Lys | Lys | Asn | Gly | Gly | Leu | Gly | Asp | Val |      |
| 515 |     |     |     |     | 520 |     |     |     |     | 525 |     |     |     |     |     |      |
| gaa | ctg | gct | aat | ctt | ctt | cag | gat | aaa | gga | cta | gat | cca | aat | ttt | tcg | 1689 |
| Glu | Leu | Ala | Asn | Leu | Leu | Gln | Asp | Lys | Gly | Leu | Asp | Pro | Asn | Phe | Ser |      |
| 530 |     |     |     |     | 535 |     |     |     |     | 540 |     |     |     |     | 545 |      |
| tac | atg | ctg | aaa | gac | aaa | gtt | atg | gat | cca | cgt | att | tta | gct | ttg | cta | 1737 |
| Tyr | Met | Leu | Lys | Asp | Lys | Val | Met | Asp | Pro | Arg | Ile | Leu | Ala | Leu | Leu |      |
|     |     |     |     | 550 |     |     |     |     | 555 |     |     |     |     | 560 |     |      |
| cag | agg | agc | agc | ttg | gat | gca | gat | aga | gag | cat | caa | gat | gac | gta | gat | 1785 |
| Gln | Arg | Ser | Ser | Leu | Asp | Ala | Asp | Arg | Glu | His | Gln | Asp | Asp | Val | Asp |      |
|     |     |     | 565 |     |     |     |     | 570 |     |     |     |     | 575 |     |     |      |
| gtc | aca | gct | act | gat | tca | gat | aga | ttg | gat | acc | act | att | gca | aat | cag | 1833 |
| Val | Thr | Ala | Thr | Asp | Ser | Asp | Arg | Leu | Asp | Thr | Thr | Ile | Ala | Asn | Gln |      |
|     |     | 580 |     |     |     |     | 585 |     |     |     |     | 590 |     |     |     |      |
| att | tct | ctg | tca | gaa | gaa | cta | agg | aga | agt | ggt | cta | gaa | aaa | tgg | ttg | 1881 |
| Ile | Ser | Leu | Ser | Glu | Glu | Leu | Arg | Arg | Ser | Gly | Leu | Glu | Lys | Trp | Leu |      |
| 595 |     |     |     |     | 600 |     |     |     |     | 605 |     |     |     |     |     |      |
| aac | att | tca | agg | cta | ata | ttc | cat | cat | tta | gct | gga | tct | cca | ata | cgt | 1929 |
| Asn | Ile | Ser | Arg | Leu | Ile | Phe | His | His | Leu | Ala | Gly | Ser | Pro | Ile | Arg |      |
| 610 |     |     |     |     | 615 |     |     |     |     | 620 |     |     |     |     | 625 |      |
| gct | ttt | att | gtt | ttc | aca | gta | atg | ttt | ata | ata | gag | act | gct | act | gtg | 1977 |
| Ala | Phe | Ile | Val | Phe | Thr | Val | Met | Phe | Ile | Ile | Glu | Thr | Ala | Thr | Val |      |
|     |     |     |     | 630 |     |     |     |     | 635 |     |     |     |     | 640 |     |      |
| gct | atc | tat | cgg | cca | gag | acc | atc | aag | gtg | ata | aat | gca | aca | cat | gaa | 2025 |
| Ala | Ile | Tyr | Arg | Pro | Glu | Thr | Ile | Lys | Val | Ile | Asn | Ala | Thr | His | Glu |      |
|     |     |     | 645 |     |     |     |     | 650 |     |     |     |     | 655 |     |     |      |
| cag | ttt | gaa | ttt | ggt | ttc | tcg | ata | ctg | ctt | ctg | tca | cca | gtt | gtc | tgc | 2073 |
| Gln | Phe | Glu | Phe | Gly | Phe | Ser | Ile | Leu | Leu | Leu | Ser | Pro | Val | Val | Cys |      |
|     |     | 660 |     |     |     |     | 665 |     |     |     |     | 670 |     |     |     |      |
| tcc | att | atg | gca | ttc | att | tgg | tct | ctg | cgt | gct | gaa | gaa | atg | ttg | atg | 2121 |
| Ser | Ile | Met | Ala | Phe | Ile | Trp | Ser | Leu | Arg | Ala | Glu | Glu | Met | Leu | Met |      |
| 675 |     |     |     |     | 680 |     |     |     |     | 685 |     |     |     |     |     |      |
| aca | tcc | aag | ccc | cag | aag | tat | ggt | ttc | att | gca | tgg | cta | ctg | agc | aca | 2169 |
| Thr | Ser | Lys | Pro | Gln | Lys | Tyr | Gly | Phe | Ile | Ala | Trp | Leu | Leu | Ser | Thr |      |
| 690 |     |     |     |     | 695 |     |     |     |     | 700 |     |     |     |     | 705 |      |
| tgt | gtt | ggt | ttg | ttt | ctc | tct | ttc | tta | agc | aaa | tca | tct | gtt | ata | ttg | 2217 |
| Cys | Val | Gly | Leu | Phe | Leu | Ser | Phe | Leu | Ser | Lys | Ser | Ser | Val | Ile | Leu |      |
|     |     |     |     | 710 |     |     |     |     | 715 |     |     |     |     | 720 |     |      |
| ggc | ctg | tct | ctc | acg | gta | cca | ctt | atg | gtg | gct | tgc | ctc | tca | ttt | gct | 2265 |
| Gly | Leu | Ser | Leu | Thr | Val | Pro | Leu | Met | Val | Ala | Cys | Leu | Ser | Phe | Ala |      |
|     |     |     | 725 |     |     |     |     | 730 |     |     |     |     | 735 |     |     |      |
| gtt | ccc | ata | tgg | ata | cgc | aat | ggt | tac | agt | ttc | tgg | att | cct | gga | agg | 2313 |

| | |
|---|---|
| Val Pro Ile Trp Ile Arg Asn Gly Tyr Ser Phe Trp Ile Pro Gly Arg<br>    740        745        750 | |
| gag ttt gca aat cgt gaa aat gtt agt caa gct cca gga gag aaa gag<br>Glu Phe Ala Asn Arg Glu Asn Val Ser Gln Ala Pro Gly Glu Lys Glu<br>755        760        765 | 2361 |
| cgg gct ctc ttt gtt atc acc att gct gtt ttc act gca tca att att<br>Arg Ala Leu Phe Val Ile Thr Ile Ala Val Phe Thr Ala Ser Ile Ile<br>770       775        780        785 | 2409 |
| ggc ctt ggt gca ata gtg tca gca aag cct tta gac gct cta ggc tat<br>Gly Leu Gly Ala Ile Val Ser Ala Lys Pro Leu Asp Ala Leu Gly Tyr<br>        790        795        800 | 2457 |
| aaa gga tgg gat gct gat aag aac agc tcc tat tct ccc tat gca aca<br>Lys Gly Trp Asp Ala Asp Lys Asn Ser Ser Tyr Ser Pro Tyr Ala Thr<br>        805        810        815 | 2505 |
| tca atg tat ctt gga tgg gca ttg tct tca aca att gct gtg att acc<br>Ser Met Tyr Leu Gly Trp Ala Leu Ser Ser Thr Ile Ala Val Ile Thr<br>    820        825        830 | 2553 |
| aca ggg ttg ata cct att gtt gct tgg ttt gca aca tac cgg ttt tca<br>Thr Gly Leu Ile Pro Ile Val Ala Trp Phe Ala Thr Tyr Arg Phe Ser<br>835        840        845 | 2601 |
| cct tca tca gct ata tgt gtt ggc ctc ttt gca act gtt ctt gtg tct<br>Pro Ser Ser Ala Ile Cys Val Gly Leu Phe Ala Thr Val Leu Val Ser<br>850       855        860        865 | 2649 |
| ttt tgc ggt gca tcc tac tgg gga gtg gta aat tca cga gag gat ggt<br>Phe Cys Gly Ala Ser Tyr Trp Gly Val Val Asn Ser Arg Glu Asp Gly<br>        870        875        880 | 2697 |
| gtt cct cta aag gct gat ttc ctt gca gca tta ctt ccc ttg ctt tgc<br>Val Pro Leu Lys Ala Asp Phe Leu Ala Ala Leu Leu Pro Leu Leu Cys<br>        885        890        895 | 2745 |
| att cca gca ttt ttc tca ctg ttc act ggg ctt tac aaa tgg aag gat<br>Ile Pro Ala Phe Phe Ser Leu Phe Thr Gly Leu Tyr Lys Trp Lys Asp<br>    900        905        910 | 2793 |
| gat gat tgg aag att tct cgt ggt gtt tac ctt ttt gtt ggc atg gga<br>Asp Asp Trp Lys Ile Ser Arg Gly Val Tyr Leu Phe Val Gly Met Gly<br>915        920        925 | 2841 |
| atg ttg ctg ttg ttt ggt gca gtt gca gct gtt att gtc aca atc agg<br>Met Leu Leu Leu Phe Gly Ala Val Ala Ala Val Ile Val Thr Ile Arg<br>930        935        940        945 | 2889 |
| ccc tgg act gtt gga gtt gct tgc ctc gta gcc att ctg ttc ctt gta<br>Pro Trp Thr Val Gly Val Ala Cys Leu Val Ala Ile Leu Phe Leu Val<br>        950        955        960 | 2937 |
| ttt gtt att ggg gtc atc cac tac tgg aca tct aac aac ttc tat cta<br>Phe Val Ile Gly Val Ile His Tyr Trp Thr Ser Asn Asn Phe Tyr Leu<br>        965        970        975 | 2985 |
| acg agg act cag atg ttg ctt gtt tgt tcc att gct ttt ctc tta gcc<br>Thr Arg Thr Gln Met Leu Leu Val Cys Ser Ile Ala Phe Leu Leu Ala<br>    980        985        990 | 3033 |
| ttg gct gcc ttc ctg atg ggt tta ttt cac gga aag cct ttt gtt gga<br>Leu Ala Ala Phe Leu Met Gly Leu Phe His Gly Lys Pro Phe Val Gly<br>995        1000       1005 | 3081 |
| gca tct ata ggt tat ttc tca ttt ata ttt ctt ctc act gga agg gct<br>Ala Ser Ile Gly Tyr Phe Ser Phe Ile Phe Leu Leu Thr Gly Arg Ala<br>1010       1015       1020       1025 | 3129 |
| ttg act gtc ctt cta tca ccg cca atc gta gtg tat tcg cca aga gta<br>Leu Thr Val Leu Leu Ser Pro Pro Ile Val Val Tyr Ser Pro Arg Val<br>        1030       1035       1040 | 3177 |
| ttg cct gta tac gtt tat gat gct cat gca gac tct gct aaa aat gtt<br>Leu Pro Val Tyr Val Tyr Asp Ala His Ala Asp Ser Ala Lys Asn Val<br>        1045       1050       1055 | 3225 |

-continued

| | |
|---|---|
| agc tat gcc ttt ctt att ctg tat ggg att gca tta gca act gaa gtt<br>Ser Tyr Ala Phe Leu Ile Leu Tyr Gly Ile Ala Leu Ala Thr Glu Val<br>     1060                   1065                  1070 | 3273 |
| tgg ggt gtt att gct agt cta ata atg aat cca cca ttt gtt ggg gct<br>Trp Gly Val Ile Ala Ser Leu Ile Met Asn Pro Pro Phe Val Gly Ala<br>1075                  1080                  1085 | 3321 |
| ggc gtt tct gct act act ctt gta att gct ttc agt ttt gct gtt tct<br>Gly Val Ser Ala Thr Thr Leu Val Ile Ala Phe Ser Phe Ala Val Ser<br>1090                  1095                  1100                  1105 | 3369 |
| cga cca tgc ctg act ctt aag atg atg gag gat gca gtt cat ttt ctc<br>Arg Pro Cys Leu Thr Leu Lys Met Met Glu Asp Ala Val His Phe Leu<br>               1110                  1115                  1120 | 3417 |
| agc aag gat aca gtt gtg caa gcg atg tca cgg tct gct aat aaa act<br>Ser Lys Asp Thr Val Val Gln Ala Met Ser Arg Ser Ala Asn Lys Thr<br>               1125                  1130                  1135 | 3465 |
| aga aat gct ata tct ggg act tac tca gca cct cag agg tcc gca agt<br>Arg Asn Ala Ile Ser Gly Thr Tyr Ser Ala Pro Gln Arg Ser Ala Ser<br>               1140                  1145                  1150 | 3513 |
| tct gct gct ctt ttg gtt gga gat cct gct ctt aca ttg gac agg gct<br>Ser Ala Ala Leu Leu Val Gly Asp Pro Ala Leu Thr Leu Asp Arg Ala<br>               1155                  1160                  1165 | 3561 |
| ggg aac ttt gtg ctt cct agg gct gat gtt atg aaa ctg aga gat cgt<br>Gly Asn Phe Val Leu Pro Arg Ala Asp Val Met Lys Leu Arg Asp Arg<br>1170                  1175                  1180                  1185 | 3609 |
| ttg aga aat gaa gaa att gct gca gga tct ttc tta tgt gga gta aaa<br>Leu Arg Asn Glu Glu Ile Ala Ala Gly Ser Phe Leu Cys Gly Val Lys<br>                        1190                  1195                  1200 | 3657 |
| gat tgt tta cta att tgc ccc cag tcc ctg tca aac ata gat tat cgg<br>Asp Cys Leu Leu Ile Cys Pro Gln Ser Leu Ser Asn Ile Asp Tyr Arg<br>               1205                  1210                  1215 | 3705 |
| agg aat atg tgt gcc cat gca cgt att ttg gct ttg gaa gaa gca att<br>Arg Asn Met Cys Ala His Ala Arg Ile Leu Ala Leu Glu Glu Ala Ile<br>               1220                  1225                  1230 | 3753 |
| gat aca gaa tgg gtg tat atg tgg gac aaa ttt ggt ggt tat tta ctt<br>Asp Thr Glu Trp Val Tyr Met Trp Asp Lys Phe Gly Gly Tyr Leu Leu<br>               1235                  1240                  1245 | 3801 |
| ctg ttg ctt gga ttg act gcc aaa gct gaa caa ata cag gat gaa gtt<br>Leu Leu Leu Gly Leu Thr Ala Lys Ala Glu Gln Ile Gln Asp Glu Val<br>1250                  1255                  1260                  1265 | 3849 |
| cgt cta aga ctc ttt ttg gat agc ata ggc ctt tcc gat ttg agt gcc<br>Arg Leu Arg Leu Phe Leu Asp Ser Ile Gly Leu Ser Asp Leu Ser Ala<br>               1270                  1275                  1280 | 3897 |
| aaa gaa att aag aaa tgg atg cct gaa gat cgg agg caa ttt gag ctt<br>Lys Glu Ile Lys Lys Trp Met Pro Glu Asp Arg Arg Gln Phe Glu Leu<br>               1285                  1290                  1295 | 3945 |
| att caa gaa agc tac ata agg gaa aaa gaa atg gaa gag gag gct ttg<br>Ile Gln Glu Ser Tyr Ile Arg Glu Lys Glu Met Glu Glu Glu Ala Leu<br>               1300                  1305                  1310 | 3993 |
| atg caa aga cga gag gaa gaa ggg aag gga aga gaa agg agg agg gca<br>Met Gln Arg Arg Glu Glu Glu Gly Lys Gly Arg Glu Arg Arg Arg Ala<br>               1315                  1320                  1325 | 4041 |
| ttg cta gag aga gag gag cga aaa tgg aag gag ctc gaa ata tca ttg<br>Leu Leu Glu Arg Glu Glu Arg Lys Trp Lys Glu Leu Glu Ile Ser Leu<br>1330                  1335                  1340                  1345 | 4089 |
| ctt tct tcc att cca aat act gga agc agg gat gct gca gct atg gca<br>Leu Ser Ser Ile Pro Asn Thr Gly Ser Arg Asp Ala Ala Ala Met Ala<br>               1350                  1355                  1360 | 4137 |
| gca gct gtc aga gct gtt gga ggt gat tct gcc ctg gaa gat tct ttt<br>Ala Ala Val Arg Ala Val Gly Gly Asp Ser Ala Leu Glu Asp Ser Phe<br>               1365                  1370                  1375 | 4185 |

```
gca aga gat agg gtc tct tca ata gcc aat cac ata cga aag gca caa            4233
Ala Arg Asp Arg Val Ser Ser Ile Ala Asn His Ile Arg Lys Ala Gln
    1380                1385                1390 ttg gct cgg cga gca gaa cag act ggt att cca ggc act ata tgc ata            4281
Leu Ala Arg Arg Ala Glu Gln Thr Gly Ile Pro Gly Thr Ile Cys Ile
1395                1400                1405 ctc gat gat gaa ccg agg agt act ggt cgt cat tgt gga gaa ctt gac            4329
Leu Asp Asp Glu Pro Arg Ser Thr Gly Arg His Cys Gly Glu Leu Asp
1410                1415                1420                1425 ttg tgc ctc tgt caa agt caa aag gtt act ttg tct att gct gtc atg            4377
Leu Cys Leu Cys Gln Ser Gln Lys Val Thr Leu Ser Ile Ala Val Met
                1430                1435                1440 gtt cag cct gta tct ggc cca gtg tgt ctt ttt gga agt gaa ttc caa            4425
Val Gln Pro Val Ser Gly Pro Val Cys Leu Phe Gly Ser Glu Phe Gln
            1445                1450                1455 aag gtt tgt tgg gaa atc tta gtg gca gga tca gaa cag ggt atg gaa            4473
Lys Val Cys Trp Glu Ile Leu Val Ala Gly Ser Glu Gln Gly Met Glu
        1460                1465                1470 gct gga caa gtt ggt ctt cga tta gta act aag ggt gaa agg atg act            4521
Ala Gly Gln Val Gly Leu Arg Leu Val Thr Lys Gly Glu Arg Met Thr
1475                1480                1485 act gtt gct aaa gag tgg aat att ggt gcg tct agt att gca gat ggc            4569
Thr Val Ala Lys Glu Trp Asn Ile Gly Ala Ser Ser Ile Ala Asp Gly
1490                1495                1500                1505 agg tgg cat ctt gtc act gta act tta gat gcc gac cta ggt gaa gca            4617
Arg Trp His Leu Val Thr Val Thr Leu Asp Ala Asp Leu Gly Glu Ala
                1510                1515                1520 act tct ttc att gat gga gtt tat gat gga tat cag aat ggg ttg ccg            4665
Thr Ser Phe Ile Asp Gly Val Tyr Asp Gly Tyr Gln Asn Gly Leu Pro
            1525                1530                1535 ttg cca aca gat aac ggt att tgg gaa cct gga act gat att tgg gtt            4713
Leu Pro Thr Asp Asn Gly Ile Trp Glu Pro Gly Thr Asp Ile Trp Val
        1540                1545                1550 ggt gct agg cca ccc atg gac tta gat gcc ttt ggt agg tca gat agc            4761
Gly Ala Arg Pro Pro Met Asp Leu Asp Ala Phe Gly Arg Ser Asp Ser
1555                1560                1565 gaa ggt tct gac tca aag atg cag atc atg gat gct ttt cta tgg gga            4809
Glu Gly Ser Asp Ser Lys Met Gln Ile Met Asp Ala Phe Leu Trp Gly
1570                1575                1580                1585 aga tgt ctc agt gaa gat gag gtt act gtt tta cat act gcc atg tct            4857
Arg Cys Leu Ser Glu Asp Glu Val Thr Val Leu His Thr Ala Met Ser
                1590                1595                1600 cct gct gag tat gga ttt ttt gac ctt gca ccc ggc gat gct tgg cat            4905
Pro Ala Glu Tyr Gly Phe Phe Asp Leu Ala Pro Gly Asp Ala Trp His
            1605                1610                1615 gga agt tat tct gca agg gtg gat gac tgg gaa agc gaa gaa gct tat            4953
Gly Ser Tyr Ser Ala Arg Val Asp Asp Trp Glu Ser Glu Glu Ala Tyr
        1620                1625                1630 gag ctt tat gat caa ggg gat gtc gaa tgg gat gga cag tac tca agt            5001
Glu Leu Tyr Asp Gln Gly Asp Val Glu Trp Asp Gly Gln Tyr Ser Ser
1635                1640                1645 ggt agg aaa cgt ccg gta cat gat gct gta gct att gac ctt gac tcc            5049
Gly Arg Lys Arg Pro Val His Asp Ala Val Ala Ile Asp Leu Asp Ser
1650                1655                1660                1665 ttt gct agg aga cca aga aaa cca agg ttt gag aca cgt gat gaa gtc            5097
Phe Ala Arg Arg Pro Arg Lys Pro Arg Phe Glu Thr Arg Asp Glu Val
                1670                1675                1680 aac cag cgt atg ctt tct gtt gaa agg gct gtc agg gat gct ctt atc            5145
Asn Gln Arg Met Leu Ser Val Glu Arg Ala Val Arg Asp Ala Leu Ile
```

-continued

```
                      1685                  1690                  1695
gcg aaa gga gag aga aac ttc act gat caa gag ttc cct cca gag gat      5193
Ala Lys Gly Glu Arg Asn Phe Thr Asp Gln Glu Phe Pro Pro Glu Asp
            1700                  1705                  1710 cgt tct tta ttt gta gat ccg atg aat cca cct ctg aaa ctg cag gtt      5241
Arg Ser Leu Phe Val Asp Pro Met Asn Pro Pro Leu Lys Leu Gln Val
        1715                  1720                  1725 gtt tct gag tgg atg agg cct tct gac ata gca aag gat ata tct atc      5289
Val Ser Glu Trp Met Arg Pro Ser Asp Ile Ala Lys Asp Ile Ser Ile
1730                  1735                  1740                  1745 agt tgt cag cct tgc ttg ttt tcg ggt tct gtg aat tcc tca gat gtg      5337
Ser Cys Gln Pro Cys Leu Phe Ser Gly Ser Val Asn Ser Ser Asp Val
                1750                  1755                  1760 tgt cag ggt cgg ttg gga gac tgt tgg ttc cta agt gca gtc gca gtt      5385
Cys Gln Gly Arg Leu Gly Asp Cys Trp Phe Leu Ser Ala Val Ala Val
            1765                  1770                  1775 tta act gag atg tct cgg ata tca gaa gtt ata atc act ccc gag tac      5433
Leu Thr Glu Met Ser Arg Ile Ser Glu Val Ile Ile Thr Pro Glu Tyr
        1780                  1785                  1790 aat gat gaa ggg att tat aca gtc aga ttc tgt att cag ggt gag tgg      5481
Asn Asp Glu Gly Ile Tyr Thr Val Arg Phe Cys Ile Gln Gly Glu Trp
    1795                  1800                  1805 gtg gcc gtg gtt gtt gat gat tgg att cct tgc gag tct ccg ggg aaa      5529
Val Ala Val Val Val Asp Asp Trp Ile Pro Cys Glu Ser Pro Gly Lys
1810                  1815                  1820                  1825 cca gca ttt gct act agt aga aag caa aac gag ctt tgg gta tcc att      5577
Pro Ala Phe Ala Thr Ser Arg Lys Gln Asn Glu Leu Trp Val Ser Ile
                1830                  1835                  1840 ctt gag aag gct tat gca aaa ctt cat ggc tct tat gag gca ttg gaa      5625
Leu Glu Lys Ala Tyr Ala Lys Leu His Gly Ser Tyr Glu Ala Leu Glu
            1845                  1850                  1855 ggt ggg ctt gtt caa gat gct cta gtc gat ctc aca gga gga gct ggt      5673
Gly Gly Leu Val Gln Asp Ala Leu Val Asp Leu Thr Gly Gly Ala Gly
        1860                  1865                  1870 gaa gag att gat atg cga agt cct caa gcc caa ctt gat ctt gct agt      5721
Glu Glu Ile Asp Met Arg Ser Pro Gln Ala Gln Leu Asp Leu Ala Ser
    1875                  1880                  1885 gga aga ttg tgg tcg cag ttg ttg cat ttc aaa caa gaa ggt ttt ctt      5769
Gly Arg Leu Trp Ser Gln Leu Leu His Phe Lys Gln Glu Gly Phe Leu
1890                  1895                  1900                  1905 ctt ggt gct gga agt cct tct gga tct gat gct cac atc tca tca agt      5817
Leu Gly Ala Gly Ser Pro Ser Gly Ser Asp Ala His Ile Ser Ser Ser
                1910                  1915                  1920 ggc att gtt cag gga cat gcg tac tca att ttg cag gta aga gaa gtt      5865
Gly Ile Val Gln Gly His Ala Tyr Ser Ile Leu Gln Val Arg Glu Val
            1925                  1930                  1935 gat ggc cac aaa ctc atc caa atc aga aat cca tgg gca aat gaa gtt      5913
Asp Gly His Lys Leu Ile Gln Ile Arg Asn Pro Trp Ala Asn Glu Val
        1940                  1945                  1950 gaa tgg aat gga cca tgg tca gac tcg tca cca gag tgg acg gaa cgg      5961
Glu Trp Asn Gly Pro Trp Ser Asp Ser Ser Pro Glu Trp Thr Glu Arg
    1955                  1960                  1965 atg aag cat aag ctc atg cat gtt cca cag tcg aag aat ggg gta ttc      6009
Met Lys His Lys Leu Met His Val Pro Gln Ser Lys Asn Gly Val Phe
1970                  1975                  1980                  1985 tgg atg tct tgg caa gat ttt cag att cac ttt cgg tca ata tat gtt      6057
Trp Met Ser Trp Gln Asp Phe Gln Ile His Phe Arg Ser Ile Tyr Val
                1990                  1995                  2000 tgt cgt gtt tat cca cct gag atg cgt tac tct gtc cat ggg caa tgg      6105
```

| | | | | |
|---|---|---|---|---|
| Cys Arg Val Tyr Pro Glu Met Arg Tyr Ser Val His Gly Gln Trp | | | | |
| 2005 | | 2010 | | 2015 |

```
cgt ggc tac aat gca ggt ggt tgc caa gat tat gac tcg tgg cac caa     6153
Arg Gly Tyr Asn Ala Gly Gly Cys Gln Asp Tyr Asp Ser Trp His Gln
        2020            2025            2030 aat cca cag tat cga ctt aga gta aca gga cgt gat gca cta tac cct     6201
Asn Pro Gln Tyr Arg Leu Arg Val Thr Gly Arg Asp Ala Leu Tyr Pro
    2035            2040            2045 gtt cac gtt ttt att acc ctt act cag ggt gtt ggt ttc tct aga aag     6249
Val His Val Phe Ile Thr Leu Thr Gln Gly Val Gly Phe Ser Arg Lys
2050            2055            2060            2065 acg aat ggt ttt cgg aac tac caa tct agc cat gat tct tca atg ttt     6297
Thr Asn Gly Phe Arg Asn Tyr Gln Ser Ser His Asp Ser Ser Met Phe
        2070            2075            2080 tac att gga atg agg ata ctc aag aca cag ggc tgc cgt gct gct tac     6345
Tyr Ile Gly Met Arg Ile Leu Lys Thr Gln Gly Cys Arg Ala Ala Tyr
    2085            2090            2095 aat atc tac atg cat gaa agc gct ggt gga aca gat tac gtt aac tcg     6393
Asn Ile Tyr Met His Glu Ser Ala Gly Gly Thr Asp Tyr Val Asn Ser
2100            2105            2110 agg gag ata tca tgc gaa ctg gtc ttg gat cct tat ccc aaa ggg tac     6441
Arg Glu Ile Ser Cys Glu Leu Val Leu Asp Pro Tyr Pro Lys Gly Tyr
        2115            2120            2125 aca att gtg cca act acc atc cac cct ggg gag gaa gca cct ttt gtt     6489
Thr Ile Val Pro Thr Thr Ile His Pro Gly Glu Glu Ala Pro Phe Val
2130            2135            2140            2145 ttg tca gtt ttt tca aaa gca tca atc aga cta gag gct gtt t           6532
Leu Ser Val Phe Ser Lys Ala Ser Ile Arg Leu Glu Ala Val
            2150            2155 agttcaagat tgagatccca tgtgtttgat ggtagctgcg tctgctgggc acccgtgcac   6592
gcaggatcca gctgtgggtt ctcgggaact agataatggg tataggaatt gcctcctgga   6652
caacttcaat caatcttgct gcatgcaagt acctaagttc ggttgcttgt tgcagatctg   6712
acaaacggca atgcttcttg tgctgaaggg aaaggagaga aggcatgatc catggttctt   6772
tggtagctgc gcaaagtgca gggtgagagg cttggttcaa tgtttgtaga tagccgtggt   6832
aactgacctg gtagcccatc ctatgtatag gtgtcccgtt taccctgtaa atgctataga   6892
gttaggttag gtagcctgtc gttcctgtta acgcataggg ctcttatgca gctgtgaaat   6952
gtcttgttgg caagctgcag ttttgctgat ttgagcgtgg agtagtcggc catagctgtt   7012
cccattggtt tgccctgtat gtaatcggaa tctgatgtca ttcaatgaac ctattttttg   7072
ggtgccatgc gaagctgtct aaaaaaaaaa aaaaaaa                            7110
```

```
<210> SEQ ID NO 24
<211> LENGTH: 2159
<212> TYPE: PRT
<213> ORGANISM: zea mays

<400> SEQUENCE: 24
```

```
Met Glu Gly Glu Gly His His Gly Val Val Leu Ala Cys Ser Ile Cys
1               5                   10                  15

Gly Phe Leu Phe Ala Val Leu Ser Pro Phe Ser Phe Trp Val Leu Trp
            20                  25                  30

Ala Val Asn Trp Arg Pro Trp Arg Leu Tyr Ser Trp Ile Tyr Ala Arg
        35                  40                  45

Lys Trp Pro Thr Tyr Val Gln Gly Pro Gln Leu Ser Thr Leu Cys Ser
50                  55                  60
```

-continued

```
Leu Leu Thr Leu Cys Ala Trp Leu Val Val Ile Ser Pro Ile Ala Val
 65                  70                  75                  80

Leu Leu Val Trp Gly Ser Val Leu Ile Ala Leu Met Glu Arg Asn Ile
                 85                  90                  95

Ile Gly Leu Ala Val Ile Met Ala Gly Val Ala Leu Leu Leu Ser Phe
            100                 105                 110

Tyr Ser Ile Met Leu Trp Trp Arg Thr Gln Trp Gln Ser Ser Lys Ala
            115                 120                 125

Val Ala Tyr Leu Leu Leu Leu Ala Val Cys Leu Leu Cys Ala Tyr Asp
            130                 135                 140

Phe Cys Ala Ile Tyr Val Thr Ala Gly Ala Ser Ala Ser Glu Leu Asn
145                 150                 155                 160

Ser Pro Ser Gly Phe Phe Phe Gly Val Ser Val Ile Ser Leu Ala Ile
                165                 170                 175

Asn Met Leu Phe Ile Cys Lys Ile Leu Phe Asn Val Ser Gly Phe Asp
            180                 185                 190

Val Asp Glu Tyr Val Arg Arg Ser Tyr Lys Phe Ala Tyr Ser Asp Cys
            195                 200                 205

Val Glu Val Ala Pro Val Ser Cys Ser Pro Glu Pro Pro Asp Pro Ser
            210                 215                 220

Glu Leu Tyr Met Thr Lys Ser Ser Arg Val Lys His Leu Gly Leu Leu
225                 230                 235                 240

Tyr Ile Ser Ser Leu Leu Val Leu Val Gly Tyr Ser Ile Leu Tyr Gly
                245                 250                 255

Leu Thr Ser Lys Glu Ala Arg Trp Leu Gly Ala Leu Thr Ser Val Ala
            260                 265                 270

Val Val Ile Leu Asp Trp Asn Leu Gly Leu Cys Ser Phe Arg Phe Glu
            275                 280                 285

Leu Leu Lys Ser Arg Met Ile Val Leu Phe Val Ala Gly Thr Ser Arg
290                 295                 300

Ala Phe Leu Val Ser Phe Gly Val His Tyr Trp Tyr Leu Gly His Cys
305                 310                 315                 320

Ile Ser Tyr Ala Phe Val Ala Ser Val Leu Leu Ser Ala Ala Val Ser
                325                 330                 335

Ser Trp Leu Ser Ile Ser Asn Pro Ser Val Ala Arg Ile Asp Ala Leu
            340                 345                 350

Arg Ser Thr Val Ile Lys Leu Arg Glu Gly Phe Arg Arg Lys Gly Gln
            355                 360                 365

Asn Ser Ser Asn Ser Ser Glu Gly Cys Gly Ser Ser Val Lys Arg
            370                 375                 380

Ser Ser Gly Ser Val Glu Ala Gly Gln Asn Gly Asn Ala Met Asp Ser
385                 390                 395                 400

Met Tyr Arg Ser Asn Ser Gln Ser Asp Gly Val Asn Trp Ser Ser Ile
                405                 410                 415

Pro Phe Asp Arg Ser Asn Ser Cys Gln Glu Gly Arg Ser Ser Asp Lys
            420                 425                 430

Asn Ile Asp Ser Ala Arg Ala Ser Leu Ala His Arg Ser Asn Ser Cys
            435                 440                 445

Leu Ser Ala Val Gln Asp Ser Glu Thr Ala Val Val Ser Val Asp Arg
            450                 455                 460

His Gly Asp Pro Ile Thr Ser Leu Val Cys Ser Ser Ser Gly Leu Glu
465                 470                 475                 480

Ser His Gly Cys Glu Pro Ser Gly Ser Ala Thr Thr Ser Gly Asn Gln
```

-continued

```
                485                 490                 495
Gln Leu Leu Asp Leu Asn Leu Ala Ala Ile Phe Gln Asp Arg Leu Asn
            500                 505                 510
Asp Pro Arg Ile Ser Ser Met Leu Lys Lys Asn Gly Gly Leu Gly Asp
            515                 520                 525
Val Glu Leu Ala Asn Leu Leu Gln Asp Lys Gly Leu Asp Pro Asn Phe
            530                 535                 540
Ser Tyr Met Leu Lys Asp Lys Val Met Asp Pro Arg Ile Leu Ala Leu
545                 550                 555                 560
Leu Gln Arg Ser Ser Leu Asp Ala Asp Arg Glu His Gln Asp Asp Val
            565                 570                 575
Asp Val Thr Ala Thr Asp Ser Asp Arg Leu Asp Thr Thr Ile Ala Asn
            580                 585                 590
Gln Ile Ser Leu Ser Glu Glu Leu Arg Arg Ser Gly Leu Glu Lys Trp
            595                 600                 605
Leu Asn Ile Ser Arg Leu Ile Phe His His Leu Ala Gly Ser Pro Ile
            610                 615                 620
Arg Ala Phe Ile Val Phe Thr Val Met Phe Ile Ile Glu Thr Ala Thr
625                 630                 635                 640
Val Ala Ile Tyr Arg Pro Glu Thr Ile Lys Val Ile Asn Ala Thr His
            645                 650                 655
Glu Gln Phe Glu Phe Gly Phe Ser Ile Leu Leu Ser Pro Val Val
            660                 665                 670
Cys Ser Ile Met Ala Phe Ile Trp Ser Leu Arg Ala Glu Glu Met Leu
            675                 680                 685
Met Thr Ser Lys Pro Gln Lys Tyr Gly Phe Ile Ala Trp Leu Leu Ser
            690                 695                 700
Thr Cys Val Gly Leu Phe Leu Ser Phe Leu Ser Lys Ser Ser Val Ile
705                 710                 715                 720
Leu Gly Leu Ser Leu Thr Val Pro Leu Met Val Ala Cys Leu Ser Phe
            725                 730                 735
Ala Val Pro Ile Trp Ile Arg Asn Gly Tyr Ser Phe Trp Ile Pro Gly
            740                 745                 750
Arg Glu Phe Ala Asn Arg Glu Asn Val Ser Gln Ala Pro Gly Glu Lys
            755                 760                 765
Glu Arg Ala Leu Phe Val Ile Thr Ile Ala Val Phe Thr Ala Ser Ile
            770                 775                 780
Ile Gly Leu Gly Ala Ile Val Ser Ala Lys Pro Leu Asp Ala Leu Gly
785                 790                 795                 800
Tyr Lys Gly Trp Asp Ala Asp Lys Asn Ser Ser Tyr Ser Pro Tyr Ala
            805                 810                 815
Thr Ser Met Tyr Leu Gly Trp Ala Leu Ser Ser Thr Ile Ala Val Ile
            820                 825                 830
Thr Thr Gly Leu Ile Pro Ile Ala Trp Phe Ala Thr Tyr Arg Phe
            835                 840                 845
Ser Pro Ser Ser Ala Ile Cys Val Gly Leu Phe Ala Thr Val Leu Val
850                 855                 860
Ser Phe Cys Gly Ala Ser Tyr Trp Gly Val Val Asn Ser Arg Glu Asp
865                 870                 875                 880
Gly Val Pro Leu Lys Ala Asp Phe Leu Ala Leu Leu Pro Leu Leu
            885                 890                 895
Cys Ile Pro Ala Phe Phe Ser Leu Phe Thr Gly Leu Tyr Lys Trp Lys
            900                 905                 910
```

-continued

```
Asp Asp Asp Trp Lys Ile Ser Arg Gly Val Tyr Leu Phe Val Gly Met
        915                 920                 925
Gly Met Leu Leu Leu Phe Gly Ala Val Ala Val Ile Val Thr Ile
        930                 935                 940
Arg Pro Trp Thr Val Gly Val Ala Cys Leu Val Ala Ile Leu Phe Leu
945                 950                 955                 960
Val Phe Val Ile Gly Val Ile His Tyr Trp Thr Ser Asn Asn Phe Tyr
                965                 970                 975
Leu Thr Arg Thr Gln Met Leu Leu Val Cys Ser Ile Ala Phe Leu Leu
                980                 985                 990
Ala Leu Ala Ala Phe Leu Met Gly Leu Phe His Gly Lys Pro Phe Val
        995                 1000                1005
Gly Ala Ser Ile Gly Tyr Phe Ser Phe Ile Phe Leu Leu Thr Gly Arg
        1010                1015                1020
Ala Leu Thr Val Leu Leu Ser Pro Pro Ile Val Val Tyr Ser Pro Arg
1025                1030                1035                1040
Val Leu Pro Val Tyr Val Tyr Asp Ala His Ala Asp Ser Ala Lys Asn
                1045                1050                1055
Val Ser Tyr Ala Phe Leu Ile Leu Tyr Gly Ile Ala Leu Ala Thr Glu
                1060                1065                1070
Val Trp Gly Val Ile Ala Ser Leu Ile Met Asn Pro Pro Phe Val Gly
                1075                1080                1085
Ala Gly Val Ser Ala Thr Thr Leu Val Ile Ala Phe Ser Phe Ala Val
        1090                1095                1100
Ser Arg Pro Cys Leu Thr Leu Lys Met Met Glu Asp Ala Val His Phe
1105                1110                1115                1120
Leu Ser Lys Asp Thr Val Val Gln Ala Met Ser Arg Ser Ala Asn Lys
                1125                1130                1135
Thr Arg Asn Ala Ile Ser Gly Thr Tyr Ser Ala Pro Gln Arg Ser Ala
                1140                1145                1150
Ser Ser Ala Ala Leu Leu Val Gly Asp Pro Ala Leu Thr Leu Asp Arg
        1155                1160                1165
Ala Gly Asn Phe Val Leu Pro Arg Ala Asp Val Met Lys Leu Arg Asp
        1170                1175                1180
Arg Leu Arg Asn Glu Glu Ile Ala Ala Gly Ser Phe Leu Cys Gly Val
1185                1190                1195                1200
Lys Asp Cys Leu Leu Ile Cys Pro Gln Ser Leu Ser Asn Ile Asp Tyr
                1205                1210                1215
Arg Arg Asn Met Cys Ala His Ala Arg Ile Leu Ala Leu Glu Glu Ala
                1220                1225                1230
Ile Asp Thr Glu Trp Val Tyr Met Trp Asp Lys Phe Gly Gly Tyr Leu
        1235                1240                1245
Leu Leu Leu Leu Gly Leu Thr Ala Lys Ala Glu Gln Ile Gln Asp Glu
        1250                1255                1260
Val Arg Leu Arg Leu Phe Leu Asp Ser Ile Gly Leu Ser Asp Leu Ser
1265                1270                1275                1280
Ala Lys Glu Ile Lys Lys Trp Met Pro Glu Asp Arg Arg Gln Phe Glu
                1285                1290                1295
Leu Ile Gln Glu Ser Tyr Ile Arg Glu Lys Met Glu Glu Ala
                1300                1305                1310
Leu Met Gln Arg Arg Glu Glu Glu Gly Lys Gly Arg Glu Arg Arg
        1315                1320                1325
```

-continued

```
Ala Leu Leu Glu Arg Glu Glu Arg Lys Trp Lys Leu Glu Ile Ser
    1330                1335                1340
Leu Leu Ser Ser Ile Pro Asn Thr Gly Ser Arg Asp Ala Ala Met
1345                1350                1355                1360
Ala Ala Ala Val Arg Ala Val Gly Gly Asp Ser Ala Leu Glu Asp Ser
                1365                1370                1375
Phe Ala Arg Asp Arg Val Ser Ser Ile Ala Asn His Ile Arg Lys Ala
            1380                1385                1390
Gln Leu Ala Arg Arg Ala Glu Gln Thr Gly Ile Pro Gly Thr Ile Cys
        1395                1400                1405
Ile Leu Asp Asp Glu Pro Arg Ser Thr Gly Arg His Cys Gly Glu Leu
    1410                1415                1420
Asp Leu Cys Leu Cys Gln Ser Gln Lys Val Thr Leu Ser Ile Ala Val
1425                1430                1435                1440
Met Val Gln Pro Val Ser Gly Pro Val Cys Leu Phe Gly Ser Glu Phe
                1445                1450                1455
Gln Lys Val Cys Trp Glu Ile Leu Val Ala Gly Ser Glu Gln Gly Met
            1460                1465                1470
Glu Ala Gly Gln Val Gly Leu Arg Leu Val Thr Lys Gly Glu Arg Met
        1475                1480                1485
Thr Thr Val Ala Lys Glu Trp Asn Ile Gly Ala Ser Ser Ile Ala Asp
    1490                1495                1500
Gly Arg Trp His Leu Val Thr Val Thr Leu Asp Ala Asp Leu Gly Glu
1505                1510                1515                1520
Ala Thr Ser Phe Ile Asp Gly Val Tyr Asp Gly Tyr Gln Asn Gly Leu
                1525                1530                1535
Pro Leu Pro Thr Asp Asn Gly Ile Trp Glu Pro Gly Thr Asp Ile Trp
            1540                1545                1550
Val Gly Ala Arg Pro Pro Met Asp Leu Asp Ala Phe Gly Arg Ser Asp
        1555                1560                1565
Ser Glu Gly Ser Asp Ser Lys Met Gln Ile Met Asp Ala Phe Leu Trp
    1570                1575                1580
Gly Arg Cys Leu Ser Glu Asp Glu Val Thr Val Leu His Thr Ala Met
1585                1590                1595                1600
Ser Pro Ala Glu Tyr Gly Phe Phe Asp Leu Ala Pro Gly Asp Ala Trp
                1605                1610                1615
His Gly Ser Tyr Ser Ala Arg Val Asp Asp Trp Glu Ser Glu Glu Ala
            1620                1625                1630
Tyr Glu Leu Tyr Asp Gln Gly Asp Val Glu Trp Asp Gly Gln Tyr Ser
        1635                1640                1645
Ser Gly Arg Lys Arg Pro Val His Asp Ala Val Ala Ile Asp Leu Asp
    1650                1655                1660
Ser Phe Ala Arg Arg Pro Arg Lys Pro Arg Phe Glu Thr Arg Asp Glu
1665                1670                1675                1680
Val Asn Gln Arg Met Leu Ser Val Glu Arg Ala Val Arg Asp Ala Leu
                1685                1690                1695
Ile Ala Lys Gly Glu Arg Asn Phe Thr Asp Gln Glu Phe Pro Pro Glu
            1700                1705                1710
Asp Arg Ser Leu Phe Val Asp Pro Met Asn Pro Leu Lys Leu Gln
        1715                1720                1725
Val Val Ser Glu Trp Met Arg Pro Ser Asp Ile Ala Lys Asp Ile Ser
    1730                1735                1740
Ile Ser Cys Gln Pro Cys Leu Phe Ser Gly Ser Val Asn Ser Ser Asp
```

-continued

```
            1745                1750                1755                1760
        Val Cys Gln Gly Arg Leu Gly Asp Cys Trp Phe Leu Ser Ala Val Ala
                    1765                1770                1775
        Val Leu Thr Glu Met Ser Arg Ile Ser Glu Val Ile Ile Thr Pro Glu
                    1780                1785                1790
        Tyr Asn Asp Glu Gly Ile Tyr Thr Val Arg Phe Cys Ile Gln Gly Glu
                    1795                1800                1805
        Trp Val Ala Val Val Asp Asp Trp Ile Pro Cys Glu Ser Pro Gly
                    1810                1815                1820
        Lys Pro Ala Phe Ala Thr Ser Arg Lys Gln Asn Glu Leu Trp Val Ser
        1825                1830                1835                1840
        Ile Leu Glu Lys Ala Tyr Ala Lys Leu His Gly Ser Tyr Glu Ala Leu
                    1845                1850                1855
        Glu Gly Gly Leu Val Gln Asp Ala Leu Val Asp Leu Thr Gly Gly Ala
                    1860                1865                1870
        Gly Glu Glu Ile Asp Met Arg Ser Pro Gln Ala Gln Leu Asp Leu Ala
                    1875                1880                1885
        Ser Gly Arg Leu Trp Ser Gln Leu Leu His Phe Lys Gln Glu Gly Phe
                    1890                1895                1900
        Leu Leu Gly Ala Gly Ser Pro Ser Gly Ser Asp Ala His Ile Ser Ser
        1905                1910                1915                1920
        Ser Gly Ile Val Gln Gly His Ala Tyr Ser Ile Leu Gln Val Arg Glu
                    1925                1930                1935
        Val Asp Gly His Lys Leu Ile Gln Ile Arg Asn Pro Trp Ala Asn Glu
                    1940                1945                1950
        Val Glu Trp Asn Gly Pro Trp Ser Asp Ser Ser Pro Glu Trp Thr Glu
                    1955                1960                1965
        Arg Met Lys His Lys Leu Met His Val Pro Gln Ser Lys Asn Gly Val
                    1970                1975                1980
        Phe Trp Met Ser Trp Gln Asp Phe Gln Ile His Phe Arg Ser Ile Tyr
        1985                1990                1995                2000
        Val Cys Arg Val Tyr Pro Pro Glu Met Arg Tyr Ser Val His Gly Gln
                    2005                2010                2015
        Trp Arg Gly Tyr Asn Ala Gly Gly Cys Gln Asp Tyr Asp Ser Trp His
                    2020                2025                2030
        Gln Asn Pro Gln Tyr Arg Leu Arg Val Thr Gly Arg Asp Ala Leu Tyr
                    2035                2040                2045
        Pro Val His Val Phe Ile Thr Leu Thr Gln Gly Val Gly Phe Ser Arg
                    2050                2055                2060
        Lys Thr Asn Gly Phe Arg Asn Tyr Gln Ser Ser His Asp Ser Ser Met
        2065                2070                2075                2080
        Phe Tyr Ile Gly Met Arg Ile Leu Lys Thr Gln Gly Cys Arg Ala Ala
                    2085                2090                2095
        Tyr Asn Ile Tyr Met His Glu Ser Ala Gly Gly Thr Asp Tyr Val Asn
                    2100                2105                2110
        Ser Arg Glu Ile Ser Cys Glu Leu Val Leu Asp Pro Tyr Pro Lys Gly
                    2115                2120                2125
        Tyr Thr Ile Val Pro Thr Thr Ile His Pro Gly Glu Glu Ala Pro Phe
                    2130                2135                2140
        Val Leu Ser Val Phe Ser Lys Ala Ser Ile Arg Leu Glu Ala Val
        2145                2150                2155
```

<210> SEQ ID NO 25

-continued

```
<211> LENGTH: 25411
<212> TYPE: DNA
<213> ORGANISM: zea mays
<220> FEATURE:
<221> NAME/KEY: CDS
<222> LOCATION: (2682)...(23733)
<223> OTHER INFORMATION: dek1/calpain genomic DNA from Mo17
<220> FEATURE:
<221> NAME/KEY: misc_feature
<222> LOCATION: (1)...(25411)
<223> OTHER INFORMATION: n = A,T,C or G

<400> SEQUENCE: 25
accgttggtg gaggctgact gtcgtatggt gcaccggaca gtccggtgca caccggacat     60
gtccggtgca ccagccacgt caccaatgcc gttggattcc aaccgttgga gcttctgtct    120
tctgggcccg cctggatgtc cggtgcacac cggacatgta ctgttcaatg tccggtgcgc    180
cagtatgggc gtgcctgact tctgcgcgct tctggcgcgc attgaatgcg cctgcaggtg    240
accgttggcg cgaagtagcc gttgctccgc agttgcaccg gacagtccgg tgtacaccgg    300
acatgtccgg tgaattatag cggagcagct gctgcgcgtt cccgaggctg gcgagttccg    360
gaggccgctc ttccttggag caccggacac tgtccggtgt acaccagaca gtccggtgaa    420
ttatagcgga gtgcctctgg aaattcccga aggtgtcaag tttgagttgg agtcctctgg    480
tgcaccggac actgtccggt gtacaccgga cagttcggtg ccccagacc agaggtgcct     540
tcggttgcct ctttgctcct tgttgaatc caaaacttat ctttttattg gctgagtgtg     600
aacctttttac acatgtataa tctatacact tgggcaaact agttagtcca attatttgtg   660
ttgggtattt caaccaccaa aattatttag gaactaggtg taagcctaat tcctttcac    720
atgcgcacct tgttgaccgc acgccacctc caccaaggcc gccgcccca cgaccacacg    780
ccgccactcc gctgcggtcc cccgaaggct ccctccccga dactgccctc cacctcgcgt    840
gcctcgttga cgagtggcct catgtcgtgg ggtccgtgcg cttgaccgcg agccgagttt    900
cgcttcgaca tcatttcgga cggctcgcag atgttgtcct ccatctcata acagtatgac    960
acacatttgt ataaaagtta ttgtggtatt ataggtttcc gttgcaacac acggacactc   1020
acctagtaaa ttgtagaatg caaagcgagc actacaacat aaaatcttta ttattagagc   1080
acggaaaaca atttttaacg aatatctttt ttatgcgtaa caatgtttct gtttcacata   1140
aaccactgtc cagcataaaa atatttcatg ttcacttcaa aaatcacaat acaaataaaa   1200
acgtttctac tttaggaaaa tattattatg gctttatgcc attttttttg gcttgtgaaa   1260
ttatatgtta ctgtaaaaat gcttccgatt taatagaaaa atggtggacc tcaataaaac   1320
atataaaaat ttatgttttt gctactctct ctatcccaaa ttaaaattta ttttagcttt   1380
tatcggattc atacattagt tatatatata tatataggtt cgtaatcatc catatgaact   1440
gaatatagaa atatagagct aaaactactt ttatttaagg ggatgaggga gtatatttta   1500
atttcgttat tatctaaaat caatgttgta ctgacttcca agaagaacta taaaaatttt   1560
aaaaataaaa aataataaat aaatttccga agaaatgaaa caaaccgccc tgtagagccc   1620
gtgcgggtgc gcccaacaac cccttccgct gccttcccac ttccgtccgc agtccgctgc   1680
attgctcgcg tcgcgtgtgt tctgtctgtc actctcgccc agtcgccctc ctcttgctct   1740
ccgacgactg gtgggctgcc gctgccgccg ccgccgccct acgccaggtg ctgaggcttt   1800
catcggtctc ttcgtcggtg tctttgccgg cgtcgagcac ccgccaggta ctgccacggt   1860
cctacccctt ctcttcccct catgctgtgc gaggctgagc accgaaaccc taacctcttt   1920
agctatttga caagcctcct accttcgaag cttttgcaaa aattattggg tgtacatgtg   1980
```

```
tacacccatg tccctttact ggttccgccc ccgtaaagac taagctgaaa ccatggaaac    2040
aaattcagga atttcgagtt atatctaata gcattgatgg aattaacatc aagtcgatca    2100
caaggaagct aatttctagt ttccccatgc acaagcaacc caacccgtct ttgagtaatt    2160
tctaatctgt atcaaacatt gaggctacat atctggtaga tcccttttgt tgtgtctgga    2220
agcagatttg aactggcatg gatgtagacc gttaaaggtg gtaccaagca aaatggactt    2280
gttaatacat tcttgtgtgc ataaacttac catttcttac tagaaggaat agtcaaatta    2340
tctccaatta aacctaattc aaaacagttc aatgtaatgg agccaacttg ttgattatta    2400
agtcaccaaa ttacataggt ggagataaac tttggggagt tttaactgat ggcctgtttg    2460
gtacatgcca atgctctgta tatggtaaca cactaggcat ttgctagtta ctactaggat    2520
tagccaaatc attatcatat ttcttgggat ctgtgaattg gttacttaac actgaactgc    2580
atgctcgagt gtcatttagt gctctttgct cttatgttgt accttttctt gcaggctatc    2640 catgatttt gcctacaaaa ggtgattgaa aagggggag g atg gaa ggg gag gga    2696
                                           Met Glu Gly Glu Gly
                                            1               5 cac cac gga gtt gtt ttg gca tgc agc atc tgt ggg ttc ctc ttc gct    2744
His His Gly Val Val Leu Ala Cys Ser Ile Cys Gly Phe Leu Phe Ala
             10                  15                  20 gtc ctt agc cct ttc agc ttt tgg gtt tta tgg gct gtg aat tgg cgg    2792
Val Leu Ser Pro Phe Ser Phe Trp Val Leu Trp Ala Val Asn Trp Arg
         25                  30                  35 cca tgg agg tta tac agg tat gct gca gaa gtt tta tat ctt tct ctc    2840
Pro Trp Arg Leu Tyr Arg Tyr Ala Ala Glu Val Leu Tyr Leu Ser Leu
     40                  45                  50 tcg ggc tca act aat att tta ctt ttt tgt tgt tgt ctg tta tct cgt    2888
Ser Gly Ser Thr Asn Ile Leu Leu Phe Cys Cys Cys Leu Leu Ser Arg
 55                  60                  65 ttg tat tct gtc ggt tct cac taa aac tgc atg cct ttt ctt tgt aca    2936
Leu Tyr Ser Val Gly Ser His  *  Asn Cys Met Pro Phe Leu Cys Thr
 70                  75                  80 att gac tac cat aaa caa agc agg aaa ccc att ttt tgt ttt tgt att    2984
Ile Asp Tyr His Lys Gln Ser Arg Lys Pro Ile Phe Cys Phe Cys Ile
 85                  90                  95                 100 agg gat att aga tct tcg ctt cct ata ttt ctt tgt tca ctt ttg caa    3032
Arg Asp Ile Arg Ser Ser Leu Pro Ile Phe Leu Cys Ser Leu Leu Gln
                105                 110                 115 ggt cta tat cta taa tcg cat act ttt agt ttc ata gtg aaa tgg ctg    3080
Gly Leu Tyr Leu  *  Ser His Thr Phe Ser Phe Ile Val Lys Trp Leu
            120                 125                 130 tgc cat ttt cat aca atc tat aaa aac tgt ttt tta tat aca ggc gaa    3128
Cys His Phe His Thr Ile Tyr Lys Asn Cys Phe Leu Tyr Thr Gly Glu
            135                 140                 145 agg gcc tct agc tga att ggt tag gtg gtc tga gta gca ctt ctc agg    3176
Arg Ala Ser Ser  *  Ile Gly  *  Val Val  *  Val Ala Leu Leu Arg
        150                 155                     160 tcc tgg ggt cga ctc ccc gtg gga gcg aat ttt agg ctg tgg tta aaa    3224
Ser Trp Gly Arg Leu Pro Val Gly Ala Asn Phe Arg Leu Trp Leu Lys
                165                 170                 175 aaa atc ctc tcg tct gtc cca cgt caa agc ata ggt cta agg ctc ggc    3272
Lys Ile Leu Ser Ser Val Pro Arg Gln Ser Ile Gly Leu Arg Leu Gly
                180                 185                 190 ccc ggt cgc ggt cgt tct gac atg ggc ttc gat gcc gct gtg tat ggg    3320
Pro Gly Arg Gly Arg Ser Asp Met Gly Phe Asp Ala Ala Val Tyr Gly
        195                 200                 205
```

-continued

| | | | | | | | | | | | | | | | |
|---|---|---|---|---|---|---|---|---|---|---|---|---|---|---|---|
| tgg | ggc | agg | ggt | ttg | ggg | gtt | ttc | tcg | acc | tgt | gta | aaa | agg | tct | tct | 3368 |
| Trp | Gly | Arg | Gly | Leu | Gly | Val | Phe | Ser | Thr | Cys | Val | Lys | Arg | Ser | Ser | |
| 210 | | | | 215 | | | | | 220 | | | | | | | |

| tct | taa | tac | aat | act | tgg | ggg | ctg | tct | tac | ccc | ccg | cag | gtc | gag | ttt | 3416 |
| Ser | * | Tyr | Asn | Thr | Trp | Gly | Leu | Ser | Tyr | Pro | Pro | Gln | Val | Glu | Phe | |
| 225 | | | | | 230 | | | | | 235 | | | | | | |

| tct | tat | ata | cag | cta | tgt | gag | aga | cct | cta | agt | atc | cat | cta | gtt | ctt | 3464 |
| Ser | Tyr | Ile | Gln | Leu | Cys | Glu | Arg | Pro | Leu | Ser | Ile | His | Leu | Val | Leu | |
| 240 | | | | | 245 | | | | | 250 | | | | | 255 | |

| gga | tat | gtt | gtt | cca | caa | tgc | aag | tca | att | ggg | gaa | att | aac | act | tca | 3512 |
| Gly | Tyr | Val | Val | Pro | Gln | Cys | Lys | Ser | Ile | Gly | Glu | Ile | Asn | Thr | Ser | |
| | | | | 260 | | | | | 265 | | | | | 270 | | |

| ata | gtt | cat | tta | ttg | caa | tat | ctc | tgt | tct | ata | gcc | ctg | ttc | tat | act | 3560 |
| Ile | Val | His | Leu | Leu | Gln | Tyr | Leu | Cys | Ser | Ile | Ala | Leu | Phe | Tyr | Thr | |
| | | | 275 | | | | | 280 | | | | | 285 | | | |

| cga | tag | agc | cat | aga | ggt | tga | gtt | gtc | ata | gta | tgc | atc | cta | ttt | ggg | 3608 |
| Arg | * | Ser | His | Arg | Gly | * | Val | Val | Ile | Val | Cys | Ile | Leu | Phe | Gly | |
| | | | 290 | | | | | 295 | | | | | 300 | | | |

| aca | cag | gtg | gta | gga | tgg | cct | gat | tgt | tac | gcc | cca | tag | tcc | gac | cag | 3656 |
| Thr | Gln | Val | Val | Gly | Trp | Pro | Asp | Cys | Tyr | Ala | Pro | * | Ser | Asp | Gln | |
| | | | 305 | | | | | 310 | | | | | 315 | | | |

| ctc | gag | tga | act | aca | cat | ttc | cac | caa | ccc | act | tac | act | ttc | atc | ctc | 3704 |
| Leu | Glu | * | Thr | Thr | His | Phe | His | Gln | Pro | Thr | Tyr | Thr | Phe | Ile | Leu | |
| | | | | 320 | | | | | 325 | | | | | 330 | | |

| act | tca | tgt | aaa | aat | ggt | taa | gct | agt | gtt | agt | ggc | atg | aac | ttt | aga | 3752 |
| Thr | Ser | Cys | Lys | Asn | Gly | * | Ala | Ser | Val | Ser | Gly | Met | Asn | Phe | Arg | |
| | | | 335 | | | | | 340 | | | | | 345 | | | |

| aac | ctt | ata | tga | taa | tct | aat | cca | ccc | tta | caa | agc | aat | gtg | ggt | ata | 3800 |
| Asn | Leu | Ile | * | * | Ser | Asn | Pro | Pro | Leu | Gln | Ser | Asn | Val | Gly | Ile | |
| | | | | | 350 | | | | | 355 | | | | | 360 | |

| aac | ccc | agc | aat | ctc | aca | tca | aca | cac | aac | ata | ggc | cac | cat | ggt | tta | 3848 |
| Asn | Pro | Ser | Asn | Leu | Thr | Ser | Thr | His | Asn | Ile | Gly | His | His | Gly | Leu | |
| | | | | 365 | | | | | 370 | | | | | 375 | | |

| aat | tcg | aac | tgg | gcc | agt | tgt | cac | act | gat | gtt | atc | aac | tat | ccc | ttt | 3896 |
| Asn | Ser | Asn | Trp | Ala | Ser | Cys | His | Thr | Asp | Val | Ile | Asn | Tyr | Pro | Phe | |
| | | | 380 | | | | | 385 | | | | | 390 | | | |

| ggt | ttt | gtg | act | gcg | tgg | ttt | atg | tgc | att | gtg | gac | tta | act | tat | att | 3944 |
| Gly | Phe | Val | Thr | Ala | Trp | Phe | Met | Cys | Ile | Val | Asp | Leu | Thr | Tyr | Ile | |
| | | | 395 | | | | | 400 | | | | | 405 | | | |

| gtg | gac | tgt | gaa | gtg | gag | ggt | tag | tag | gtt | tgg | tat | gag | taa | cac | tgt | 3992 |
| Val | Asp | Cys | Glu | Val | Glu | Gly | * | * | Val | Trp | Tyr | Glu | * | His | Cys | |
| | 410 | | | | | 415 | | | | | | | | 420 | | |

| aca | cca | tca | tac | ttt | ctg | gtt | ctg | tca | aac | act | ctg | ttt | cat | gta | taa | 4040 |
| Thr | Pro | Ser | Tyr | Phe | Leu | Val | Leu | Ser | Asn | Thr | Leu | Phe | His | Val | * | |
| | | | | 425 | | | | | 430 | | | | | 435 | | |

| act | tgt | tac | taa | cct | tgg | tga | tta | gcg | agg | acg | atc | tct | cca | tta | gag | 4088 |
| Thr | Cys | Tyr | * | Pro | Trp | * | Leu | Ala | Arg | Thr | Ile | Ser | Pro | Leu | Glu | |
| | | | | 440 | | | | | 445 | | | | | 450 | | |

| gag | ata | atc | ttt | tac | tat | ata | aag | cgt | cag | ttc | cta | tgg | ttt | cac | ggt | 4136 |
| Glu | Ile | Ile | Phe | Tyr | Tyr | Ile | Lys | Arg | Gln | Phe | Leu | Trp | Phe | His | Gly | |
| | | | | 455 | | | | | 460 | | | | | 465 | | |

| ttc | aca | gtc | gtc | atg | tgt | tag | caa | caa | atc | tct | act | ata | taa | aac | acc | 4184 |
| Phe | Thr | Val | Val | Met | Cys | * | Gln | Gln | Ile | Ser | Thr | Ile | * | Asn | Thr | |
| | | | | 470 | | | | | 475 | | | | | 480 | | |

| agt | ttc | cat | ggt | tcc | acg | gtc | gtt | gtg | ccg | tgc | gtc | acc | ctt | ccc | ctt | 4232 |
| Ser | Phe | His | Gly | Ser | Thr | Val | Val | Val | Pro | Cys | Val | Thr | Leu | Pro | Leu | |
| | | | | 485 | | | | | 490 | | | | | 495 | | |

| tct | gct | tta | tgc | aaa | aat | tgt | gca | caa | atg | ggg | gtt | tga | acc | ttg | gtt | 4280 |
| Ser | Ala | Leu | Cys | Lys | Asn | Cys | Ala | Gln | Met | Gly | Val | * | Thr | Leu | Val | |
| | | | | 500 | | | | | 505 | | | | | 510 | | |

-continued

| | | | | | | | | | | | | | | | |
|---|---|---|---|---|---|---|---|---|---|---|---|---|---|---|---|
| gtt | ggc | tcc | aca | ttc | aca | ccc | acc | taa | cca | aca | gaa | cac | aca | tat | ttt | 4328 |
| Val | Gly | Ser | Thr | Phe | Thr | Pro | Thr | * | Pro | Thr | Glu | His | Thr | Tyr | Phe |
| | | | 515 | | | | | 520 | | | | | 525 | | |

```
gtt ggc tcc aca ttc aca ccc acc taa cca aca gaa cac aca tat ttt     4328
Val Gly Ser Thr Phe Thr Pro Thr  *  Pro Thr Glu His Thr Tyr Phe
            515                 520                 525 tgt gtt tta tta aaa caa agt cta ccc ata tga tat ata gaa acc gta     4376
Cys Val Leu Leu Lys Gln Ser Leu Pro Ile  *  Tyr Ile Glu Thr Val
            530                 535                 540 gca atg cac gac atc tga cta gta ata tat aga gca cct gat gaa tcg     4424
Ala Met His Asp Ile  *  Leu Val Ile Tyr Arg Ala Pro Asp Glu Ser
            545                 550                 555 tat gac cac tta aca gaa ata tgg ctt tga agt ttg aac ttc tgc cgt     4472
Tyr Asp His Leu Thr Glu Ile Trp Leu  *  Ser Leu Asn Phe Cys Arg
            560                 565                 570 gtt atg tgt tta cca gaa aaa gtt acc tta aat act gat gtt aaa ttt     4520
Val Met Cys Leu Pro Glu Lys Val Thr Leu Asn Thr Asp Val Lys Phe
            575                 580                 585 agc tat tat ttt atg ctt att tat tta tat ttt att gtg acc act tgc     4568
Ser Tyr Tyr Phe Met Leu Ile Tyr Leu Tyr Phe Ile Val Thr Thr Cys
            590                 595                 600 cct gac tat tgg gtt gtc tca ttt ctg tct caa tct gtt aac ttt ttt     4616
Pro Asp Tyr Trp Val Val Ser Phe Leu Ser Gln Ser Val Asn Phe Phe
            605                 610                 615 cct tct gtt ttg tga cac agt tgg ata tat gca agg aaa tgg cca aca     4664
Pro Ser Val Leu  *  His Ser Trp Ile Tyr Ala Arg Lys Trp Pro Thr
620                 625                 630 tat gtt caa gga cct caa ttg agc aca ctt tgc agc ctt ttg aca ctt     4712
Tyr Val Gln Gly Pro Gln Leu Ser Thr Leu Cys Ser Leu Leu Thr Leu
635                 640                 645                 650 tgt gca tgg ctt gtt gtc att tcc cct ata gca gtt ctg ctc gca tgg     4760
Cys Ala Trp Leu Val Val Ile Ser Pro Ile Ala Val Leu Leu Ala Trp
            655                 660                 665 gga agc gtc ctt att gct ctt ctg gaa agg aat ata att ggt tta gct     4808
Gly Ser Val Leu Ile Ala Leu Leu Glu Arg Asn Ile Ile Gly Leu Ala
            670                 675                 680 gtt ata atg acg ggt gtt gct ttg ctc ctg tca ttc tac tct ata atg     4856
Val Ile Met Thr Gly Val Ala Leu Leu Leu Ser Phe Tyr Ser Ile Met
            685                 690                 695 ctc tgg tgg aga aca caa tgg caa agc tca agt atg tta tct ttg ctt     4904
Leu Trp Trp Arg Thr Gln Trp Gln Ser Ser Ser Met Leu Ser Leu Leu
    700                 705                 710 tat ctt gat taa cct agc gtt tat ttc tct tgg caa ctg gat cct ata     4952
Tyr Leu Asp  *  Pro Ser Val Tyr Phe Ser Trp Gln Leu Asp Pro Ile
715                 720                 725 tat ata tat ata tat ata tat cta tat aca tac ata cat ata tat ata     5000
Tyr Ile Tyr Ile Tyr Ile Tyr Leu Tyr Thr Tyr Ile His Ile Tyr Ile
730                 735                 740                 745 tag aga gag ata tcc aca ctt aat ttc tgg tca tgg ctt cat gaa taa     5048
 *  Arg Glu Ile Ser Thr Leu Asn Phe Trp Ser Trp Leu His Glu  *
        750                 755 aaa ttt tga ccg aca gag gag gaa cta ggt tta tga att aat ttt ttt     5096
Lys Phe  *  Pro Thr Glu Glu Glu Leu Gly Leu  *  Ile Asn Phe Phe
760                 765                 770 gat caa cat acg agg agt ggc att gta aat aag aag aaa tag gca acc     5144
Asp Gln His Thr Arg Ser Gly Ile Val Asn Lys Lys Lys  *  Ala Thr
    775                 780                 785 aga ttc gag cct aag aag act cgg atc tgg gtg gtg gtg ggg ttg tgc     5192
Arg Phe Glu Pro Lys Lys Thr Arg Ile Trp Val Val Val Gly Leu Cys
    790                 795                 800 att gag act tcc cac caa cta agg tag gcc caa ttc ttg tgg ggt tca     5240
Ile Glu Thr Ser His Gln Leu Arg  *  Ala Gln Phe Leu Trp Gly Ser
```

```
                    805                 810                 815
tgg tct gat att ttg aaa ttt ggt gtt cac cta taa tat tca cca aga      5288
Trp Ser Asp Ile Leu Lys Phe Gly Val His Leu  *  Tyr Ser Pro Arg
820                 825                 830 aat tta tta cct cag aaa ttt gaa tta taa aga ata ctg tta caa aac      5336
Asn Leu Leu Pro Gln Lys Phe Glu Leu  *  Arg Ile Leu Leu Gln Asn
835                 840                 845 atg ttt ttc cgc atg aaa gct gtg tgc cat tat att aag aag aag tgg      5384
Met Phe Phe Arg Met Lys Ala Val Cys His Tyr Ile Lys Lys Lys Trp
850                 855                 860                 865 aga ttt aga aac cct cta ccc tca ccc caa aat aag tta cgt atc agc      5432
Arg Phe Arg Asn Pro Leu Pro Ser Pro Gln Asn Lys Leu Arg Ile Ser
                    870                 875                 880 aca tca ttt aaa aca ttt cta aaa tgc gat tta taa atg ttt tca gta      5480
Thr Ser Phe Lys Thr Phe Leu Lys Cys Asp Leu  *  Met Phe Ser Val
                    885                 890                 895 gtt gtc act gtc att att gat ctt gtt gtg tta act aat gac atg ttt      5528
Val Val Thr Val Ile Ile Asp Leu Val Val Leu Thr Asn Asp Met Phe
                    900                 905                 910 att gca gag gct gtt gct tac ctt ctc ctt ctg gca gta ggc ctg cta      5576
Ile Ala Glu Ala Val Ala Tyr Leu Leu Leu Leu Ala Val Gly Leu Leu
                    915                 920                 925 tgt gcc tac gac ttt tgt gct att tat gtg aca gct ggt gct agt gct      5624
Cys Ala Tyr Asp Phe Cys Ala Ile Tyr Val Thr Ala Gly Ala Ser Ala
930                 935                 940 tcc gag ctt aat tct cca tca ggg ttc ttc ttc ggg gtg tct gta ata      5672
Ser Glu Leu Asn Ser Pro Ser Gly Phe Phe Phe Gly Val Ser Val Ile
945                 950                 955                 960 tca ttg gcc atc aat atg ctt ttt ata tgt aaa ata ctg ttt aat ggt      5720
Ser Leu Ala Ile Asn Met Leu Phe Ile Cys Lys Ile Leu Phe Asn Gly
                    965                 970                 975 aaa gct tct gtt ttc tgt ttt tca ctt gtc tgt caa tat gtt taa ctc      5768
Lys Ala Ser Val Phe Cys Phe Ser Leu Val Cys Gln Tyr Val  *  Leu
                    980                 985                 990 atc atg att aac ttc act ttc ttg cgc att tta tgc aca gta agt gga      5816
Ile Met Ile Asn Phe Thr Phe Leu Arg Ile Leu Cys Thr Val Ser Gly
                    995                 1000                1005 ttt gat gtt gat gaa tat gtg cgg agg tca tac aaa ttt gcc tat tct      5864
Phe Asp Val Asp Glu Tyr Val Arg Arg Ser Tyr Lys Phe Ala Tyr Ser
                    1010                1015                1020 gac tgt gtt gaa gtg gct cct gtt tca tgc tct cct gag cca ccg gat      5912
Asp Cys Val Glu Val Ala Pro Val Ser Cys Ser Pro Glu Pro Pro Asp
                    1025                1030                1035 cct agt gaa tta tac atg aca aaa tcc agc agg taa att gac ttc tat      5960
Pro Ser Glu Leu Tyr Met Thr Lys Ser Ser Arg  *  Ile Asp Phe Tyr
1040                1045                1050 ttt ttc cta tca tac aat ctt gta act tgt ata cct aat tat tta tca      6008
Phe Phe Leu Ser Tyr Asn Leu Val Thr Cys Ile Pro Asn Tyr Leu Ser
1055                1060                1065                1070 ata ctg ttt tac tag taa ttt ttt tga gga atg ggt ttt gcg cat tat      6056
Ile Leu Phe Tyr  *   *  Phe Phe  *  Gly Met Gly Phe Ala His Tyr
                         1075                1080 atg tcc act ggc aaa atc agg agt gta gct tta ata aag ttt cca gct      6104
Met Ser Thr Gly Lys Ile Arg Ser Val Ala Leu Ile Lys Phe Pro Ala
1085                1090                1095 acg ctc act gga tag att tag tga ctg gaa ttt aag aat agt aga gaa      6152
Thr Leu Thr Gly  *  Ile  *   *  Leu Glu Phe Lys Asn Ser Arg Glu
1100                1105                1110 ggc cca aaa ctt att att ttt tca cta ttg tgt ttt tgg tct gtg tgc      6200
```

-continued

| | | |
|---|---|---|
| Gly Pro Lys Leu Ile Ile Phe Ser Leu Leu Cys Phe Trp Ser Val Cys<br>   1115      1120      1125 | | |
| atg atg tgc ttg gat tta tat ggt tat att gtg gaa tgg tgg gag tgc<br>Met Met Cys Leu Asp Leu Tyr Gly Tyr Ile Val Glu Trp Trp Glu Cys<br>   1130      1135      1140 | | 6248 |
| taa att cta tcc ata ctt gtg ctt cca act caa ata agt cac atg ttt<br>\* Ile Leu Ser Ile Leu Val Leu Pro Thr Gln Ile Ser His Met Phe<br>   1145      1150      1155 | | 6296 |
| ctt tgt att ata ttt ttc ttt atc att ttg aga aaa tgt tca cag ctt<br>Leu Cys Ile Ile Phe Phe Phe Ile Ile Leu Arg Lys Cys Ser Gln Leu<br>1160      1165      1170      1175 | | 6344 |
| cta acc tgg taa tgc agg gtc aag cat tta ggg ctt ctc tac att agc<br>Leu Thr Trp \* Cys Arg Val Lys His Leu Gly Leu Leu Tyr Ile Ser<br>         1180      1185      1190 | | 6392 |
| tct ctg ctt gtg ctt gtt ggt tat tcc atc ttg tac ggt ctt acg tca<br>Ser Leu Leu Val Leu Val Gly Tyr Ser Ile Leu Tyr Gly Leu Thr Ser<br>   1195      1200      1205 | | 6440 |
| aaa gaa gct cgt tgg ttg ggt gct tta act tca gtt gca gtt gtt atc<br>Lys Glu Ala Arg Trp Leu Gly Ala Leu Thr Ser Val Ala Val Val Ile<br>   1210      1215      1220 | | 6488 |
| ctt ggt aac gtt ttt tct tcc ttg cat cat tga att ttc act ctg tat<br>Leu Gly Asn Val Phe Ser Ser Leu His His \* Ile Phe Thr Leu Tyr<br>   1225      1230      1235 | | 6536 |
| ctg ttt ctt gac ctc tta ttt tgc ttt cta cag act gga atc tgg gct<br>Leu Phe Leu Asp Leu Leu Phe Cys Phe Leu Gln Thr Gly Ile Trp Ala<br>   1240      1245      1250 | | 6584 |
| tat gtt cat tta gat ttg agc ttc tta aaa gta gga tga tag tgt tat<br>Tyr Val His Leu Asp Leu Ser Phe Leu Lys Val Gly \*  \* Cys Tyr<br>   1255      1260      1265 | | 6632 |
| ttg tgg ctg gaa cat caa ggg ctt tcc ttg tat cct ttg gag tgc att<br>Leu Trp Leu Glu His Gln Gly Leu Ser Leu Tyr Pro Leu Glu Cys Ile<br>   1270      1275      1280 | | 6680 |
| act ggt ttg tat tca ata ttc atc tct ttc ttt gta ttg ata aac att<br>Thr Gly Leu Tyr Ser Ile Phe Ile Ser Phe Phe Val Leu Ile Asn Ile<br>   1285      1290      1295 | | 6728 |
| tgg gac cta gta ttc ttc tgc ctc ttt gct aac tag ctg tta cat tag<br>Trp Asp Leu Val Phe Phe Cys Leu Phe Ala Asn \* Leu Leu His \*<br>1300      1305      1310 | | 6776 |
| gta cct tgg cca ttg cat cag cta tgc ttt tgt agc atc tgt gct ttt<br>Val Pro Trp Pro Leu His Gln Leu Cys Phe Cys Ser Ile Cys Ala Phe<br>   1315      1320      1325 | | 6824 |
| atc tgc tgc tgt ttc ttc ctg gct ttc tat ttc aaa ccc ctc agt tgc<br>Ile Cys Cys Cys Phe Phe Leu Ala Phe Tyr Phe Lys Pro Leu Ser Cys<br>1330      1335      1340      1345 | | 6872 |
| aag gat aga cgc cct aag aag tac agt aat aaa gct acg aga ggg att<br>Lys Asp Arg Arg Pro Lys Lys Tyr Ser Asn Lys Ala Thr Arg Gly Ile<br>   1350      1355      1360 | | 6920 |
| tcg aag aaa agg aca aaa tag ttc ttc aaa ttc atc aga agg ctg tgg<br>Ser Lys Lys Arg Thr Lys \* Phe Phe Lys Phe Ile Arg Arg Leu Trp<br>   1365      1370      1375 | | 6968 |
| ctc tag tgt gaa gcg tag tag cgg tag tgt tga agc tgg tca aaa tgg<br>Leu \* Cys Glu Ala \*  \* Arg \* Cys \* Ser Trp Ser Lys Trp<br>   1380           1385 | | 7016 |
| taa tgc aac gga ttc tat gta cag aag caa ctc aca aag cga tgg tgt<br>\* Cys Asn Gly Phe Tyr Val Gln Lys Gln Leu Thr Lys Arg Trp Cys<br>   1390      1395      1400 | | 7064 |
| caa ttg gag cag tat tcc ttt tga tcg atc aaa cag ttg tca aga agg<br>Gln Leu Glu Gln Tyr Ser Phe \* Ser Ile Lys Gln Leu Ser Arg Arg<br>   1405      1410      1415 | | 7112 |

| | | |
|---|---|---|
| ccg gag ctc tga caa gaa cat aga tag tgc acg tgc aag ctt agc tca<br>Pro Glu Leu * Gln Glu His Arg * Cys Thr Cys Lys Leu Ser Ser<br>　　　1420　　　　　　　　　1425　　　　　　　　1430 | | 7160 |
| tcg gag taa ttc atg ctt atc tgc tgt cca aga ctc tga aac cgc tgt<br>Ser Glu * Phe Met Leu Ile Cys Cys Pro Arg Leu * Asn Arg Cys<br>　　　　　　1435　　　　　　　　1440　　　　　　　　1445 | | 7208 |
| tgt ttc agt aga tag gca tgg aga tcc cac tac ttc act tgt ttg ttc<br>Cys Phe Ser Arg * Ala Trp Arg Ser His Tyr Phe Thr Cys Leu Phe<br>　　　　　　　　1450　　　　　　　1455　　　　　　　　1460 | | 7256 |
| tag cag tgg ttt gga aag tca tgg ctg tga gcc tag tgg atc agc cac<br>* Gln Trp Phe Gly Lys Ser Trp Leu * Ala * Trp Ile Ser His<br>　　　　　　　1465　　　　　　　　　　　　　1470 | | 7304 |
| cac ctc agg taa tca aca gct att gga ttt gaa cct ggc agc aat att<br>His Leu Arg * Ser Thr Ala Ile Gly Phe Glu Pro Gly Ser Asn Ile<br>　　　1475　　　　　　　　　1480　　　　　　　　1485 | | 7352 |
| tca gga cag att aaa tga tcc aag gat ttc atc tat gct aaa aaa gaa<br>Ser Gly Gln Ile Lys * Ser Lys Asp Phe Ile Tyr Ala Lys Lys Glu<br>　　　1490　　　　　　　　　1495　　　　　　　　1500 | | 7400 |
| cgg tgg act tgg aga tgt aga act ggc taa tct tct tca gga taa agg<br>Arg Trp Thr Trp Arg Cys Arg Thr Gly * Ser Ser Ser Gly * Arg<br>　　　1505　　　　　　　　1510　　　　　　　　　1515 | | 7448 |
| act aga tcc aaa ttt ttc ata cat gct gaa aga caa agt tat gga tcc<br>Thr Arg Ser Lys Phe Phe Ile His Ala Glu Arg Gln Ser Tyr Gly Ser<br>　　　1520　　　　　　　　　1525　　　　　　　　1530 | | 7496 |
| acg tat ttt ggc ttt gct aca gag gag cag ctt gga tgc aga tag aga<br>Thr Tyr Phe Gly Phe Ala Thr Glu Glu Gln Leu Gly Cys Arg * Arg<br>　　　1535　　　　　　　　　1540　　　　　　　　1545 | | 7544 |
| gca tca aga tga cgt aga tgt cac agc tac tga ttc aga tag att gga<br>Ala Ser Arg * Arg Arg Cys His Ser Tyr * Phe Arg * Ile Gly<br>　　　1550　　　　　　　　　1555　　　　　　　　1560 | | 7592 |
| tac cac tat tgc aaa tca gat ttc tct gtc aga aga act aag gag aag<br>Tyr His Tyr Cys Lys Ser Asp Phe Ser Val Arg Arg Thr Lys Glu Lys<br>　　　　　　1565　　　　　　　　1570　　　　　　　　1575 | | 7640 |
| tgg tct aga aaa atg gtt gaa cat ttc aag gct aat att cca tca ttt<br>Trp Ser Arg Lys Met Val Glu His Phe Lys Ala Asn Ile Pro Ser Phe<br>　　　1580　　　　　　　　　1585　　　　　　　　1590 | | 7688 |
| agc tgg atc tcc aat acg tgc ttt tat tgt ttt cac agt aat gtt tat<br>Ser Trp Ile Ser Asn Thr Cys Phe Tyr Cys Phe His Ser Asn Val Tyr<br>　　　1595　　　　　　　　　1600　　　　　　　　1605 | | 7736 |
| aat aga gac tgc tac tgt ggc tat cta tcg acc aga gac cat caa ggt<br>Asn Arg Asp Cys Tyr Cys Gly Tyr Leu Ser Thr Arg Asp His Gln Gly<br>1610　　　　　　　　1615　　　　　　　　1620　　　　　　　　1625 | | 7784 |
| gat aaa tgc aac aca tga aca ggt aaa ttg ttg cag tac aat gta att<br>Asp Lys Cys Asn Thr * Thr Gly Lys Leu Leu Gln Tyr Asn Val Ile<br>　　　　　　1630　　　　　　　　1635　　　　　　　　1640 | | 7832 |
| cct ttg aaa gtt tgg cta tta gtt tga cca ata gag att ttc tta att<br>Pro Leu Lys Val Trp Leu Leu Val * Pro Ile Glu Ile Phe Leu Ile<br>　　　　　　　　1645　　　　　　　1650　　　　　　　　1655 | | 7880 |
| tgg cag ttt gaa ttt ggt ttc tcg ata ctg ctt ctg tca cca gtt gtc<br>Trp Gln Phe Glu Phe Gly Phe Ser Ile Leu Leu Leu Ser Pro Val Val<br>　　　　　　　　　1660　　　　　　　1665　　　　　　　　1670 | | 7928 |
| tgc tcc att atg gca ttc att tgg tct ctg cgt gct gaa gaa atg ttg<br>Cys Ser Ile Met Ala Phe Ile Trp Ser Leu Arg Ala Glu Glu Met Leu<br>　　　1675　　　　　　　　　1680　　　　　　　　1685 | | 7976 |
| atg aca tcc aag ccc cag aag gtg atg cac taa aat aaa aat agt ttc<br>Met Thr Ser Lys Pro Gln Lys Val Met His * Asn Lys Asn Ser Phe<br>　　　　　　1690　　　　　　　　1695　　　　　　　　1700 | | 8024 |
| act att tgg cat acc tgg ata tga ttg ttt tat taa tat gac aac ttt<br>Thr Ile Trp His Thr Trp Ile * Leu Phe Tyr * Tyr Asp Asn Phe<br>　　　　　　　1705　　　　　　　　1710　　　　　　　　1715 | | 8072 |

| | | |
|---|---|---|
| tta ccc ata tcg aaa cta gtg cct cat act gtt ttt ggt tga aca ttt<br>Leu Pro Ile Ser Glu Leu Val Pro His Thr Val Phe Gly * Thr Phe<br>1720                          1725                     1730 | 8120 |
| act atg act agc ttc tgt gta gtg taa cat gaa tat agt taa tga gag<br>Thr Met Thr Ser Phe Cys Val Val * His Glu Tyr Ser * * Glu<br>          1735                        1740 | 8168 |
| aaa aaa atc atg tct caa atg tag taa ttc ctt acc agt ctg cac ata<br>Lys Lys Ile Met Ser Gln Met * * Phe Leu Thr Ser Leu His Ile<br>1745                          1750                        1755 | 8216 |
| taa tcg gtt tgt agt aga aaa ata ttt ttt ttt tac ctg gga gct agg<br>* Ser Val Cys Ser Arg Lys Ile Phe Phe Phe Tyr Leu Gly Ala Arg<br>      1760                        1765                     1770 | 8264 |
| tgc cta ggt atg ctg aaa cat cta atc ctg tca aca aaa att tct tat<br>Cys Leu Gly Met Leu Lys His Leu Ile Leu Ser Thr Lys Ile Ser Tyr<br>1775                        1780                       1785 | 8312 |
| att atg aca tgt gct tta tct gcc att aga tac aat gcc gta tta gtt<br>Ile Met Thr Cys Ala Leu Ser Ala Ile Arg Tyr Asn Ala Val Leu Val<br>1790                        1795                       1800                     1805 | 8360 |
| gct att gtt tta ata tta ctg gtc tca act ata aca act tgc ctt tct<br>Ala Ile Val Leu Ile Leu Leu Val Ser Thr Ile Thr Thr Cys Leu Ser<br>                  1810                        1815                       1820 | 8408 |
| ttc agt atg gtt tca ttg cat ggc tac tga gca cat gtg ttg gtt tgt<br>Phe Ser Met Val Ser Leu His Gly Tyr * Ala His Val Leu Val Cys<br>1825                        1830                       1835 | 8456 |
| ttc tct ctt tct taa ggt aca cat act tct ctt gca tct gaa aca tat<br>Phe Ser Leu Ser * Gly Thr His Thr Ser Leu Ala Ser Glu Thr Tyr<br>                  1840                        1845                       1850 | 8504 |
| tta ctg tta tag ttt tag tta ata cta att aac ctt ttg tgc ctt agt<br>Leu Leu Leu * Phe * Leu Ile Leu Ile Asn Leu Leu Cys Leu Ser<br>                  1855                        1860                       1865 | 8552 |
| tgg tta tct att tac aca aag aca taa agt ttt ata tgc ata agc aat<br>Trp Leu Ser Ile Tyr Thr Lys Thr * Ser Phe Ile Cys Ile Ser Asn<br>                  1870                        1875                       1880 | 8600 |
| aca ttg ttt caa tat act ccc tcc agt ttg caa ata gct gaa gtt ttt<br>Thr Leu Phe Gln Tyr Thr Pro Ser Ser Leu Gln Ile Ala Glu Val Phe<br>                  1885                        1890                       1895 | 8648 |
| ttt tac gac aac atg gtc aac ata gct ttg acc act act ttg tat tag<br>Phe Tyr Asp Asn Met Val Asn Ile Ala Leu Thr Thr Thr Leu Tyr *<br>               1900                        1905                       1910 | 8696 |
| agt ata aat gaa tat ctt aac taa ggg atg tgt gtg tgc ctg tgt ggg<br>Ser Ile Asn Glu Tyr Leu Asn * Gly Met Cys Val Cys Leu Cys Gly<br>              1915                        1920                       1925 | 8744 |
| tgt gca cgt gca tgt ggg tgt ctg ttg taa ggg ctc tta acc tac ata<br>Cys Ala Arg Ala Cys Gly Cys Leu Leu * Gly Leu Leu Thr Tyr Ile<br>               1930                        1935                       1940 | 8792 |
| gtt ctc ctg cat gtt caa gaa aaa aga aag tac ttt tca aaa aaa tgt<br>Val Leu Leu His Val Gln Glu Lys Arg Lys Tyr Phe Ser Lys Lys Cys<br>              1945                        1950                       1955 | 8840 |
| atg tat aat tgt atg tga tct tca gtt ttc tta act aaa tat ctt tta<br>Met Tyr Asn Cys Met * Ser Ser Val Phe Leu Thr Lys Tyr Leu Leu<br>            1960                        1965                       1970 | 8888 |
| aaa gtt att tgt aat gat ttt ttt ttt aaa gtt tga ctc aaa cct tgt<br>Lys Val Ile Cys Asn Asp Phe Phe Phe Lys Val * Leu Lys Pro Cys<br>             1975                        1980                       1985 | 8936 |
| cca aag cgg caa gta ttt gca aac tgg tta act gga tgc ggc att cgt<br>Pro Lys Arg Gln Val Phe Ala Asn Trp Leu Thr Gly Cys Gly Ile Arg<br>            1990                        1995                       2000 | 8984 |
| ttt att tta ttt tgt ctt tta tgt cat aac ata ttg tca ttt tta gta<br>Phe Ile Leu Phe Cys Leu Leu Cys His Asn Ile Leu Ser Phe Leu Val | 9032 |

-continued

```
        2005                2010                2015
ttg tac tgt tag ttc att tat gca atg ctt tct tag ttt ttg cac aac    9080
Leu Tyr Cys  *  Phe Ile Tyr Ala Met Leu Ser  *  Phe Leu His Asn
2020                2025                2030 aaa tcg tgt gac tta tta tgt gtc tag agt ggg cca atg cag tta gtc    9128
Lys Ser Cys Asp Leu Leu Cys Val  *  Ser Gly Pro Met Gln Leu Val
2035                2040                2045 aaa gca tga aga tgt gtt ttt aga gca taa agg taa gct gcg cca aaa    9176
Lys Ala  *  Arg Cys Val Phe Arg Ala  *  Arg  *  Ala Ala Pro Lys
2050                2055                2060 tag aca tga aaa gtg tca ttg agg caa gaa aac ata atg gat tta cca    9224
 *  Thr  *  Lys Val Ser Leu Arg Gln Glu Asn Ile Met Asp Leu Pro
            2065                2070                2075 att tag ata ttt tag cac ata caa gta agc ata ttc taa ctc agc act    9272
Ile  *  Ile Phe  *  His Ile Gln Val Ser Ile Phe  *  Leu Ser Thr
                2080                2085 aga aac aga aaa tgt gaa tat ata cca ttc gtt aat tgg gaa cag aag    9320
Arg Asn Arg Lys Cys Glu Tyr Ile Pro Phe Val Asn Trp Glu Gln Lys
            2090                2095                2100 gga cct gtc aag ggc gtg gta gtt caa ggt agc tgg acc tcg gct aag    9368
Gly Pro Val Lys Gly Val Val Val Gln Gly Ser Trp Thr Ser Ala Lys
2105                2110                2115                2120 gga cct gcc aag ggc gtt caa ggt agc tgg cct tga cta agg gac ctg    9416
Gly Pro Ala Lys Gly Val Gln Gly Ser Trp Pro  *  Leu Arg Asp Leu
            2125                2130                2135 tca agg gtg ggc cgg ggg gga tca agg tag ctg gac ctc ggc tac ata    9464
Ser Arg Val Gly Arg Gly Gly Ser Arg  *  Leu Asp Leu Gly Tyr Ile
            2140                2145                2150 gtt cat agt ttt ggt ttg taa tgg tgt ggg gtt gtt ttc cta gac acc    9512
Val His Ser Phe Gly Leu  *  Trp Cys Gly Val Val Phe Leu Asp Thr
            2155                2160                2165 cta tgg tga ggg ggt gaa att aag aga gat ggg gaa gat tgg aaa aca    9560
Leu Trp  *  Gly Gly Glu Ile Lys Arg Asp Gly Glu Asp Trp Lys Thr
            2170                2175                2180 ata tgt tat tgc tta atg ttt gat cac cac cct tag aga taa ata ggc    9608
Ile Cys Tyr Cys Leu Met Phe Asp His His Pro  *  Arg  *  Ile Gly
            2185                2190 tat tgg cct cta ata acc tga ggt gga aac tcc tag aat taa ggc cag    9656
Tyr Trp Pro Leu Ile Thr  *  Gly Gly Asn Ser  *  Asn  *  Gly Gln
2195                2200                2205 aat tgg cca tgc aaa caa cat ggt cac ttt cct ctt gtc caa cgt ggt    9704
Asn Trp Pro Cys Lys Gln His Gly His Phe Pro Leu Val Gln Arg Gly
            2210                2215                2220 gat cac gct cgt cat ggt gcg gcg cgc ggt gat tgc ggc cct tgt ggt    9752
Asp His Ala Arg His Gly Ala Ala Arg Gly Asp Cys Gly Pro Cys Gly
            2225                2230                2235 gtc act agt gca ggc ttg gtg aga gta gtg ggc ccc aca aga cat ctc    9800
Val Thr Ser Ala Gly Leu Val Arg Val Val Gly Pro Thr Arg His Leu
2240                2245                2250                2255 tcc tct aca agc agc tct ttc tcg agc taa aat gaa gga tgg cac tcg    9848
Ser Ser Thr Ser Ser Ser Phe Ser Ser  *  Asn Glu Gly Trp His Ser
            2260                2265                2270 atg aag ttg tcg atg tct tcc cat att gtg gat aac aca agc tcg cct    9896
Met Lys Leu Ser Met Ser Ser His Ile Val Asp Asn Thr Ser Ser Pro
            2275                2280                2285 ttc cac tgt att aag acc cgg tgg aca tca tgg aca agg tga gtg tgt    9944
Phe His Cys Ile Lys Thr Arg Trp Thr Ser Trp Thr Arg  *  Val Cys
            2290                2295                2300 acg acg tgt ttt ggt tac cgg gca gcg gca ccg ttg tga atg atc gac    9992
```

-continued

```
Thr Thr Cys Phe Gly Tyr Arg Ala Ala Ala Pro Leu  *  Met Ile Asp
        2305                2310                    2315 aat gga ggg ggt gtt tgg tgg cct gca gac aga cta ttg aga agg cca    10040
Asn Gly Gly Gly Val Trp Trp Pro Ala Asp Arg Leu Leu Arg Arg Pro
        2320                2325                    2330 acg tgg aaa aca tca tgg agc cgt gcc tgg tgc gga aga gct agt cga    10088
Thr Trp Lys Thr Ser Trp Ser Arg Ala Trp Cys Gly Arg Ala Ser Arg
        2335                2340                    2345 atg gcg aca tcg ttg atg agt tcg gtg atg tgg ttt gcc ctg tag aag    10136
Met Ala Thr Ser Leu Met Ser Ser Val Met Trp Phe Ala Leu  *  Lys
        2350                2355                    2360 cgt ggc ttg agc ttt cct ttg gtc gtg gct ggc agg agg ctg gag ctc    10184
Arg Gly Leu Ser Phe Pro Leu Val Val Ala Gly Arg Arg Leu Glu Leu
        2365                2370                    2375 gga gac gga gtc aca acc aca ccc aat cac cca caa cgt agg ata ttg    10232
Gly Asp Gly Val Thr Thr Thr Pro Asn His Pro Gln Arg Arg Ile Leu
2380                2385                    2390                    2395 cac aat gga gct tgt cat agt ggt gct ttt gga cgg cct gcg cct gct    10280
His Asn Gly Ala Cys His Ser Gly Ala Phe Gly Arg Pro Ala Pro Ala
                2400                2405                    2410 cta ggt ggt agc gga cat tcg cta gaa att cat ttc tat ttg cca tgt    10328
Leu Gly Gly Ser Gly His Ser Leu Glu Ile His Phe Tyr Leu Pro Cys
        2415                2420                    2425 tct tgg cca tcg cca caa cct gtc tcg ttg ggt tcg tag gag tgg atg    10376
Ser Trp Pro Ser Pro Gln Pro Val Ser Leu Gly Ser  *  Glu Trp Met
        2430                2435                    2440 atg ggg tag ttg tcg cgg tct tag acc gcc tta aat gta ttg tct aga    10424
Met Gly  *  Leu Ser Arg Ser  *  Thr Ala Leu Asn Val Leu Ser Arg
        2445                2450                    2455 ggg aga aac tgt atg tgt tct ttt aga tgt act cgg ccc agg gta gcc    10472
Gly Arg Asn Cys Met Cys Ser Phe Arg Cys Thr Arg Pro Arg Val Ala
        2460                2465                    2470 ggc tag cca ccg atg ggg acg ata gcc aga gaa gcg gca cag gta cat    10520
Gly  *  Pro Pro Met Gly Thr Ile Ala Arg Glu Ala Ala Gln Val His
        2475                2480                    2485 gac gat gac acg gtt gtt cgt ctc tgt atg agc att gga act tag ttg    10568
Asp Asp Asp Thr Val Val Arg Leu Cys Met Ser Ile Gly Thr  *  Leu
        2490                2495                    2500 tct tgt gta gtt tgg cgc caa tcg gcc cat gag gcg cat gag ctc cca    10616
Ser Cys Val Val Trp Arg Gln Ser Ala His Glu Ala His Glu Leu Pro
        2505                2510                    2515 cta gga tgt gga ggt gaa gat ggg gtc aag gtt gga gac cat caa ttg    10664
Leu Gly Cys Gly Gly Glu Asp Gly Val Lys Val Gly Asp His Gln Leu
        2520                2525                    2530 ggg cat gcc atg cag gcg gac cat gtt ggt gaa gaa agc cga cgc cac    10712
Gly His Ala Met Gln Ala Asp His Val Gly Glu Glu Ser Arg Arg His
2535                2540                    2545                    2550 aga ctg aca tgt agg ggt gag cca aca aca tga agt ggt tgt agt tac    10760
Arg Leu Thr Cys Arg Gly Glu Pro Thr Thr  *  Ser Gly Cys Ser Tyr
        2555                2560                    2565 tgc aac ggt tga cca gag gat cac aag ctc gct ctt gat gcg agg caa    10808
Cys Asn Gly  *  Pro Glu Asp His Lys Leu Ala Leu Asp Ala Arg Gln
                2570                2575                    2580 ggc cta gat gaa gtc tag ctc gat gtc aga cca tac caa caa agg gag    10856
Gly Leu Asp Glu Val  *  Leu Asp Val Arg Pro Tyr Gln Gln Arg Glu
                2585                2590                    2595 ggg cac gag tag tcc aac caa atg aaa atg ttc tga ctt gta gcg ctg    10904
Gly His Glu  *  Ser Asn Gln Met Lys Met Phe  *  Leu Val Ala Leu
                2600                2605
```

```
                                                     -continued aca agt agc tcg ccc ctg gtg cat tta gtg gtg ggt gcg ctg aag ccc     10952
Thr Ser Ser Ser Pro Leu Val His Leu Val Val Gly Ala Leu Lys Pro
2610                2615                2620                2625 tcg tgg ctg tcg tca tgg aca ata gcc acc aac cct gcg agt agg gga     11000
Ser Trp Leu Ser Ser Trp Thr Ile Ala Thr Asn Pro Ala Ser Arg Gly
                    2630                2635                2640 gac gtt ggg acg att aga ggt gtg agt tgt agg cca cca tgc tgt cga     11048
Asp Val Gly Thr Ile Arg Gly Val Ser Cys Arg Pro Pro Cys Cys Arg
            2645                2650                2655 tga tgg atc agg gtg tga caa gct ggc ttg cga caa ttt tgg cgt aga     11096
 *  Trp Ile Arg Val  *  Gln Ala Gly Leu Arg Gln Phe Trp Arg Arg
                2660                2665                2670 tgg cta cca agg cta ggt tcg tgg ctt aca cct ggc gga ggc ggt cga     11144
Trp Leu Pro Arg Leu Gly Ser Trp Leu Thr Pro Gly Gly Gly Gly Arg
        2675                2680                2685 tga agt caa atc agg ggc gaa aga tgg tga gga tgg cac tgt cgt cgg     11192
 *  Ser Gln Ile Arg Gly Glu Arg Trp  *  Gly Trp His Cys Arg Arg
            2690                2695                2700 tgt tgc gcc tag aga aaa agc tga cga taa agt tca tgg tgc cgg gtt     11240
Cys Cys Ala  *  Arg Lys Ser  *  Arg  *  Ser Ser Trp Cys Arg Val
                2705                2710 tgt act cga tgg tga aat tga agc cca aca act tgc cca ccc aat gat     11288
Cys Thr Arg Trp  *  Asn  *  Ser Pro Thr Thr Cys Pro Pro Asn Asp
2715                2720                2725 gct ctg aaa acg tgg caa gac att ggt cta gga gaa att tca aac tgc     11336
Ala Leu Lys Thr Trp Gln Asp Ile Gly Leu Gly Glu Ile Ser Asn Cys
        2730                2735                2740 aag ttc tca cta gga agc gat gac acc gaa gat agg gat gcc aat ggc     11384
Lys Phe Ser Leu Gly Ser Asp Asp Thr Glu Asp Arg Asp Ala Asn Gly
2745                2750                2755                2760 gta tgg cat gca tga ggt cga tta att ctc gct tgt acg cgt cga ggg     11432
Val Trp His Ala  *  Gly Arg Leu Ile Leu Ala Cys Thr Arg Arg Gly
            2765                2770                2775 agc ggt ggg ata tgg cga cat gcc taa tga gga agg tga caa ggt gct     11480
Ser Gly Gly Ile Trp Arg His Ala  *   *  Gly Arg  *  Gln Gly Ala
                2780                2785 taa ttg gat gat cac gac cca aac ccg ttt gaa gag gcg cca cac tct     11528
 *  Leu Asp Asp His Asp Pro Asn Pro Phe Glu Glu Ala Pro His Ser
        2790                2795                2800 cgg aga ggg cta gtg ttg ggg ctg tcg taa tca ccg tct tca ggg cct     11576
Arg Arg Gly Leu Val Leu Gly Leu Ser  *  Ser Pro Ser Ser Gly Pro
2805                2810                2815 aga agg cca acc aca gga agg cgt cct tgt gaa gga gca tgg tga ggg     11624
Arg Arg Pro Thr Thr Gly Arg Arg Pro Cys Glu Gly Ala Trp  *  Gly
2820                2825                2830 gtg tcg tga ggt ggc tga tgc att gca cag gtc gaa cga cat gat gag     11672
Val Ser  *  Gly Gly  *  Cys Ile Ala Gln Val Glu Arg His Asp Glu
2835                    2840                2845 gaa ctc aga gaa cct gtt gtg tgt cca gaa cga tgt ttt gtc gac aat     11720
Glu Leu Arg Glu Pro Val Val Cys Pro Glu Arg Cys Phe Val Asp Asn
        2850                2855                2860 tgc tct tga tgc gga gat cga gct tgt tga aga act tgg cgt tgt aga     11768
Cys Ser  *  Cys Gly Asp Arg Ala Cys  *  Arg Thr Trp Arg Cys Arg
2865                2870                2875 gct agg agt ttg tcg acg acg ggt ttg ggg aag gca tcc ttc acg aca     11816
Ala Arg Ser Leu Ser Thr Thr Gly Leu Gly Lys Ala Ser Phe Thr Thr
            2880                2885                2890 atg gtg ttg agg gcc tca tag ttg aca tag aat tgc caa gag tcg tcg     11864
Met Val Leu Arg Ala Ser  *  Leu Thr  *  Asn Cys Gln Glu Ser Ser
2895                        2900                2905
```

```
gcc ttc ctg acc agg agc acc ggt gag gag aag gcg cat gag ccg tgg      11912
Ala Phe Leu Thr Arg Ser Thr Gly Glu Glu Lys Ala His Glu Pro Trp
        2910                2915                2920 tgg atc agg ccc tag gct agc atg gtg gtg cac tgg cac tcc aac tca      11960
Trp Ile Arg Pro  *  Ala Ser Met Val Val His Trp His Ser Asn Ser
        2925                2930                2935 ttc ttg tgg gtc gcc gga tag cag cgg tag ggg cag aca acc act ggt      12008
Phe Leu Trp Val Ala Gly  *  Gln Arg  *  Gly Gln Thr Thr Thr Gly
        2940                2945                2950 tgc gcc ctc aga cca tgg tga tgt ggt gct cat gag tgt gtg gtg gag      12056
Cys Ala Leu Arg Pro Trp  *  Cys Gly Ala His Glu Cys Val Val Glu
        2955                2960                2965 tcc cta ggg ctc gat gaa gac gaa gca act cgg cga gta ggg cct cca      12104
Ser Leu Gly Leu Asp Glu Asp Glu Ala Thr Arg Arg Val Gly Pro Pro
        2970                2975                2980 tgt ggt tgt tgc tcg tgc agg tct gca aag ctg cgt tgg gcg gtc cag      12152
Cys Gly Cys Cys Ser Cys Arg Ser Ala Lys Leu Arg Trp Ala Val Gln
        2985                2990                2995 cca cgc cat gcc agt tca cat gat ggt cat ggt gcc aga atg aca ccg      12200
Pro Arg His Ala Ser Ser His Asp Gly His Gly Ala Arg Met Thr Pro
3000                3005                3010                3015 tga tag cgc caa aat ccc ata gga tgg gcg cga gtg aca tga gcc att      12248
 *   *  Arg Gln Asn Pro Ile Gly Trp Ala Arg Val Thr  *  Ala Ile
                3020                3025 ggg tcc cca aca tga tgt cgc aac cta cca gca aat agg tca ctt gaa      12296
Gly Ser Pro Thr  *  Cys Arg Asn Leu Pro Ala Asn Arg Ser Leu Glu
        3030                3035                3040 aag ctt tgt cgt cga tgt aca aag gcg tcc cac gga aca cgc cta gat      12344
Lys Leu Cys Arg Arg Cys Thr Lys Ala Ser His Gly Thr Arg Leu Asp
        3045                3050                3055 agg gaa cac act cac cat ttg cca tga tta cct tca tgt tgt cat ggt      12392
Arg Glu His Thr His His Leu Pro  *  Leu Pro Ser Cys Cys His Gly
3060                3065                3070 tct gag cct cct tgg ctt tga aat tgt atg tgt gtt tat ttg gta aac      12440
Ser Glu Pro Pro Trp Leu  *  Asn Cys Met Cys Val Tyr Leu Val Asn
3075                3080                3085 ata gag gtc tag ttt tgt taa aaa aaa tta aat atc tct ttc tga att      12488
Ile Glu Val  *  Phe Cys  *  Lys Lys Leu Asn Ile Ser Phe  *  Ile
3090                3095                3100 att aaa aaa tac tct ttg tat atc tag cga ata tct tta tga ctt tgg      12536
Ile Lys Lys Tyr Ser Leu Tyr Ile  *  Arg Ile Ser Leu  *  Leu Trp
        3105                3110                3115 aag ctt tat gtc tgc aat caa tta atg cat ttt att ggt gaa aca tat      12584
Lys Leu Tyr Val Cys Asn Gln Leu Met His Phe Ile Gly Glu Thr Tyr
        3120                3125                3130 ctg cat ttt ggt cta aaa gtc atc ttt ttt tgc tct gca gca aat cat      12632
Leu His Phe Gly Leu Lys Val Ile Phe Phe Cys Ser Ala Ala Asn His
        3135                3140                3145 cag tta tat tgg gcc tgt ctc tca cgg tac cac tta tgg tgg ctt gcc      12680
Gln Leu Tyr Trp Ala Cys Leu Ser Arg Tyr His Leu Trp Trp Leu Ala
        3150                3155                3160 tct cat ttg ctg ttc cca tat gga tac gca atg gtt aca gtt tct gga      12728
Ser His Leu Leu Phe Pro Tyr Gly Tyr Ala Met Val Thr Val Ser Gly
3165                3170                3175                3180 ttc ctg gaa ggg agt ttg caa atc gtg aaa atg tta gtc aag ctc cag      12776
Phe Leu Glu Gly Ser Leu Gln Ile Val Lys Met Leu Val Lys Leu Gln
            3185                3190                3195 gag aga aag agg ttt gtt gtt cgg ttc ttt ata aga ttg caa cta cca      12824
Glu Arg Lys Arg Phe Val Val Arg Phe Phe Ile Arg Leu Gln Leu Pro
```

-continued

```
                3200                3205                3210
act agg gat ttt ctg gtc aca tgc ata agt gta acg ttg atc tat tca     12872
Thr Arg Asp Phe Leu Val Thr Cys Ile Ser Val Thr Leu Ile Tyr Ser
            3215                3220                3225 atc tct ttg ttt agt cag aag gag ata ctg aat tgc gag ttt gcg acc     12920
Ile Ser Leu Phe Ser Gln Lys Glu Ile Leu Asn Cys Glu Phe Ala Thr
            3230                3235                3240 cag tct aat gtt gaa aac tgg att tac ctg aat atg tct att tca tgt     12968
Gln Ser Asn Val Glu Asn Trp Ile Tyr Leu Asn Met Ser Ile Ser Cys
3245                3250                3255                3260 caa tct ttt cca tat gtg ctc gtc ata ttt gca tgg cca tgt cat gtt     13016
Gln Ser Phe Pro Tyr Val Leu Val Ile Phe Ala Trp Pro Cys His Val
                3265                3270                3275 ttt agc aca tca aat aaa atg cct aat ttg tag cac aga ttt tac taa     13064
Phe Ser Thr Ser Asn Lys Met Pro Asn Leu  *  His Arg Phe Tyr  *
            3280                3285                3290 gat tat tgt aga taa ttt aga atc gaa cta tcc aat att ggc aat taa     13112
Asp Tyr Cys Arg  *  Phe Arg Ile Glu Leu Ser Asn Ile Gly Asn  *
                3295                3300 gaa aag act tat tag tgt tgc tta ccg ttt tct ttt tct ggt ttc agc     13160
Glu Lys Thr Tyr  *  Cys Cys Leu Pro Phe Ser Phe Ser Gly Phe Ser
3305                3310                3315 ggg ctc tct ttg tta tca cca ttg ctg ttt tca ctg cat caa tta ttg     13208
Gly Leu Ser Leu Leu Ser Pro Leu Leu Phe Ser Leu His Gln Leu Leu
3320                3325                3330                3335 gcc ttg gtg caa tag tgt cag caa agc ctt tag acg ctc tag gct ata     13256
Ala Leu Val Gln  *  Cys Gln Gln Ser Leu  *  Thr Leu  *  Ala Ile
                3340                3345 aag ggt ggg atg ctg ata aga aca gct cct att ctc cct atg caa cat     13304
Lys Gly Gly Met Leu Ile Arg Thr Ala Pro Ile Leu Pro Met Gln His
3350                3355                3360 caa tgt atc ttg gat ggg cat tgt ctt caa caa ttg ctg tga tta cca     13352
Gln Cys Ile Leu Asp Gly His Cys Leu Gln Gln Leu Leu  *  Leu Pro
3365                3370                3375 cag ggt tga tac cta ttg ttg ctt ggt ttg caa cat acc ggt ttt cac     13400
Gln Gly  *  Tyr Leu Leu Leu Gly Leu Gln His Thr Gly Phe His
3380                3385                3390 ctt cat cag cta tat gtg ttg gcc tct ttg caa gta cgt tcg tct tga     13448
Leu His Gln Leu Tyr Val Leu Ala Ser Leu Gln Val Arg Ser Ser  *
3395                3400                3405 tcc ttt ttt cgg aaa aaa tac ttt aaa tat tga ata gaa gag att gca     13496
Ser Phe Phe Arg Lys Lys Tyr Phe Lys Tyr  *  Ile Glu Glu Ile Ala
3410                3415                3420 gct gtt cta att cat gct ttt ctg cag ctg ttc ttg tgt ctt ttt gcg     13544
Ala Val Leu Ile His Ala Phe Leu Gln Leu Phe Leu Cys Leu Phe Ala
3425                3430                3435                3440 gtg cat cct act ggg gag tgg taa att cac gag agg atg gtg ctc ctc     13592
Val His Pro Thr Gly Glu Trp  *  Ile His Glu Arg Met Val Leu Leu
                3445                3450                3455 taa agg ctg att tcc ttg cag cat tac ttc cct tgc ttt gca ttc cag     13640
 *  Arg Leu Ile Ser Leu Gln His Tyr Phe Pro Cys Phe Ala Phe Gln
            3460                3465                3470 cat ttt tct cac tgt tca ctg ggc ttt aca aat ggt ata aaa agg act     13688
His Phe Ser His Cys Ser Leu Gly Phe Thr Asn Gly Ile Lys Arg Thr
                3475                3480                3485 gtc ttt agc att tta ttc ccc tct gta ttt ctg atc cac tga gat caa     13736
Val Phe Ser Ile Leu Phe Pro Ser Val Phe Leu Ile His  *  Asp Gln
            3490                3495                3500 aat tgc aaa taa ttt cag gaa gga tga tga ttg gaa gat ttc tcg tgg     13784
```

| | | |
|---|---|---|
| Asn Cys Lys * Phe Gln Glu Gly * * Leu Glu Asp Phe Ser Trp<br>3505 3510 | | |
| cgt tta cct ttt tgt tgg cat ggg aat gtt gct gtt gtt tgg tgc ggt<br>Arg Leu Pro Phe Cys Trp His Gly Asn Val Ala Val Val Trp Cys Gly<br>3515 3520 3525 3530 | 13832 | |
| tgc agc tgt tat tgt cac aat cag gcc ctg gac tgt aag taa agt tta<br>Cys Ser Cys Tyr Cys His Asn Gln Ala Leu Asp Cys Lys * Ser Leu<br>3535 3540 3545 | 13880 | |
| tgt gac ctg gga cgt tag ttt tca att aca ata ggc tat aat tca cat<br>Cys Asp Leu Gly Arg * Phe Ser Ile Thr Ile Gly Tyr Asn Ser His<br>3550 3555 3560 | 13928 | |
| gtc atc ttt ata cag gtt gga gtt gct tgc ctc gta gcc att ctg ttc<br>Val Ile Phe Ile Gln Val Gly Val Ala Cys Leu Val Ala Ile Leu Phe<br>3565 3570 3575 | 13976 | |
| ctt gta ttt gtt att ggg gtc atc cac tac tgg aca tct aac aac ttc<br>Leu Val Phe Val Ile Gly Val Ile His Tyr Trp Thr Ser Asn Asn Phe<br>3580 3585 3590 | 14024 | |
| tat cta acg agg aca cag atg ctg ctt gtt tgt tcc att gct ttt ctc<br>Tyr Leu Thr Arg Thr Gln Met Leu Leu Val Cys Ser Ile Ala Phe Leu<br>3595 3600 3605 | 14072 | |
| tta gcc ttg gct gcc ttc ctg atg ggt tta ttt cac ggt gac tga tga<br>Leu Ala Leu Ala Ala Phe Leu Met Gly Leu Phe His Gly Asp * *<br>3610 3615 3620 | 14120 | |
| tct ttt ttc tat gcc cat ctg tcc ttt att tca ctt tgt tta ttg gtt<br>Ser Phe Phe Tyr Ala His Leu Ser Phe Ile Ser Leu Cys Leu Leu Val<br>3625 3630 3635 | 14168 | |
| tga gtt att gct atc att tag tct tgt att tac ttg gct tct gaa ctt<br>* Val Ile Ala Ile Ile * Ser Cys Ile Tyr Leu Ala Ser Glu Leu<br>3640 3645 3650 | 14216 | |
| tgc agg aaa gcc ttt tgt tgg agc atc tat agg tta ttt ctc att tat<br>Cys Arg Lys Ala Phe Cys Trp Ser Ile Tyr Arg Leu Phe Leu Ile Tyr<br>3655 3660 3665 | 14264 | |
| att tct tct cac tgg aag ggc ttt gac tgt aag ttt tgt cat gca cta<br>Ile Ser Ser His Trp Lys Gly Phe Asp Cys Lys Phe Cys His Ala Leu<br>3670 3675 3680 | 14312 | |
| aga taa ctg ttg ctg atc gct ttc tag ttc tca gta tac tgt aga att<br>Arg * Leu Leu Leu Ile Ala Phe * Phe Ser Val Tyr Cys Arg Ile<br>3685 3690 3695 | 14360 | |
| ttc ttc taa tgc tga atg gtg tgc cct tct cag gtc ctt cta tca ccg<br>Phe Phe * Cys * Met Val Cys Pro Ser Gln Val Leu Leu Ser Pro<br>3700 3705 3710 | 14408 | |
| cca atc gta gtg tat tcg cca aga gta ttg cct gta tac gtt tat gat<br>Pro Ile Val Val Tyr Ser Pro Arg Val Leu Pro Val Tyr Val Tyr Asp<br>3715 3720 3725 | 14456 | |
| gct cat gca gac tct gct aaa aat gtt agg tac aag tat att ctt tct<br>Ala His Ala Asp Ser Ala Lys Asn Val Arg Tyr Lys Tyr Ile Leu Ser<br>3730 3735 3740 | 14504 | |
| cgt gct acc tgt ttg cct ttt ttg agt tca ggg ttg gtc ata atg tat<br>Arg Ala Thr Cys Leu Pro Phe Leu Ser Ser Gly Leu Val Ile Met Tyr<br>3745 3750 3755 3760 | 14552 | |
| tct tat ctc tgt tct gtc cca tcc taa aag ttc tag ttt cag ttg aga<br>Ser Tyr Leu Cys Ser Val Pro Ser * Lys Phe * Phe Gln Leu Arg<br>3765 3770 | 14600 | |
| aca tgt tct aat gtt gtc ttt ttt ttt aca gct atg cct ttc tta ttc<br>Thr Cys Ser Asn Val Val Phe Phe Phe Thr Ala Met Pro Phe Leu Phe<br>3775 3780 3785 3790 | 14648 | |
| tgt atg gga ttg cat tag caa ctg aag ttt ggg gtg tta ttg cta gtc<br>Cys Met Gly Leu His * Gln Leu Lys Phe Gly Val Leu Leu Leu Val<br>3795 3800 3805 | 14696 | |

```
                                                         -continued taa taa tga atc cac cat ttg ttg ggg ctg gcg ttt ctg cta cta ctc    14744
 *   *   *  Ile His His Leu Leu Gly Leu Ala Phe Leu Leu Leu Leu
                     3810                3815 ttg taa ttg ctt tca gtt ttg ctg ttt ctc gac cct gcc tga ctc tta    14792
Leu  *  Leu Leu Ser Val Leu Leu Phe Leu Asp Pro Ala  *  Leu Leu
        3820                3825                3830 agg ttg gta att tgc tgc agc tag tac tag taa gat ttc gta ctc ctt    14840
Arg Leu Val Ile Cys Cys Ser  *  Tyr  *   *  Asp Phe Val Leu Leu
        3835                3840                            3845 ttt tta tat gat taa tat aaa ata aat aca tat ctt ttt taa aaa tca    14888
Phe Leu Tyr Asp  *  Tyr Lys Ile Asn Thr Tyr Leu Phe  *  Lys Ser
                    3850                3855 atc aga tga tgg agg atg cag ttc att ttc tca gca agg ata cag ttg    14936
Ile Arg  *  Trp Arg Met Gln Phe Ile Phe Ser Ala Arg Ile Gln Leu
3860            3865                3870 tgc aag cga tgt cac ggt ctg cta ata aag tat gtt tta tat ttg tat    14984
Cys Lys Arg Cys His Gly Leu Leu Ile Lys Tyr Val Leu Tyr Leu Tyr
3875            3880                3885                3890 tat taa gat att caa cat aag tta ttt gtg tgc atg ctt tta tac att    15032
Tyr  *  Asp Ile Gln His Lys Leu Phe Val Cys Met Leu Leu Tyr Ile
                    3895                3900                3905 tct cca ttt tta gtt aga aac att tca acc agt ctc tag ttt gct tgc    15080
Ser Pro Phe Leu Val Arg Asn Ile Ser Thr Ser Leu  *  Phe Ala Cys
                3910                3915                3920 tta tta gca tct cgt gct gag atc tag ttc aga act gtt cat gct taa    15128
Leu Leu Ala Ser Arg Ala Glu Ile  *  Phe Arg Thr Val His Ala  *
                3925                3930 tct gac gca tcc aag ttc tgt cat agt cct gtc att gtg tac att ggg    15176
Ser Asp Ala Ser Lys Phe Cys His Ser Pro Val Ile Val Tyr Ile Gly
3935            3940                3945                3950 atc tgt gta aat tac tat cga caa aat att tta aat cta tct cag aag    15224
Ile Cys Val Asn Tyr Tyr Arg Gln Asn Ile Leu Asn Leu Ser Gln Lys
        3955                3960                3965 ctc gtc act tgt agg att gcc att gca att aga atc ctt tga aat aat    15272
Leu Val Thr Cys Arg Ile Ala Ile Ala Ile Arg Ile Leu  *  Asn Asn
        3970                3975                        3980 tca caa tgt ttg gat ctg tac atg aca gta tgt ttt tcc aga cta gaa    15320
Ser Gln Cys Leu Asp Leu Tyr Met Thr Val Cys Phe Ser Arg Leu Glu
        3985                3990                3995 atg cta tat ctg gga ctt act cag cac ctc aga ggt ccg caa gtt ctg    15368
Met Leu Tyr Leu Gly Leu Thr Gln His Leu Arg Gly Pro Gln Val Leu
        4000                4005                4010 ctg ctc ttt tgg ttg gag atc ctg ctc tta cat tgg aca ggg ctg gga    15416
Leu Leu Phe Trp Leu Glu Ile Leu Leu Leu His Trp Thr Gly Leu Gly
        4015                4020                4025 act ttg tgc ttc cta ggg ctg atg tta tga aac tga gag atc gtt tga    15464
Thr Leu Cys Phe Leu Gly Leu Met Leu  *  Asn  *  Glu Ile Val  *
4030                4035                        4040 gaa atg aag aaa ttg ctg cag gat ctt tct tat gtg gag taa aag att    15512
Glu Met Lys Lys Leu Leu Gln Asp Leu Ser Tyr Val Glu  *  Lys Ile
        4045                4050                4055 gtt tac taa ttt gcc ccc agt ccc tgt caa aca tag att atc gga gga    15560
Val Tyr  *  Phe Ala Pro Ser Pro Cys Gln Thr  *  Ile Ile Gly Gly
            4060                4065                4070 ata tgt gtg ccc atg cac gta ttt tgg ctt tgg aag aag caa ttg ata    15608
Ile Cys Val Pro Met His Val Phe Trp Leu Trp Lys Lys Gln Leu Ile
        4075                4080                4085 cgg aat ggg tgt ata tgt ggg aca aat ttg gtg gtt att tac ttc tgt    15656
Arg Asn Gly Cys Ile Cys Gly Thr Asn Leu Val Val Ile Tyr Phe Cys
        4090                4095                4100
```

-continued

```
tgc ttg gat tga ctg cca aag ctg aac aaa tac agg tat gta ttt ggt     15704
Cys Leu Asp  *  Leu Pro Lys Leu Asn Lys Tyr Arg Tyr Val Phe Gly
    4105            4110                4115 atg ttg tac aat ttt tta gac ccc aat ttg tta gcg att aat ggt gtg     15752
Met Leu Tyr Asn Phe Leu Asp Pro Asn Leu Leu Ala Ile Asn Gly Val
    4120            4125                4130 aag cat ttc tgt att gtt tca gga tga agt tcg tct aag act ctt ttt     15800
Lys His Phe Cys Ile Val Ser Gly  *  Ser Ser Lys Thr Leu Phe
4135            4140                4145 gga tag cat agg cct ttc cga ttt gag tgc caa aga aat taa gaa atg     15848
Gly  *  His Arg Pro Phe Arg Phe Glu Cys Gln Arg Asn  *  Glu Met
4150            4155                4160 gat gcc tga aga tcg gag gca att tga gct tat tca aga aag gta ttt     15896
Asp Ala  *  Arg Ser Glu Ala Ile  *  Ala Tyr Ser Arg Lys Val Phe
    4165            4170                4175 ttt gtc tgt tac tat tag tta tac tac tga agg gca ggc cta gtg cag     15944
Phe Val Cys Tyr Tyr  *  Leu Tyr Tyr  *  Arg Ala Gly Leu Val Gln
    4180            4185                4190 tgg tga gag ctg tct tac caa gtc acc agg tcg cag gtt cga agc agt     15992
Trp  *  Glu Leu Ser Tyr Gln Val Thr Arg Ser Gln Val Arg Ser Ser
        4195            4200                4205 ccc tcc gca ttt gcg ggg gaa agg ctt gtc tca gtt tag ggg gtg ttt     16040
Pro Ser Ala Phe Ala Gly Glu Arg Leu Val Ser Val  *  Gly Val Phe
            4210            4215                4220 ggc ttc can nnn nnn nnn nnn nnn ncc cta gac ccc aac tca tgc       16088
Gly Phe Xaa Xaa Xaa Xaa Xaa Xaa Xaa Leu Asp Pro Asn Ser Cys
            4225            4230                4235 agg agc cta tgg cac tga gtc tgc ctc ctt tta caa tta gtt ata cca     16136
Arg Ser Leu Trp His  *  Val Cys Leu Leu Leu Gln Leu Val Ile Pro
            4240            4245                4250 tta ttg tat gac aca taa aat aaa aat cat att gca gcc att gct att     16184
Leu Leu Tyr Asp Thr  *  Asn Lys Asn His Ile Ala Ala Ile Ala Ile
            4255            4260                4265 cct ttg tta ttt gtg tct aca gct aca taa ggg aaa aag aaa tgg aag     16232
Pro Leu Leu Phe Val Ser Thr Ala Thr  *  Gly Lys Lys Lys Trp Lys
            4270            4275                4280 agg agg ctt tga tgc aaa gac gag agg aag aag gga agg gaa gag aaa     16280
Arg Arg Leu  *  Cys Lys Asp Glu Arg Lys Lys Gly Arg Glu Glu Lys
            4285            4290                4295 gga gga ggg cat tgc tag aga gag agg agc gaa aat gga agg agc tcg     16328
Gly Gly Gly His Cys  *  Arg Glu Arg Ser Glu Asn Gly Arg Ser Ser
            4300            4305                4310 aaa tat cat tgc ttt ctt cca ttc cta ata ctg aag gca ggg atg ctg     16376
Lys Tyr His Cys Phe Leu Pro Phe Leu Ile Leu Glu Ala Gly Met Leu
            4315            4320                4325 cag cta tgg cag cag ctg tca gag ctg ttg gag gtg att ctg ccc tgg     16424
Gln Leu Trp Gln Gln Leu Ser Glu Leu Leu Glu Val Ile Leu Pro Trp
            4330            4335                4340 aag att ctt ttg caa gag ata ggg tct ctt caa tag cca atc aca tac     16472
Lys Ile Leu Leu Gln Glu Ile Gly Ser Leu Gln  *  Pro Ile Thr Tyr
4345            4350            4355 gaa agg cac aat tgg ctc ggc gag cag aac agg tta tgt cct ctg att     16520
Glu Arg His Asn Trp Leu Gly Glu Gln Asn Arg Leu Cys Pro Leu Ile
4360            4365                4370            4375 acc ctt aat ttc atc aag tta tga aac aca cct gcc atc att tga gcg     16568
Thr Leu Asn Phe Ile Lys Leu  *  Asn Thr Pro Ala Ile Ile  *  Ala
            4380                4385 ctg tag aac tgt aat tta tct ttg agt gca tgt ttt ttt ttc gaa cac     16616
Leu  *  Asn Cys Asn Leu Ser Leu Ser Ala Cys Phe Phe Phe Glu His
```

-continued

| | |
|---|---|
| 4390            4395            4400 | |
| aca gga gag ctg cgt ata att ata tta aga aga aga gga cca aag gtt<br>Thr Gly Glu Leu Arg Ile Ile Ile Leu Arg Arg Arg Gly Pro Lys Val<br>4405            4410            4415            4420 | 16664 |
| aca gaa aac ccg aaa gaa ata gcc agg ttt tag gca tct aag gag cct<br>Thr Glu Asn Pro Lys Glu Ile Ala Arg Phe  *  Ala Ser Lys Glu Pro<br>      4425            4430            4435 | 16712 |
| aga acc tag cct aaa aac tac caa tct ttg agt gca tgt tag gca taa<br>Arg Thr  *  Pro Lys Asn Tyr Gln Ser Leu Ser Ala Cys  *  Ala  *<br>         4440            4445 | 16760 |
| aca tcc ctg ggt att tgt tgt ctg ttt tgt gtc tca tct gga gct ggt<br>Thr Ser Leu Gly Ile Cys Cys Leu Phe Cys Val Ser Ser Gly Ala Gly<br>      4450            4455            4460 | 16808 |
| aat ctt aca aca aat aag tat tcc ctc cag tca ata ata gtt tat gct<br>Asn Leu Thr Thr Asn Lys Tyr Ser Leu Gln Ser Ile Ile Val Tyr Ala<br>4465            4470            4475            4480 | 16856 |
| atg aca ctt cag aaa aaa gca tat gga tac atg tat ctg agg gca aat<br>Met Thr Leu Gln Lys Lys Ala Tyr Gly Tyr Met Tyr Leu Arg Ala Asn<br>         4485            4490            4495 | 16904 |
| aag cag caa aat aac cat ttt ggc ctc taa tta att gaa gct gtg atg<br>Lys Gln Gln Asn Asn His Phe Gly Leu  *  Leu Ile Glu Ala Val Met<br>      4500            4505            4510 | 16952 |
| cac atg aac tgc aaa ggt cag gcc caa gca acg tga gta cta gtg ata<br>His Met Asn Cys Lys Gly Gln Ala Gln Ala Thr  *  Val Leu Val Ile<br>      4515            4520            4525 | 17000 |
| tta cta gtt gaa tgg agt ttc ctg gaa ttg cat taa cga ccg ttg ggg<br>Leu Leu Val Glu Trp Ser Phe Leu Glu Leu His  *  Arg Pro Leu Gly<br>      4530            4535            4540 | 17048 |
| agg taa tgg act aat ggg gtc acc cat atc ctg tcc ccg cac act atc<br>Arg  *  Trp Thr Asn Gly Val Thr His Ile Leu Ser Pro His Thr Ile<br>         4545            4550            4555 | 17096 |
| cat tcc caa att atc caa tcc aaa tat tga ggg taa tac tta tga ata<br>His Ser Gln Ile Ile Gln Ser Lys Tyr  *  Gly  *  Tyr Leu  *  Ile<br>         4560            4565 | 17144 |
| aac taa tgg gta ata gat gga gct aat ccc tgt cgc tgc ctc cac tac<br>Asn  *  Trp Val Ile Asp Gly Ala Asn Pro Cys Arg Cys Leu His Tyr<br>4570            4575            4580 | 17192 |
| aac gct aca tcg ttg gtg cgg gct tgc tgt cca ccg cct tcc tcc agg<br>Asn Ala Thr Ser Leu Val Arg Ala Cys Cys Pro Pro Pro Ser Ser Arg<br>4585            4590            4595            4600 | 17240 |
| gac tcg tca atc ggg tac acc gaa tga ggt gct gag cac cga cat ggt<br>Asp Ser Ser Ile Gly Tyr Thr Glu  *  Gly Ala Glu His Arg His Gly<br>         4605            4610            4615 | 17288 |
| atc aga gtt tga tgt gct gcc aac gtg gat gtg cca tgc cgg ggc cag<br>Ile Arg Val  *  Cys Ala Ala Asn Val Asp Val Pro Cys Arg Gly Gln<br>         4620            4625            4630 | 17336 |
| cac ccg tgc tgt agt cgc ccc gtg gtc ctg ggt tga ata tgt gga tag<br>His Pro Cys Cys Ser Arg Pro Val Val Leu Gly  *  Ile Cys Gly  *<br>      4635            4640 | 17384 |
| gaa ggg gga agg gga ttc tag tag cag cag gtt gag cgc aag ccg caa<br>Glu Gly Gly Arg Gly Phe  *   *  Gln Gln Val Glu Arg Lys Pro Gln<br>4645            4650            4655 | 17432 |
| tga tgg ctc gac ttg aat ctg agg ata tgc agg ggg att cta gaa gca<br> *  Trp Leu Asp Leu Asn Leu Arg Ile Cys Arg Gly Ile Leu Glu Ala<br>         4660            4665            4670 | 17480 |
| gca ggt tga gtg caa gct gca atg ctg gct gct gag ctg tgg cgc tgg<br>Ala Gly  *  Val Gln Ala Ala Met Leu Ala Ala Glu Leu Trp Arg Trp<br>      4675            4680            4685 | 17528 |
| tgg tgt cag gcg tga tgg cca gtg tgt gca agc cta gtg gag gcc aaa | 17576 |

```
                                                          -continued

Trp Cys Gln Ala  *  Trp Pro Val Cys Ala Ser Leu Val Glu Ala Lys
    4690              4695                4700 ttg ccc ccc tct ttg cca taa ctc ctt tat atg gtt gct act ttg cca    17624
Leu Pro Pro Ser Leu Pro  *  Leu Leu Tyr Met Val Ala Thr Leu Pro
    4705                4710                4715 agg aat ctg cat gtc ctc atg cat gcg agc acg cct ttc cct atc cac    17672
Arg Asn Leu His Val Leu Met His Ala Ser Thr Pro Phe Pro Ile His
    4720                4725                4730 att agt tgc cta ttc ctt ggc cag caa ttg tca agc ttt cat att ata    17720
Ile Ser Cys Leu Phe Leu Gly Gln Gln Leu Ser Ser Phe His Ile Ile
4735            4740                4745                4750 ctt tga tat tgt cct cat gta gcc act aaa ttt cca ctc ctt gat tct    17768
Leu  *  Tyr Cys Pro His Val Ala Thr Lys Phe Pro Leu Leu Asp Ser
                4755                4760                4765 acc tca ccc tgc gcc act gat tgt gtg ccc tgt gca tcc gcg gtg gta    17816
Thr Ser Pro Cys Ala Thr Asp Cys Val Pro Cys Ala Ser Ala Val Val
                4770                4775                4780 gcg ccc agg ggc aag aac ata ttg cga ggt gct tag ggt cgg gac agg    17864
Ala Pro Arg Gly Lys Asn Ile Leu Arg Gly Ala  *  Gly Arg Asp Arg
            4785                4790                4795 gac aaa tag ggt cga gat caa gtc gac gta ctt atg cct ggt gag ggt    17912
Asp Lys  *  Gly Arg Asp Gln Val Asp Val Leu Met Pro Gly Glu Gly
                4800                4805                4810 ggt gga cct aga cac cga tgg cca ctt cga cga ggg att cat ctg cct    17960
Gly Gly Pro Arg His Arg Trp Pro Leu Arg Arg Gly Ile His Leu Pro
            4815                4820                4825 tac atg cca cat atg cca cac ttc ttg acc ttg act ggc atg aca cca    18008
Tyr Met Pro His Met Pro His Phe Leu Thr Leu Thr Gly Met Thr Pro
    4830                4835                4840 agg gta tgt gac cac aca tgt ctt cat ggc gtg gcc att gac cac acg    18056
Arg Val Cys Asp His Thr Cys Leu His Gly Val Ala Ile Asp His Thr
    4845                4850                4855 ctt gtc gga gtt ctt gag gaa ggg cgt cgg tgg atc ttt gtt gat tgg    18104
Leu Val Gly Val Leu Glu Glu Gly Arg Arg Trp Ile Phe Val Asp Trp
4860            4865                4870                4875 tca aaa gca gtt gtc aat gta ttg ttt gtt tgt ggg tag gtg gtt acc    18152
Ser Lys Ala Val Val Asn Val Leu Phe Val Cys Gly  *  Val Val Thr
                4880                4885                4890 cgg taa tat cca cta ata tca tac ctg tac cca tga tta gat ggg taa    18200
Arg  *  Tyr Pro Leu Ile Ser Tyr Leu Tyr Pro  *  Leu Asp Gly  *
                4895                4900 ttg ata ccc tcc cta aac tct aca tgt att ggt ttg tgt acg tgt att    18248
Leu Ile Pro Ser Leu Asn Ser Thr Cys Ile Gly Leu Cys Thr Cys Ile
    4905                4910                4915 gga tac cta gtg gca tga tca aat cac ata ttt cat tct acc tcc atc    18296
Gly Tyr Leu Val Ala  *  Ser Asn His Ile Phe His Ser Thr Ser Ile
4920            4925                4930 cca caa aga gta gtt gtc cta agt caa aca atc tta atc taa ttt tat    18344
Pro Gln Arg Val Val Val Leu Ser Gln Thr Ile Leu Ile  *  Phe Tyr
4935            4940                4945 tga gaa aag tac cta tac tta tga att atg ata cca aat aag taa tat    18392
 *  Glu Lys Tyr Leu Tyr Leu  *  Ile Met Ile Pro Asn Lys  *  Tyr
    4950                4955                4960 taa aaa aac ctc gac ctg cgg ggg gta aga caa ccc tgg gca tta aca    18440
 *  Lys Asn Leu Asp Leu Arg Gly Val Arg Gln Pro Leu Gly Ile Thr
            4965                4970                4975 tta aga ata aga cct cac gta ggt cga gaa aac ccc tga acc ctt gcc    18488
Leu Arg Ile Arg Pro His Val Gly Arg Glu Asn Pro  *  Thr Leu Ala
    4980                4985                4990
```

```
cca ccc ata cac atc ggc atc gta gcc tat ggg aga acg acc acg gcc    18536
Pro Pro Ile His Ile Gly Ile Val Ala Tyr Gly Arg Thr Thr Thr Ala
        4995                5000                5005 agg cgt tag gcc tat gct ttg gtg tgg gac aga cga ggg gat ttt ttt    18584
Arg Arg  *  Ala Tyr Ala Leu Val Trp Asp Arg Arg Gly Asp Phe Phe
    5010                5015                5020 aac ctc acc cga agt ctg ctc cca tgg gga gtc aaa ctc aag aca tga    18632
Asn Leu Thr Arg Ser Leu Leu Pro Trp Gly Val Lys Leu Lys Thr  *
    5025                5030                5035 gga gtg cca ctc tga cca tct aac caa ctc agc tag aag aaa gac ctg    18680
Gly Val Pro Leu  *  Pro Ser Asn Gln Leu Ser  *  Lys Lys Asp Leu
    5040                5045                5050 acc ttg ccc tgc tgc ttt ttt ggc cac ctt agg gtg tta ggg tca gtt    18728
Thr Leu Pro Cys Cys Phe Phe Gly His Leu Arg Val Leu Gly Ser Val
    5055                5060                5065 taa gtt ttg ttg tat ctg ttc ttt gga cct tta ttc tct ctt aat ata    18776
 *  Val Leu Leu Tyr Leu Phe Phe Gly Pro Leu Phe Ser Leu Asn Ile
        5070                5075                5080 atg atg cac aac tct cct gcg cgt ttg aga aaa aaa gtt gat acc ttt    18824
Met Met His Asn Ser Pro Ala Arg Leu Arg Lys Lys Val Asp Thr Phe
    5085                5090                5095 ttt aca aat ttg ttc aaa cat agg ata att taa ctt agg aaa aaa cta    18872
Phe Thr Asn Leu Phe Lys His Arg Ile Ile  *  Leu Arg Lys Lys Leu
5100                5105                5110 gaa tgt cac ttt gtg gga tcg agg tag tac taa ata aga gca taa gag    18920
Glu Cys His Phe Val Gly Ser Arg  *  Tyr  *  Ile Arg Ala  *  Glu
5115                5120                5125 taa aaa tat ccc tac ctt aat atc tca aaa cct gtt gga atc aac ctt    18968
 *  Lys Tyr Pro Tyr Leu Asn Ile Ser Lys Pro Val Gly Ile Asn Leu
        5130                5135                5140 gac tag agg gag tat cat gga aaa att taa acc gct gac cac ctg gaa    19016
Asp  *  Arg Glu Tyr His Gly Lys Ile  *  Thr Ala Asp His Leu Glu
    5145                5150                5155 gcc ttc ttg ttt tgc ttt ttt agc aat gca ttg tac atg tat tct ttc    19064
Ala Phe Leu Phe Cys Phe Phe Ser Asn Ala Leu Tyr Met Tyr Ser Phe
    5160                5165                5170 tgt ttt tag tgt ttt tct cca atg ctt gta tat cta att tgt tgt gaa    19112
Cys Phe  *  Cys Phe Ser Pro Met Leu Val Tyr Leu Ile Cys Cys Glu
        5175                5180                5185 tgt gga aca gac tgg tat tcc agg cac tat atg cat act cga tga tga    19160
Cys Gly Thr Asp Trp Tyr Ser Arg His Tyr Met His Thr Arg  *   *
    5190                5195                5200 acc gag gag tac tgg tcg tca ttg tgg aga act tga ctt gtg cct ctg    19208
Thr Glu Glu Tyr Trp Ser Ser Leu Trp Arg Thr  *  Leu Val Pro Leu
    5205                5210                5215 tca aag tca aaa ggt tac ttt gtc tat tgc tgt cat ggt tca gcc tgt    19256
Ser Lys Ser Lys Gly Tyr Phe Val Tyr Cys Cys His Gly Ser Ala Cys
    5220                5225                5230 atc tgg ccc agt gtg tct ttt tgg aag tga att cca aaa ggt ttg ctg    19304
Ile Trp Pro Ser Val Ser Phe Trp Lys  *  Ile Pro Lys Gly Leu Leu
    5235                5240                5245 gga aat ctt agt ggc agg atc aga aca ggg tat gga agc tgg aca agt    19352
Gly Asn Leu Ser Gly Arg Ile Arg Thr Gly Tyr Gly Ser Trp Thr Ser
    5250                5255                5260 tgg tct tcg att agt gac taa ggg tga aag gat gac tac tgt tgc taa    19400
Trp Ser Ser Ile Ser Asp  *  Gly  *  Lys Asp Asp Tyr Cys Cys  *
    5265                5270                5275 aga gtg gaa tat tgg tgc gtc tag tat tgc aga tgg cag gta tcc cct    19448
Arg Val Glu Tyr Trp Cys Val  *  Tyr Cys Arg Trp Gln Val Ser Pro
    5280                5285                5290
```

-continued

| | |
|---|---|
| att cac aac tat tgc att atg cat agc aaa taa aat caa agg cag cca<br>Ile His Asn Tyr Cys Ile Met His Ser Lys \* Asn Gln Arg Gln Pro<br>             5295                           5300                           5305 | 19496 |
| tcc tcg ggt ttg ttg ttt tgg tac tgg cat gtg tgt tgg aac tgt gag<br>Ser Ser Gly Leu Leu Phe Trp Tyr Trp His Val Cys Trp Asn Cys Glu<br>             5310                           5315                           5320 | 19544 |
| gca gtt ggg gca tat att cta tca tga agc tct cct gct tgt tca tga<br>Ala Val Gly Ala Tyr Ile Leu Ser \* Ser Ser Pro Ala Cys Ser \*<br>             5325                           5330                           5335 | 19592 |
| aaa aaa aac taa tta tgt ttt act tac gat ggc aat ccc tga tgc agg<br>Lys Lys Asn \* Leu Cys Phe Thr Tyr Asp Gly Asn Pro \* Cys Arg<br>             5340                           5345                           5350 | 19640 |
| ttc ggt gtt ttt ata cct gtt gcg agt atg tgt gag ttt act taa agt<br>Phe Gly Val Phe Ile Pro Val Ala Ser Met Cys Glu Phe Thr \* Ser<br>             5355                           5360                           5365 | 19688 |
| ttg tac ggg att ttt tgt tga tga aca ttt ctt cta tac tcg ctt ttg<br>Leu Tyr Gly Ile Phe Cys \* \* Thr Phe Leu Leu Tyr Ser Leu Leu<br>             5370                                                 5375 | 19736 |
| aat tat tac ttg ttg ggt tca gac ctg ttc act tct gca tca taa act<br>Asn Tyr Tyr Leu Leu Gly Ser Asp Leu Phe Thr Ser Ala Ser \* Thr<br>5380                           5385                           5390 | 19784 |
| atg gtg tta ctt tag tta gac tct gat gcg aac cat att tgg aag caa<br>Met Val Leu Leu \* Leu Asp Ser Asp Ala Asn His Ile Trp Lys Gln<br>5395                           5400                           5405 | 19832 |
| tta tag ctg cca tgt aaa ttt gca ggt ggc atc ttg tca ctg taa ctt<br>Leu \* Leu Pro Cys Lys Phe Ala Gly Gly Ile Leu Ser Leu \* Leu<br>5410                           5415                           5420 | 19880 |
| tag atg ccg acc tag gtg aag caa ctt cct tca ttg atg gag ttt atg<br>\* Met Pro Thr \* Val Lys Gln Leu Pro Ser Leu Met Glu Phe Met<br>             5425                           5430                           5435 | 19928 |
| atg gat atc aga atg ggt tgc cgt tgc caa cag ata acg gta ttt ggg<br>Met Asp Ile Arg Met Gly Cys Arg Cys Gln Gln Ile Thr Val Phe Gly<br>             5440                           5445                           5450 | 19976 |
| aac ccg gaa ctg ata ttt ggg ttg gtg cta ggc cac cca tgg act tag<br>Asn Pro Glu Leu Ile Phe Gly Leu Val Leu Gly His Pro Trp Thr \*<br>             5455                           5460                           5465 | 20024 |
| atg cct ttg gta ggt cag ata gcg aag gtt ctg act caa aga tgc aga<br>Met Pro Leu Val Gly Gln Ile Ala Lys Val Leu Thr Gln Arg Cys Arg<br>             5470                           5475                           5480 | 20072 |
| tca tgg atg ctt tca tat ggg gaa gat gtc tca gtg aag atg agg tta<br>Ser Trp Met Leu Phe Tyr Gly Glu Asp Val Ser Val Lys Met Arg Leu<br>5485                           5490                           5495                           5500 | 20120 |
| ctg ttt tac ata ctg cca tgt ctc ctg ctg agt atg gat ttt ttg acc<br>Leu Phe Tyr Ile Leu Pro Cys Leu Leu Leu Ser Met Asp Phe Leu Thr<br>             5505                           5510                           5515 | 20168 |
| ttg cac ccg gcg atg ctt ggc atg gaa gtt att ctg caa ggg tat tgc<br>Leu His Pro Ala Met Leu Gly Met Glu Val Ile Leu Gln Gly Tyr Cys<br>             5520                           5525                           5530 | 20216 |
| ttt tac cta taa att ctg cac cag ttt ttt gtg atg tct tga atc gag<br>Phe Tyr Leu \* Ile Leu His Gln Phe Phe Val Met Ser \* Ile Glu<br>             5535                           5540                           5545 | 20264 |
| agg gaa tat gat att gaa tgt gtt ttt ctt atg tta ctg ttt cat tca<br>Arg Glu Tyr Asp Ile Glu Cys Val Phe Leu Met Leu Leu Phe His Ser<br>             5550                           5555                           5560 | 20312 |
| ggt gga tga ctg gga aag cga aga agc tta tga gct tta tga tca agg<br>Gly Gly \* Leu Gly Lys Arg Arg Ser Leu \* Ala Leu \* Ser Arg<br>             5565                           5570                           5575 | 20360 |
| gga tgt cga atg gga tgg aca gta ctc aag tgg tag gaa acg ccc ggt<br>Gly Cys Arg Met Gly Trp Thr Val Leu Lys Trp \* Glu Thr Pro Gly | 20408 |

-continued

|  |  |  |  |  |  |  |  |  |  |  |  |  |
|---|---|---|---|---|---|---|---|---|---|---|---|---|
| | 5580 | | | 5585 | | | | 5590 | | | | |
| aca | tga | tgc | tgt | agc | tat | tga | cct | tga | ctc | ctt | tgc | tag | gag | acc | aag | 20456 |
| Thr | * | Cys | Cys | Ser | Tyr | * | Pro | * | Leu | Leu | Cys | * | Glu | Thr | Lys | |
| | | | | 5595 | | | | | | 5600 | | | | | | |
| aaa | acc | aag | gtt | tga | gac | acg | tga | tga | agt | caa | cca | gcg | tat | gct | ttc | 20504 |
| Lys | Thr | Lys | Val | * | Asp | Thr | * | * | Ser | Gln | Pro | Ala | Tyr | Ala | Phe | |
| | | 5605 | | | | | 5610 | | | | | 5615 | | | | |
| tgt | tga | aag | ggc | tgt | cag | gga | tgc | tct | tat | cgc | gaa | agg | aga | gag | aaa | 20552 |
| Cys | * | Lys | Gly | Cys | Gln | Gly | Cys | Ser | Tyr | Arg | Glu | Arg | Arg | Glu | Lys | |
| | | | 5620 | | | | | 5625 | | | | | 5630 | | | |
| ctt | cac | tga | tca | aga | gtt | ccc | tcc | aga | aga | tcg | ttc | ttt | att | tgt | aga | 20600 |
| Leu | His | * | Ser | Arg | Val | Pro | Ser | Arg | Arg | Ser | Phe | Phe | Ile | Cys | Arg | |
| | | | | 5635 | | | | | 5640 | | | | | 5645 | | |
| tcc | gat | gaa | tcc | acc | tct | gaa | act | gca | ggt | atc | ata | tgc | aca | tct | cat | 20648 |
| Ser | Asp | Glu | Ser | Thr | Ser | Glu | Thr | Ala | Gly | Ile | Ile | Cys | Thr | Ser | His | |
| | | | | | 5650 | | | | | 5655 | | | | | 5660 | |
| gct | ctt | gtg | aaa | aat | att | ggt | taa | gtt | cct | gac | atg | ttt | taa | ttt | gtg | 20696 |
| Ala | Leu | Val | Lys | Asn | Ile | Gly | * | Val | Pro | Asp | Met | Phe | * | Phe | Val | |
| | | | | 5665 | | | | | 5670 | | | | | 5675 | | |
| agt | ttt | agg | ttg | ttt | ctg | agt | gga | tga | ggc | ctt | ctg | aca | tag | caa | agg | 20744 |
| Ser | Phe | Arg | Leu | Phe | Leu | Ser | Gly | * | Gly | Leu | Leu | Thr | * | Gln | Arg | |
| | | | | 5680 | | | | | | 5685 | | | | | | |
| aga | tat | cta | tca | gtt | gtc | agc | ctt | gct | tgt | ttt | cgg | gtt | ctg | tga | att | 20792 |
| Arg | Tyr | Leu | Ser | Val | Val | Ser | Leu | Ala | Cys | Phe | Arg | Val | Leu | * | Ile | |
| 5690 | | | | | 5695 | | | | | 5700 | | | | | | |
| cct | cag | atg | tgt | gtc | agg | tat | att | ttt | ctg | ttt | tct | act | ttt | gtg | cag | 20840 |
| Pro | Gln | Met | Cys | Val | Arg | Tyr | Ile | Phe | Leu | Phe | Ser | Thr | Phe | Val | Gln | |
| 5705 | | | | | 5710 | | | | | 5715 | | | | | 5720 | |
| cca | gaa | ttg | tgg | taa | agg | gga | att | tag | ggc | atc | ctt | att | tat | tat | cag | 20888 |
| Pro | Glu | Leu | Trp | * | Arg | Gly | Ile | * | Gly | Ile | Leu | Ile | Tyr | Tyr | Gln | |
| | | | | 5725 | | | | | | 5730 | | | | | | |
| aat | tga | gat | ccg | gtt | tgc | aca | aac | ctt | tcc | agg | gtc | ggt | tgg | gag | act | 20936 |
| Asn | * | Asp | Pro | Val | Cys | Thr | Asn | Leu | Phe | Arg | Val | Gly | Trp | Glu | Thr | |
| 5735 | | | | | 5740 | | | | | | 5745 | | | | | |
| gtt | ggt | tcc | taa | gtg | cag | tcg | cag | ttt | taa | ctg | aga | tgt | ctc | gga | tat | 20984 |
| Val | Gly | Ser | * | Val | Gln | Ser | Gln | Phe | * | Leu | Arg | Cys | Leu | Gly | Tyr | |
| 5750 | | | | | 5755 | | | | | | 5760 | | | | | |
| cag | aag | tta | taa | tca | ctc | ctg | agt | aca | atg | atg | aag | gga | ttt | ata | cag | 21032 |
| Gln | Lys | Leu | * | Ser | Leu | Leu | Ser | Thr | Met | Met | Lys | Gly | Phe | Ile | Gln | |
| | 5765 | | | | | 5770 | | | | | 5775 | | | | | |
| tca | gat | tct | gta | ttc | agg | tac | cca | ata | ttt | caa | tgt | tta | aac | cat | ttg | 21080 |
| Ser | Asp | Ser | Val | Phe | Arg | Tyr | Pro | Ile | Phe | Gln | Cys | Leu | Asn | His | Leu | |
| | 5780 | | | | | 5785 | | | | | 5790 | | | | | |
| act | gat | aag | tac | ttg | aat | tgc | tcc | ttt | tct | att | aat | aca | cta | gcc | ttg | 21128 |
| Thr | Asp | Lys | Tyr | Leu | Asn | Cys | Ser | Phe | Ser | Ile | Asn | Thr | Leu | Ala | Leu | |
| 5795 | | | | | 5800 | | | | | 5805 | | | | | 5810 | |
| tgt | cat | ttg | gtc | agt | atg | tta | tct | agg | aag | gtt | cag | ttg | att | cat | ttt | 21176 |
| Cys | His | Leu | Val | Ser | Met | Leu | Ser | Arg | Lys | Val | Gln | Leu | Ile | His | Phe | |
| | | | | 5815 | | | | | 5820 | | | | | 5825 | | |
| gca | aag | ttt | ata | ata | cag | tta | tct | taa | aat | gtt | aga | cca | aaa | aat | cac | 21224 |
| Ala | Lys | Phe | Ile | Ile | Gln | Leu | Ser | * | Asn | Val | Arg | Pro | Lys | Asn | His | |
| | | | | 5830 | | | | | 5835 | | | | | 5840 | | |
| ggt | gaa | gtt | tac | cat | ttg | aca | atc | ata | tgt | cca | gtt | taa | cat | tag | agt | 21272 |
| Gly | Glu | Val | Tyr | His | Leu | Thr | Ile | Ile | Cys | Pro | Val | * | His | * | Ser | |
| | | | | 5845 | | | | | 5850 | | | | | 5855 | | |
| tct | att | tct | gaa | gca | aat | gtg | tac | atc | atg | cta | cat | gca | tcg | ata | aca | 21320 |
| Ser | Ile | Ser | Glu | Ala | Asn | Val | Tyr | Ile | Met | Leu | His | Ala | Ser | Ile | Thr | |
| | | | | | 5860 | | | | | 5865 | | | | | 5870 | |
| tat | tta | act | gtg | tca | gga | aaa | ata | aat | tat | ttt | att | agt | ttt | ttt | gaa | 21368 |

-continued

| | | |
|---|---|---|
| Tyr Leu Thr Val Ser Gly Lys Ile Asn Tyr Phe Ile Ser Phe Phe Glu<br>5875              5880              5885 | | |
| ggg aaa acc gta gga aat tcc cta cag tga aat ata ttg aat taa att<br>Gly Lys Thr Val Gly Asn Ser Leu Gln * Asn Ile Leu Asn * Ile<br>5890              5895              5900 | 21416 | |
| agg aaa aat aag gac gac cac tgg aca aaa ccg aaa aag agg aaa aag<br>Arg Lys Asn Lys Asp Asp His Trp Thr Lys Pro Lys Lys Arg Lys Lys<br>5905              5910              5915 | 21464 | |
| gaa agg ggg gaa agg caa aga aca tcc caa att aca act cca ata act<br>Glu Arg Gly Glu Arg Gln Arg Thr Ser Gln Ile Thr Thr Pro Ile Thr<br>5920              5925              5930 | 21512 | |
| agc aag ata taa ggg ata att att tta tta gta gtt cat tgg tct gca<br>Ser Lys Ile * Gly Ile Ile Ile Leu Leu Val Val His Trp Ser Ala<br>5935              5940              5945 | 21560 | |
| ata ttt act gga gcc atg ttg gag tca tct tgg atg tgt act gct cta<br>Ile Phe Thr Gly Ala Met Leu Glu Ser Ser Trp Met Cys Thr Ala Leu<br>5950              5955              5960 | 21608 | |
| tgg aga tat ata ctg cat gat tgg ttg att ggg ccc cgc gcc cag gcc<br>Trp Arg Tyr Ile Leu His Asp Trp Leu Ile Gly Pro Arg Ala Gln Ala<br>5965              5970              5975              5980 | 21656 | |
| ccg tgc atg cgt tga ccg cgc ttg ggc gtg tgc ttg gtt ggc tgc acg<br>Pro Cys Met Arg * Pro Arg Leu Gly Val Cys Leu Val Gly Cys Thr<br>5985              5990              5995 | 21704 | |
| gca gcg acg gag cct gtg tgc aca ggt gca agg tag gtt ttt taa ccc<br>Ala Ala Thr Glu Pro Val Cys Thr Gly Ala Arg * Val Phe * Pro<br>6000              6005 | 21752 | |
| tcg ttg gct tgc atg cgt ggg gaa gta aga atc atc cgt ttc aac cga<br>Ser Leu Ala Cys Met Arg Gly Glu Val Arg Ile Ile Arg Phe Asn Arg<br>6010              6015              6020              6025 | 21800 | |
| tgc agg cct ccg cga gtc agg cgc gga ggc tgc tag caa cca aac agg<br>Cys Arg Pro Pro Arg Val Arg Arg Gly Gly Cys * Gln Pro Asn Arg<br>6030              6035              6040 | 21848 | |
| agg ata atg tat att act aaa aat agt agc tta gtt ata ctt cac ctc<br>Arg Ile Met Tyr Ile Thr Lys Asn Ser Ser Leu Val Ile Leu His Leu<br>6045              6050              6055 | 21896 | |
| tgc aat gta agt act tgc ttc cct caa tac ttt tta tgc cct gac ctg<br>Cys Asn Val Ser Thr Cys Phe Pro Gln Tyr Phe Leu Cys Pro Asp Leu<br>6060              6065              6070 | 21944 | |
| gta agt ccc tca gtg aca cac tga cac cta tct ata aac ctg agg ttg<br>Val Ser Pro Ser Val Thr His * His Leu Ser Ile Asn Leu Arg Leu<br>6075              6080              6085 | 21992 | |
| gta aga aaa tac ctt tct gtt act gat ccc atg tgg ttt ccg tgt gtt<br>Val Arg Lys Tyr Leu Ser Val Thr Asp Pro Met Trp Phe Pro Cys Val<br>6090              6095              6100 | 22040 | |
| gtt gat ata gat ttc agg agt gat atc ttt ata tca caa tac aaa ttg<br>Val Asp Ile Asp Phe Arg Ser Asp Ile Phe Ile Ser Gln Tyr Lys Leu<br>6105              6110              6115 | 22088 | |
| gct gta gtt ggt gta acc cag aag gga aaa aca gtg cac atg aag agc<br>Ala Val Val Gly Val Thr Gln Lys Gly Lys Thr Val His Met Lys Ser<br>6120              6125              6130              6135 | 22136 | |
| act tgt aat atg ttt ttt att agg gct taa cac taa tgc att gtt ttc<br>Thr Cys Asn Met Phe Phe Ile Arg Ala * His * Cys Ile Val Phe<br>6140              6145 | 22184 | |
| ccc tct gac tta ata ttt agc tta cat tgt gga gac tag aga tgt ttt<br>Pro Ser Asp Leu Ile Phe Ser Leu His Cys Gly Asp * Arg Cys Phe<br>6150              6155              6160 | 22232 | |
| atg aat tat ctt aca cta atc tga ttt tct ctg tat ttt aaa aaa ctc<br>Met Asn Tyr Leu Thr Leu Ile * Phe Ser Leu Tyr Phe Lys Lys Leu<br>6165              6170              6175 | 22280 | |

```
ttc tct gag tta tag ttc tta tgt ttt ata ttt tcc caa ggg tga gtg      22328
Phe Ser Glu Leu  *  Phe Leu Cys Phe Ile Phe Ser Gln Gly  *  Val
6180                6185                6190 ggt ggc tgt ggt tgt tga tga ttg gat tcc ttg cga gtc tcc ggg aa       22376
Gly Gly Cys Gly Cys  *   *  Leu Asp Ser Leu Arg Val Ser Gly Glu
    6195                6200                6205 acc agc att tgc tac tag tag aaa gca aaa cga gct ttg ggt atc cat      22424
Thr Ser Ile Cys Tyr  *   *  Lys Ala Lys Arg Ala Leu Gly Ile His
        6210                6215                6220 tct tga gaa ggc tta tgc aaa act tca tgg ctc tta tga ggc att gga      22472
Ser  *  Glu Gly Leu Cys Lys Thr Ser Trp Leu Leu  *  Gly Ile Gly
            6225                6230                    6235 agg tgg gct tgt tca aga tgc tct agt cga tct cac agg agg agc tgg      22520
Arg Trp Ala Cys Ser Arg Cys Ser Ser Arg Ser His Arg Arg Ser Trp
                6240                6245                6250 tga aga gat tga tat gcg aag tcc tca agc cca act tga tct tgc tag      22568
 *  Arg Asp  *  Tyr Ala Lys Ser Ser Ser Pro Thr  *  Ser Cys  *
                    6255                6260 tgg aag att gtg gtc gca gtt gtt gca ttt caa aca aga agg ttt tct      22616
Trp Lys Ile Val Val Ala Val Val Ala Phe Gln Thr Arg Arg Phe Ser
            6265                6270                6275 tct tgg tgc tgg aag tcc ttc tgg atc tga tgc tca cat ctc atc aag      22664
Ser Trp Cys Trp Lys Ser Phe Trp Ile  *  Cys Ser His Leu Ile Lys
6280                6285                6290 tgg cat tgt tca ggg aca tgc gta ctc aat ttt gca ggt ttg ctc tag      22712
Trp His Cys Ser Gly Thr Cys Val Leu Asn Phe Ala Gly Leu Leu  *
6295                6300                6305 ttt aga taa ttc tat ctg aga tac tgg gta act gtc agc ttt tca cta      22760
Phe Arg  *  Phe Tyr Leu Arg Tyr Trp Val Thr Val Ser Phe Ser Leu
6310                6315                6320 ctc ccg gga caa gtt tac aca att ata cat tat ttc agg taa gag aag      22808
Leu Pro Gly Gln Val Tyr Thr Ile Ile His Tyr Phe Arg  *  Glu Lys
6325                6330                6335 ttg atg gcc aca aac tca tcc aaa tca gaa atc cat ggg caa atg aag      22856
Leu Met Ala Thr Asn Ser Ser Lys Ser Glu Ile His Gly Gln Met Lys
6340                6345                6350                6355 ttg aat gga atg gac cat ggt cag act cgt cac cag agt gga cgg aac      22904
Leu Asn Gly Met Asp His Gly Gln Thr Arg His Gln Ser Gly Arg Asn
        6360                6365                6370 gga tga agc ata agc tca tgc atg ttc cac agg tac ttg tct ctt gat      22952
Gly  *  Ser Ile Ser Ser Cys Met Phe His Arg Tyr Leu Ser Leu Asp
            6375                6380                6385 att ttt ttt gca tgt cat atc aca cta gtt ggt ggc aaa cca cag ctt      23000
Ile Phe Phe Ala Cys His Ile Thr Leu Val Gly Gly Lys Pro Gln Leu
                6390                6395                6400 att gat aat cga gat aat tca ttg cac cgc tat aaa caa aat gta cca      23048
Ile Asp Asn Arg Asp Asn Ser Leu His Arg Tyr Lys Gln Asn Val Pro
            6405                6410                6415 tgt aag ttt gat ttc atc tct aca gat ctt gac ttc aat ccc cct tgt      23096
Cys Lys Phe Asp Phe Ile Ser Thr Asp Leu Asp Phe Asn Pro Pro Cys
        6420                6425                6430 ctc tcc atc ctt gca gtc gaa gaa tgg ggt att ctg gat gtc ttg gca      23144
Leu Ser Ile Leu Ala Val Glu Glu Trp Gly Ile Leu Asp Val Leu Ala
6435                6440                6445                6450 aga ttt tca gat tca ctt tcg gtc aat cta tgt ttg tcg tgt tta tcc      23192
Arg Phe Ser Asp Ser Leu Ser Val Asn Leu Cys Leu Ser Cys Leu Ser
        6455                6460                6465 acc tga gat gcg tta ctc tgt cca tgg gca atg gcg tgg tta caa tgc      23240
Thr  *  Asp Ala Leu Leu Cys Pro Trp Ala Met Ala Trp Leu Gln Cys
            6470                6475                6480
```

```
agg tgg ttg cca aga tta tga ctc atg gca cca aaa tcc aca gta tcg    23288
Arg Trp Leu Pro Arg Leu  *  Leu Met Ala Pro Lys Ser Thr Val Ser
            6485            6490            6495 act tag agt aac agg acg tga tgc act ata ccc tgt tca tgt ttt tat    23336
Thr  *  Ser Asn Arg Thr  *  Cys Thr Ile Pro Cys Ser Cys Phe Tyr
            6500            6505            6510 tac cct tac tca ggt atg ttg gaa cct acc tat caa cct aac acc agg    23384
Tyr Pro Tyr Ser Gly Met Leu Glu Pro Thr Tyr Gln Pro Asn Thr Arg
            6515            6520            6525 aga agc aca atg atg ttt tat ctg tgt aaa ttt cat gct ttt cag ggt    23432
Arg Ser Thr Met Met Phe Tyr Leu Cys Lys Phe His Ala Phe Gln Gly
            6530            6535            6540 gtt ggt ttc tct aga aag acg aat ggt ttt cgg aac tac caa tct agc    23480
Val Gly Phe Ser Arg Lys Thr Asn Gly Phe Arg Asn Tyr Gln Ser Ser
            6545            6550            6555 cat gat tct tca atg ttt tac att gga atg agg ata ctc aag aca cag    23528
His Asp Ser Ser Met Phe Tyr Ile Gly Met Arg Ile Leu Lys Thr Gln
            6560            6565            6570 ggc tgc cgt gct gct tac aat atc tac atg cat gaa agc gct ggt gga    23576
Gly Cys Arg Ala Ala Tyr Asn Ile Tyr Met His Glu Ser Ala Gly Gly
6575            6580            6585            6590 aca gat tac gtt aac tcg agg gag ata tca tgc gaa ctg gtc ttg gat    23624
Thr Asp Tyr Val Asn Ser Arg Glu Ile Ser Cys Glu Leu Val Leu Asp
            6595            6600            6605 cct tat ccc aaa ggg tac aca att gtg cca act acc atc cac cct ggg    23672
Pro Tyr Pro Lys Gly Tyr Thr Ile Val Pro Thr Thr Ile His Pro Gly
            6610            6615            6620 gag gaa gca cct ttt gtt ttg tca gtt ttt tca aaa gca tca atc aga    23720
Glu Glu Ala Pro Phe Val Leu Ser Val Phe Ser Lys Ala Ser Ile Arg
            6625            6630            6635 cta gag gct gtt t aattcaagat tgagatccca tgtgtttggt ggtagctgcg      23773
Leu Glu Ala Val
   6640 tctgctgggc actcgtgcac gcaggatcca gctgtgggtt ctcgtgaact agataattgg  23833 taagtgttgt attgagttac ctgtacagaa gtatgaagtg gtagttaacc cagggtgccc  23893 caaactacaa ccatcctata tttcacgtgc cgctatattc tcatcattca ttcaggttca  23953 aaacagagga gttggactaa ctggccttat aaccgtttca gggtatagga attgcctcct  24013 ggacaacttc aatgaatctt gctgcatgca agtacataag ttcggttgct tgttgcagaa  24073 ctgacaaacg gcaatgcttc ttgtgctgaa gggaaaggag agaaggcatg atccatggtt  24133 cttttggtagc tgcgcaaagt gcagggtgag aggcttggtt caatgtttgt agatagccgt  24193 ggtaactgac ctggtagccc atcctatgta taggtgtccc gtttaccctg taaatgctat   24253 agagttaggt taggtagcct gtcgttcctg ttaacgcata gggctcttat gcagctgtga   24313 aatgtcttgt tagcaagctg cagttttgct gatttgagcg tggagtagtc ggccatagct   24373 gttcccattg gtttgccctg tatgtaatcg gaatctgatg tcattcaatg aacctatttt   24433 ttgggtgcca tgcgaagctg tctaagattt gagtctcttc atgcatcaaa ttatgcatca   24493 tcctcgctgg aaaaataaaa actctaccaa acatagacga ttatttggtt cctttctcg    24553 tcgatgtttc cttatgacca aagttgttag gtttgatagt tcgatggcca agataatttg   24613 agaaaaaaat gacttcttcc attttgttat tattaataac ctattaccag tttcggggca   24673 atccaagttc caatcagtgc acacattagt taattttgta ctgcattttt ttatcaaata   24733 taaaaaaagt agtagtcaaa atagcataaa ccaaccaaca aactaaacca tggtacgtac   24793
```

-continued

| | |
|---|---|
| atgttagtgc tacgtcatat cgacaacgca gcctgccgat catatatcat cttccttaga | 24853 |
| tgtcagtgta tcctgcccga ttgctgctgc ggcagcagcc ccgggatgaa tgcacgccg | 24913 |
| agctgtggga gccagtgctg gccctggatg aagctctcga cggtgtactt ctgcagcgcg | 24973 |
| tgctggtagg tgatgttctt gatacccctc cacttgacgc gttcgctcat gttggcgccg | 25033 |
| ggcccgtggt tttccacctc ggcgtagtag caggtgctga ggccgaagtc gccgagccac | 25093 |
| ggcagccagc cctgcgggtc gatgaacccg ccgatctccg actggatgta gagcgtgcgc | 25153 |
| gagtgctcct tccacgggcg gcccaggaag gtcctgaacc ggccgacgct cttctcgaac | 25213 |
| tccgggtgcg gcgcgacggt gcagttgtgg atgacggtgc cgcccaccga ccgcctctcc | 25273 |
| ttgcggccct gcgccgtgac gatgttctgc tggttgtcca tgcacttgcg cacctggatg | 25333 |
| aggcagttct ggaacaccac ctgcgcgttg ccgaagatga agtcgatggt gcccgtgatg | 25393 |
| acgcagtcgc ggtagtac | 25411 |

<210> SEQ ID NO 26
<211> LENGTH: 7094
<212> TYPE: DNA
<213> ORGANISM: Arabidopsis thaliana
<220> FEATURE:
<221> NAME/KEY: CDS
<222> LOCATION: (120)...(6570)
<223> OTHER INFORMATION: cDNA

<400> SEQUENCE: 26

| | |
|---|---|
| cttggttggt tttaagctgc ggatttgatg atttgtgcgc aagcttgggg tttcagcttt | 60 |
| tttttgtgat ggaattttga tttccgagtt gcatggtgtt gtaggtggga gaagaagcc | 119 |

| | |
|---|---|
| atg gaa ggg gat gag cga gga gtc tta ctt gct tgt gta att tcg ggt<br>Met Glu Gly Asp Glu Arg Gly Val Leu Leu Ala Cys Val Ile Ser Gly<br>1               5                   10                  15 | 167 |
| acc ctt ttc acg gtt ttc ggt tcg ggt tcg ttt tgg ata ctt tgg gct<br>Thr Leu Phe Thr Val Phe Gly Ser Gly Ser Phe Trp Ile Leu Trp Ala<br>           20                  25                  30 | 215 |
| gtt aat tgg cgg cca tgg cgt ctc tac agt tgg atc ttt gct aga aaa<br>Val Asn Trp Arg Pro Trp Arg Leu Tyr Ser Trp Ile Phe Ala Arg Lys<br>       35                  40                  45 | 263 |
| tgg cca aaa gta ttg caa ggt cct cag ctt gat ata cta tgt ggt gtt<br>Trp Pro Lys Val Leu Gln Gly Pro Gln Leu Asp Ile Leu Cys Gly Val<br>   50                  55                  60 | 311 |
| cta tct ctt ttt gct tgg att gtg gta gta tcc cct att gca atc ttg<br>Leu Ser Leu Phe Ala Trp Ile Val Val Val Ser Pro Ile Ala Ile Leu<br>65                  70                  75                  80 | 359 |
| ata gga tgg ggt tct tgg ctg att gtg ata ttg gat cga cat atc att<br>Ile Gly Trp Gly Ser Trp Leu Ile Val Ile Leu Asp Arg His Ile Ile<br>               85                  90                  95 | 407 |
| ggg ctg gcg ata ata atg gct gga aca gcc ctt tta ctg gca ttc tac<br>Gly Leu Ala Ile Ile Met Ala Gly Thr Ala Leu Leu Leu Ala Phe Tyr<br>           100                 105                 110 | 455 |
| tca atc atg ctt tgg tgg agg acc cag tgg caa agc tca aga gct gtc<br>Ser Ile Met Leu Trp Trp Arg Thr Gln Trp Gln Ser Ser Arg Ala Val<br>       115                 120                 125 | 503 |
| gct tta ctt ctc ctt ctt ggt gtt gcc tta cta tgt gcg tat gaa ctc<br>Ala Leu Leu Leu Leu Leu Gly Val Ala Leu Leu Cys Ala Tyr Glu Leu<br>   130                 135                 140 | 551 |
| tgt gct gtc tat gtt acg gct ggt gcg cat gca tct cag caa tat tct<br>Cys Ala Val Tyr Val Thr Ala Gly Ala His Ala Ser Gln Gln Tyr Ser<br>145                 150                 155                 160 | 599 |
| cct tct ggt ttc ttt ttc ggt gta tca gca atc gcg ttg gca att aac | 647 |

```
                                                                -continued

Pro Ser Gly Phe Phe Phe Gly Val Ser Ala Ile Ala Leu Ala Ile Asn
            165                 170                 175 atg cta ttt atc tgc cgc atg gtc ttt aat gga aat ggt tta gat gtg        695
Met Leu Phe Ile Cys Arg Met Val Phe Asn Gly Asn Gly Leu Asp Val
            180                 185                 190 gac gaa tat gta agg agg gca tat aaa ttt gct tat tca gat tgt ata        743
Asp Glu Tyr Val Arg Arg Ala Tyr Lys Phe Ala Tyr Ser Asp Cys Ile
            195                 200                 205 gaa gtg ggt cct gtg gct tgt ttg cct gaa cct cct gat cct aat gaa        791
Glu Val Gly Pro Val Ala Cys Leu Pro Glu Pro Pro Asp Pro Asn Glu
210                 215                 220 tta tat ccc cgg caa acc agc agg gct tca cat ctt ggc ctt ctg tac        839
Leu Tyr Pro Arg Gln Thr Ser Arg Ala Ser His Leu Gly Leu Leu Tyr
225                 230                 235                 240 ctg ggc tca ctc gta gtt ctc ctt gcc tac tca gtc cta tat ggt ctc        887
Leu Gly Ser Leu Val Val Leu Leu Ala Tyr Ser Val Leu Tyr Gly Leu
                245                 250                 255 aca gct agg gaa tca cgt tgg ctt gga gga atc aca tca gct gca gtt        935
Thr Ala Arg Glu Ser Arg Trp Leu Gly Gly Ile Thr Ser Ala Ala Val
            260                 265                 270 att gtt ctt gac tgg aat att ggg gca tgc ttg tat ggg ttt aag ctt        983
Ile Val Leu Asp Trp Asn Ile Gly Ala Cys Leu Tyr Gly Phe Lys Leu
            275                 280                 285 ctt cag aat cgt gtt ctg gca ctt ttt gtt gct ggc ata tcc cgt ctt       1031
Leu Gln Asn Arg Val Leu Ala Leu Phe Val Ala Gly Ile Ser Arg Leu
        290                 295                 300 ttc cta ata tgt ttt ggc ata cac tac tgg tac cta ggg cat tgt att       1079
Phe Leu Ile Cys Phe Gly Ile His Tyr Trp Tyr Leu Gly His Cys Ile
305                 310                 315                 320 agt tac att ttc gta gca tca gtt cta tca ggt gct gct gtt tct cgg       1127
Ser Tyr Ile Phe Val Ala Ser Val Leu Ser Gly Ala Ala Val Ser Arg
                325                 330                 335 cat cta tct ata aca gac cca tca gct gca aga aga gat gcc tta cag       1175
His Leu Ser Ile Thr Asp Pro Ser Ala Ala Arg Arg Asp Ala Leu Gln
            340                 345                 350 agc aca gtg atc cgc ttg aga gaa ggt ttt cgg aga aaa gag cag aat       1223
Ser Thr Val Ile Arg Leu Arg Glu Gly Phe Arg Arg Lys Glu Gln Asn
            355                 360                 365 agt tct tca agt tct tca gat ggt tgt ggc tca agt ata aaa aga agt       1271
Ser Ser Ser Ser Ser Ser Asp Gly Cys Gly Ser Ser Ile Lys Arg Ser
370                 375                 380 agt agt atc gat gct ggc cat act ggt tgt act aat gaa gca aat cgt       1319
Ser Ser Ile Asp Ala Gly His Thr Gly Cys Thr Asn Glu Ala Asn Arg
385                 390                 395                 400 acg gca gaa tct tgc acg gct gac aat cta act cga aca ggc agc tct       1367
Thr Ala Glu Ser Cys Thr Ala Asp Asn Leu Thr Arg Thr Gly Ser Ser
                405                 410                 415 cag gag gga atc aat agc gac aaa agc gaa gaa agt gga aga cca agc       1415
Gln Glu Gly Ile Asn Ser Asp Lys Ser Glu Glu Ser Gly Arg Pro Ser
            420                 425                 430 tta ggt tta cgt agt agt tca tgt cgt tct gtg gtc caa gag ccc gaa       1463
Leu Gly Leu Arg Ser Ser Ser Cys Arg Ser Val Val Gln Glu Pro Glu
            435                 440                 445 gca gga acg tct tat ttt atg gac aaa gtt tct gat caa aat aac act       1511
Ala Gly Thr Ser Tyr Phe Met Asp Lys Val Ser Asp Gln Asn Asn Thr
450                 455                 460 ctt gtt gtt tgt tcg agc agt ggt cta gat agc caa ggt tac gag tct       1559
Leu Val Val Cys Ser Ser Ser Gly Leu Asp Ser Gln Gly Tyr Glu Ser
465                 470                 475                 480
```

-continued

| | | |
|---|---|---|
| agc aca tcg aat tct gca aac cag cag ctt ttg gat atg aat ttg gct<br>Ser Thr Ser Asn Ser Ala Asn Gln Gln Leu Leu Asp Met Asn Leu Ala<br>                        485                      490                495 | 1607 |
| ctt gct ttc cag gac cag tta aac aat cct agg ata gcc tcg ata ctt<br>Leu Ala Phe Gln Asp Gln Leu Asn Asn Pro Arg Ile Ala Ser Ile Leu<br>                      500                      505                    510 | 1655 |
| aag aag aaa gca aaa gaa ggt gat ctt gaa ctg act aat ttg ctg caa<br>Lys Lys Lys Ala Lys Glu Gly Asp Leu Glu Leu Thr Asn Leu Leu Gln<br>                      515                      520                    525 | 1703 |
| gac aag ggg ttg gac cct aac ttt gct gta atg ttg aag gaa aaa aac<br>Asp Lys Gly Leu Asp Pro Asn Phe Ala Val Met Leu Lys Glu Lys Asn<br>530                      535                      540 | 1751 |
| ttg gat cct act ata ttg gca cta ctt cag agg agt agt ttg gat gca<br>Leu Asp Pro Thr Ile Leu Ala Leu Leu Gln Arg Ser Ser Leu Asp Ala<br>545                      550                      555                560 | 1799 |
| gat aga gat cac cgc gac aat act gat att aca atc att gac tca aac<br>Asp Arg Asp His Arg Asp Asn Thr Asp Ile Thr Ile Ile Asp Ser Asn<br>                      565                      570                    575 | 1847 |
| agt gtt gac aat act ttg cca aat cag att tct tta tcc gaa gaa ttg<br>Ser Val Asp Asn Thr Leu Pro Asn Gln Ile Ser Leu Ser Glu Glu Leu<br>                      580                      585                    590 | 1895 |
| aga ctc cgt gga cta gag aag tgg ctt aag ttg tct aga ctt ctt ctg<br>Arg Leu Arg Gly Leu Glu Lys Trp Leu Lys Leu Ser Arg Leu Leu Leu<br>                 595                      600                    605 | 1943 |
| cac cat gta gcg ggg aca cca gag aga gca tgg ggc ctc ttt agt ctt<br>His His Val Ala Gly Thr Pro Glu Arg Ala Trp Gly Leu Phe Ser Leu<br>        610                      615                    620 | 1991 |
| gtc ttt atc ctt gaa aca atc att gtg gcc att ttt cgc cca aag acc<br>Val Phe Ile Leu Glu Thr Ile Ile Val Ala Ile Phe Arg Pro Lys Thr<br>625                      630                      635                640 | 2039 |
| atc acg att ata aat tct agt cat caa cag ttc gaa ttt ggt ttc tct<br>Ile Thr Ile Ile Asn Ser Ser His Gln Gln Phe Glu Phe Gly Phe Ser<br>                      645                      650                    655 | 2087 |
| gtg ctg cta ttg tca cct gtt gtc tgt tca ata atg gct ttt ctt cgg<br>Val Leu Leu Leu Ser Pro Val Val Cys Ser Ile Met Ala Phe Leu Arg<br>                      660                      665                    670 | 2135 |
| tct ctt caa gtt gag gaa atg gcc ttg aca tca aaa tct cgc aag tat<br>Ser Leu Gln Val Glu Glu Met Ala Leu Thr Ser Lys Ser Arg Lys Tyr<br>               675                      680                    685 | 2183 |
| ggc ttt gtt gcc tgg ctt ctg agc aca tca gtt gga ttg tca ctc tcg<br>Gly Phe Val Ala Trp Leu Leu Ser Thr Ser Val Gly Leu Ser Leu Ser<br>690                      695                      700 | 2231 |
| ttc ttg agt aaa tcg tca gta ctt ctg gga ata tcc ttg act gtg ccc<br>Phe Leu Ser Lys Ser Ser Val Leu Leu Gly Ile Ser Leu Thr Val Pro<br>705                      710                      715                720 | 2279 |
| ctc atg gca gca tgc ctg tct att gct gtt ccc ata tgg atg cat aat<br>Leu Met Ala Ala Cys Leu Ser Ile Ala Val Pro Ile Trp Met His Asn<br>                      725                      730                    735 | 2327 |
| ggg tac caa ttt tgg gtt cca cag tta tca tgt ggt gac cag gca aga<br>Gly Tyr Gln Phe Trp Val Pro Gln Leu Ser Cys Gly Asp Gln Ala Arg<br>                   740                      745                    750 | 2375 |
| gat tta cga tct ccc agg ata aag ggg ttt att ctt tgg att tgt gtt<br>Asp Leu Arg Ser Pro Arg Ile Lys Gly Phe Ile Leu Trp Ile Cys Val<br>               755                      760                    765 | 2423 |
| gtg ttg ttt gcg ggt tct gta att tct ctt ggt gcg att ata tct gct<br>Val Leu Phe Ala Gly Ser Val Ile Ser Leu Gly Ala Ile Ile Ser Ala<br>                      770                      775                    780 | 2471 |
| aaa cct ttg gat gat tta aag tat aag ctg ttt agt gcc aga gaa aac<br>Lys Pro Leu Asp Asp Leu Lys Tyr Lys Leu Phe Ser Ala Arg Glu Asn<br>785                      790                      795                800 | 2519 |

-continued

| | |
|---|---|
| aac gtc acg tca cca tat aca tct tct gta tac ctt ggt tgg gca atg<br>Asn Val Thr Ser Pro Tyr Thr Ser Ser Val Tyr Leu Gly Trp Ala Met<br>805                      810                   815 | 2567 |
| tca tct gga att gct tta gta gtt acc gcc att cta cca ata gtt tca<br>Ser Ser Gly Ile Ala Leu Val Val Thr Ala Ile Leu Pro Ile Val Ser<br>    820                     825                 830 | 2615 |
| tgg ttt gca act tat agg ttt tcc cac tct tct gct gtc tgt ctc atg<br>Trp Phe Ala Thr Tyr Arg Phe Ser His Ser Ser Ala Val Cys Leu Met<br>       835                   840             845 | 2663 |
| ata ttc tca gtt gtt ctc gtg gca ttt tgt gga act tca tat ttg gaa<br>Ile Phe Ser Val Val Leu Val Ala Phe Cys Gly Thr Ser Tyr Leu Glu<br>850                      855                 860 | 2711 |
| gtt gta aaa tct aga gat gat cag ttg ccc aca aag ggt gat ttc ctt<br>Val Val Lys Ser Arg Asp Asp Gln Leu Pro Thr Lys Gly Asp Phe Leu<br>865                     870               875             880 | 2759 |
| gcg gcc ttg ctt cca ctt gca tgc att ccg gcg ctg ctt tca cta tgc<br>Ala Ala Leu Leu Pro Leu Ala Cys Ile Pro Ala Leu Leu Ser Leu Cys<br>             885                 890             895 | 2807 |
| tgt ggg atg gtt aaa tgg aag gac gat tgt tgg ata ctc tct cga ggt<br>Cys Gly Met Val Lys Trp Lys Asp Asp Cys Trp Ile Leu Ser Arg Gly<br>900                      905                 910 | 2855 |
| gta tat gtt ttc ttt tca ata ggt ctt ctt ctt ttt ggt gcg ata<br>Val Tyr Val Phe Phe Ser Ile Gly Leu Leu Leu Phe Gly Ala Ile<br>    915                   920                 925 | 2903 |
| gca gct gtc att gca gtc aaa cca tgg acg ata ggc gta tct ttt ctc<br>Ala Ala Val Ile Ala Val Lys Pro Trp Thr Ile Gly Val Ser Phe Leu<br>930                      935                 940 | 2951 |
| tta gtt ctt ttc ctt atg gtg gta aca att ggt gta atc cat ctt tgg<br>Leu Val Leu Phe Leu Met Val Val Thr Ile Gly Val Ile His Leu Trp<br>945                     950                 955             960 | 2999 |
| gcg tca aac aat ttc tat tta acc agg aaa cag aca tcc ttt gtc tgc<br>Ala Ser Asn Asn Phe Tyr Leu Thr Arg Lys Gln Thr Ser Phe Val Cys<br>               965                 970             975 | 3047 |
| ttt ctt gct ctt ctt ttg ggt ttg gcc gca ttc ctt ctc gga tgg cat<br>Phe Leu Ala Leu Leu Leu Gly Leu Ala Ala Phe Leu Leu Gly Trp His<br>             980                 985                 990 | 3095 |
| caa gat aaa gca ttt gct gga gca tct gtt ggt tac ttt aca ttc ctg<br>Gln Asp Lys Ala Phe Ala Gly Ala Ser Val Gly Tyr Phe Thr Phe Leu<br>995                     1000               1005 | 3143 |
| tct ctg ttg gct gga aga gca tta gct gtt ctt cta tcc cca cca att<br>Ser Leu Leu Ala Gly Arg Ala Leu Ala Val Leu Leu Ser Pro Pro Ile<br>    1010                 1015               1020 | 3191 |
| gta gta tat tct cca agg gtg cta cca gta tat gtc tac gat gct cat<br>Val Val Tyr Ser Pro Arg Val Leu Pro Val Tyr Val Tyr Asp Ala His<br>1025                 1030               1035              1040 | 3239 |
| gct gat tgc gga aag aat gtc agt gct gca ttt ctt gtc ctg tat gga<br>Ala Asp Cys Gly Lys Asn Val Ser Ala Ala Phe Leu Val Leu Tyr Gly<br>               1045               1050              1055 | 3287 |
| att gct ttg gca aca gaa ggc tgg ggt gtt gtt gct agt ctg ata att<br>Ile Ala Leu Ala Thr Glu Gly Trp Gly Val Val Ala Ser Leu Ile Ile<br>        1060               1065               1070 | 3335 |
| tat cct ccg ttt gcg ggt gct gct gta tca gct atc acc ctt gta gta<br>Tyr Pro Pro Phe Ala Gly Ala Ala Val Ser Ala Ile Thr Leu Val Val<br>               1075               1080              1085 | 3383 |
| gcc ttt ggg ttt gct gtt tct cgc cca tgt ttg act ctt gag atg atg<br>Ala Phe Gly Phe Ala Val Ser Arg Pro Cys Leu Thr Leu Glu Met Met<br>1090                 1095               1100 | 3431 |
| gag gtt gct gta cgc ttt ctt agc aag gat act ata gtg caa gct atc<br>Glu Val Ala Val Arg Phe Leu Ser Lys Asp Thr Ile Val Gln Ala Ile | 3479 |

-continued

| | | |
|---|---|---|
| tct cga tct gcc acg aaa aca aga aat gct cta tcc ggc acg tat tca<br>Ser Arg Ser Ala Thr Lys Thr Arg Asn Ala Leu Ser Gly Thr Tyr Ser<br>                     1125                       1130                       1135 | 3527 |

```
1105                1110                1115                1120 tct cga tct gcc acg aaa aca aga aat gct cta tcc ggc acg tat tca        3527
Ser Arg Ser Ala Thr Lys Thr Arg Asn Ala Leu Ser Gly Thr Tyr Ser
            1125                1130                1135 gct ccc caa agg tcc gcc agc tct gca gct ctt ctg gtt ggg gat ccc        3575
Ala Pro Gln Arg Ser Ala Ser Ser Ala Ala Leu Leu Val Gly Asp Pro
            1140                1145                1150 tct gca atg cgt gat aaa gca ggg aac ttt gtg ctt cct aga gat gat        3623
Ser Ala Met Arg Asp Lys Ala Gly Asn Phe Val Leu Pro Arg Asp Asp
            1155                1160                1165 gtc atg aaa tta agg gat cgt ctc agg aac gaa gaa aga gtt gct gga        3671
Val Met Lys Leu Arg Asp Arg Leu Arg Asn Glu Glu Arg Val Ala Gly
            1170                1175                1180 tca atc ttc tac aaa atg caa tgc agg aaa gga ttc cgt cat gaa cca        3719
Ser Ile Phe Tyr Lys Met Gln Cys Arg Lys Gly Phe Arg His Glu Pro
1185                1190                1195                1200 cct aca aat gta gat tat aga aga gac atg tgt gcc cat gca aga gtt        3767
Pro Thr Asn Val Asp Tyr Arg Arg Asp Met Cys Ala His Ala Arg Val
            1205                1210                1215 ttg gca ctg gaa gag gca att gat aca gaa tgg gtg tat atg tgg gac        3815
Leu Ala Leu Glu Glu Ala Ile Asp Thr Glu Trp Val Tyr Met Trp Asp
            1220                1225                1230 aaa ttt ggt ggt tat tta cta cta ttg tta ggt ttg aca gct aag gcg        3863
Lys Phe Gly Gly Tyr Leu Leu Leu Leu Gly Leu Thr Ala Lys Ala
            1235                1240                1245 gag aga gtt cag gat gag gta cgg ttg cgg ctc ttc tta gat agc att        3911
Glu Arg Val Gln Asp Glu Val Arg Leu Arg Leu Phe Leu Asp Ser Ile
            1250                1255                1260 ggg ttc tcg gat tta agt gcc aga aaa atc agt aaa tgg aag cca gag        3959
Gly Phe Ser Asp Leu Ser Ala Arg Lys Ile Ser Lys Trp Lys Pro Glu
1265                1270                1275                1280 gat aga aga caa ttc gaa att att caa gag agt tat ctg aga gag aaa        4007
Asp Arg Arg Gln Phe Glu Ile Ile Gln Glu Ser Tyr Leu Arg Glu Lys
            1285                1290                1295 gag atg gaa gag gaa agc ctt atg cag aga cgt gaa gaa gaa ggg aga        4055
Glu Met Glu Glu Glu Ser Leu Met Gln Arg Arg Glu Glu Glu Gly Arg
            1300                1305                1310 ggt aaa gaa aga agg aaa gct ctt ttg gag aag gaa gag cgc aaa tgg        4103
Gly Lys Glu Arg Arg Lys Ala Leu Leu Glu Lys Glu Glu Arg Lys Trp
            1315                1320                1325 aag gaa att gaa gcg tcc ctt att cca tct att cct aat gct ggt agc        4151
Lys Glu Ile Glu Ala Ser Leu Ile Pro Ser Ile Pro Asn Ala Gly Ser
            1330                1335                1340 agg gag gca gca gcc atg gca gct gca ata cgt gct gtt ggg ggt gat        4199
Arg Glu Ala Ala Ala Met Ala Ala Ala Ile Arg Ala Val Gly Gly Asp
1345                1350                1355                1360 tct gtc ctt gag gat tcc ttc gca aga gag agg gtc tcg ggt att gca        4247
Ser Val Leu Glu Asp Ser Phe Ala Arg Glu Arg Val Ser Gly Ile Ala
            1365                1370                1375 cgt agg ata cgc act gct caa cta gaa cga cgt gca caa cag act gga        4295
Arg Arg Ile Arg Thr Ala Gln Leu Glu Arg Arg Ala Gln Gln Thr Gly
            1380                1385                1390 ata tct ggg gca gtt tgt gtt ctt gat gat gaa cca atg ata agt ggt        4343
Ile Ser Gly Ala Val Cys Val Leu Asp Asp Glu Pro Met Ile Ser Gly
            1395                1400                1405 aaa cat tgc ggc caa atg gac tca agt gtc tgt caa agt cag aag att        4391
Lys His Cys Gly Gln Met Asp Ser Ser Val Cys Gln Ser Gln Lys Ile
1410                1415                1420 agc ttt tcc gtt aca gca atg atc caa tcc gat tct gga cct gta tgt        4439
```

```
                                                               -continued

Ser Phe Ser Val Thr Ala Met Ile Gln Ser Asp Ser Gly Pro Val Cys
1425                1430                1435                1440 ctt ttt ggc act gaa ttt caa aag aaa gta tgt tgg gag att ctg gtt    4487
Leu Phe Gly Thr Glu Phe Gln Lys Lys Val Cys Trp Glu Ile Leu Val
                    1445                1450                1455 gct ggt tct gag caa gga att gag gct ggc caa gtt ggg ctt agg ttg    4535
Ala Gly Ser Glu Gln Gly Ile Glu Ala Gly Gln Val Gly Leu Arg Leu
                1460                1465                1470 ata aca aaa ggt gag agg cag aca acc gtt gct aga gag tgg tat att    4583
Ile Thr Lys Gly Glu Arg Gln Thr Thr Val Ala Arg Glu Trp Tyr Ile
            1475                1480                1485 ggt gca acc agc ata act gat gga agg tgg cat aca gtg aca atc aca    4631
Gly Ala Thr Ser Ile Thr Asp Gly Arg Trp His Thr Val Thr Ile Thr
        1490                1495                1500 att gat gct gat gcg ggg gaa gct act tgt tac ata gat ggt ggg ttt    4679
Ile Asp Ala Asp Ala Gly Glu Ala Thr Cys Tyr Ile Asp Gly Gly Phe
1505                1510                1515                1520 gat ggc tac cag aat ggg tta cct cta agt att ggc agt gcc att tgg    4727
Asp Gly Tyr Gln Asn Gly Leu Pro Leu Ser Ile Gly Ser Ala Ile Trp
                    1525                1530                1535 gaa caa gga gct gaa gtt tgg ttg ggt gtt agg cca cct ata gat gtt    4775
Glu Gln Gly Ala Glu Val Trp Leu Gly Val Arg Pro Pro Ile Asp Val
                1540                1545                1550 gat gca ttc ggg aga tca gat agt gat ggc gtc gaa tca aag atg cat    4823
Asp Ala Phe Gly Arg Ser Asp Ser Asp Gly Val Glu Ser Lys Met His
            1555                1560                1565 att atg gat gtt ttc ctt tgg ggg aaa tgc tta agt gaa gaa gag gcc    4871
Ile Met Asp Val Phe Leu Trp Gly Lys Cys Leu Ser Glu Glu Glu Ala
        1570                1575                1580 gct tct ttg cat gca gcc att ggc atg gct gac tta gac atg att gat    4919
Ala Ser Leu His Ala Ala Ile Gly Met Ala Asp Leu Asp Met Ile Asp
1585                1590                1595                1600 ttg tct gat gac aat tgg caa tgg acg gat tca ccc ccc aga gtc gat    4967
Leu Ser Asp Asp Asn Trp Gln Trp Thr Asp Ser Pro Pro Arg Val Asp
                    1605                1610                1615 ggt tgg gat agt gat cct gcc gat gtt gat ctc tat gat agg gat gac    5015
Gly Trp Asp Ser Asp Pro Ala Asp Val Asp Leu Tyr Asp Arg Asp Asp
                1620                1625                1630 gta gat tgg gat gga caa tat tcc agt ggg agg aaa aga aga tca ggt    5063
Val Asp Trp Asp Gly Gln Tyr Ser Ser Gly Arg Lys Arg Arg Ser Gly
            1635                1640                1645 cgg gat ttt gta atg agt gtc gat tcc ttt gcc agg aga cac agg aaa    5111
Arg Asp Phe Val Met Ser Val Asp Ser Phe Ala Arg Arg His Arg Lys
        1650                1655                1660 ccc agg atg gag aca caa gaa gat ata aat caa aga atg cgt tca gtt    5159
Pro Arg Met Glu Thr Gln Glu Asp Ile Asn Gln Arg Met Arg Ser Val
1665                1670                1675                1680 gag ttg gct gtc aaa gaa gct ctc tct gca cga ggt gat aag caa ttt    5207
Glu Leu Ala Val Lys Glu Ala Leu Ser Ala Arg Gly Asp Lys Gln Phe
                    1685                1690                1695 act gac cag gaa ttt cct cca aat gat cgc tct tta ttt gtg gat aca    5255
Thr Asp Gln Glu Phe Pro Pro Asn Asp Arg Ser Leu Phe Val Asp Thr
                1700                1705                1710 caa aat ccc cca tca aaa ttg cag gtt gtt tct gaa tgg atg aga cct    5303
Gln Asn Pro Pro Ser Lys Leu Gln Val Val Ser Glu Trp Met Arg Pro
            1715                1720                1725 gac tcc att gtg aaa gaa aac ggt agt gat tcc cgt ccc tgc ctg ttc    5351
Asp Ser Ile Val Lys Glu Asn Gly Ser Asp Ser Arg Pro Cys Leu Phe
        1730                1735                1740
```

| | |
|---|---|
| tct ggg gat gca aat cct tca gat gtt tgc cag ggg cgt ttg ggg gat<br>Ser Gly Asp Ala Asn Pro Ser Asp Val Cys Gln Gly Arg Leu Gly Asp<br>1745              1750                   1755                   1760 | 5399 |
| tgt tgg ttc tta agc gcc gtt gca gtt ttg aca gag gtt tca cga ata<br>Cys Trp Phe Leu Ser Ala Val Ala Val Leu Thr Glu Val Ser Arg Ile<br>                   1765                   1770                   1775 | 5447 |
| tct gaa gtg atc att act cct gaa tac aac gag gaa ggg atc tac act<br>Ser Glu Val Ile Ile Thr Pro Glu Tyr Asn Glu Glu Gly Ile Tyr Thr<br>1780              1785                   1790 | 5495 |
| gtt cgt ttt tgt att cag ggt gag tgg gtt cct gtt gtt atc gat gac<br>Val Arg Phe Cys Ile Gln Gly Glu Trp Val Pro Val Val Ile Asp Asp<br>                   1795                   1800                   1805 | 5543 |
| tgg att cca tgt gaa tca cct ggt aaa cca gct ttt gct act agc aga<br>Trp Ile Pro Cys Glu Ser Pro Gly Lys Pro Ala Phe Ala Thr Ser Arg<br>    1810                   1815                   1820 | 5591 |
| aag ctc aat gaa ctc tgg gtc tcc atg gtg gag aaa gca tat gcc aag<br>Lys Leu Asn Glu Leu Trp Val Ser Met Val Glu Lys Ala Tyr Ala Lys<br>1825              1830                   1835                   1840 | 5639 |
| ctc cat ggt tct tat gag gca ctg gag ggg gga ctg gtt cag gat gct<br>Leu His Gly Ser Tyr Glu Ala Leu Glu Gly Gly Leu Val Gln Asp Ala<br>                   1845                   1850                   1855 | 5687 |
| ctt gtc gac cta act gga gga gct ggt gag gag att gac ttg cgg agt<br>Leu Val Asp Leu Thr Gly Gly Ala Gly Glu Glu Ile Asp Leu Arg Ser<br>    1860                   1865                   1870 | 5735 |
| gct caa gca caa ata gat ctt gca agt ggc aga ttg tgg tct caa ttg<br>Ala Gln Ala Gln Ile Asp Leu Ala Ser Gly Arg Leu Trp Ser Gln Leu<br>1875              1880                   1885 | 5783 |
| tta cgt ttt aaa caa gag ggg ttc tta ctt ggt gct gga agt cca tca<br>Leu Arg Phe Lys Gln Glu Gly Phe Leu Leu Gly Ala Gly Ser Pro Ser<br>                   1890                   1895                   1900 | 5831 |
| gga tct gat gtt cat gta tct tcc agt ggc att gtg caa ggg cat gct<br>Gly Ser Asp Val His Val Ser Ser Ser Gly Ile Val Gln Gly His Ala<br>1905              1910                   1915                   1920 | 5879 |
| tac tcc gtc tta cag gtg aga gag gtt gat ggg cac aga ctt gtt cag<br>Tyr Ser Val Leu Gln Val Arg Glu Val Asp Gly His Arg Leu Val Gln<br>                   1925                   1930                   1935 | 5927 |
| att cga aat cca tgg gct aat gaa gtt gag tgg aat ggt ccc tgg tca<br>Ile Arg Asn Pro Trp Ala Asn Glu Val Glu Trp Asn Gly Pro Trp Ser<br>    1940                   1945                   1950 | 5975 |
| gac tca tcc cca gag tgg act gat agg atg aag cac aag ctg aag cat<br>Asp Ser Ser Pro Glu Trp Thr Asp Arg Met Lys His Lys Leu Lys His<br>1955              1960                   1965 | 6023 |
| gtt cca cag tca aaa gaa ggt ata ttc tgg atg tct tgg caa gat ttc<br>Val Pro Gln Ser Lys Glu Gly Ile Phe Trp Met Ser Trp Gln Asp Phe<br>                   1970                   1975                   1980 | 6071 |
| cag att cat ttc aga tca ata tat gtg tgt cgg gtt tac ccc cgt gag<br>Gln Ile His Phe Arg Ser Ile Tyr Val Cys Arg Val Tyr Pro Arg Glu<br>1985              1990                   1995                   2000 | 6119 |
| atg cgc tac tct gta aat ggc caa tgg cga ggt tat agt gcc ggt ggc<br>Met Arg Tyr Ser Val Asn Gly Gln Trp Arg Gly Tyr Ser Ala Gly Gly<br>                   2005                   2010                   2015 | 6167 |
| tgc caa gat tat agc tca tgg cat caa aat cca caa ttc agg ctg agg<br>Cys Gln Asp Tyr Ser Ser Trp His Gln Asn Pro Gln Phe Arg Leu Arg<br>    2020                   2025                   2030 | 6215 |
| gca act ggt tct gat gca tct tta cca att cat gtg ttc atc acc tta<br>Ala Thr Gly Ser Asp Ala Ser Leu Pro Ile His Val Phe Ile Thr Leu<br>2035              2040                   2045 | 6263 |
| act cag ggc gta ggt ttc tcg aga aca act cct gga ttt cgt aac tac<br>Thr Gln Gly Val Gly Phe Ser Arg Thr Thr Pro Gly Phe Arg Asn Tyr<br>                   2050                   2055                   2060 | 6311 |

-continued

```
caa tca agc cat gat tca cag ttg ttc tat atc gga ttg agg att ctt      6359
Gln Ser Ser His Asp Ser Gln Leu Phe Tyr Ile Gly Leu Arg Ile Leu
2065                2070                2075                2080 aaa act cgt gga cgt cgt gct gct tac aac ata ttt ctt cat gaa tct      6407
Lys Thr Arg Gly Arg Arg Ala Ala Tyr Asn Ile Phe Leu His Glu Ser
            2085                2090                2095 gtt ggt gga aca gac tat gtg aat tcc cgt gag att tca tgt gaa atg      6455
Val Gly Gly Thr Asp Tyr Val Asn Ser Arg Glu Ile Ser Cys Glu Met
        2100                2105                2110 gtt ctt gac cct gat cct aag ggt tat act att gtc cca acc acg ata      6503
Val Leu Asp Pro Asp Pro Lys Gly Tyr Thr Ile Val Pro Thr Thr Ile
    2115                2120                2125 cac cca ggg gaa gaa gca cct ttt gtc ctt tca gtc ttc aca aaa gca      6551
His Pro Gly Glu Glu Ala Pro Phe Val Leu Ser Val Phe Thr Lys Ala
2130                2135                2140 tcc att gtt ctt gaa gct t tgtagtgccc gtattgtcag atggctctct           6600
Ser Ile Val Leu Glu Ala
2145            2150 cagcaacctg catgccatga aatcatccaa gtgcttgcgt tgtttaagga accagacggc    6660
ttacgtctca atgttaagac ttgttttgcc cacgatccac gcaacattag agaagactta   6720
actccctctg caacagcgtc tgatctgata gctggccatc acattattgg tgaatctatg   6780
aagtctcggg ataaaatgtt ttagttagtg tcctgatttt gaaccacgaa gttaactgct   6840
cagaggatag ataatttgca ctggagaaag cacttttcag gcatggctca ccggcattcc   6900
atctcgatct tgagacacgc atcaaatgta catttgtagg tattgcgaca agtacagatt   6960
tattaaatgt agaataacta cttcataact gaggaaacaa ggagagacat aggagacttg   7020
tgacttgttg ggtaaaggtt tggtattcgg tagtgatagc tgcagttttg gttggtgtgt   7080
tgtaatattc agac                                                     7094
```

<210> SEQ ID NO 27
<211> LENGTH: 2150
<212> TYPE: PRT
<213> ORGANISM: Arabidopsis thaliana

<400> SEQUENCE: 27

```
Met Glu Gly Asp Glu Arg Gly Val Leu Leu Ala Cys Val Ile Ser Gly
1               5                   10                  15

Thr Leu Phe Thr Val Phe Gly Ser Gly Ser Phe Trp Ile Leu Trp Ala
            20                  25                  30

Val Asn Trp Arg Pro Trp Arg Leu Tyr Ser Trp Ile Phe Ala Arg Lys
        35                  40                  45

Trp Pro Lys Val Leu Gln Gly Pro Gln Leu Asp Ile Leu Cys Gly Val
    50                  55                  60

Leu Ser Leu Phe Ala Trp Ile Val Val Ser Pro Ile Ala Ile Leu
65                  70                  75                  80

Ile Gly Trp Gly Ser Trp Leu Ile Val Ile Leu Asp Arg His Ile Ile
                85                  90                  95

Gly Leu Ala Ile Ile Met Ala Gly Thr Ala Leu Leu Ala Phe Tyr
            100                 105                 110

Ser Ile Met Leu Trp Trp Arg Thr Gln Trp Gln Ser Ser Arg Ala Val
        115                 120                 125

Ala Leu Leu Leu Leu Leu Gly Val Ala Leu Leu Cys Ala Tyr Glu Leu
    130                 135                 140

Cys Ala Val Tyr Val Thr Ala Gly Ala His Ala Ser Gln Gln Tyr Ser
```

-continued

```
            145                 150                 155                 160
        Pro Ser Gly Phe Phe Gly Val Ser Ala Ile Ala Leu Ala Ile Asn
                        165                 170                 175
        Met Leu Phe Ile Cys Arg Met Val Phe Asn Gly Asn Gly Leu Asp Val
                        180                 185                 190
        Asp Glu Tyr Val Arg Arg Ala Tyr Lys Phe Ala Tyr Ser Asp Cys Ile
                        195                 200                 205
        Glu Val Gly Pro Val Ala Cys Leu Pro Glu Pro Pro Asp Pro Asn Glu
                        210                 215                 220
        Leu Tyr Pro Arg Gln Thr Ser Arg Ala Ser His Leu Gly Leu Leu Tyr
        225                 230                 235                 240
        Leu Gly Ser Leu Val Val Leu Leu Ala Tyr Ser Val Leu Tyr Gly Leu
                        245                 250                 255
        Thr Ala Arg Glu Ser Arg Trp Leu Gly Gly Ile Thr Ser Ala Ala Val
                        260                 265                 270
        Ile Val Leu Asp Trp Asn Ile Gly Ala Cys Leu Tyr Gly Phe Lys Leu
                        275                 280                 285
        Leu Gln Asn Arg Val Leu Ala Leu Phe Val Ala Gly Ile Ser Arg Leu
                        290                 295                 300
        Phe Leu Ile Cys Phe Gly Ile His Tyr Trp Tyr Leu Gly His Cys Ile
        305                 310                 315                 320
        Ser Tyr Ile Phe Val Ala Ser Val Leu Ser Gly Ala Ala Val Ser Arg
                        325                 330                 335
        His Leu Ser Ile Thr Asp Pro Ser Ala Ala Arg Arg Asp Ala Leu Gln
                        340                 345                 350
        Ser Thr Val Ile Arg Leu Arg Glu Gly Phe Arg Arg Lys Glu Gln Asn
                        355                 360                 365
        Ser Ser Ser Ser Ser Ser Asp Gly Cys Gly Ser Ser Ile Lys Arg Ser
                        370                 375                 380
        Ser Ser Ile Asp Ala Gly His Thr Gly Cys Thr Asn Glu Ala Asn Arg
        385                 390                 395                 400
        Thr Ala Glu Ser Cys Thr Ala Asp Asn Leu Thr Arg Thr Gly Ser Ser
                        405                 410                 415
        Gln Glu Gly Ile Asn Ser Asp Lys Ser Glu Glu Ser Gly Arg Pro Ser
                        420                 425                 430
        Leu Gly Leu Arg Ser Ser Ser Cys Arg Ser Val Val Gln Glu Pro Glu
                        435                 440                 445
        Ala Gly Thr Ser Tyr Phe Met Asp Lys Val Ser Asp Gln Asn Asn Thr
                        450                 455                 460
        Leu Val Val Cys Ser Ser Ser Gly Leu Asp Ser Gln Gly Tyr Glu Ser
        465                 470                 475                 480
        Ser Thr Ser Asn Ser Ala Asn Gln Gln Leu Leu Asp Met Asn Leu Ala
                        485                 490                 495
        Leu Ala Phe Gln Asp Gln Leu Asn Asn Pro Arg Ile Ala Ser Ile Leu
                        500                 505                 510
        Lys Lys Lys Ala Lys Glu Gly Asp Leu Glu Leu Thr Asn Leu Leu Gln
                        515                 520                 525
        Asp Lys Gly Leu Asp Pro Asn Phe Ala Val Met Leu Lys Glu Lys Asn
                        530                 535                 540
        Leu Asp Pro Thr Ile Leu Ala Leu Leu Gln Arg Ser Ser Leu Asp Ala
        545                 550                 555                 560
        Asp Arg Asp His Arg Asp Asn Thr Asp Ile Thr Ile Ile Asp Ser Asn
                        565                 570                 575
```

```
Ser Val Asp Asn Thr Leu Pro Asn Gln Ile Ser Leu Ser Glu Glu Leu
            580                 585                 590

Arg Leu Arg Gly Leu Glu Lys Trp Leu Lys Leu Ser Arg Leu Leu Leu
        595                 600                 605

His His Val Ala Gly Thr Pro Glu Arg Ala Trp Gly Leu Phe Ser Leu
    610                 615                 620

Val Phe Ile Leu Glu Thr Ile Val Ala Ile Phe Arg Pro Lys Thr
625                 630                 635                 640

Ile Thr Ile Ile Asn Ser Ser His Gln Gln Phe Glu Phe Gly Phe Ser
                645                 650                 655

Val Leu Leu Ser Pro Val Val Cys Ser Ile Met Ala Phe Leu Arg
                660                 665                 670

Ser Leu Gln Val Glu Glu Met Ala Leu Thr Ser Lys Ser Arg Lys Tyr
            675                 680                 685

Gly Phe Val Ala Trp Leu Leu Ser Thr Ser Val Gly Leu Ser Leu Ser
        690                 695                 700

Phe Leu Ser Lys Ser Ser Val Leu Leu Gly Ile Ser Leu Thr Val Pro
705                 710                 715                 720

Leu Met Ala Ala Cys Leu Ser Ile Ala Val Pro Ile Trp Met His Asn
                725                 730                 735

Gly Tyr Gln Phe Trp Val Pro Gln Leu Ser Cys Gly Asp Gln Ala Arg
            740                 745                 750

Asp Leu Arg Ser Pro Arg Ile Lys Gly Phe Ile Leu Trp Ile Cys Val
        755                 760                 765

Val Leu Phe Ala Gly Ser Val Ile Ser Leu Gly Ala Ile Ile Ser Ala
770                 775                 780

Lys Pro Leu Asp Asp Leu Lys Tyr Lys Leu Phe Ser Ala Arg Glu Asn
785                 790                 795                 800

Asn Val Thr Ser Pro Tyr Thr Ser Ser Val Tyr Leu Gly Trp Ala Met
            805                 810                 815

Ser Ser Gly Ile Ala Leu Val Val Thr Ala Ile Leu Pro Ile Val Ser
            820                 825                 830

Trp Phe Ala Thr Tyr Arg Phe Ser His Ser Ser Ala Val Cys Leu Met
        835                 840                 845

Ile Phe Ser Val Val Leu Val Ala Phe Cys Gly Thr Ser Tyr Leu Glu
        850                 855                 860

Val Val Lys Ser Arg Asp Asp Gln Leu Pro Thr Lys Gly Asp Phe Leu
865                 870                 875                 880

Ala Ala Leu Leu Pro Leu Ala Cys Ile Pro Ala Leu Leu Ser Leu Cys
                885                 890                 895

Cys Gly Met Val Lys Trp Lys Asp Asp Cys Trp Ile Leu Ser Arg Gly
            900                 905                 910

Val Tyr Val Phe Phe Ser Ile Gly Leu Leu Leu Phe Gly Ala Ile
        915                 920                 925

Ala Ala Val Ile Ala Val Lys Pro Trp Thr Ile Gly Val Ser Phe Leu
930                 935                 940

Leu Val Leu Phe Leu Met Val Val Thr Ile Gly Val Ile His Leu Trp
945                 950                 955                 960

Ala Ser Asn Asn Phe Tyr Leu Thr Arg Lys Gln Thr Ser Phe Val Cys
            965                 970                 975

Phe Leu Ala Leu Leu Leu Gly Leu Ala Ala Phe Leu Leu Gly Trp His
            980                 985                 990
```

```
Gln Asp Lys Ala Phe Ala Gly Ala Ser Val Gly Tyr Phe Thr Phe Leu
        995                 1000                1005

Ser Leu Leu Ala Gly Arg Ala Leu Ala Val Leu Leu Ser Pro Pro Ile
    1010                1015                1020

Val Val Tyr Ser Pro Arg Val Leu Pro Val Tyr Val Asp Ala His
1025                1030                1035                1040

Ala Asp Cys Gly Lys Asn Val Ser Ala Ala Phe Leu Val Leu Tyr Gly
                    1045                1050                1055

Ile Ala Leu Ala Thr Glu Gly Trp Gly Val Val Ala Ser Leu Ile Ile
                1060                1065                1070

Tyr Pro Pro Phe Ala Gly Ala Ala Val Ser Ala Ile Thr Leu Val Val
            1075                1080                1085

Ala Phe Gly Phe Ala Val Ser Arg Pro Cys Leu Thr Leu Glu Met Met
        1090                1095                1100

Glu Val Ala Val Arg Phe Leu Ser Lys Asp Thr Ile Val Gln Ala Ile
1105                1110                1115                1120

Ser Arg Ser Ala Thr Lys Thr Arg Asn Ala Leu Ser Gly Thr Tyr Ser
                    1125                1130                1135

Ala Pro Gln Arg Ser Ala Ser Ala Ala Leu Leu Val Gly Asp Pro
                1140                1145                1150

Ser Ala Met Arg Asp Lys Ala Gly Asn Phe Val Leu Pro Arg Asp Asp
            1155                1160                1165

Val Met Lys Leu Arg Asp Arg Leu Arg Asn Glu Glu Arg Val Ala Gly
        1170                1175                1180

Ser Ile Phe Tyr Lys Met Gln Cys Arg Lys Gly Phe Arg His Glu Pro
1185                1190                1195                1200

Pro Thr Asn Val Asp Tyr Arg Arg Asp Met Cys Ala His Ala Arg Val
                    1205                1210                1215

Leu Ala Leu Glu Glu Ala Ile Asp Thr Glu Trp Val Tyr Met Trp Asp
                1220                1225                1230

Lys Phe Gly Gly Tyr Leu Leu Leu Leu Gly Leu Thr Ala Lys Ala
            1235                1240                1245

Glu Arg Val Gln Asp Glu Val Arg Leu Arg Leu Phe Leu Asp Ser Ile
        1250                1255                1260

Gly Phe Ser Asp Leu Ser Ala Arg Lys Ile Ser Lys Trp Lys Pro Glu
1265                1270                1275                1280

Asp Arg Arg Gln Phe Glu Ile Ile Gln Glu Ser Tyr Leu Arg Glu Lys
                    1285                1290                1295

Glu Met Glu Glu Glu Ser Leu Met Gln Arg Arg Glu Glu Gly Arg
                1300                1305                1310

Gly Lys Glu Arg Arg Lys Ala Leu Leu Glu Lys Glu Arg Lys Trp
            1315                1320                1325

Lys Glu Ile Glu Ala Ser Leu Ile Pro Ser Ile Pro Asn Ala Gly Ser
        1330                1335                1340

Arg Glu Ala Ala Ala Met Ala Ala Ala Ile Arg Ala Val Gly Gly Asp
1345                1350                1355                1360

Ser Val Leu Glu Asp Ser Phe Ala Arg Glu Arg Val Ser Gly Ile Ala
                    1365                1370                1375

Arg Arg Ile Arg Thr Ala Gln Leu Glu Arg Arg Ala Gln Gln Thr Gly
                1380                1385                1390

Ile Ser Gly Ala Val Cys Val Leu Asp Asp Glu Pro Met Ile Ser Gly
            1395                1400                1405

Lys His Cys Gly Gln Met Asp Ser Ser Val Cys Gln Ser Gln Lys Ile
```

-continued

```
            1410                1415                1420
Ser Phe Ser Val Thr Ala Met Ile Gln Ser Asp Ser Gly Pro Val Cys
1425                1430                1435                1440

Leu Phe Gly Thr Glu Phe Gln Lys Lys Val Cys Trp Glu Ile Leu Val
            1445                1450                1455

Ala Gly Ser Glu Gln Gly Ile Glu Ala Gly Gln Val Gly Leu Arg Leu
            1460                1465                1470

Ile Thr Lys Gly Glu Arg Gln Thr Thr Val Ala Arg Glu Trp Tyr Ile
            1475                1480                1485

Gly Ala Thr Ser Ile Thr Asp Gly Arg Trp His Thr Val Thr Ile Thr
            1490                1495                1500

Ile Asp Ala Asp Ala Gly Glu Ala Thr Cys Tyr Ile Asp Gly Gly Phe
1505                1510                1515                1520

Asp Gly Tyr Gln Asn Gly Leu Pro Leu Ser Ile Gly Ser Ala Ile Trp
            1525                1530                1535

Glu Gln Gly Ala Glu Val Trp Leu Gly Val Arg Pro Pro Ile Asp Val
            1540                1545                1550

Asp Ala Phe Gly Arg Ser Asp Ser Asp Gly Val Glu Ser Lys Met His
            1555                1560                1565

Ile Met Asp Val Phe Leu Trp Gly Lys Cys Leu Ser Glu Glu Glu Ala
            1570                1575                1580

Ala Ser Leu His Ala Ala Ile Gly Met Ala Asp Leu Asp Met Ile Asp
1585                1590                1595                1600

Leu Ser Asp Asp Asn Trp Gln Trp Thr Asp Ser Pro Pro Arg Val Asp
            1605                1610                1615

Gly Trp Asp Ser Asp Pro Ala Asp Val Asp Leu Tyr Asp Arg Asp Asp
            1620                1625                1630

Val Asp Trp Asp Gly Gln Tyr Ser Ser Gly Arg Lys Arg Arg Ser Gly
            1635                1640                1645

Arg Asp Phe Val Met Ser Val Asp Ser Phe Ala Arg Arg His Arg Lys
            1650                1655                1660

Pro Arg Met Glu Thr Gln Glu Asp Ile Asn Gln Arg Met Arg Ser Val
1665                1670                1675                1680

Glu Leu Ala Val Lys Glu Ala Leu Ser Ala Arg Gly Asp Lys Gln Phe
            1685                1690                1695

Thr Asp Gln Glu Phe Pro Pro Asn Asp Arg Ser Leu Phe Val Asp Thr
            1700                1705                1710

Gln Asn Pro Pro Ser Lys Leu Gln Val Val Ser Glu Trp Met Arg Pro
            1715                1720                1725

Asp Ser Ile Val Lys Glu Asn Gly Ser Asp Ser Arg Pro Cys Leu Phe
            1730                1735                1740

Ser Gly Asp Ala Asn Pro Ser Asp Val Cys Gln Gly Arg Leu Gly Asp
1745                1750                1755                1760

Cys Trp Phe Leu Ser Ala Val Ala Val Leu Thr Glu Val Ser Arg Ile
            1765                1770                1775

Ser Glu Val Ile Ile Thr Pro Glu Tyr Asn Glu Glu Gly Ile Tyr Thr
            1780                1785                1790

Val Arg Phe Cys Ile Gln Gly Glu Trp Val Pro Val Ile Asp Asp
            1795                1800                1805

Trp Ile Pro Cys Glu Ser Pro Gly Lys Pro Ala Phe Ala Thr Ser Arg
            1810                1815                1820

Lys Leu Asn Glu Leu Trp Val Ser Met Val Glu Lys Ala Tyr Ala Lys
1825                1830                1835                1840
```

Leu His Gly Ser Tyr Glu Ala Leu Glu Gly Gly Leu Val Gln Asp Ala
            1845                1850                1855

Leu Val Asp Leu Thr Gly Gly Ala Gly Glu Glu Ile Asp Leu Arg Ser
        1860                1865                1870

Ala Gln Ala Gln Ile Asp Leu Ala Ser Gly Arg Leu Trp Ser Gln Leu
            1875                1880                1885

Leu Arg Phe Lys Gln Glu Gly Phe Leu Leu Gly Ala Gly Ser Pro Ser
        1890                1895                1900

Gly Ser Asp Val His Val Ser Ser Ser Gly Ile Val Gln Gly His Ala
1905                1910                1915                1920

Tyr Ser Val Leu Gln Val Arg Glu Val Asp Gly His Arg Leu Val Gln
            1925                1930                1935

Ile Arg Asn Pro Trp Ala Asn Glu Val Glu Trp Asn Gly Pro Trp Ser
        1940                1945                1950

Asp Ser Ser Pro Glu Trp Thr Asp Arg Met Lys His Lys Leu Lys His
        1955                1960                1965

Val Pro Gln Ser Lys Glu Gly Ile Phe Trp Met Ser Trp Gln Asp Phe
    1970                1975                1980

Gln Ile His Phe Arg Ser Ile Tyr Val Cys Arg Val Tyr Pro Arg Glu
1985                1990                1995                2000

Met Arg Tyr Ser Val Asn Gly Gln Trp Arg Gly Tyr Ser Ala Gly Gly
            2005                2010                2015

Cys Gln Asp Tyr Ser Ser Trp His Gln Asn Pro Gln Phe Arg Leu Arg
        2020                2025                2030

Ala Thr Gly Ser Asp Ala Ser Leu Pro Ile His Val Phe Ile Thr Leu
            2035                2040                2045

Thr Gln Gly Val Gly Phe Ser Arg Thr Thr Pro Gly Phe Arg Asn Tyr
        2050                2055                2060

Gln Ser Ser His Asp Ser Gln Leu Phe Tyr Ile Gly Leu Arg Ile Leu
2065                2070                2075                2080

Lys Thr Arg Gly Arg Arg Ala Ala Tyr Asn Ile Phe Leu His Glu Ser
            2085                2090                2095

Val Gly Gly Thr Asp Tyr Val Asn Ser Arg Glu Ile Ser Cys Glu Met
            2100                2105                2110

Val Leu Asp Pro Asp Pro Lys Gly Tyr Thr Ile Val Pro Thr Thr Ile
        2115                2120                2125

His Pro Gly Glu Glu Ala Pro Phe Val Leu Ser Val Phe Thr Lys Ala
    2130                2135                2140

Ser Ile Val Leu Glu Ala
2145                2150

<210> SEQ ID NO 28
<211> LENGTH: 20035
<212> TYPE: DNA
<213> ORGANISM: Arabidopsis thaliana
<220> FEATURE:
<221> NAME/KEY: CDS
<222> LOCATION: (4001)...(14037)
<223> OTHER INFORMATION: genomic DNA sequence

<400> SEQUENCE: 28
tgggaggagt ggtgcatctt agcacggcga agttagctag aggtttctta gtgtgtttat    60
gtctttgggg ttttttctcg ctatcatacg ccgcaaggtc cggcgtatca aagcagaagt   120
ttgaagtgaa gaaacatttg aacaggctga acaaacctgc tgtcaaaagc attcaggtat   180

```
atatatttt   tttttagtgt   tttggtttct   tctatttgga   ttggttttg   atagacaaat    240 gagagatctt  tagaacatta   tcataatctt   atgattcact   tatttctctc  tccttcctgc    300
tacacataat  gattcgattt   acttttattt   tattaacgat   tccataaaag  ttatggtcat    360
aattaaggat  tttgacttga   aatgttaatg   ttactttgtt   gttgaacaga  gttcagatgg    420
tgatgtgatt  gactgtgttc   caatctcaaa   gcaaccagct   tttgatcatc  cgttcctcaa    480
agatcacaag  attcaggtct   agagaataaa   acataactg    atttagatct  ggctttgtgt    540
tttatgttgt  aagtgctgat   gttttttatat  atactttgtt   ttttttttaga tgaagcctaa    600 ttaccaccct  gaaggactct   ttgatgacaa   caaagtgtct   gctcctaaat  caaatgagaa    660
agaagggcat  attcctcagt   tgtggcatcg   atatggtaaa   tgttctgaag  gaactattcc    720
catgaggagg  acaaaggaag   atgatgtttt   gagagcaagt   tcagttaaaa  gatatggcaa    780
gaagaagcgt  agaagtgtcc   ctttacctaa   atctgcagaa   cctgacctta  ttaaccaaag    840
tggtcaccag  gtgagactaa   gtgtgaatgt   gttgtgaatc   ttttttattt  ttgttggttt    900
ctggatctga  gatgttttgt   tttggtttca   tgaattgtag   catgccatag  cttatgtaga    960
aggagataag  tactatggag   ctaaggctac   tataaatgtg   tgggagccaa  agatacagca   1020
gcagaatgag  ttcagcttgt   cacagatatg   gcttcttggt   ggctcattcg  gacaagatct   1080
taatagcatc  gaagctggtt   ggcaggtact   acaatgttat   cccaacgaga  aacatataag   1140
aaatgtgaat  aagatttgtg   tgtgattctt   ttttcatgtt   tagaatattg  actcttgttg   1200
cttttattta  caggtgagcc   cggatctgta   tggtgacaat   aacacgagac  tcttcactta   1260
ctggactgta  agatcctaac   actcccacct   aatcaagttc   ttactgtcat  atctttctgt   1320
ttctgcttat  atttctctgt   tgtatcttac   gttaccaaat   tatttgcaga  gtgatgcata   1380
tcaagctacc  ggttgctaca   atcttctttg   ctccggtttt   attcaaatca  acagtgacat   1440
agcaatggga  gcaagcattt   ccccggtctc   tggatatcgt   aactcgcagt  acgatatcag   1500
tattctgatc  tggaaggtat   gttaagccat   aaagagataa   gtttgacgca  atccataaga   1560
caagaaaagc  tgaaatggtc   tgttaacttt   tttcacagga   tcctaaagag  ggacactggt   1620
ggatgcaatt  tgggaacggc   tatgttttag   gctattggcc   atcttttctc  ttctcctact   1680
tgacagaaag  tgcatcgatg   attgaatggg   gaggagaagt   cgtgaactca  caatcagatg   1740
gccagcacac  ttcaacacaa   atgggcagtg   gtaaatttcc   agaagaaggc  tttagcaaag   1800
caagttactt  caggaacatt   caggtggttg   atgggtcaaa   caacctcaag  gcacctaaag   1860
gacttggaac  attcactgaa   cagtctaact   gttatgatgt   tcaaaccgga  agcaatgatg   1920 attgggtca   ttacttttac   tatgaggcc   ctggtaaaaa   ccagaagtgt  ccataagcta   1980
ggctccaagt  agtagtggct   cgtctctcga   gttatcttgt   cttgtgaatt  caccttgttt   2040 cttttctacac acactcactc   aaatccgcct   tcttgggtag   ttttaggga   tggttaaagt   2100 tatgtaatgg  taaagtttg    gtgtcttttt   ctccatgtaa   gtaggtgggg  aagaagtgga   2160
aaggtgtggc  ttaagtttct   ttgaaaactc   agaaactttg   gcccttagtg  taattttact   2220
ttgtctcctt  tgtattgtga   tttgtttaaa   caagtgaatg   aatctctctt  tctcactctt   2280
attaacaaat  aatttcaggg   aattaatatt   aacttttgcc   ttaatctctt  tataaaccta   2340
ctctctaatg  ccctttttg    acaattagag   atttactt    gttttctcat  cacctttgg    2400 taaatttgac  ttcacattta   gagagagaga   gagtaaaatg   atctaaaaat  ggtcatggat   2460
tgcatttgaa  aattgtattt   ggtgatgact   gatttcatga   actgtctctc  tttggatgat   2520
gatcttttgc  aaatgggtga   atcatattta   ttttttccac   ttttttcaca  ataaagttcc   2580
```

-continued

```
aagcatatac aattatgaag tacacatata ctgaatttac aacaaaactt ttcctacaac   2640
cttctaattt taaatatgct attttcttaa gtgaaaaagt taaatattaa tattgtagat   2700
ctgccttttg aaaataaata tggtcttgta tgttcagtag actatctttg acttaatcgg   2760
cttaaatttg ggattaaaga aattagaaac aagaaaacaa tttaaaaatt ctaatttgta   2820
ttatatcata tagttgatga tttaaatttt gtgacagaga cattggtctt ccacttcttt   2880
tttcctggtt atgagctttg agcctataac ctgaatttga cttacttaaa cttatttagt   2940
aattatacta tttattcatg aattaggtac tattttatca ttcttgtctt cttctttttt   3000
ctttcctacc ataatactat ttttattttc ttttaatcac acatatcaca atattatact   3060
tctgttttgt tttgtgcatt taacactttt tgtctaaatt aatattggat tggataaaat   3120
attgagtgta ataagataac atataaattc aggtaataaa aaccaattaa aaacagatgt   3180
aagtcttttt ttgacaaatc ttaatttagc taaatccgta tctaaatcat tccattctca   3240
ctgaccaata aatactcaga gcgtgtacac cacttgatat ctcattggct catggttcac   3300
acgcgcgtgt agcgtttgtt cggacagaac catagcttta tttattttat taaattaatt   3360
gtgttttttt ttccacaaga acttttttctc tctctacaat acgtcgtctc tttgaggaag   3420
agagagagtg agaaaaaggt agtagcttct tttttttagt ttacgggttc acacattcaa   3480
agggtagggt tttaatctta ccttctctct ctatccattt cccaaaacct gagaaacaaa   3540
tttctctgag atttattcaa aaaaaaatca acattttgca gaaagcaaaa gcaagaaaac   3600
cctaaaagga agctaatttg tgtttcacaa gctcttcaga gtgtgagccc tatctttctg   3660
ttttctctac tttacagctt gattcttctg attttaaacc ctagtgaacc aaatctgtat   3720
ccaagatgtc tcattttgct tgaaggctgc taaagtttcg attttttaagc gatcccttc   3780 tgcttcgatg ccactgcaca gtaagctcat ttcggtcaag taggtaaggt ttctaaactt   3840
aagctgggtt ttgtgaaatt taggtttggt ttttgtgttc ttggttggtt ttaagctgcg   3900
gatttgatga tttgtgcgca agcttggggt ttcagctttt ttttttgtga tggaattttg   3960
atttccgagt tgcatggtgt tgtaggtggg agaagaagcc atg gaa ggg gat gag   4015
                                              Met Glu Gly Asp Glu
                                                1               5 cga gga gtc tta ctt gct tgt gta att tcg ggt acc ctt ttc acg gtt   4063
Arg Gly Val Leu Leu Ala Cys Val Ile Ser Gly Thr Leu Phe Thr Val
         10                  15                  20 ttc ggt tcg ggt tcg ttt tgg ata ctt tgg gct gtt aat tgg cgg cca   4111
Phe Gly Ser Gly Ser Phe Trp Ile Leu Trp Ala Val Asn Trp Arg Pro
     25                  30                  35 tgg cgt ctc tac agg taa aca agt cca ttc ata tgt ttg ggc agc tct   4159
Trp Arg Leu Tyr Arg  *  Thr Ser Pro Phe Ile Cys Leu Gly Ser Ser
         40                  45                  50 agg tgt tgt ttt gtc ata tat ggc gct tga tag agt tgc ttt gta tga   4207
Arg Cys Cys Phe Val Ile Tyr Gly Ala  *   *  Ser Cys Phe Val  *
         55                  60                  65 gta gta ttg aca tag aac cat agt tag tga atg att ttg gaa tgt gtt   4255
Val Val Leu Thr  *  Asn His Ser  *   *  Met Ile Leu Glu Cys Val
         70                  75 cta ttt ttg cag ttg gat ctt tgc tag aaa atg gcc aaa agt att gca   4303
Leu Phe Leu Gln Leu Asp Leu Cys  *  Lys Met Ala Lys Ser Ile Ala
     80                  85                  90 agg tcc tca gct tga tat act atg tgg tgt tct atc tct ttt tgc ttg   4351
Arg Ser Ser Ala  *  Tyr Thr Met Trp Cys Ser Ile Ser Phe Cys Leu
     95                  100                 105
```

```
                                                              -continued gat tgt ggt agt atc ccc tat tgc aat ctt gat agg atg ggg ttc ttg        4399
Asp Cys Gly Ser Ile Pro Tyr Cys Asn Leu Asp Arg Met Gly Phe Leu
    110             115             120 gct gat tgt gat att gga tcg aca tat cat tgg gct ggc gat aat aat        4447
Ala Asp Cys Asp Ile Gly Ser Thr Tyr His Trp Ala Gly Asp Asn Asn
125             130             135             140 ggc tgg aac agc cct ttt act ggc att cta ctc aat cat gct ttg gtg        4495
Gly Trp Asn Ser Pro Phe Thr Gly Ile Leu Leu Asn His Ala Leu Val
            145             150             155 gag gac cca gtg gca aag ctc aag tat gtt tac cat cta ctc ttt ctg        4543
Glu Asp Pro Val Ala Lys Leu Lys Tyr Val Tyr His Leu Leu Phe Leu
            160             165             170 act taa ttc aca aca ttc ttc tgg tgt tat att ctt gat aat agt ggt        4591
Thr  *  Phe Thr Thr Phe Phe Trp Cys Tyr Ile Leu Asp Asn Ser Gly
        175             180             185 ggc acg tag tgt tag tgt atg aag tat ccg atg tag gaa tgg gaa caa        4639
Gly Thr  *  Cys  *  Cys Met Lys Tyr Pro Met  *  Glu Trp Glu Gln
        190             195             200 agc aga aca tac ctg aca cat cac tac tta ttg tga atg aac tat tga        4687
Ser Arg Thr Tyr Leu Thr His His Tyr Leu Leu  *  Met Asn Tyr  *
            205             210 act tct ttc tta cat tct cgt ttg aac aaa cag gag ctg tcg ctt tac        4735
Thr Ser Phe Leu His Ser Arg Leu Asn Lys Gln Glu Leu Ser Leu Tyr
215             220             225             230 ttc tcc ttc ttg gtg ttg cct tac tat gtg cgt atg aac tct gtg ctg        4783
Phe Ser Phe Leu Val Leu Pro Tyr Tyr Val Arg Met Asn Ser Val Leu
            235             240             245 tct atg tta cgg ctg gtg cgc atg cat ctc agc aat att ctc ctt ctg        4831
Ser Met Leu Arg Leu Val Arg Met His Leu Ser Asn Ile Leu Leu Leu
            250             255             260 gtt tct ttt tcg gtg tat cag caa tcg cgt tgg caa tta aca tgc tat        4879
Val Ser Phe Ser Val Tyr Gln Gln Ser Arg Trp Gln Leu Thr Cys Tyr
            265             270             275 tta tct gcc gca tgg tct tta atg gta aag ttt acc cag tcc tta atc        4927
Leu Ser Ala Ala Trp Ser Leu Met Val Lys Phe Thr Gln Ser Leu Ile
            280             285             290 aac atg caa ttg ctg tgt att caa ctt tat cag tct act taa ttc ttt        4975
Asn Met Gln Leu Leu Cys Ile Gln Leu Tyr Gln Ser Thr  *  Phe Phe
295             300             305 gta tta gct caa agc aaa tct tcc gta tct att aac atg cat act ttt        5023
Val Leu Ala Gln Ser Lys Ser Ser Val Ser Ile Asn Met His Thr Phe
310             315             320             325 taa cct cca acc tca att taa gtt gtt gaa act ttg cga aat ttt cca        5071
 *  Pro Pro Thr Ser Ile  *  Val Val Glu Thr Leu Arg Asn Phe Pro
            330             335 tca ccg cag gaa atg gtt tag atg tgg acg aat atg taa gga ggg cat        5119
Ser Pro Gln Glu Met Val  *  Met Trp Thr Asn Met  *  Gly Gly His
340             345             350 ata aat ttg ctt att cag att gta tag aag tgg gtc ctg tgg ctt gtt        5167
Ile Asn Leu Leu Ile Gln Ile Val  *  Lys Trp Val Leu Trp Leu Val
            355             360             365 tgc ctg aac ctc ctg atc cta atg aat tat atc ccc ggc aaa cca gca        5215
Cys Leu Asn Leu Leu Ile Leu Met Asn Tyr Ile Pro Gly Lys Pro Ala
            370             375             380 ggt aag ttc ttg ttg ctc tct acc tag aaa ttc aat aat att ttg gca        5263
Gly Lys Phe Leu Leu Leu Ser Thr  *  Lys Phe Asn Asn Ile Leu Ala
385             390             395 tag ctg gcc tct tat gtt atg att gtt cct gaa ttt tgc aat caa caa        5311
 *  Leu Ala Ser Tyr Val Met Ile Val Pro Glu Phe Cys Asn Gln Gln
            400             405             410
```

-continued

| | |
|---|---|
| act att gaa tac ttg gaa cca acc taa atc tga aca gga ttc agg gct<br>Thr Ile Glu Tyr Leu Glu Pro Thr * Ile * Thr Gly Phe Arg Ala<br>415                        420                                    425 | 5359 |
| agt aat ctt gcc gtt tct ctc tag ctt ttt ttt ttt tcg ccc aac agg<br>Ser Asn Leu Ala Val Ser Leu * Leu Phe Phe Phe Ser Pro Asn Arg<br>430                        435                                    440 | 5407 |
| tgg tgt gga tgg tgt tat gat ttg ttt ata ctg agc gct gaa atg ttc<br>Trp Cys Gly Trp Cys Tyr Asp Leu Phe Ile Leu Ser Ala Glu Met Phe<br>445                        450                                    455 | 5455 |
| tca ttc ata ttt tta tca atc agc tat aat ctt ttt tct tgc ata tat<br>Ser Phe Ile Phe Leu Ser Ile Ser Tyr Asn Leu Phe Ser Cys Ile Tyr<br>460                        465                        470                        475 | 5503 |
| gta ggg ctt cac atc ttg gcc ttc tgt acc tgg gct cac tcg tag ttc<br>Val Gly Leu His Ile Leu Ala Phe Cys Thr Trp Ala His Ser * Phe<br>                        480                        485                            490 | 5551 |
| tcc ttg cct act cag tcc tat atg gtc tca cag cta ggg aat cac gtt<br>Ser Leu Pro Thr Gln Ser Tyr Met Val Ser Gln Leu Gly Asn His Val<br>                495                        500                        505 | 5599 |
| ggc ttg gag gaa tca cat cag ctg cag tta ttg ttc ttg gta aaa aga<br>Gly Leu Glu Glu Ser His Gln Leu Gln Leu Leu Phe Leu Val Lys Arg<br>            510                        515                        520 | 5647 |
| taa aaa tta ttt act tat att taa agt tga agc agg cta ctt gat tat<br>* Lys Leu Phe Thr Tyr Ile * Ser * Ser Arg Leu Leu Asp Tyr<br>                525                               530                        535 | 5695 |
| tcc tca act cat ctt cat gct taa tat ttt cat gta gac tgg aat att<br>Ser Ser Thr His Leu His Ala * Tyr Phe His Val Asp Trp Asn Ile<br>                540                               545                        550 | 5743 |
| ggg gca tgc ttg tat ggg ttt aag ctt ctt cag aat cgt gtt ctg gca<br>Gly Ala Cys Leu Tyr Gly Phe Lys Leu Leu Gln Asn Arg Val Leu Ala<br>                  555                        560                        565 | 5791 |
| ctt ttt gtt gct ggc ata tcc cgt ctt ttc cta ata tgt ttt ggc ata<br>Leu Phe Val Ala Gly Ile Ser Arg Leu Phe Leu Ile Cys Phe Gly Ile<br>                570                               575                        580 | 5839 |
| cac tac tgg ttt gtt tct gag cta aaa agc ttg tta ctt atc tat aga<br>His Tyr Trp Phe Val Ser Glu Leu Lys Ser Leu Leu Leu Ile Tyr Arg<br>            585                        590                        595 | 5887 |
| tct aaa gtt tgt ccc ctt cat ggc atg taa gat att atc cgt tct gtt<br>Ser Lys Val Cys Pro Leu His Gly Met * Asp Ile Ile Arg Ser Val<br>600                        605                                    610 | 5935 |
| gtt gca ggt acc tag ggc att gta tta gtt aca ttt tcg tag cat cag<br>Val Ala Gly Thr * Gly Ile Val Leu Val Thr Phe Ser * His Gln<br>            615                        620                        625 | 5983 |
| ttc tat cag gtg ctg ctg ttt ctc ggc atc tat cta taa cag acc cat<br>Phe Tyr Gln Val Leu Leu Phe Leu Gly Ile Tyr Leu * Gln Thr His<br>                630                             635                        640 | 6031 |
| cag ctg caa gaa gag atg cct tac aga gca cag tga tcc gct tga gag<br>Gln Leu Gln Glu Glu Met Pro Tyr Arg Ala Gln * Ser Ala * Glu<br>            645                        650                        655 | 6079 |
| aag gtt ttc gga gaa aag agc aga ata gtt ctt caa gtt ctt cag atg<br>Lys Val Phe Gly Glu Lys Ser Arg Ile Val Leu Gln Val Leu Gln Met<br>                660                             665                        670 | 6127 |
| gtt gtg gct caa gta taa aaa gaa gta gta gta tcg atg ctg gcc ata<br>Val Val Ala Gln Val * Lys Glu Val Val Val Ser Met Leu Ala Ile<br>            675                        680                        685 | 6175 |
| ctg gtt gta cta atg aag caa atc gta cgg cag aat ctt gca cgg ctg<br>Leu Val Val Leu Met Lys Gln Ile Val Arg Gln Asn Leu Ala Arg Leu<br>            690                        695                        700 | 6223 |
| aca atc taa ctc gaa cag gca gct ctc agg agg gaa tca ata gcg aca<br>Thr Ile * Leu Glu Gln Ala Ala Leu Arg Arg Glu Ser Ile Ala Thr | 6271 |

```
                                          -continued
      705                   710                   715
aaa gcg aag aaa gtg gaa gac caa gct tag gtt tac gta gta gtt cat    6319
Lys Ala Lys Lys Val Glu Asp Gln Ala  *  Val Tyr Val Val Val His
720                 725                 730 gtt ctg tgg tcc aag agc ccg aag cag gaa cgt ctt att tta tgg        6367
Val Leu Trp Ser Lys Ser Pro Lys Gln Glu Arg Leu Ile Leu Trp
    735                 740                 745 aca aag ttt ctg atc aaa ata aca ctc ttg ttg ttt gtt cga gca gtg    6415
Thr Lys Phe Leu Ile Lys Ile Thr Leu Leu Leu Phe Val Arg Ala Val
750                 755                 760                 765 gtc tag ata gcc aag gtt acg agt cta gca cat cga att ctg caa acc    6463
Val  *  Ile Ala Lys Val Thr Ser Leu Ala His Arg Ile Leu Gln Thr
        770                 775                 780 agc agc ttt tgg ata tga att tgg ctc ttg ctt tcc agg acc agt taa    6511
Ser Ser Phe Trp Ile  *  Ile Trp Leu Leu Leu Ser Arg Thr Ser  *
            785                 790 aca atc cta gga tag cct cga tac tta aga aga aag caa aag aag gtg    6559
Thr Ile Leu Gly  *  Pro Arg Tyr Leu Arg Arg Lys Gln Lys Lys Val
795                 800                 805 atc ttg aac tga cta att tgc tgc aag aca agg ggt tgg acc cta act    6607
Ile Leu Asn  *  Leu Ile Cys Cys Lys Thr Arg Gly Trp Thr Leu Thr
810                 815                 820 ttg ctg taa tgt tga agg aaa aaa act tgg atc cta cta tat tgg cac    6655
Leu Leu  *  Cys  *  Arg Lys Lys Thr Trp Ile Leu Leu Tyr Trp His
825                 830                 835 tac ttc aga gga gta gtt tgg atg cag ata gag atc acc gcg aca ata    6703
Tyr Phe Arg Gly Val Val Trp Met Gln Ile Glu Ile Thr Ala Thr Ile
    840                 845                 850 ctg ata tta caa tca ttg act caa aca gtg ttg aca ata ctt tgc caa    6751
Leu Ile Leu Gln Ser Leu Thr Gln Thr Val Leu Thr Ile Leu Cys Gln
855                 860                 865                 870 atc aga ttt ctt tat ccg aag aat tga gac tcc gtg gac tag aga agt    6799
Ile Arg Phe Leu Tyr Pro Lys Asn  *  Asp Ser Val Asp  *  Arg Ser
            875                 880 ggc tta agt tgt cta gac ttc ttc tgc acc atg tag cgg gga cac cag    6847
Gly Leu Ser Cys Leu Asp Phe Phe Cys Thr Met  *  Arg Gly His Gln
885                 890                 895 aga gag cat ggg gcc tct tta gtc ttg tct tta tcc ttg aaa caa tca    6895
Arg Glu His Gly Ala Ser Leu Val Leu Ser Leu Ser Leu Lys Gln Ser
900                 905                 910                 915 ttg tgg cca ttt ttc gcc caa aga cca tca cga tta taa att cta gtc    6943
Leu Trp Pro Phe Phe Ala Gln Arg Pro Ser Arg Leu  *  Ile Leu Val
            920                 925                 930 atc aac agg tga gtt cca ccc tct gat tta ttg tct ctg tgg aaa aaa    6991
Ile Asn Arg  *  Val Pro Pro Ser Asp Leu Leu Ser Leu Trp Lys Lys
                935                 940                 945 ttt tgg gtc ttg ttt tgg ctt caa att act gcc agt tta ctc aaa ttg    7039
Phe Trp Val Leu Phe Trp Leu Gln Ile Thr Ala Ser Leu Leu Lys Leu
            950                 955                 960 atc ctt gta gtt taa atg aag gtt att cgt acc ttt gct aac tca ctt    7087
Ile Leu Val Val  *  Met Lys Val Ile Arg Thr Phe Ala Asn Ser Leu
        965                 970                 975 gtt atc taa ttg tag ttc gaa ttt ggt ttc tct gtg ctg cta ttg tca    7135
Val Ile  *  Leu  *  Phe Glu Phe Gly Phe Ser Val Leu Leu Leu Ser
                980                 985                 990 cct gtt gtc tgt tca ata atg gct ttt ctt cgg tct ctt caa gtt gag    7183
Pro Val Val Cys Ser Ile Met Ala Phe Leu Arg Ser Leu Gln Val Glu
            995                 1000                1005 gaa atg gcc ttg aca tca aaa tct cgc aag gta tgg ctc gtc tct ttg    7231
```

```
Glu Met Ala Leu Thr Ser Lys Ser Arg Lys Val Trp Leu Val Ser Leu
        1010                1015                1020 gtt tag tat gtt cat tag tac ttg ttg tgg aca atg cat ata ccc tgt      7279
Val  *  Tyr Val His  *  Tyr Leu Leu Trp Thr Met His Ile Pro Cys
            1025                1030                1035 gat gtt tta att gtt cta aat tat gtt atg ttt cta tgt ttt cag tat      7327
Asp Val Leu Ile Val Leu Asn Tyr Val Met Phe Leu Cys Phe Gln Tyr
        1040                1045                1050 ggc ttt gtt gcc tgg ctt ctg agc aca tca gtt gga ttg tca ctc tcg      7375
Gly Phe Val Ala Trp Leu Leu Ser Thr Ser Val Gly Leu Ser Leu Ser
        1055                1060                1065 ttc ttg agg tac tac gat ttt ttt atc ttc att gga cag cta cca act      7423
Phe Leu Arg Tyr Tyr Asp Phe Phe Ile Phe Ile Gly Gln Leu Pro Thr
        1070                1075                1080 ttt cgc aca atg gtc aca gga tta tgt cat tca ttg gac agc tac caa      7471
Phe Arg Thr Met Val Thr Gly Leu Cys His Ser Leu Asp Ser Tyr Gln
1085            1090                1095                1100 ctt ttc tca ctt ggt cat ttt tat gtt ctc att aca aac atc atg cat      7519
Leu Phe Ser Leu Gly His Phe Tyr Val Leu Ile Thr Asn Ile Met His
            1105                1110                1115 gct tca att ttg cag taa atc gtc agt act tct ggg aat atc ctt gac      7567
Ala Ser Ile Leu Gln  *  Ile Val Ser Thr Ser Gly Asn Ile Leu Asp
        1120                1125                1130 tgt gcc cct cat ggc agc atg cct gtc tat tgc tgt tcc cat atg gat      7615
Cys Ala Pro His Gly Ser Met Pro Val Tyr Cys Cys Ser His Met Asp
        1135                1140                1145 gca taa tgg gta cca att ttg ggt tcc aca gtt atc atg tgg tga cca      7663
Ala  *  Trp Val Pro Ile Leu Gly Ser Thr Val Ile Met Trp  *  Pro
        1150                1155                1160 ggc aag aga ttt acg atc tcc cag gat aaa ggt ctg tgt gtt ttc cct      7711
Gly Lys Arg Phe Thr Ile Ser Gln Asp Lys Gly Leu Cys Val Phe Pro
        1165                1170                1175 gac ctg gtt gca agt atc tct ctt tgt caa tta aat atc tct aac taa      7759
Asp Leu Val Ala Ser Ile Ser Leu Cys Gln Leu Asn Ile Ser Asn  *
        1180                1185                1190 act ttc ttt cca ttt tag ggg ttt att ctt tgg att tgt gtt gtg ttg      7807
Thr Phe Phe Pro Phe  *  Gly Phe Ile Leu Trp Ile Cys Val Val Leu
        1195                1200                1205 ttt gcg ggt tct gta att tct ctt ggt gcg att ata tct gct aaa cct      7855
Phe Ala Gly Ser Val Ile Ser Leu Gly Ala Ile Ile Ser Ala Lys Pro
        1210                1215                1220 ttg gat gat tta aag tat aag ctg ttt agt gcc aga gaa aac aac gtc      7903
Leu Asp Asp Leu Lys Tyr Lys Leu Phe Ser Ala Arg Glu Asn Asn Val
        1225                1230                1235 acg tca cca tat aca tct tct gta tac ctt ggt tgg gca atg tca tct      7951
Thr Ser Pro Tyr Thr Ser Ser Val Tyr Leu Gly Trp Ala Met Ser Ser
1240            1245                1250                1255 gga att gct tta gta gtt acc gcc att cta cca ata gtt tca tgg ttt      7999
Gly Ile Ala Leu Val Val Thr Ala Ile Leu Pro Ile Val Ser Trp Phe
        1260                1265                1270 gca act tat agg ttt tcc cac tct tct gct gtc tgt ctc atg ata ttc      8047
Ala Thr Tyr Arg Phe Ser His Ser Ser Ala Val Cys Leu Met Ile Phe
        1275                1280                1285 tca ggt aat ttg tgt ttc tgt tag ttt gct cac att tgg ttg gga ttt      8095
Ser Gly Asn Leu Cys Phe Cys  *  Phe Ala His Ile Trp Leu Gly Phe
        1290                1295                1300 ttt tcc ttc tcg aag tga tcc tta tat ttc ttt tcc tct act ttc tag      8143
Phe Ser Phe Ser Lys  *  Ser Leu Tyr Phe Phe Ser Ser Thr Phe  *
        1305                1310                1315
```

| | |
|---|---:|
| ttg ttc tcg tgg cat ttt gtg gaa ctt cat att tgg aag ttg taa aat<br>Leu Phe Ser Trp His Phe Val Glu Leu His Ile Trp Lys Leu * Asn<br>             1320                  1325                1330 | 8191 |
| cta gag atg atc agt tgc cca caa agg gtg att tcc ttg cgg cct tgc<br>Leu Glu Met Ile Ser Cys Pro Gln Arg Val Ile Ser Leu Arg Pro Cys<br>1335                  1340                  1345 | 8239 |
| ttc cac ttg cat gca ttc cgg cgc tgc ttt cac tat gct gtg gga tgg<br>Phe His Leu His Ala Phe Arg Arg Cys Phe His Tyr Ala Val Gly Trp<br>1350                  1355                  1360 | 8287 |
| tta aat ggt gga tga cta ttt cct cac gtt gcc tat aaa tcc ttc ctc<br>Leu Asn Gly Gly * Leu Phe Pro His Val Ala Tyr * Ile Leu Leu<br>1365                  1370                  1375 | 8335 |
| tca gtt tca atg aga tcg tcc ttt taa atg ttt tgt ggt tgt tct ttg<br>Ser Val Ser Met Arg Ser Ser Phe * Met Phe Cys Gly Cys Ser Leu<br>1380                  1385                  1390 | 8383 |
| cag gaa gga cga ttg ttg gat act ctc tcg agg tgt ata tgt ttt ctt<br>Gln Glu Gly Arg Leu Leu Asp Thr Leu Ser Arg Cys Ile Cys Phe Leu<br>             1395                  1400                1405 | 8431 |
| ttc aat agg tct tct tct tct ttt tgg tgc gat agc agc tgt cat tgc<br>Phe Asn Arg Ser Ser Ser Ser Phe Trp Cys Asp Ser Ser Cys His Cys<br>             1410                  1415                1420 | 8479 |
| agt caa acc atg gac ggt aaa tgc aaa ttg ctt aca taa ttc tca aag<br>Ser Gln Thr Met Asp Gly Lys Cys Lys Leu Leu Thr * Phe Ser Lys<br>1425                  1430                  1435 | 8527 |
| ttt ttg gct tac ttt tct caa tct gat aca tct ttg tgt ttc aat aat<br>Phe Leu Ala Tyr Phe Ser Gln Ser Asp Thr Ser Leu Cys Phe Asn Asn<br>1440                  1445                  1450                1455 | 8575 |
| aac aga tag gcg tat ctt ttc tct tag ttc ttt tcc tta tgg tgg taa<br>Asn Arg * Ala Tyr Leu Phe Ser * Phe Phe Ser Leu Trp Trp *<br>                      1460                            1465 | 8623 |
| caa ttg gtg taa tcc atc ttt ggg cgt caa aca att tct att taa cca<br>Gln Leu Val * Ser Ile Phe Gly Arg Gln Thr Ile Ser Ile * Pro<br>1470                  1475                  1480 | 8671 |
| gga aac aga cat cct ttg tct gct ttc ttg ctc ttc ttt tgg gtt tgg<br>Gly Asn Arg His Pro Leu Ser Ala Phe Leu Leu Phe Phe Trp Val Trp<br>             1485                  1490                1495 | 8719 |
| ccg cat tcc ttc tcg gat ggc atc aag gtg agg att gcc cat atc tta<br>Pro His Ser Phe Ser Asp Gly Ile Lys Val Arg Ile Ala His Ile Leu<br>             1500                  1505                1510 | 8767 |
| ttt taa act ctt cgt aga ggt gag acc tac tct agt gac aca gca att<br>Phe * Thr Leu Arg Arg Gly Glu Thr Tyr Ser Ser Asp Thr Ala Ile<br>1515                  1520                  1525 | 8815 |
| tca taa ttt ttt tgc aga taa agc att tgc tgg agc atc tgt tgg tta<br>Ser * Phe Phe Cys Arg * Ser Ile Cys Trp Ser Ile Cys Trp Leu<br>1530                  1535                  1540 | 8863 |
| ctt tac att cct gtc tct gtt ggc tgg aag agc att agc tgt gag ttc<br>Leu Tyr Ile Pro Val Ser Val Gly Trp Lys Ser Ile Ser Cys Glu Phe<br>1545                  1550                  1555 | 8911 |
| aac aga act gtg gct ttt tct gtt tct gta ttc aac cgg aat att aac<br>Asn Arg Thr Val Ala Phe Ser Val Ser Val Phe Asn Arg Asn Ile Asn<br>1560                  1565                  1570                1575 | 8959 |
| gat tat tct cgt agg ttc ttc tat ccc cac caa ttg tag tat att ctc<br>Asp Tyr Ser Arg Arg Phe Phe Tyr Pro His Gln Leu * Tyr Ile Leu<br>             1580                  1585                1590 | 9007 |
| caa ggg tgc tac cag tat atg tct acg atg ctc atg ctg att gcg aaa<br>Gln Gly Cys Tyr Gln Tyr Met Ser Thr Met Leu Met Leu Ile Ala Glu<br>             1595                  1600                1605 | 9055 |
| aga atg tca ggt atg cag cca ctt gag tac ccc taa tag tat tgc atc<br>Arg Met Ser Gly Met Gln Pro Leu Glu Tyr Pro * * Tyr Cys Ile<br>             1610                  1615                1620 | 9103 |

-continued

| | |
|---|---|
| tgc tga tct gaa atg acc ata aag gat taa gct gat cga ctc tca tat<br>Cys * Ser Glu Met Thr Ile Lys Asp * Ala Asp Arg Leu Ser Tyr<br>                      1625                                 1630 | 9151 |
| gct ttt cta ttg att gca ttg gga ttt ctc tag tgc tgc att tct tgt<br>Ala Phe Leu Leu Ile Ala Leu Gly Phe Leu * Cys Cys Ile Ser Cys<br>1635                      1640                           1645 | 9199 |
| cct gta tgg aat tgc ttt ggc aac aga agg ctg ggg tgt tgt tgc tag<br>Pro Val Trp Asn Cys Phe Gly Asn Arg Arg Leu Gly Cys Cys Cys *<br>                1650                         1655                         1660 | 9247 |
| tct gat aat tta tcc tcc gtt tgc ggg tgc tgc tgt atc agc tat cac<br>Ser Asp Asn Leu Ser Ser Val Cys Gly Cys Cys Cys Ile Ser Tyr His<br>1665                      1670                         1675                     1680 | 9295 |
| cct tgt agt agc ctt tgg gtt tgc tgt ttc tcg ccc atg ttt gac tct<br>Pro Cys Ser Ser Leu Trp Val Cys Cys Phe Ser Pro Met Phe Asp Ser<br>                      1685                        1690                     1695 | 9343 |
| tga ggt tag ttt tct ggt tgt ttg att tat ttg ttc ctt aaa ata aag<br>* Gly * Phe Ser Gly Cys Leu Ile Tyr Leu Phe Leu Lys Ile Lys<br>                           1700                        1705                     1710 | 9391 |
| att agt ggt tag tgg ttc att taa atc act tcg cta att cct tct gat<br>Ile Ser Gly * Trp Phe Ile * Ile Thr Ser Leu Ile Pro Ser Asp<br>                      1715                                1720 | 9439 |
| gtt ctt cag atg atg gag gtt gct gta cgc ttt ctt agc aag gat act<br>Val Leu Gln Met Met Glu Val Ala Val Arg Phe Leu Ser Lys Asp Thr<br>1725                      1730                         1735                     1740 | 9487 |
| ata gtg caa gct atc tct cga tct gcc acg aaa gta agt tac act ctg<br>Ile Val Gln Ala Ile Ser Arg Ser Ala Thr Lys Val Ser Tyr Thr Leu<br>                      1745                        1750                     1755 | 9535 |
| atg tgt ctc ttg aaa atc ata ttg ata ttc tat tat tgg cct tat ttc<br>Met Cys Leu Leu Lys Ile Ile Leu Ile Phe Tyr Tyr Trp Pro Tyr Phe<br>1760                      1765                         1770 | 9583 |
| aac aca ttc acg taa tat gga gct cca tgg gat gta tga ttt att ccg<br>Asn Thr Phe Thr * Tyr Gly Ala Pro Trp Asp Val * Phe Ile Pro<br>                      1775                        1780                     1785 | 9631 |
| tct ttg caa ctt gtt aat tac aga caa gaa atg ctc tat ccg gca cgt<br>Ser Leu Gln Leu Val Asn Tyr Arg Gln Glu Met Leu Tyr Pro Ala Arg<br>                      1790                        1795                     1800 | 9679 |
| att cag ctc ccc aaa ggt ccg cca gct ctg cag ctc ttc tgg ttg ggg<br>Ile Gln Leu Pro Lys Gly Pro Pro Ala Leu Gln Leu Phe Trp Leu Gly<br>                1805                         1810                     1815 | 9727 |
| atc cct ctg caa tgc gtg ata aag cag gga act ttg tgc ttc cta gag<br>Ile Pro Leu Gln Cys Val Ile Lys Gln Gly Thr Leu Cys Phe Leu Glu<br>1820                      1825                         1830 | 9775 |
| atg atg tca tga aat taa ggg atc gtc tca gga acg aag aaa gag ttg<br>Met Met Ser * Asn * Gly Ile Val Ser Gly Thr Lys Lys Glu Leu<br>1835                      1840                         1845 | 9823 |
| ctg gat caa tct tct aca aaa tgc aat gca gga aag gat tcc gtc atg<br>Leu Asp Gln Ser Ser Thr Lys Cys Asn Ala Gly Lys Asp Ser Val Met<br>1850                      1855                         1860 | 9871 |
| aac cac cta caa atg tag att ata gaa gag aca tgt gtg ccc atg caa<br>Asn His Leu Gln Met * Ile Ile Glu Glu Thr Cys Val Pro Met Gln<br>1865                      1870                         1875 | 9919 |
| gag ttt tgg cac tgg aag agg caa ttg ata cag aat ggg tgt ata tgt<br>Glu Phe Trp His Trp Lys Arg Gln Leu Ile Gln Asn Gly Cys Ile Cys<br>1880                      1885                        1890                     1895 | 9967 |
| ggg aca aat ttg gtg gtt att tac tac tat tgt tag gtt tga cag cta<br>Gly Thr Asn Leu Val Val Ile Tyr Tyr Tyr Cys * Val * Gln Leu<br>                      1900                        1905 | 10015 |
| agg cgg aga gag ttc agg tga atc ctg att cta aat ttt cat ata ttc<br>Arg Arg Arg Glu Phe Arg * Ile Leu Ile Leu Asn Phe His Ile Phe | 10063 |

-continued

| | | |
|---|---|---|
| 1910 | 1915 | 1920 |

| | | |
|---|---|
| ttc tct atg tat gtc taa cac ggg att att aca atg ttg tag gat gag<br>Phe Ser Met Tyr Val * His Gly Ile Ile Thr Met Leu * Asp Glu<br>1925                                    1930                                  1935 | 10111 |
| gta cgg ttg cgc ctc ttc tta gat agc att ggg ttc tcg gat tta agt<br>Val Arg Leu Arg Leu Phe Leu Asp Ser Ile Gly Phe Ser Asp Leu Ser<br>1940                                   1945                                 1950 | 10159 |
| gcc aga aaa atc agt aaa tgg aag cca gag gat aga aga caa ttc gaa<br>Ala Arg Lys Ile Ser Lys Trp Lys Pro Glu Asp Arg Arg Gln Phe Glu<br>1955                                  1960                              1965                     1970 | 10207 |
| att att caa gag agg tat atg ttt ctt ata att atg tgg ttt gac gaa<br>Ile Ile Gln Glu Arg Tyr Met Phe Leu Ile Ile Met Trp Phe Asp Glu<br>                        1975                                  1980                                1985 | 10255 |
| gct gaa ctc tta gac tgt tgc cta tca ttt tct ttt gtg ttg taa att<br>Ala Glu Leu Leu Asp Cys Cys Leu Ser Phe Ser Phe Val Leu * Ile<br>                        1990                                  1995                                2000 | 10303 |
| tta gtt atc tga gag aga aag aga tgg aag agg aaa gcc tta tgc aga<br>Leu Val Ile * Glu Arg Lys Arg Trp Lys Arg Lys Ala Leu Cys Arg<br>                        2005                                  2010                                2015 | 10351 |
| gac gtg aag aag aag gga gag gta aag aaa gaa gga aag ctc ttt tgg<br>Asp Val Lys Lys Lys Gly Glu Val Lys Lys Glu Gly Lys Leu Phe Trp<br>                        2020                                  2025                                2030 | 10399 |
| aga agg aag agc gca aat gga agg aaa ttg aag cgt ccc tta ttc cat<br>Arg Arg Lys Ser Ala Asn Gly Arg Lys Leu Lys Arg Pro Leu Phe His<br>                2035                                  2040                                2045 | 10447 |
| cta ttc cta atg ctg gta gca ggg agg cag cag cca tgg cag ctg caa<br>Leu Phe Leu Met Leu Val Ala Gly Arg Gln Gln Pro Trp Gln Leu Gln<br>2050                                  2055                                  2060 | 10495 |
| tac gtg ctg ttg ggg gtg att ctg tcc ttg agg att cct tcg caa gag<br>Tyr Val Leu Leu Gly Val Ile Leu Ser Leu Arg Ile Pro Ser Gln Glu<br>2065                                  2070                                  2075                                2080 | 10543 |
| aga ggg tct cgg gta ttg cac gta gga tac gca ctg ctc aac tag aac<br>Arg Gly Ser Arg Val Leu His Val Gly Tyr Ala Leu Leu Asn * Asn<br>                        2085                                  2090                                2095 | 10591 |
| gac gtg cac aac agg tta aaa ctt att ttt ata ttc tgc aag tgt tct<br>Asp Val His Asn Arg Leu Lys Leu Ile Phe Ile Phe Cys Lys Cys Ser<br>                        2100                                  2105                                2110 | 10639 |
| ttc tta tga tgc tga tta atg gag aat taa cta aga aaa gtt att acc<br>Phe Leu * Cys * Leu Met Glu Asn * Leu Arg Lys Val Ile Thr<br>                                        2115                                              2120 | 10687 |
| aga ctg gaa tat ctg ggg cag ttt gtg ttc ttg atg atg aac caa tga<br>Arg Leu Glu Tyr Leu Gly Gln Phe Val Phe Leu Met Met Asn Gln *<br>2125                                  2130                                  2135 | 10735 |
| taa gtg gta aac att gcg gcc aaa tgg act caa gtg tct gtc aaa gtc<br>* Val Val Asn Ile Ala Ala Lys Trp Thr Gln Val Ser Val Lys Val<br>                        2140                                  2145                                2150 | 10783 |
| aga aga tta gct ttt ccg tta cag caa tga tcc aat ccg att ctg gac<br>Arg Arg Leu Ala Phe Pro Leu Gln Gln * Ser Asn Pro Ile Leu Asp<br>2155                                  2160                                  2165 | 10831 |
| ctg tat gtc ttt ttg gca ctg aat ttc aaa aga aag tat gtt ggg aga<br>Leu Tyr Val Phe Leu Ala Leu Asn Phe Lys Arg Lys Tyr Val Gly Arg<br>2170                                  2175                                  2180                                2185 | 10879 |
| ttc tgg ttg ctg gtt ctg agc aag gaa ttg agg ctg gcc aag ttg ggc<br>Phe Trp Leu Leu Val Leu Ser Lys Glu Leu Arg Leu Ala Lys Leu Gly<br>                        2190                                  2195                                2200 | 10927 |
| tta ggt tga taa caa aag gtg aga ggc aga caa ccg ttg cta gag agt<br>Leu Gly * * Gln Lys Val Arg Gly Arg Gln Pro Leu Leu Glu Ser<br>                                        2205                                      2210                                2215 | 10975 |
| ggt ata ttg gtg caa cca gca taa ctg atg gaa ggt cta act ctt ttt | 11023 |

```
Gly Ile Leu Val Gln Pro Ala  *  Leu Met Glu Gly Leu Thr Leu Phe
             2220                2225                2230 ccc ctc agt ttc cat att gca aaa ttt act tcg agg act ttt atg atc    11071
Pro Leu Ser Phe His Ile Ala Lys Phe Thr Ser Arg Thr Phe Met Ile
             2235                2240                2245 cat att tct cat gat ctg gtt tgg caa aag ttt ccg atg tta tca tgg    11119
His Ile Ser His Asp Leu Val Trp Gln Lys Phe Pro Met Leu Ser Trp
             2250                2255                2260 att tct gtc ata ttt ata tat tag ctg ttt caa tca cag gtg gca tac    11167
Ile Ser Val Ile Phe Ile Tyr  *  Leu Phe Gln Ser Gln Val Ala Tyr
             2265                2270                2275 agt gac aat cac aat tga tgc tga tgc ggg gga agc tac ttg tta cat    11215
Ser Asp Asn His Asn  *  Cys  *  Cys Gly Gly Ser Tyr Leu Leu His
             2280                2285                2290 aga tgg tgg gtt tga tgg cta cca gaa tgg gtt acc tct aag tat tgg    11263
Arg Trp Trp Val  *  Trp Leu Pro Glu Trp Val Thr Ser Lys Tyr Trp
             2295                2300                2305 cag tgc cat ttg gga aca agg agc tga agt ttg gtt ggg tgt tag gcc    11311
Gln Cys His Leu Gly Thr Arg Ser  *  Ser Leu Val Gly Cys  *  Ala
             2310                2315                2320 acc tat aga tgt tga tgc att cgg gag atc aga tag tga tgg cgt cga    11359
Thr Tyr Arg Cys  *  Cys Ile Arg Glu Ile Arg  *   *  Trp Arg Arg
             2325                2330 atc aaa gat gca tat tat gga tgt ttt cct ttg ggg gaa atg ctt aag    11407
Ile Lys Asp Ala Tyr Tyr Gly Cys Phe Pro Leu Gly Glu Met Leu Lys
             2335                2340                2345 tga aga aga ggc cgc ttc ttt gca tgc agc cat tgg cat ggc tga ctt    11455
 *  Arg Arg Gly Arg Phe Phe Ala Cys Ser His Trp His Gly  *  Leu
             2350                2355                2360 aga cat gat tga ttt gtc tga tga caa ttg gca atg gac gga ttc acc    11503
Arg His Asp  *  Phe Val  *   *  Gln Leu Ala Met Asp Gly Phe Thr
             2365                2370                2375 ccc cag agt atg ttt tcc ttc tgt tga ctg ttg gca tat ttt ttc agt    11551
Pro Gln Ser Met Phe Ser Phe Cys  *  Leu Leu Ala Tyr Phe Phe Ser
             2380                2385                2390 ccg atg ttt gtt aaa agg cta atg tta aaa cct att cta att ttt gtt    11599
Pro Met Phe Val Lys Arg Leu Met Leu Lys Pro Ile Leu Ile Phe Val
             2395                2400                2405 gat tcc ttt ctc ttt tta cca ggt cga tgg ttg gga tag tga tcc tgc    11647
Asp Ser Phe Leu Phe Leu Pro Gly Arg Trp Leu Gly  *   *  Ser Cys
             2410                2415                2420 cga tgt tga tct cta tga tag gga tga cgt aga ttg gga tgg aca ata    11695
Arg Cys  *  Ser Leu  *   *  Gly  *  Arg Arg Leu Gly Trp Thr Ile
             2425                2430 ttc cag tgg gag gaa aag aag atc agg tcg gga ttt tgt aat gag tgt    11743
Phe Gln Trp Glu Glu Lys Lys Ile Arg Ser Gly Phe Cys Asn Glu Cys
             2435                2440                2445 cga ttc ctt tgc cag gag aca cag gaa acc cag gat gga gac aca aga    11791
Arg Phe Leu Cys Gln Glu Thr Gln Glu Thr Gln Asp Gly Asp Thr Arg
2450                 2455                2460                2465 aga tat aaa tca aag aat gcg ttc agt tga gtt ggc tgt caa aga agc    11839
Arg Tyr Lys Ser Lys Asn Ala Phe Ser  *  Val Gly Cys Gln Arg Ser
             2470                2475                2480 tct ctc tgc acg agg tga taa gca att tac tga cca gga att tcc tcc    11887
Ser Leu Cys Thr Arg  *   *  Ala Ile Tyr  *  Pro Gly Ile Ser Ser
             2485                2490 aaa tga tcg ctc ttt att tgt gga tac aca aaa tcc ccc atc aaa att    11935
Lys  *  Ser Leu Phe Ile Cys Gly Tyr Thr Lys Ser Pro Ile Lys Ile
             2495                2500                2505
```

-continued

```
gca ggt atg gat tgt taa att ttt ctc att ttt tct gtt ttt agt taa      11983
Ala Gly Met Asp Cys  *  Ile Phe Leu Ile Phe Ser Val Phe Ser  *
        2510                2515                2520 ata tca ttt taa gtg att ata tat ctg gac aca aaa tct gcc ttc aca      12031
Ile Ser Phe  *  Val Ile Ile Tyr Leu Asp Thr Lys Ser Ala Phe Thr
        2525                2530                2535 tag atc aag taa aac taa caa ctt gat ggg aac tct aac ctt ttg agt      12079
 *  Ile Lys  *  Asn  *  Gln Leu Asp Gly Asn Ser Asn Leu Leu Ser
        2540                2545                2550 gtc ata att tca ggt tgt ttc tga atg gat gag acc tga ctc cat tgt      12127
Val Ile Ile Ser Gly Cys Phe  *  Met Asp Glu Thr  *  Leu His Cys
        2555                2560 gaa aga aaa cgg tag tga ttc ccg tcc ctg cct gtt ctc tgg gga tgc      12175
Glu Arg Lys Arg  *   *  Phe Pro Ser Leu Pro Val Leu Trp Gly Cys
2565                2570                2575 aaa tcc ttc aga tgt ttg cca ggt ttg atc act tac ttt ttc tgt tca      12223
Lys Ser Phe Arg Cys Leu Pro Gly Leu Ile Thr Tyr Phe Phe Cys Ser
        2580                2585                2590 gtt act ttt tcc tga ccg tct tgt atg cat gtc aat tca aaa tga tcc      12271
Val Thr Phe Ser  *  Pro Ser Cys Met His Val Asn Ser Lys  *  Ser
2595                2600                2605 cag aga ttt att ctt gcg att ggg tta act tgt ttt ata ggg gcg ttt      12319
Gln Arg Phe Ile Leu Ala Ile Gly Leu Thr Cys Phe Ile Gly Ala Phe
        2610                2615                2620 ggg gga ttg ttg gtt ctt aag cgc cgt tgc agt ttt gac aga ggt ttc      12367
Gly Gly Leu Leu Val Leu Lys Arg Arg Cys Ser Phe Asp Arg Gly Phe
2625                2630                2635                2640 acg aat atc tga agt gat cat tac tcc tga ata caa cga gga agg gat      12415
Thr Asn Ile  *  Ser Asp His Tyr Ser  *  Ile Gln Arg Gly Arg Asp
                    2645                2650 cta cac tgt tcg ttt ttg tat tca ggt tcc tgt ctc aaa cat tct ttc      12463
Leu His Cys Ser Phe Leu Tyr Ser Gly Ser Cys Leu Lys His Ser Phe
2655                2660                2665                2670 acg gca ctt ctt tgt tct ctt gat tgt agc atc gtg cag gtt ctt cta      12511
Thr Ala Leu Leu Cys Ser Leu Asp Cys Ser Ile Val Gln Val Leu Leu
                2675                2680                2685 tga ttt gtg tac aat cag agg ttt gaa gtt tga ttg ctt tcc cct tgc      12559
 *  Phe Val Tyr Asn Gln Arg Phe Glu Val  *  Leu Leu Ser Pro Cys
        2690                2695                2700 agg gtg agt ggg ttc ctg ttg tta tcg atg act gga ttc cat gtg aat      12607
Arg Val Ser Gly Phe Leu Leu Leu Ser Met Thr Gly Phe His Val Asn
                2705                2710                2715 cac ctg gta aac cag ctt ttg cta cta gca gaa agc tca atg aac tct      12655
His Leu Val Asn Gln Leu Leu Leu Ala Glu Ser Ser Met Asn Ser
        2720                2725                2730 ggg tct cca tgg tgg aga aag cat atg cca agc tcc atg gtt ctt atg      12703
Gly Ser Pro Trp Trp Arg Lys His Met Pro Ser Ser Met Val Leu Met
        2735                2740                2745 agg cac tgg agg ggg gac tgg ttc agg atg ctc ttg tcg acc taa ctg      12751
Arg His Trp Arg Gly Asp Trp Phe Arg Met Leu Leu Ser Thr  *  Leu
        2750                2755                2760 gag gag ctg gta agg aga ttg act tgc gga gtg ctc aag cac aaa tag      12799
Glu Glu Leu Val Arg Arg Leu Thr Cys Gly Val Leu Lys His Lys  *
        2765                2770                2775 atc ttg caa gtg gca gat tgt ggt ctc aat tgt tac gtt tta aac aag      12847
Ile Leu Gln Val Ala Asp Cys Gly Leu Asn Cys Tyr Val Leu Asn Lys
        2780                2785                2790 agg ggt tct tac ttg gtg ctg gaa gtc cat cag gat ctg atg ttc atg      12895
Arg Gly Ser Tyr Leu Val Leu Glu Val His Gln Asp Leu Met Phe Met
2795                2800                2805                2810
```

```
tat ctt cca gtg gca ttg tgc aag ggc atg ctt act ccg tct tac agg        12943
Tyr Leu Pro Val Ala Leu Cys Lys Gly Met Leu Thr Pro Ser Tyr Arg
            2815                2820                2825 tat tcc ctt ttg ctt tgg ttg cat ttg cca tat cct gag tat gag aac        12991
Tyr Ser Leu Leu Leu Trp Leu His Leu Pro Tyr Pro Glu Tyr Glu Asn
            2830                2835                2840 aca att taa tat att tac gta ctg tct ttc ttc agg tga gag agg ttg        13039
Thr Ile  *  Tyr Ile Tyr Val Leu Ser Phe Phe Arg  *  Glu Arg Leu
            2845                2850                2855 atg ggc aca gac ttg ttc aga ttc gaa atc cat ggg cta atg aag ttg        13087
Met Gly Thr Asp Leu Phe Arg Phe Glu Ile His Gly Leu Met Lys Leu
            2860                2865                2870 agt gga atg gtc cct ggt cag act cat ccc cag agt gga ctg ata gga        13135
Ser Gly Met Val Pro Gly Gln Thr His Pro Gln Ser Gly Leu Ile Gly
            2875                2880                2885 tga agc aca agc tga agc atg ttc cac agg tag ttt ctc ttg cgc tta        13183
 *  Ser Thr Ser  *  Ser Met Phe His Arg  *  Phe Leu Leu Arg Leu
            2890                2895                2900 act tct tta cag ctc att cct tgt gtt cct tga att ctc tta gtc cga        13231
Thr Ser Leu Gln Leu Ile Pro Cys Val Pro  *  Ile Leu Leu Val Arg
            2905                2910                2915 tta ggg gga cta tat ttc aga aac tgg taa aag att ttg ctt tat tgt        13279
Leu Gly Gly Leu Tyr Phe Arg Asn Trp  *  Lys Ile Leu Leu Tyr Cys
            2920                2925                2930 taa caa ggg gac aca cat gga caa aac ata gtg ctc aca aac aca tag        13327
 *  Gln Gly Asp Thr His Gly Gln Asn Ile Val Leu Thr Asn Thr  *
            2935                2940                2945 tta ggt gta aat ata tgt aat tat gct atg gtt tct tca agt aaa gta        13375
Leu Gly Val Asn Ile Cys Asn Tyr Ala Met Val Ser Ser Ser Lys Val
            2950                2955                2960 tat tgc gta ctg atc ctg tgc att ctg tta aac agt caa aag aag gta        13423
Tyr Cys Val Leu Ile Leu Cys Ile Leu Leu Asn Ser Gln Lys Lys Val
            2965                2970                2975 tat tct gga tgt ctt ggc aag att tcc aga ttc att tca gat caa tat        13471
Tyr Ser Gly Cys Leu Gly Lys Ile Ser Arg Phe Ile Ser Asp Gln Tyr
            2980                2985                2990 atg tgt gtc ggg ttt acc ccc gtg aga tgc gct act ctg taa atg gcc        13519
Met Cys Val Gly Phe Thr Pro Val Arg Cys Ala Thr Leu  *  Met Ala
            2995                3000                3005 aat ggc gag gtt ata gtg ccg gtg gct gcc aag att ata gct cat ggc        13567
Asn Gly Glu Val Ile Val Pro Val Ala Ala Lys Ile Ile Ala His Gly
            3010                3015                3020 atc aaa atc cac aat tca ggc tga ggg caa ctg gtt ctg atg cat ctt        13615
Ile Lys Ile His Asn Ser Gly  *  Gly Gln Leu Val Leu Met His Leu
3025            3030                3035 tac caa ttc atg tgt tca tca cct taa ctc agg cac atg cta tcc ctt        13663
Tyr Gln Phe Met Cys Ser Ser Pro  *  Leu Arg His Met Leu Ser Leu
3040            3045                3050 gat gga aac ttt ttc tat cta taa ttc ttt tgt aat tat cct cag ctc        13711
Asp Gly Asn Phe Phe Tyr Leu  *  Phe Phe Cys Asn Tyr Pro Gln Leu
3055            3060                3065 att ctc cca atg tta ctt aca ggg cgt agg ttt ctc gag aac aac tcc        13759
Ile Leu Pro Met Leu Leu Thr Gly Arg Arg Phe Leu Glu Asn Asn Ser
3070            3075                3080                3085 tgg att tcg taa cta cca atc aag cca tga ttc aca gtt gtt cta tat        13807
Trp Ile Ser  *  Leu Pro Ile Lys Pro  *  Phe Thr Val Val Leu Tyr
                    3090                3095 cgg att gag gat tct taa aac tcg tgg acg tcg tgc tgc tta caa cat        13855
Arg Ile Glu Asp Ser  *  Asn Ser Trp Thr Ser Cys Cys Leu Gln His
```

-continued

```
     3100                3105                3110
att  tct tca tga atc tgt tgg tgg aac aga cta tgt gaa ttc ccg tga             13903
Ile  Ser Ser  *  Ile Cys Trp Trp Asn Arg Leu Cys Glu Phe Pro  *
     3115                3120                3125
gat  ttc atg tga aat ggt tct tga ccc tga tcc taa ggg tta tac tat             13951
Asp  Phe Met  *  Asn Gly Ser  *  Pro  *  Ser  *  Gly Leu Tyr Tyr
     3130                3135                         3140
tgt  ccc aac cac gat aca ccc agg gga aga agc acc ttt tgt cct ttc             13999
Cys  Pro Asn His Asp Thr Pro Arg Gly Arg Ser Thr Phe Cys Pro Phe
               3145                3150                3155
agt  ctt cac aaa agc atc cat tgt tct tga agc ttt gt agtgccgta                14047
Ser  Leu His Lys Ser Ile His Cys Ser  *  Ser Phe
                    3160                3165
```
ttgtcagatg gctctctcag caacctgcat gccatgaaat catccaagtg cttgtgttgt    14107
ttaaggaacc agacggctta cgtctcaatg ttaagacttg ttttgcccac gatccacgca    14167
acattagaga aggtaaattt cttaacctttt ctgcaaggat tgctcttttc ctatcctcac    14227
tcactgttcc tcattcagac ttaactccct ccgcaacagc gtctgatctg atagctggcc    14287
atcacattat tggtgaatct atgaagtctc gggataaaat gttttagtta ttgtcctgat    14347
tttgaaccac gaagttaact gctcagagga tagataattt gcactggaga aagcactttt    14407
caggcatggc tcaccggcat tccatctcga tcttgagaca cgcatcaaat gtacatttgt    14467
aggtattgcg acaagtacag atttattaaa tgtagaataa ctacttcata actgaggaaa    14527
caaggagaga aataggagac ttgtgacttg ttgggtaaag gttggtatt cggtagtggt    14587 agctgcagtt ttggttggtg tgttgtaata ttcagacact aatctgtgtg cagatttcgt    14647
ttcaactcta atatatgagg gctctctttc tctctcgttc tctttcacta tctctcttaa    14707
tctgtgtttg gagttctctt tacactcgct cacccatttg taaatggaga ttctagaact    14767
tctcaacagg aaccgctgtt gtgtacatga attgtctatt tgcagatcaa ctagtataaa    14827
accaagcaaa aggtaagaaa agagacagat taagaagata ggttagcttt gaaagcaaaa    14887
gatccgtcaa aaatacaagt gcctcatagt taacctgtag taatgaagag aggcatctca    14947
aaatgcaacg aaaaagtgaa atacaccttc ctaccccctcg ccaaaatctt gaatatctca    15007
tttaagttct ttcttcgacg gttcttcact ccgaatcgct ttccatgctc cccattgcct    15067
tcaatcctct tggtctctac atgaaaatat gaatgtatca cacctctctg ctagtacata    15127
aacattaact tctacagaga aactagaaag agaaaaatct gatagatacc ttcttttgaag    15187 tcttcttctc tcttacttca tatctctctt tgcacagatc tgataaccaa gctcctggac    15247
tcaccagctg cattatacat aacaatcatg agataaaaat ggttatgaag aacacaaacg    15307
ttaagttttc aaagagactc acaagcaatg tcttctgaac caatttggct cgcttcttag    15367
gtctttgagg aagcttgcaa cctttcatag ccaaaaaatc ttcttccttc tctttatttg    15427
acaaagctat atacaacttt ggccacacat gcttctttgt ttcttttcaca ggttccttaa    15487 taattttccc actctcatct attcccatcg aacccccttgt tgtataatac ctatcttcct    15547
tctcgggcga cgccataaac gatctccgca cattgactag agaatcagtg atcctatcac    15607
cgcagaaaca taacaatatc ttacatataa aaaaacttga aaaatatcac ttttttccccc    15667 aataatactt acttgttagg acggttaaga tgtcgagaag gtgagcctct ctcagaagag    15727
acagcacgag aaatgagttt acgtttagtc aaacaatcag ttgatttgcc attggcaagg    15787 cttttgatctt tcttcacttt catacatcta actcttttcc tctcacccca ttgcaacaca    15847
aaatctgcct ctgtggttcc acttcctctt tgtcccttta cctcctccat tacacaacac    15907

```
tcactttctt tctcttaacc ttaaacaacc aacaaagaaa cataaactca gacattgaaa   15967
actcttccag aaatagacca aacaaatcta gaacaaccac taagaaactt ctgtttacaa   16027 aagggaaaa  agttctgttt acaaatcata ctcgtttctg atttctaaca aatactgaaa   16087
caaaaccaca gattaagata gacaaatcag gactaatttg tagagacaag acacactaac   16147
ctcaagatct gcaactttaa ctcagcgact tatcttccag aatcaccct  caaagcagca   16207 atatccaaaa acaatattaa aaaaatcaga aaaaaaatag actaaaatct ataaatcaga   16267
tagtgtttac agcagaatcg attcttcaat actatataga acacaaacac accattgtca   16327
tataaataca gaaacaatag ctttaccaaa aaaataaacc caaaaaagaa gagcataaac   16387
acttacaaga gtgaaactag atgaaaccaa agacagaaac ttgggatgaa caatttttta   16447
ggtgaaatgg agaaaaaaag ttgttccctt ttcttctctc agaagatgga tagattcaaa   16507
ctccacaaaa aaatagaaaa agaatttgta atctggattt tcttttaata tctcgatgag   16567
accagaagat cgaaacactg tttatctatc ttctttaaac acacacacac acaaaagaaa   16627
taaaaactgc ttaccctctg gtctttactg cgacgctcac cttttttttt tttttttta    16687 atatgccatt ttattatttt tgctcatttt aatttaataa tgaaaaaat  aatgtgattg    16747 ataacaaccg tcagatatgt aatggatggt gagatgggct tctagaagtt aaaaaaagcc    16807
taagcctgtt gtgtttgata aaagagtgaa ctcgttatgg ggactaacga atcatgttat    16867
gacatgtgta ttgtttttgt cgagtacacg ttagtacggt ttcagtggat aataaacacc    16927
atgccatatg tccggcgaga agatccaaaa taagattttg cgctaagaca gtaaaaaggt    16987
tttgtcccac gcgccaatga catctgattt ctcagatttg aacaaaattc gcctttggct    17047
tttacagggc ggtgagtgtc acgctctaaa gatgcgtgtg tgattagatg taaacccaat    17107
tcatattcaa acttgggcta atataggctt aatttatggg ctttcgtagt gaggcttttt    17167
acagaaattt tctaattttc tcatcattta tatagtttac ttactagtga gtatttagta    17227
acttgccctc taaaaagatt ttgtcagcaa tttttttggtg atactgctgc ttcgttttac    17287
aggtctaatg aatgcagcca aggtaataga ataatcgaat gagagctttg gtcatctgtc    17347
tggtaagatc atatccgttg gatgttcaat atgttgaggc ttttaagtct gaaacagaac    17407
ttgaagatta ggttacttgt tacttttaag ttgttaataa tgagattatc aagatctttt    17467
gggttatcga gttatgtcag tagagtcttc tactgttgta ccaatttgta accctttgtta   17527 tatatatata aaatgatatg ggaaaactta tagttttttt tttctctctt cattttttgta   17587 cattcaagaa agaaaaaaga aaaaaataat aattttcttc gataataatc tccaatttt    17647 attttctata aaatttaata ttctcttttt tcaaataaat aaattcttgg ctataagtat    17707
ttctgtcaag ctaaatatat atatcaaatg aacaagtaga cattggactg ctagcttcac   17767
agagatgtac atagacgcag atatctgtaa accgtgtcta gatttcaaaa cactcttagc    17827
aaaatggaag tccagcatag taaaagagtt gtagttcttt tctgaaaaac aggtagaaat    17887
attatctctt aacctgattg agataaaaaa aacataatac ttaaatataa taagtatatt    17947 ctatatttt  taaagtatat tatatttgtg tatcttgtaa ttgtaaaaga aatttgtatt    18007
ctgtcacgag tgaatatata tatgaatttt ttttcttaaa tgtaattgtg gttctatgca    18067
tatcatatat ttctgaaatt ccaaacggct atgtgttctc ttttgtggtc agtctcagtc    18127
acatttgttt atcttacaat aatttattat ttaaatgtgt tcctctaata agcagttaaa    18187
ggaggcaaat gagttttcaa aactgcaaaa tgagatttca aaacatatttt ttgaagaaaa   18247
```

```
                                                -continued
gttaactaga ttttaatcca accaatggtc cactagattt caaagttcca acatggaact    18307
cattattatg ctttggtcgg aaaagtgtta aagttttatt tttgaatctc actttctcgt    18367
tgcggccttg tttaaactac ttgctgatct aaaacttaaa cggttccttc taattcctta    18427
aacgacggag aatttaaatt agttaatgag tagtctttat gaaaaaatca aaataaaaga    18487
gagtgaataa ttcgaaaaca aaagtaacaa acaaataatt cgtatgttta cggtgttagg    18547
gtccacaaaa gcagtccagc ctcatgcata tgattatgca taattgtatg tttgtatttt    18607
gtaagctttt ccagctattt tattttgtta tcttcttctt cggtctgttt gatttctttt    18667
tttgtatatg attttaaaaa gcatgctact gatatactaa ttcttttctt ttgtaattgg    18727
ggtagttggt cattttcata gtttggtgtg aacgttggta tgaacatcac taatttcaag    18787
gaaacactaa aacggctaat tgacccttta gtgcaatcag aatagtacat aaataaagta    18847
attgtttctt aaagaaaaaa aaattcttag atagaaggaa aaggagtatt ctagaatata    18907
gttttgatga aaaatagttc tccatataat aggtttattt ttaattaata aaatatatgt    18967
ttattgaaga aaaagaagga aatgatgctt agtaaatttg cttacaaact aagcaaaatc    19027
tctataaatt aatattttg tgcgtaaaat attttattaa tttataaaga tattaactga    19087
taaaagttaa tctaagactt gatccacttt ataatctgtg gatccgcgag attactaagt    19147
ggattaaatt ctatgattat attttctaa taacatatta atgtatttgt tataatttat    19207
gagtgtactc tccaaataat agtatatgat aaaaaatttt taatacacta aaaaaactat    19267
agaattttac ttagctcatc tcaatctcat ctagagtttg gttattaata gtactaagta    19327
atagctaatc ttttaaataa gtagaataaa aacttttttaa atacaccaac aaagttagat    19387
gtaacttctt atcctttgaa caactcatgt gaagtcacaa atacaaaatt cattacaatc    19447
aaaacaaaaa ttagtaaaaa acgttttgt gaggttggaa agaaaaaagg acagtggttg    19507
agaaaaagaa gaatgtggtt tgggccaaga gacagccaat ttgccagctg taaaatctca    19567
tacaattgtt gtataaatag acaataccat ccccacaact attatcatca caacacaaat    19627
caaaacaaga ataacaaaat ctttctctta taaattctta tttcaagaca tcaaaggaga    19687
attaatggag gcaatgaaga tgaagatgat ggtgtttatt atggttgttg cggtggcttt    19747
ctcagctgcc acggctgcta ccgttgaagc tccagctcca agcccaactt ctgatgctgc    19807
catgtttgta ccagcactgt ttgcatctgt tgttgctttg gcatctggtt tcatcttttg    19867
atcattcttt ttttcttcat tatttaattg catttgttaa tgagtttgcg tgatttgatt    19927
ctctattgtt agaatgttgc attcttattt cttaatgtaa ccatctgttt ctctatgtat    19987
ctatgtgtat tatcaattca tcactgttta tgagatcgtt tatcttaa                 20035
```